United States Patent
Jasti et al.

(10) Patent No.: US 11,555,820 B2
(45) Date of Patent: *Jan. 17, 2023

(54) NANOHOOP COMPOUNDS FOR USE IN BIOTECHNOLOGY AND METHODS OF MAKING AND USING THE SAME

(71) Applicant: University of Oregon, Eugene, OR (US)

(72) Inventors: Ramesh Jasti, Eugene, OR (US); Bruce P. Branchaud, Eugene, OR (US); Brittany White, Eugene, OR (US); Terri Lovell, Eugene, OR (US); Curtis Colwell, Eugene, OR (US)

(73) Assignee: University of Oregon, Eugene, OR (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/041,676

(22) Filed: Jul. 20, 2018

(65) Prior Publication Data

US 2019/0025315 A1 Jan. 24, 2019

Related U.S. Application Data

(60) Provisional application No. 62/535,623, filed on Jul. 21, 2017.

(51) Int. Cl.

| | | |
|---|---|---|
| *C07D 471/08* | (2006.01) | |
| *G01N 33/58* | (2006.01) | |
| *A61K 45/06* | (2006.01) | |
| *C12Q 1/6837* | (2018.01) | |
| *G01N 33/533* | (2006.01) | |
| *C07H 15/26* | (2006.01) | |
| *C07D 285/16* | (2006.01) | |
| *C07C 13/28* | (2006.01) | |
| *C07D 513/04* | (2006.01) | |
| *C07C 63/331* | (2006.01) | |
| *B82Y 5/00* | (2011.01) | |
| *B82Y 30/00* | (2011.01) | |

(52) U.S. Cl.
CPC .......... *G01N 33/582* (2013.01); *A61K 45/06* (2013.01); *C07C 13/28* (2013.01); *C07C 63/331* (2013.01); *C07D 285/16* (2013.01); *C07D 513/04* (2013.01); *C07H 15/26* (2013.01); *G01N 33/533* (2013.01); *B82Y 5/00* (2013.01); *B82Y 30/00* (2013.01); *C12Q 1/6837* (2013.01)

(58) Field of Classification Search
CPC .... G01N 33/582; G01N 33/533; A61K 45/06; C07C 13/28; C07C 63/331; C07D 285/16; C07D 513/04; C07H 15/26; B82Y 5/00; B82Y 30/00; C12Q 1/6837
See application file for complete search history.

(56) References Cited

U.S. PATENT DOCUMENTS

| | | | |
|---|---|---|---|
| 8,461,403 B2* | 6/2013 | Jasti | C07C 1/22 |
| | | | 568/626 |
| 8,895,768 B2 | 11/2014 | Yamago | |
| 9,029,551 B2 | 5/2015 | Itami et al. | |
| 9,090,473 B2 | 7/2015 | Jasti et al. | |
| 9,481,618 B2 | 11/2016 | Itami et al. | |
| 9,527,737 B2 | 12/2016 | Itami et al. | |
| 10,934,290 B2* | 3/2021 | Jasti | H01L 51/0051 |
| 2004/0202603 A1* | 10/2004 | Fischer | B01J 20/28009 |
| | | | 423/447.2 |
| 2011/0166390 A1 | 7/2011 | Jasti et al. | |
| 2012/0220790 A1 | 8/2012 | Yamago | |
| 2015/0064720 A1* | 3/2015 | Chen | G01N 33/588 |
| | | | 435/7.21 |
| 2015/0152022 A1 | 6/2015 | Jasti et al. | |
| 2016/0372684 A1 | 12/2016 | Jasti et al. | |
| 2018/0290952 A1 | 10/2018 | Jasti et al. | |

OTHER PUBLICATIONS

Kuwabara et al. (Angew. Chem. Int. Ed. 2015, vol. 54, pp. 9646-9649) (Year: 2015).*
Xue et al. (J. Org. Chem. 2014, vol. 79, pp. 9735-9739) (Year: 2014).*
Darzi et al. (J. Org. Chem. 2012, vol. 77, pp. 6624-6628, published Jul. 17, 2012) (Year: 2012).*
Nishihara et al. (J. Phys. Chem. Lett. 2012, vol. 3, pp. 3125-3128, published Oct. 12, 2012). (Year: 2012).*
Ozasa et al. Bull. Chem. Jpn., vol. 53, pp. 2610-2617, published 1980 (Year: 1980).*
Salvatella et al. (Educacion Quimica (2017), vol. 28, pp. 232-237). (Year: 2017).*
Bandyopadhyay et al. (Phys. Chem. Chem. Phys., 2016, vol. 18, pp. 20682-20690, published Jul. 6, 2016). (Year: 2016).*
Ishii et al., "Synthesis and dimerization of chloro[10]cycloparaphenylene: a directly connected cycloparaphenylene dimer," *Organic Letters*, vol. 16, pp. 2174-2176, Apr. 1, 2014.
Kikuchi et al., "Definitive evidence for the contribution of biradical character in a closed-shell molecule, derivative of 1,4-Bis-(4,5-diphenylimidazol-2-ylidene)cyclohexa-2,5-diene," *JACS Communications*, vol. 126, pp. 6526-6527, May 11, 2004.
Kubota et al., "$\eta^6$-Cycloparaphenylene transition metal complexes: synthesis, structure, photophysical properties, and application to the selective monofunctionalization of cycloparaphenylenes," *JACS*, vol. 137, pp. 1356-1361, Jan. 2015.

(Continued)

*Primary Examiner* — Tracy Vivlemore
*Assistant Examiner* — Nam P Nguyen
(74) *Attorney, Agent, or Firm* — Klarquist Sparkman, LLP

(57) ABSTRACT

Disclosed herein are embodiments of nanohoop compounds and conjugates thereof that can be used myriad biological applications. The nanohoop compounds described herein can exhibit beneficial properties that are useful in biotechnology, such as a fluorescent tag, probe, or label.

21 Claims, 10 Drawing Sheets

(56) References Cited

OTHER PUBLICATIONS

Matsui et al., "Synthesis and properties of cycloparaphenylene-2,5-pyridylidene: a nitrogen-containing carbon nanoring," *Organic Letters*, 14(7): 1888-1891, Feb. 2012.

Mutoh et al., "Entropy-controlled biradical-quinoid isomerization of a π-conjugated delocalized biradical," *Phys. Chem. Chem. Phys.*, vol. 17, pp. 1151-1155, Nov. 17, 2014.

Oki et al., "One-pot synthesis of a rice-ball-shaped cyclophane with syn-diethanoanthracene-fused dipyrrole and hexafluorobenzene," *Chem. Lett.*, vol. 46, pp. 243-244, Nov. 26, 2016.

Rio et al., "Cyclotetrahalo-p-phenylenes: simulations of halogen substituted cycloparaphenylenes and their interaction with $C_{60}$," *Phys. Chem. Chem. Phys.*, vol. 18, pp. 23257-23263, Jul. 22, 2016.

Takase et al., "Donor-acceptor segregated paracyclophanes composed of naphthobipyrrole and stacked fluoarenes," *Organic Letters*, 15(13): 3202-3205, Jun. 2013.

White, "[n]Cycloparaphenylenes as a new class of cellular imaging agents," Presentation slides dated Jul. 22, 2017.

Xia et al., "Synthesis, characterization, and computational studies of cycloparaphenylene dimers," *JACS*, vol. 134, pp. 19709-19715, Nov. 6, 2012.

Ball et al., "Stepping into the Light: Conjugated Macrocycles with Donor-Acceptor Motifs," *ACS Cent. Sci.*, 1, 416-417, Oct. 27, 2015.

Darzi et al., "Synthesis, Properties, and Design Principles of Donor-Acceptor Nanohoops," *ACS Central Science*, vol. 1, pp. 335-342, Sep. 3, 2015.

Darzi et al., "The dynamic, size-dependent properties of [5]-[12]cycloparaphenylenes," *Chem. Soc. Rev.*, vol. 44, pp. 6401-6410, Apr. 27, 2015.

Darzi, Research Presentation/Slides, Sep. 24, 2014.

Havinga et al., "A new class of small band gap organic polymer conductors," *Polymer Bulletin*, 29(119): 119-126, Aug. 1992.

Hirst "Synthesis of Nitrogen-Substituted Cycloparaphenylenes," Dissertation, May 2014.

Hirst "Synthesis of Nitrogen-Substituted Cycloparaphenylenes," Thesis Defense Presentation, May 13, 2014.

Iwamoto et al., "Selective and Random Syntheses of [n]Cycloparaphenylenes (n=8-13) and Size Dependence of Their Electronic Properties," *J. Am. Chem. Soc.*, 133(21): 8354-8361, May 4, 2011.

Iwamoto et al., "Size-Selective Encapsulation of $C_{60}$ by [10]Cycloparaphenylene: Formation of the Shortest Fullerene-Peapod," *Agnew. Chem. Int. Ed.*, vol. 50, pp. 8342-8344, Jul. 18, 2011.

Jasti et al., "Synthesis, Characterization, and Theory of [9]-, [12]-, and [18]Cycloparaphenylene: Carbon Nanohoop Structures," *J. Am. Chem. Soc.*, vol. 130, pp. 17646-17647, Dec. 4, 2008.

Xia et al., "Gram-scale synthesis and crystal structures of [8]- and [10]CPP, and the solid-state structure of $C_{60}$@[10]CPP," *Chemical Science*, vol. 3, pp. 3018-3021, Jul. 11, 2012.

Xia et al., "Synthesis, Characterization and Computational Studies of Cycloparaphenylene Dimers," *J. Am. Chem. Soc.*, 134(48): 19709-19715, Nov. 6, 2012.

Zhang et al., "Giant Cyclo[n]thiophenes with Extended π Conjugation," *Angewandte Chemie Int. Ed.*, 48(36): 6632-6635, Jun. 27, 2009.

\* cited by examiner

NANOHOOP COMPOUNDS FOR USE IN BIOTECHNOLOGY AND METHODS OF MAKING AND USING THE SAME

CROSS REFERENCE TO RELATED APPLICATIONS

This application claims the benefit of the earlier filing date of U.S. Provisional Patent Application No. 62/535,623, filed on Jul. 21, 2017, the entirety of which is incorporated herein by reference.

ACKNOWLEDGMENT OF GOVERNMENT SUPPORT

This invention was made with government support under Contract No. CHE-1255219 awarded by the National Science Foundation. The government has certain rights in the invention.

FIELD

The present disclosure concerns nanohoop compounds and methods of making nanohoop compounds, as well as their uses in biological and biotechnological applications.

BACKGROUND

The use of fluorescent dyes is prevalent throughout a variety of applications, such as biological assays, bio-imaging, sensor chemistry, dye chemistry, and the like. Several conventional dyes, however, exhibit reactivity, photoinstability, and/or low intensity fluorescence that limits their applicability across the scope of applications using dyes. For example, many conventional dyes exhibit low quantum yields that limits their intensity and/or are reactive towards nucleophiles, which can interfere with their fluorescence. New dyes are needed that avoid these disadvantages and that can be used across all applications utilizing dyes. Also needed are compounds that can be used as signal-generating species for use in biotechnological applications (e.g., immunoassays, flow cytometry, and the like) and other applications (e.g., super-resolution microscopy, data storage, and the like).

SUMMARY

Described herein are embodiments of compounds having a nanohoop structure, including embodiments that contain functionality to link nanohoops together, to a chemical moiety, a biological moiety, or both. In certain disclosed embodiments, the nanohoop can comprise a solubilizing group, a quenching moiety, or a biological moiety, and can comprise an optional linker that links the solubilizing group, the quenching moiety, or the biological moiety to the nanohoop compound (e.g., such as an aliphatic, heteroaliphatic, aryl, or heteroaryl linker). For example, the biological moiety can comprise a peptide, an oligonucleotide, a nucleoside, a nucleotide, a protein, an aptamer, a drug, a cell, an antibody, an amino acid, a lipid, a carbohydrate, a liposome, a cyclodextrin, or a porphyrin. In some embodiments, the nanohoop can be coupled to another chemical moiety directly or through a linker component. In some embodiments, the chemical moiety can be selected from an electron-donating group, an electron withdrawing group, or a functional group that facilitates coupling of the nanohoop compound with a solubilizing group, a quenching moiety, and/or a biological moiety. In particular disclosed embodiments, the compounds are nanohoop compounds comprising five or more aromatic rings, with some embodiments having at least one aromatic ring comprising a substituent or that is bound to other rings of the nanohoop compound skeleton by bonds that are meta-substituted relative to each other. In some embodiments, the nanohoop compounds can comprise fused ring systems that comprise a mixture of aromatic and non-aromatic rings.

In some embodiments, two or more nanohoop compounds can be coupled together to form a polymeric nanohoop compound.

The nanohoop compounds described herein can be used in a variety of applications, including chemical and biological applications. Solely by way of example, the nanohoop compounds can be used to make fluorescent dyes or labels. In certain embodiments, the nanohoop compounds may be used in biological assays, imaging techniques, and flow cytometry applications, such as to image cells, detect biomarkers, and the like.

Also disclosed herein are embodiments of methods used to make the nanohoop compounds and conjugates disclosed herein. In particular embodiments, the nanohoop compounds can be conjugated to a biological moiety. Kits and embodiments of methods of using the disclosed nanohoop compounds for assays and/or sample analysis are additionally described.

The foregoing and other objects, features, and advantages of the present disclosure will become more apparent from the following detailed description, which proceeds with reference to the accompanying figures.

DETAILED DESCRIPTION

I. Overview of Terms

Figure 1:
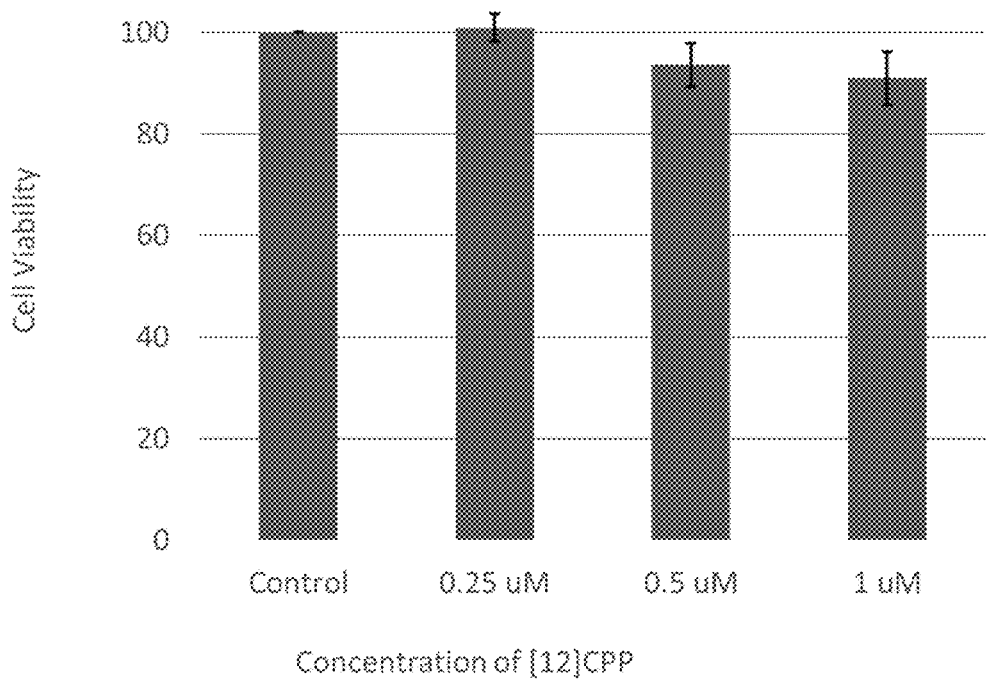
FIG. 1 is graph showing the viability of HeLa cells in the presence of varying concentrations of a nanohoop compound.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a "—" symbol at the beginning of the functional group formula; this symbol is not a part of the functional group, but instead denotes how the functional group connects to the formulas described herein. For example, a functional group with a formula "—OC(O)R$^b$" is attached to an atom of the functionalized compound by the oxygen atom of the functional group that is next to the "—" symbol.

Acyl Halide: —C(O)X, wherein X is a halogen, such as Br, F, I, or Cl.

Acyloxy: —OC(O)R$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, such as —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-10}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Alkylaryl/Alkenylaryl/Alkynylaryl: An aryl group that is or can be coupled to a compound disclosed herein, wherein the aryl group is or becomes coupled through an alkyl, alkenyl, or alkynyl group, respectively.

Alkylheteroaryl/Alkenylheteroaryl/Alkynylheteroaryl: A heteroaryl group that is or can be coupled to a compound disclosed herein, wherein the heteroaryl group is or becomes coupled through an alkyl, alkenyl, or alkynyl group, respectively.

Amide: —C(O)NR$^b$R$^c$ wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Amine: —NR$^b$R$^c$, wherein each of R$^b$ and R$^c$ independently is selected from hydrogen, aliphatic, aryl, heteroaliphatic, aliphatic-aryl, heteroaryl, aliphatic-heteroaryl, heteroaliphatic-aryl, heteroaliphatic-heteroaryl, and any combination thereof.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aryl, heteroaryl, other functional groups, or any combination thereof. In some embodiments, the aryl ring is selected from, but not limited to, phenyl, naphthyl, anthracenyl, indenyl, azulenyl, fluorenyl, tetracyanoanthaquinodimethyl, and the like.

Carboxyl: —C(O)OR$^b$, wherein R$^b$ is aliphatic, aryl, heteroaliphatic, aliphatic-aryl, heteroaryl, aliphatic-heteroaryl, heteroaliphatic-aryl, heteroaliphatic-heteroaryl, hydrogen, and any combination thereof.

Carboxylate: A-CO$_2$— anion, including salts thereof.

Electron-Accepting Group (EAG): A functional group capable of accepting electron density from the ring to which it is directly attached, such as by inductive electron withdrawal.

Electron-Donating Group (EDG): A functional group capable of donating at least a portion of its electron density into the ring to which it is directly attached, such as by resonance.

Ester: —C(O)OR$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl, or any combination thereof.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Halogen: An atom selected from fluoro, chloro, bromo, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group. Exemplary heteroaliphatic groups include, but are not limited to, aliphatic groups comprising an ether, a thioether, an ester, an amine, a carboxy, a carbonyl, or an amide.

Heteroaliphatic-aryl: An aryl group that is or can be coupled to a compound disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or two or more fused rings, which fused rings may or may not be aromatic and/or contain a heteroatom, provided that the point of attachment is through an atom of the aromatic heteroaryl group. In some embodiments, the heteroaryl ring is selected from, but not limited to, pyridinyl, quinolinyl, quinazolinyl, quinoxalinyl, benzoquinolinyl, benzoquinoxalinyl, benzoquinazolinyl, indolyl, indolinyl, benzofuranyl, benzothiophenyl, benzimidizolyl, purinyl, carbazolyl, acridinyl, phenazinyl, and the like.

Ketone: —C(O)R$^b$, wherein R$^b$ is selected from aliphatic, aryl, heteroaliphatic, aliphatic-aryl, heteroaryl, aliphatic-heteroaryl, heteroaliphatic-aryl, heteroaliphatic-heteroaryl and any combination thereof.

Nanohoop: A compound comprising linked rings, such as linked aromatic rings (or groups), that are organized to form a hoop-like structure. In some embodiments, the rings can be linked in a para-, ortho-, or meta-substituted manner, or other positional manner. In some embodiments, the rings of the nanohoop skeleton are all linked in a para-substituted manner such that the bonds connecting each ring to two other rings of the nanohoop compound are para-substituted relative to each other. In some additional embodiments, at least one ring of the nanohoop skeleton is linked in a meta-substituted manner such that the bonds connecting this ring to two other rings of the nanohoop compound are meta-substituted relative to each other.

Phosphate Ester: A —P(O)(OR$^b$)$_2$ group, wherein each R$^b$ independently is selected from aliphatic, aryl, heteroaliphatic, aliphatic-aryl, heteroaryl, aliphatic-heteroaryl, heteroaliphatic-aryl, heteroaliphatic-heteroaryl and any combination thereof.

Phosphoryl: A —P(O)(OR$^b$)$_2$ group, wherein R$^b$ is selected from hydrogen or a cationic species, such as a cationic metal or other positively charged species.

Phosphonate: A —OP(O)(OR$^b$) group, wherein R$^b$ is selected from hydrogen or a cationic species, such as a cationic metal or other positively charged species.

Quaternary Amine: —N$^+$R$^b$R$^c$R$^d$, wherein each of R$^b$, R$^c$, and R$^d$ independently are selected from hydrogen, aliphatic, aryl, heteroaliphatic, aliphatic-aryl, heteroaryl, aliphatic-heteroaryl, heteroaliphatic-aryl, heteroaliphatic-heteroaryl and any combination thereof.

Solubilizing Group: A group that, when added to a compound, renders the compound more soluble in water than without the group. Exemplary solubilizing groups include, but are not limited to, anionic groups, such as carboxylate, phosphonate, sulfonate, and the like.

Sulfonyl: —SO$_3$R$^b$, wherein R$^b$ is selected from hydrogen, aliphatic, aryl, heteroaliphatic, aliphatic-aryl, heteroaryl, aliphatic-heteroaryl, heteroaliphatic-aryl, heteroaliphatic-heteroaryl and any combination thereof.

Sulfonate: An —SO₃ anion, including salts thereof.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. In formulas and specific compounds disclosed herein, a hydrogen atom is present and completes any formal valency requirements (but may not necessarily be illustrated) wherever a functional group or other atom is not illustrated. For example, a phenyl ring that is drawn as

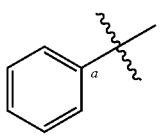

comprises a hydrogen atom attached to each carbon atom of the phenyl ring other than the "a" carbon, even though such hydrogen atoms are not illustrated.

Any functional group disclosed herein and/or defined above can be substituted or unsubstituted, unless otherwise indicated herein.

II. Introduction

Nanohoop compound embodiments disclosed herein exhibit surprisingly high extinction coefficients, photostability, and/or quantum yields that render them brighter than many commonly-used commercial dyes. In certain embodiments, the disclosed nanohoop compounds have an extinction coefficient that is 5 to 10 times larger, and/or a quantum yield that is doubled or tripled, as compared to a commercial dye. Embodiments of the disclosed nanohoop compounds also exhibit red-shifts upon tuning the size of the nanohoop, which provides the ability to make bioprobes that absorb and emit longer wavelength light. Embodiments of the nanohoop compounds can be designed such that the emitted light extends outside of the visible range, such as into the ultraviolet or infrared wavelengths. Nanohoop compound embodiments disclosed herein also exhibit long excited state lifetimes, on the order of, for example, 10 to 20 nanoseconds or more. The nanohoop compound embodiments disclosed herein are non-toxic and/or resistant to photobleaching in aqueous media. In additional embodiments, certain nanohoop compound embodiments disclosed herein have smaller nanohoop sizes (e.g., 5 rings within the nanohoop, or 6 rings within the nanohoop) and further comprise at least one ring that is connected to two other rings of the nanohoop in a meta-substituted matter, but are still able to exhibit bright fluorescence. As such, the nanohoop compound embodiments disclosed herein are suited for live cell imaging, tissue imaging, live whole animal imaging, and related techniques, as well as in microscopy and/or data storage.

Additionally, nanohoop compound embodiments disclosed herein are chemically inert to functional groups existing in biological systems (e.g., thiols, amines, and other nucleophiles) and thus are able to avoid reactions with such nucleophiles. Nanohoop compound embodiments disclosed herein also have a cyclic structure that lends to their use in biological applications as the cyclic structure provides hydrophobic pockets that can be engineered into biological systems (e.g., peptides, DNA, RNA, cell membranes etc.) to create biosynthetic systems for catalysts, sensors, assays, and the like. The hydrophobic pocket also can serve as a pore (or cavity) in which biological moieties can be contained without the need to covalently attach the biological moiety to the nanohoop compound.

The nanohoop compound embodiments and conjugates disclosed herein are useful for biomarker detection in flow cytometry. Flow cytometry is a research and clinical diagnostic tool used for identifying and monitoring many diseases, including HIV and cancer. In typical flow cytometry studies, multiple features of a sample of cells are analyzed simultaneously, typically by fluorescently-labeled antibody conjugates that target specific cell biomarkers. A limitation of flow cytometry, however, is the availability of bright fluorescent probes spanning the color spectrum that can be efficiently conjugated to antibodies. There are few available small molecule ultra violet (UV) excitable probes, and they are generally not bright enough to be useful for cytometry. Early detection of low abundant biomarkers by flow cytometry requires unusually bright fluorophores.

Nanohoop compound embodiments and conjugates described herein advantageously provide a superior level of visibility/detectability and thus are superior probes for use in flow cytometry. For example, certain nanohoop compound embodiments and conjugates disclosed herein exhibit the appropriate fluorescent properties, a lack of propensity for quenching, and low side reactivity that is useful for functioning as bright flow cytometry probes. For example, an N-hydroxy-succinimide (NHS) functionalized nanohoop can be incorporated into an antibody, to provide a nanohoop/antibody conjugate useful for flow cytometry. A useful fluorescent probe can have high photostability, extinction coefficient (s), quantum yield (QY), and/or brightness (sx QY). While many fluorescent probes are available commercially, a large number are required to carry out sophisticated experiments and many commercial probes have limitations. Fluorescein based probes suffer from inherent photostability and the fluorescence intensity is pH sensitive, which can complicate measurements. Rhodamine dyes, upon conjugation to proteins, exhibit severely decreased fluorescence due to intermolecular quenching and formation of the corresponding non-fluorescent ring-closed derivative. Fluorescence quenching is problematic when trying to identify low abundant cell populations or cell surface antigens with low expression levels. This makes investigation and detecting low abundant targets difficult, highlighting the need for bright fluorophores with minimal quenching upon conjugation. Certain drawbacks associated with many of the conventional probes may be overcome by advantageous design and use of the unique chemical and photophysical properties of the disclosed nanohoop compounds. Using the disclosed nanohoop compounds for flow cytometry can have an impact on the number of biomarkers that can be detected, and thus human disease detection.

III. Nanohoop Compounds and Conjugates

A nanohoop compound exhibits a radially oriented π-system, and may contain varying numbers of aromatic groups, such as aryl rings, heteroaryl rings, or combinations thereof. Embodiments of the nanohoop compounds and conjugates disclosed herein are fluorescent, which lends to their utility in myriad biotechnological applications. In particular embodiments, the nanohoop compounds and conjugates contain para-linked aryl or heteroaryl rings that exhibit singular aromatic ring planes that are perpendicular to the radius of the hoop, rather than parallel, and therefore the carbon atoms do not necessarily all sit in one plane of the radially oriented π-system. However, other linkages are contemplated, such as meta- or ortho-linkages between rings of the nanohoop skeleton.

The abbreviation [n]CPP is used herein to describe a nanohoop compound (or conjugate) having "n" rings, such as aromatic (e.g., aryl or heteroaryl) rings, present in the skeleton of the nanohoop compound (or conjugate), wherein n is an integer that can range, for example, from 4 to 100 or more. The abbreviation [n]mCPP is used herein to describe a nanohoop compound (or conjugate) having "n" rings, such as aromatic (e.g., aryl or heteroaryl) rings, present in the skeleton of the nanohoop compound (or conjugate), wherein n is an integer that can range, for example, from 4 to 100 or more and further wherein at least one ring of the nanohoop skeleton is bound to two other rings of the nanohoop skeleton by bonds that are meta-substituted relative to each other. The cyclic architecture of the CPP is referred to as a nanohoop. The term CPP is not limited to CPPs containing only phenyl rings, however, as a CPP may also include other rings and ring systems, such as aryl and/or heteroaryl rings, tetracyanoanthaquinodimethane, pyridyl rings, N-alkylated pyridyl rings, 2,2'-(anthracene-9,10-diylidene)dimalononitrile, furanyl, cyclopentadienyl, azolyl rings, and other ring systems groups.

In some embodiments, nanohoop compound and/or conjugate embodiments comprise a structure satisfying Formula I:

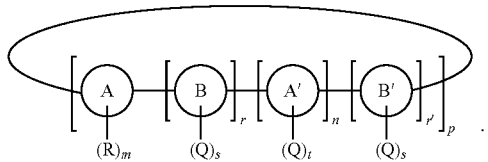

Formula I

With reference to Formula I, the "hoop-shaped" nature of the compounds is represented by the solid curved line, with in turn represents a bond formed between a carbon atom of an "A," "A'," "B," or "B'" ring and a carbon atom of another "A," "A'," "B," or "B'" ring, to form the hoop structure. In particular disclosed embodiments, the nanohoop compounds and/or conjugates described herein comprise at least one A ring having at least one R group present. In yet other embodiments, the nanohoop compounds described herein comprise at least one A ring that is bound to other rings in the nanohoop through bonds that are meta-substituted relative to one another, in which case no R groups need be present. In particular disclosed embodiments, the nanohoop compound will comprise at least four aromatic rings within the nanohoop skeleton.

Also, with reference to Formula I, each of rings A, B, A' and B' independently is an aromatic ring system (e.g., aryl ring or a heteroaryl ring);

m is an integer selected from 1 to 10, or m is zero when at least one ring A is attached to another ring A or a ring B, A', and/or B' via bonds that are meta-substituted relative to one another;

each R independently is a "linker-Z" group or a "Z" group, wherein the linker of the linker-Z group comprises an aliphatic group, a heteroaliphatic group (e.g., an ether, a thioether, an ester, an amino group, a carboxy, a carbonyl, an amido group, or any combination thereof); and Z comprises a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, another nanohoop compound, or a functional group that facilitates coupling of the nanohoop compound with a solubilizing group, a peptide, an oligonucleotide, a nucleoside, a nucleotide, a protein, an aptamer, a quenching moiety, a drug, a cell, an antibody, an amino acid, a lipid, a carbohydrate, a liposome, a cyclodextrin, or a porphyrin;

each Q independently is Z or a linker-Z group;

each of r', r and n independently is an integer selected from 0 to 24 (e.g., 0, 1, 2, 3, 4, 5, 6, 7, 8, 9, 10, 11, 12, 13, 14, 15, 16, 17, 18, 19, 20, 21, 22, 23, or 24);

each of s and t, when present, independently is an integer selected from 0 to 10 (e.g., 0, 1, 2, 3, 4, 5, 6, 7, 8, 9, or 10); and p is an integer selected from 1 to 12 (e.g., 0, 1, 2, 3, 4, 5, 6, 7, 8, 9, 10, 11, or 12), provided that, in some embodiments, when each of r, r', and n is 0, then p is at least 5, and provided that when p is 1, then at least one of r, r', or n is 4 or r, r', or n independently are integers that when taken together add up to 4.

In some embodiments, each ring B, A', and B' independently can be selected from an aromatic (e.g., aryl) ring optionally comprising a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with a solubilizing group, a peptide, an oligonucleotide, a nucleoside, a nucleotide, a protein, an aptamer, a drug, a cell, an antibody, an amino acid, a quenching moiety, a lipid, a carbohydrate, a liposome, a cyclodextrin, or a porphyrin; an aryl ring optionally comprising an electron-accepting group; a heteroaryl ring optionally comprising a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin; or a heteroaryl ring optionally comprising an electron-accepting group or one or more heteroatoms and/or substituents that are capable of accepting electron density from a core ring to which they are attached (wherein the core ring is a ring comprising two carbon atoms that each are attached to two different rings of the nanohoop compound). In some embodiments, each ring B, A', and B' independently can be selected from an aryl ring optionally comprising an electron-donating group; or a heteroaryl ring optionally comprising an electron-donating group.

In some embodiments, rings B, A', and B' can be (i) phenyl; (ii) phenyl comprising one or more linker-Z and/or Z groups as described above; (iii) phenyl comprising one or more electron-donating substituents described herein; (iv) a heteroaryl ring system having a structure satisfying a formula:

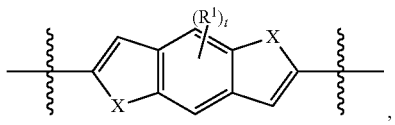

wherein X is selected from O, S, and NR$^b$ (wherein R$^b$ comprises aliphatic, aryl, heteroaliphatic, aliphatic-aryl, heteroaryl, aliphatic-heteroaryl, heteroaliphatic-aryl, or heteroaliphatic-heteroaryl), R$^1$ is selected from an electron-donating group disclosed herein, and t is 0, 1, or 2; (v) phenyl substituted with one or more electron-accepting substituents described herein; (vi) pyridinyl; (vii) pyridinyl substituted with an aliphatic or aryl group; (viii) tetracyanoanthaquinodimethyl; or (vix) a ring system having a structure satisfying a formula:

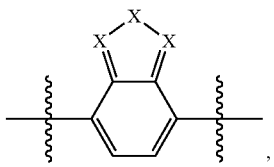

wherein each X independently is selected from O, S, N, or NR$^b$ (wherein R$^b$ is as defined above).

In some embodiments, each ring B, A', or B' independently can be selected from phenyl; benzo[1,2-b:4,5-b']dithiophenyl optionally substituted with one or more electron-donating substituents described herein; benzo[1,2-b:4,5-b']difuranyl optionally substituted with one or more electron-donating substituents described herein; 4,4-dimethyl-4H-cyclopenta[2,1-b:3,4-b']dithiophene optionally substituted with one or more electron-donating substituents described herein; 1,5-dihydropyrrolo[2,3-f]indolyl optionally substituted with one or more electron-donating substituents described herein; benzo[c][1,2,5]thiadiazolyl; benzo[c][1,2,5]oxadiazolyl; 2H-benzo[d][1,2,3]triazolyl; or tetracyanoanthaquinodimethyl.

Also with reference to the formulas described herein, particular embodiments concern compounds wherein each of rings A, A', B and B' are present and each are phenyl. In some embodiments, each of ring A and A' is aryl or heteroaryl, and each of rings B and B' is aryl. For example, each of A and A' may have the structure shown in Formula IIIF and IIIH, wherein at least one of a, b, c, and d is N, such as pyridyl, and each of B and B' may be phenyl. In further embodiments, A may be phenyl, A' may be N-methyl pyridyl, and B and B' may be phenyl. In yet additional embodiments, the nanohoop may consist of unsubstituted phenyl rings (wherein each m, s, and t are zero) and wherein at least one A phenyl ring is bound to the other phenyl rings of the nanohoop via bounds that are meta-substituted relative to one another.

In certain embodiments, and also with reference to the formulas described herein, particular embodiments concern compounds wherein the rings A, A', B and B' are independently bonded to another in any feasible manner relative to the other, such that any point of connection in a ring can be used to bond it to an adjacent ring. For 6-membered rings, this means that the rings may be bonded together in an ortho-substituted, meta-substituted or para-substituted manner, or any combination thereof. Solely by way of example, a nanohoop compound comprising 8 phenyl rings with two each of A, A', B and B', (e.g., p=2), may have all eight of the rings bonded to the other in a para-substituted manner. Alternatively, the A ring may, for example, be bonded to the B ring in an ortho-substituted manner, the B ring may be bonded to the A' ring in a para-substituted manner, the A' ring may be bonded to the B' ring in a meta-substituted manner, and the B' ring may be bonded to the A ring in a para-substituted manner. In yet other embodiments, the A ring can be bonded to the B ring in an meta-substituted manner, the B ring may be bonded to the A' ring in a para-substituted manner, the A' ring may be bonded to the B' ring in a para-substituted manner, and the B' ring may be bonded to the A ring in a meta-substituted manner. All of the various permutations of such linkages are envisioned for the disclosed nanohoop compounds regardless of the ring size.

In some embodiments of the nanohoop compounds of the formulas described herein, m is selected from 1 to 10, that is, m is 1, 2, 3, 4, 5, 6, 7, 8, 9, or 10. In further embodiments, m is selected from 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, or 2 to 3. In additional embodiments, m is at least 1, at least 2, at least 3, at least 4, no more than 1, or no more than 2. In further embodiments, m can be zero as long as one A ring is bound to other rings of the nanohoop via bonds that are meta-substituted relative to one another.

In some embodiments of the nanohoop compounds of the formulas described herein, m' is selected from 0 to 10, that is, m' is 0, 1, 2, 3, 4, 5, 6, 7, 8, 9, or 10. In further embodiments, m' is selected from 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, or 2 to 3. In additional embodiments, m' is at least 1, at least 2, at least 3, at least 4, no more than 1, or no more than 2.

In some embodiments of the nanohoop compounds of the formulas described herein, R is a linker coupled to a group Z. Alternatively, R is Z and as such Z is directly attached to ring A without an intervening linker. In some embodiments, the linker group can be a $C_{1-6}$ aliphatic group and Z can be a carboxyl group. In some embodiments, the linker group can be $C_{1-6}$ aliphatic and Z can be an amino acid, for example, glycine or isoleucine. In yet additional embodiments, the linker is -($L^a$-X-$L^b$)$_v$-, wherein each of $L^a$ and $L^b$ independently is aliphatic; X is a heteroatom, such as N, P, Se, As, O and S; and v is an integer selected from 1 to 50. In certain embodiments, X is selected from O, S, or NR$^a$ (wherein R$^a$ is hydrogen or aliphatic, such as $C_{1-6}$ aliphatic) and/or v is an integer selected from 1 to 5. In an additional embodiment, the linker is $C_{1-6}$ aliphatic-O—$C_{1-6}$ aliphatic, such as —$CH_2$—O—$CH_2CH_2CH_2$—. In further additional embodiments, the linker is a polyether (e.g., PEG) group, such as a PEG with an average molecular weight between 50 and 20,000 gm/mol.

In some embodiments of the nanohoop compounds of the formulas described herein, Z can be a solubilizing group. For example, Z is a solubilizing group comprising an anionic group, such as an anionic group selected from carboxylate, phosphonate, and sulfonate. In certain embodiments, Z is an anionic group. In particular disclosed embodiments, Z is $SO_3H$ or a salt thereof, such as $SO_3Na$.

In some embodiments of the nanohoop compounds of the formulas described herein, Z is a peptide. For example, the peptide can comprise a cell-penetrating peptide (e.g., HIV-1 Tat protein or pVEC), an oligopeptide, a peptidic drug (e.g., exenatide or nesiritide), an antibody, a protein, or any combination thereof. In some embodiments, Z is an amino acid. For example, Z is an amino acid comprising a proteinogenic amino acid, an unnatural amino acid, a non-proteinogenic amino acid, a homo amino acid, an N-methyl amino acid, an alpha-methyl amino acid, a beta amino acid, a delta amino acid, a gamma amino acid, a D-amino acid, an L-amino acid, a thio amino acid, a seleno amino acid, an amino sulfonic acid, or combinations thereof. The amino acid or peptide may comprise standard protecting groups, such as Boc or Alloc. In particular disclosed embodiments, Z is glycine, —OH, —SH, —NH$_2$, —COOH, or —SO$_3$Na.

In some embodiments of the nanohoop compounds of the formulas described herein, Z is a drug. For example, Z can comprise aspartame, captopril, enalapril, octreotide, desmopressin, or any combinations thereof. The nanohoop compound can be conjugated to a drug to act as, for example, a fluorescent label, or it can be used to form a drug analog. In yet other embodiments, the drug may be contained within a pore defined by the aromatic skeleton of a nanohoop compound. In such embodiments, the "R" group of any one of the formulas described above need not be present.

In certain embodiments of the nanohoop compounds of the formulas described herein, Z is a cell. The cell may be associated with a nanohoop compound by covalent or non-covalent interactions. The nanohoop compound may, for example, comprise an antibody or peptide that is electrostatically or covalently bound to a cell. Alternatively, the nanohoop compound can be covalently bound to a component in the cell membrane, such as a lipid, or it may be associated with the cell via hydrophobic or electrostatic interactions after being taken up by the cell. In yet additional embodiments, the nanohoop compound can be associated with the cell such that it becomes part of the membrane of the cell.

In some embodiments of the nanohoop compounds of the formulas described herein, Z is a nucleoside, a nucleotide, or a combination of nucleosides and/or nucleotides (thus forming an oligonucleoside or oligonucleotide), an aptamer, or the like. Embodiments of Z also include modified nucleosides and nucleotides. For example, natural oligonucleotides are in the D-form, but L-form oligonucleotides (Spiegelmers) are chiral inversions thereof. Nucleic acids may contain backbone modifications, such as 2' halogenation, amination, or methoxylation. Backbone phosphate linkages can be modified as well, such as with phosphorodithioate or phosphorothiolate linkages. Inverted nucleic acids are commercially available, which allow for an oligonucleotide to incorporate a 3'-3' or 5'-5' reversed linkage. Xeno-nucleic acids (XNAs) contain artificial nucleic structures, such as hexitol nucleic acids, threose nucleic acids (TNA), or locked nucleic acids (LNA), which contain a bridge between the 2' oxygen and 4' carbon. Aptamers, including pegaptanig and pegpleranib, are single-stranded DNA or RNA molecules that can bind a target with high affinity. Aptamers can have an increased resistance to nuclease degradation via the incorporation of modified nucleic acids. For example, aptamers may be made with ssDNA having dT replaced with dU residues modified in the 5-postiion, such as with benzyl or indole, to provide slow off-rate modified aptamers ("SO-MAmers"). In certain embodiments, Z may comprise a Spiegelmer, a somamer, a TNA aptamer, a XNA aptamer, a LNA aptamer, a catalytic aptamer, a thiophosphate, a phosphorodithioate, an inverted nucleic acid, a 2'-fluoro-, 2'-methoxy-, or 2'-amino-modified nucleotide or nucleoside, a nucleotide or nucleotide with a modified base, a primer, an oligonucleoside or oligonucleotide, or combinations thereof.

In some embodiments, Z is a quenching moiety that is capable of quenching (that is, reducing or eliminating) the fluorescence of the nanohoop compound when the quenching moiety enters the cavity of the nanohoop compound. In some embodiments, the quenching moiety can be any functional group and/or molecule that fits within a cavity of the nanohoop. In some embodiments, the quenching moiety can be a nanohoop compound that has fewer rings within its skeleton as compared to the nanohoop compound to which it is attached, or it can be a fullerene compound. In particular embodiments comprising a quenching moiety, the quenching moiety is attached to the nanohoop compound via a linker group that is capable of isomerizing such that the quenching moiety can be forced into the cavity of the nanohoop and then removed from the cavity so as to provide tuneable appearance and disappearance of a fluorescent signal emitted by the nanohoop compound. In such embodiments, the linker can be an aliphatic linker comprising at least one site of unsaturation, such as a double bond that can isomerize from a cis to trans configuration (or trans to cis). Isomerization of such linkers can be controlled using photoactivation techniques and/or pH dependent techniques, which are recognized by those of ordinary skill in the art with the benefit of the present disclosure. In yet additional embodiments, the quenching moiety can be attached to the nanohoop compound via a linker group that is capable of being cleaved so as to release the quenching moiety, which can then enter the cavity of the nanohoop so as to quench its fluorescent signal. In such embodiments, the linker can comprise a cleavable moiety that can be cleaved so as to release the quenching moiety. In such embodiments, the linker can comprise an ester that can be enzymatically cleaved by an enzyme, such as an esterase; an amide bond of a peptide that can be enzymatically cleaved by an enzyme, such as a protease; or a strand of DNA and/or RNA that can be enzymatically cleaved by an enzyme, such as a restriction enzyme. The size of the nanohoop compound to which the quenching moiety is attached can be modified and/or the functional groups present on the nanohoop compound can be modified so as to tune the kinetics and rate at which the quenching moiety enters the cavity of the nanohoop.

In an embodiment of the nanohoop compounds, Z is a functional group that facilitates coupling the nanohoop compound with a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin. For example, the functional group may be a halogen such that the halogen serves as a leaving group that facilitates replacement of the halogen atom with the solubilizing group, peptide, oligonucleotide, nucleoside, nucleotide, protein, aptamer, drug, cell, antibody, amino acid, lipid, carbohydrate, liposome, cyclodextrin, or porphyrin. In some embodiments, the functional group may comprise an activated ester, such as an NHS ester, or a chemical coupling agent known in the field of organic chemistry, and with the benefit of the present disclosure, as being suitable for coupling two reactive components. In certain embodiments, the functional group comprises an amine, a carboxylic acid, a hydroxyl, an alkyne, an azide, a thiol, an aldehyde, an aminooxy, a triazole, or combinations thereof.

In some embodiments of the nanohoop compounds, Q is Z or linker-Z. Thus, certain embodiments of the nanohoop compounds include compounds with Q comprising a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin. In some embodiments, Q is a solubilizing group, such as a solubilizing group comprising an anionic group (e.g., comprising a carboxyl, phosphoryl, or sulfonyl group, such as a carboxylate, phosphonate or sulfonate group). In particular disclosed embodiments, Q can be carboxyl or amine. In one embodiment, Q is the same as R, such as embodiments wherein both Q and R are carboxyl. In certain embodiments, Q is different from R, such as Q is carboxyl and R is amino. Q is not present when both s and t are 0. In certain embodiments, Q is an anionic group comprising carboxyl, an organophosphorus group, an organosulfur group, hydroxyl, thiol, or combinations thereof. In an exemplary embodiment, Q is $SO_3H$ or a salt thereof, such as $SO_3Na$.

In some embodiments of the nanohoop compounds, each of r', r and n independently is an integer selected from 0 to 24. For example, r and r' may be 0 and n may be selected from 0 to 24. In some embodiments, the nanohoop comprises only A and A' rings, and n is selected from 4, 5, 6, 7, 8, 9, and 10. In some embodiments, the nanohoop comprises only A and B rings, such that n and r' are 0 and r is selected from 0 to 24, such as 4, 5, 6, 7, 8, 9, and 10.

In certain embodiments of the nanohoop compounds, each of s and t independently is an integer selected from 0 to 10. In some embodiments, s and t are both 0. In additional embodiments, s and t are each independently selected from 0 and 5, or from 0 and 4.

In an embodiment of the nanohoop compounds, p is an integer selected from 1 to 12. For example, p is from 1 to 10, from 1 to 4, from 1 to 3, or is 1, 2, or 3.

In further embodiments of the nanohoop compounds, when each of r, r', and n is 0, then p is at least 5, and when p is 1, then at least one of r, r', or n is 4 or r, r', or n independently are integers that when taken together add up to 4.

In certain embodiments, the nanohoop compound has a structure that satisfies any one or more of Formulas IIA through III illustrated below in Table 1, wherein the illustrated variables can be as indicated above and further wherein each of a, b, c, and d, independently is selected from C or N.

TABLE 1

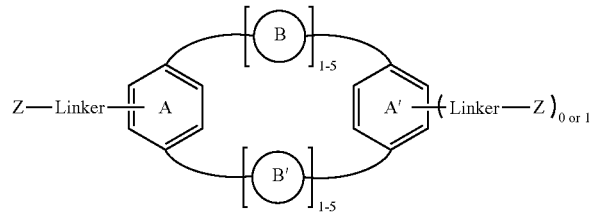

Formula IIA

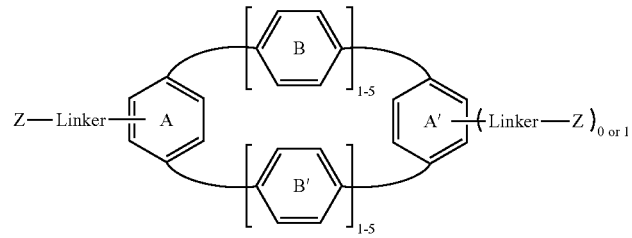

Formula IIB

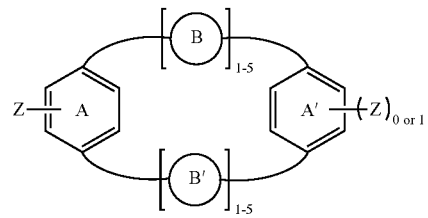

Formula IIC

TABLE 1-continued
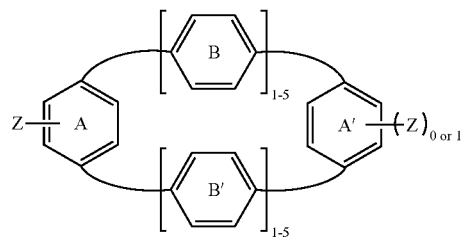
Formula IID
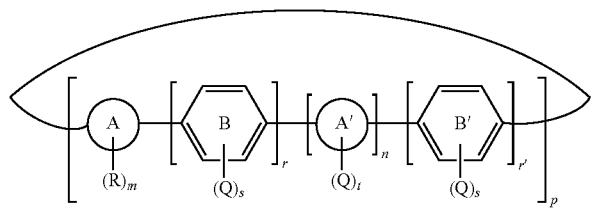
Formula IIE
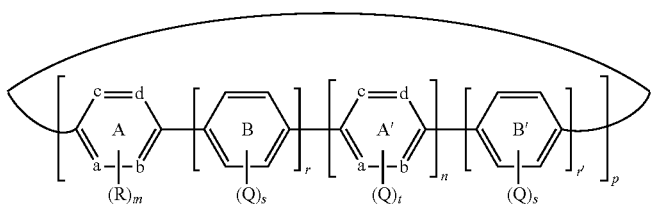
Formula IIF
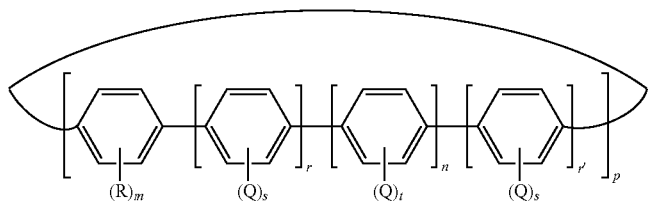
Formula IIG
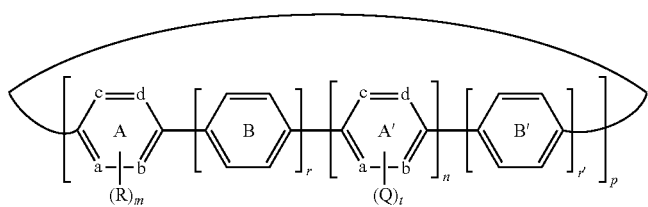
Formula IIH
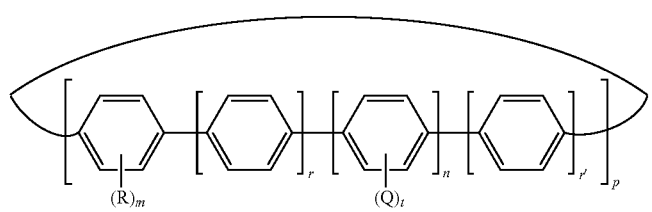
Formula III In particular disclosed embodiments, the nanohoop compounds/conjugates described herein can have structures satisfying any one or more of Formulas IIJ-IIP as illustrated in Table 2.

TABLE 2

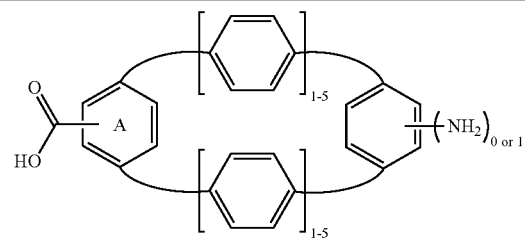

Formula IIJ

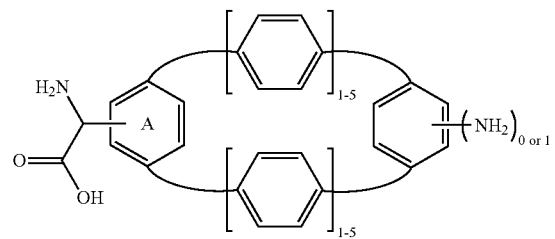

Formula IIK

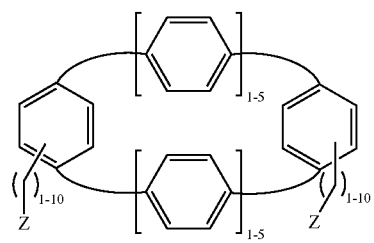

Formula IIL

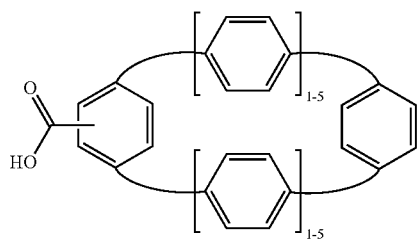

TABLE 2-continued

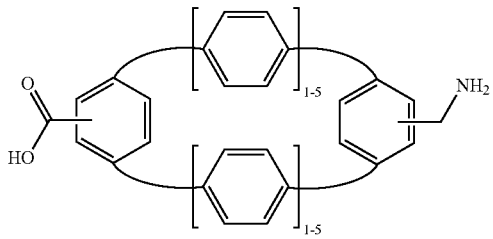

Formula IIM

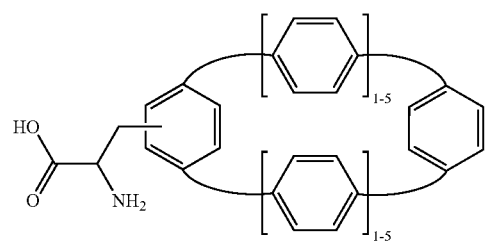

Formula IIN

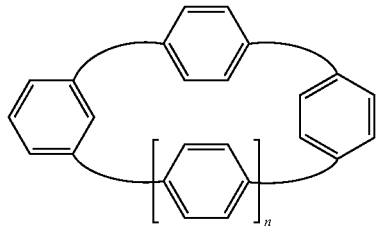

Formula IIO

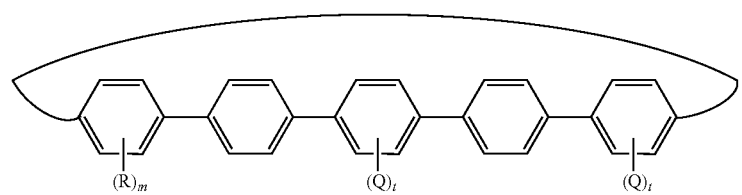

Formula IIP wherein n is an integer selected from 2 to 9, such as 3 to 9, or 4 to 9, or 5 to 9, or 7 to 9, or 1, 2, 3, 4, 5, 6, 7, 8, or 9.

In certain embodiments, the nanohoop compound has a structure that satisfies any one or more of formulas IIA, IIIB, IIIC, IIID, IIIE, IIIF, IIIG, IIIH, or IIIJ illustrated below in Table 3.

TABLE 3

Formula IIIA

TABLE 3-continued
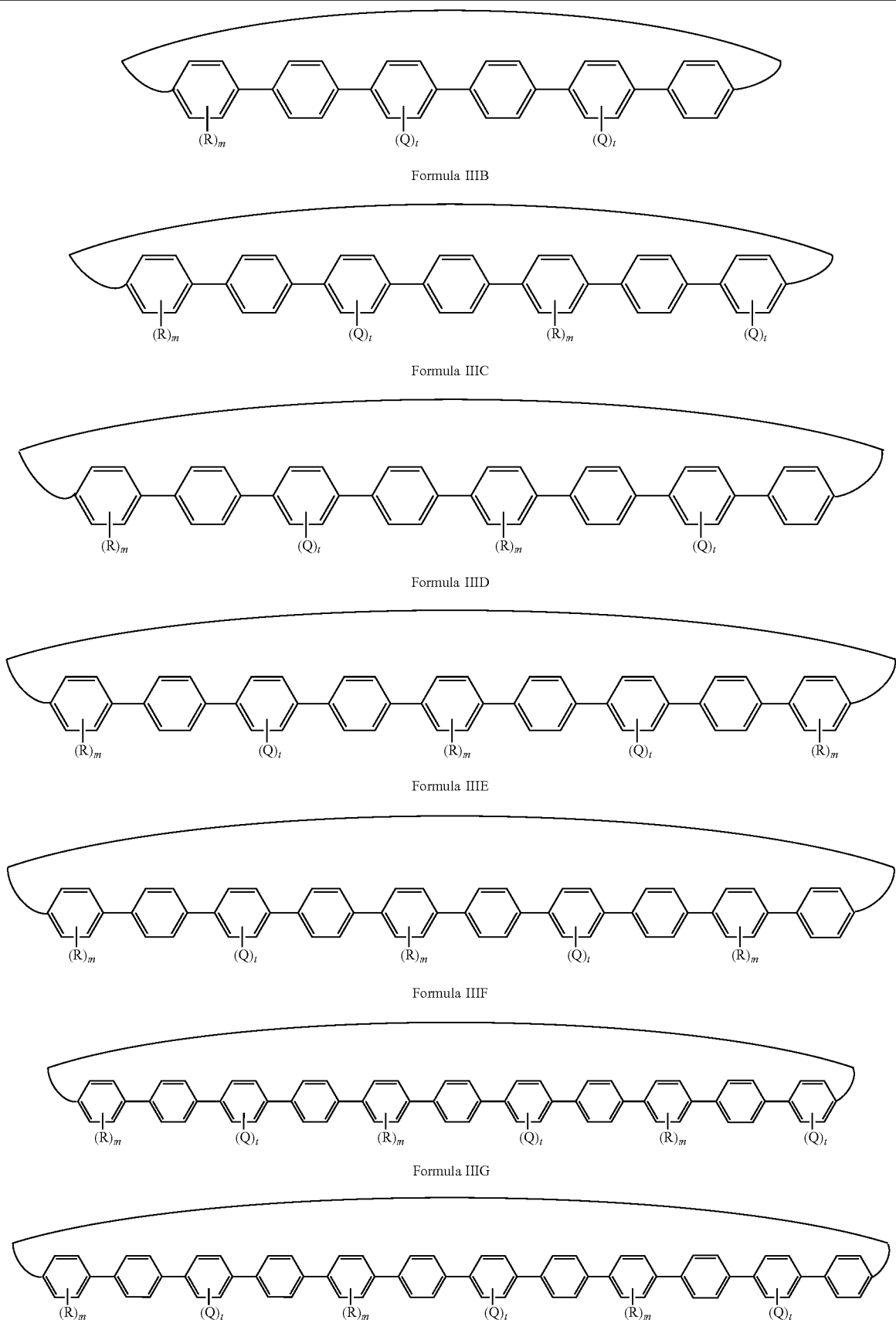

TABLE 3-continued

Formula IIIH

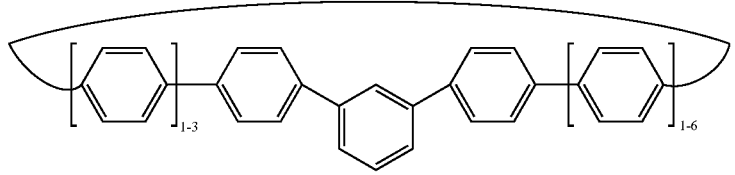

Formula IIIJ

In some embodiments of any of the formulas described above, the following variable recitations can apply:

at least one of R or Q independently comprises an anionic group;

m is an integer selected from 1 to 4; and each of t, when present, independently is an integer selected from 0 to 4.

For example, in certain embodiments of the compounds of Formula III, at least one of R or Q comprises an anionic group selected from carboxylate, phosphonate and sulfonate. In some embodiments, R is an anionic group comprising a carboxyl, an organophosphorus group, an organosulfur group, hydroxyl, thiol, or combinations thereof. In an embodiment, R is $SO_3H$ or a salt thereof, such as $SO_3Na$. In additional embodiments, Q is an anionic group comprising carboxyl, an organophosphorus group, an organosulfur group, hydroxyl, thiol, or combinations thereof. In some particular embodiments, Q is $SO_3H$ or a salt thereof, such as $SO_3Na$.

In yet additional embodiments, m is selected from 1 to 3, 1 to 2, 2 to 3, 2 to 4, at least 1, at least 2, at least 3, no more than 1, no more than 2, no more than 3, is 1, is 2 or is 3. In some embodiments, each of t is selected from 0 to 3, 0 to 2, 0 to 1, 1 to 4, 1 to 3, 1 to 2, at least 1, at least 2, at least 3, no more than 1, no more than 2, no more than 3, is 0, is 1, is 2, is 3, or is 4.

In yet additional embodiments, each of the rings A, A', B, and B' ring is phenyl; m is 1; R is linker-Z, wherein Z is a solubilizing group and the linker is $-(L^a-X-L^b)_v-$ (wherein each of $L^a$ and $L^b$ independently is $C_{1-6}$ alkyl; X is O or S; and v is 1); each of n, r, and r' is 1; each of s and t is 0; and p is 2.

In yet additional embodiments, each of the rings A, A', B and B' is phenyl; m, n, and t are each 1; R is Z, wherein Z comprises an amino group; Q comprises a carboxyl group; r and r' are each independently 1, 2, 3, 4, or 5; each of s and t is 0; and p is 1, 2 or 3.

In yet additional embodiments, each of the rings A, A', B, and B' is phenyl; m is 1; each of n, r, and r' independently is 1, 2, 3, or 4; R is Z, wherein Z comprises an amino group and a carboxyl group; each of s and t is 0; and p is 1, 2, or 3.

In yet additional embodiments, the nanohoop compounds can have structures satisfying any one or more of the formulas illustrated below in Table 4.

TABLE 4

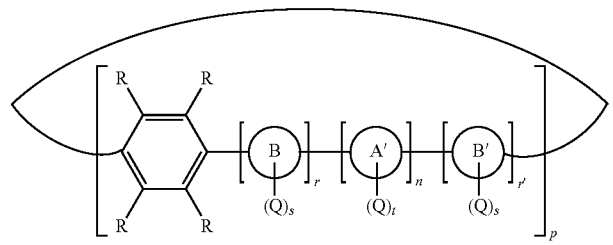

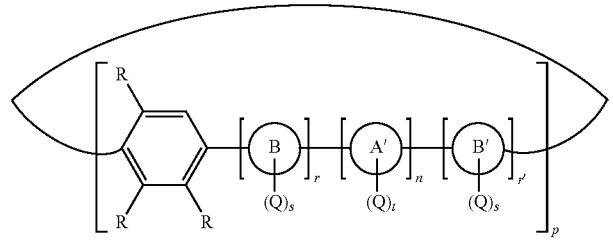

TABLE 4-continued
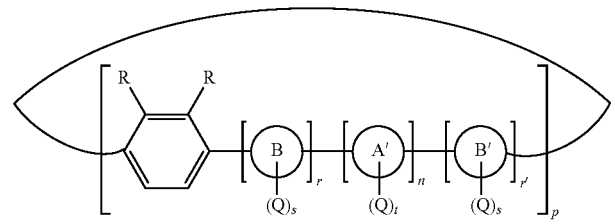
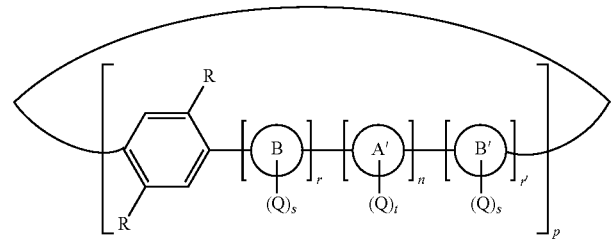
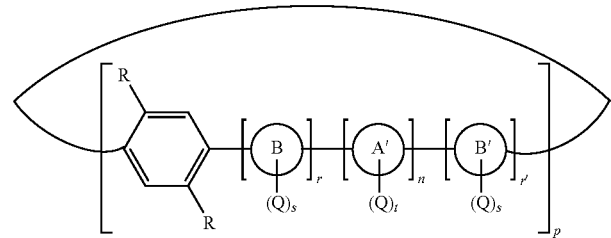
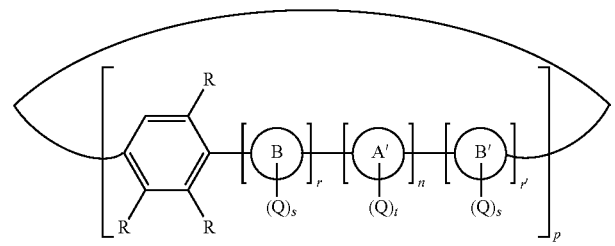
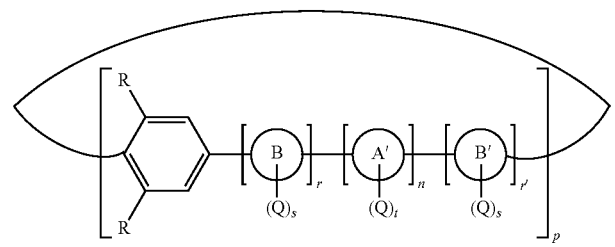
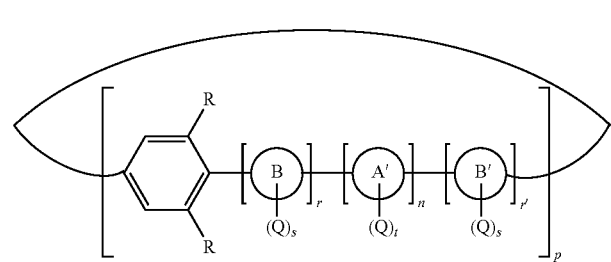

TABLE 4-continued
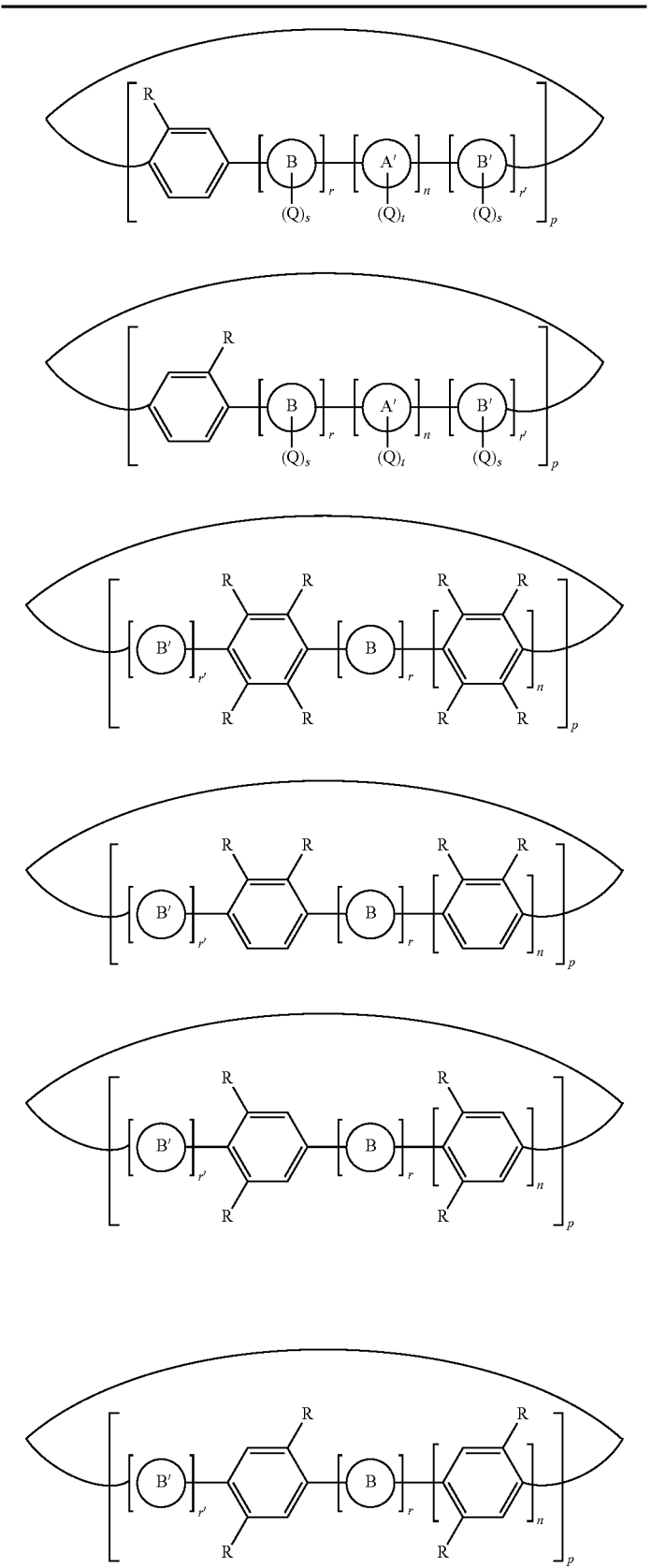

TABLE 4-continued
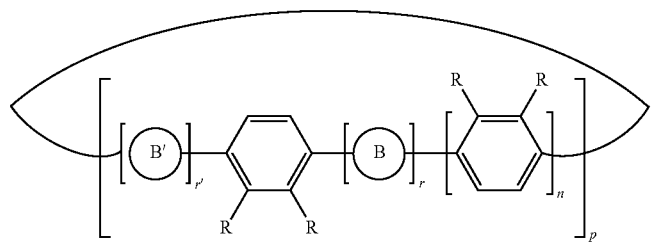
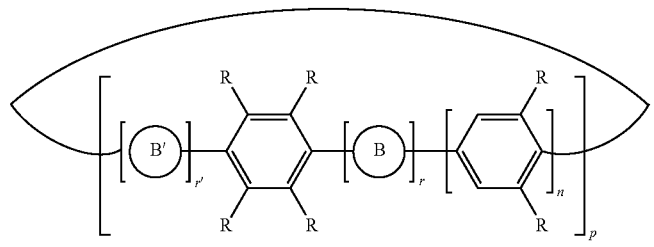
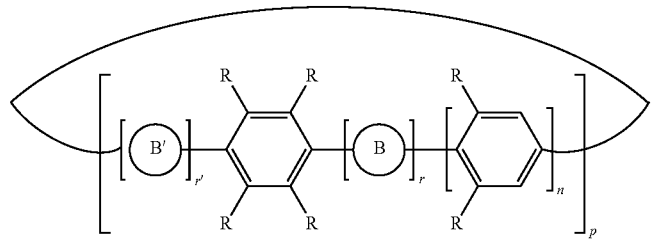
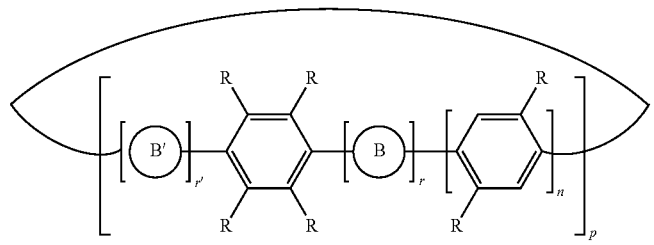
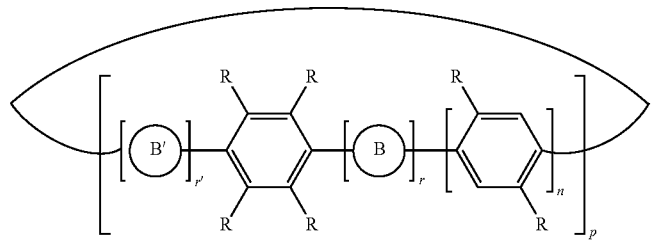
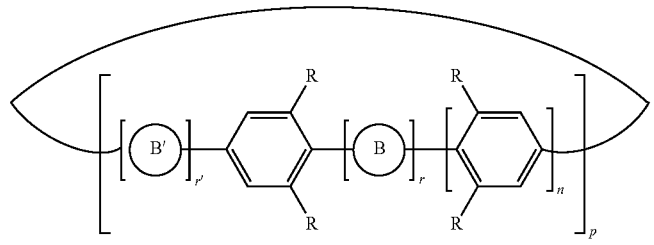

TABLE 4-continued

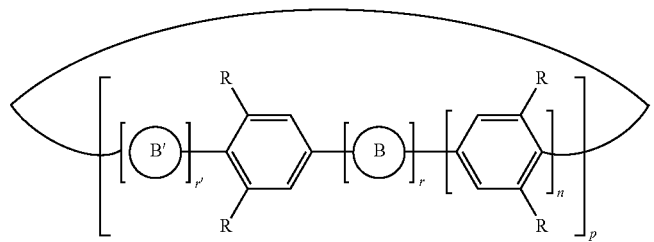

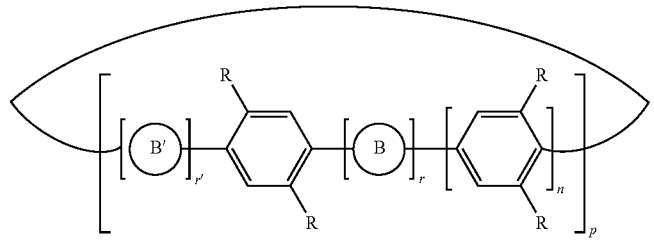

With reference to the formulas above, each circle represents a ring system, such as a single aromatic ring or a fused ring system such as those described herein. In particular disclosed embodiments, the circle represents an aryl or heteroaryl ring, such as a phenyl or pyridinyl ring. Each R illustrated in the formulas above can be the same or different as another R on the same nanohoop compound and can be selected from the R groups listed or illustrated herein.

In some embodiments, the nanohoop compound can have a structure satisfying any of the formulas below in Table 5 wherein the illustrated variables can be as recited herein.

TABLE 5

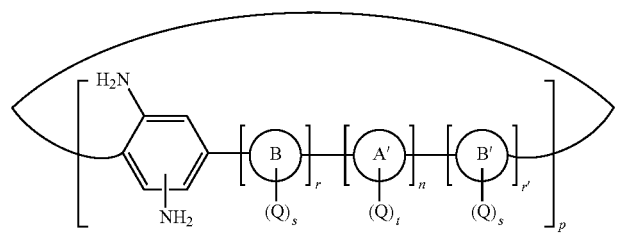

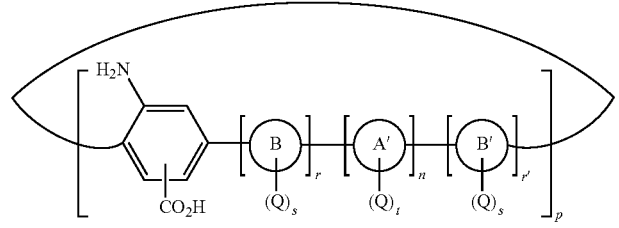

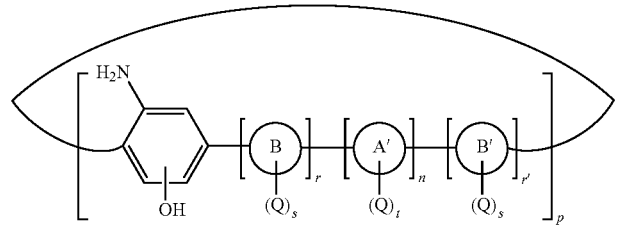

TABLE 5-continued
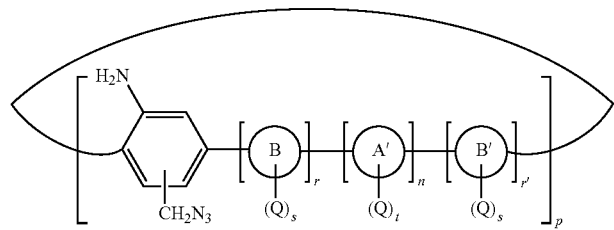
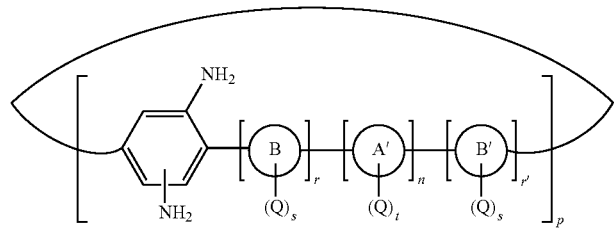
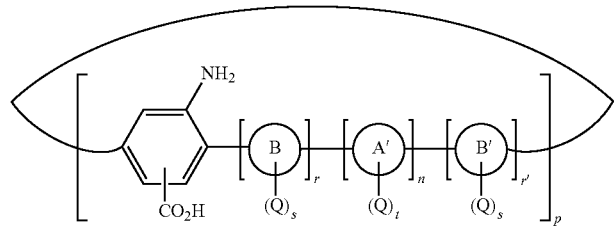
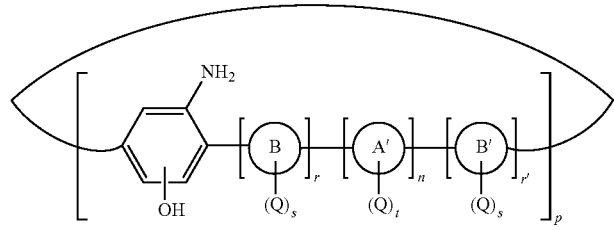
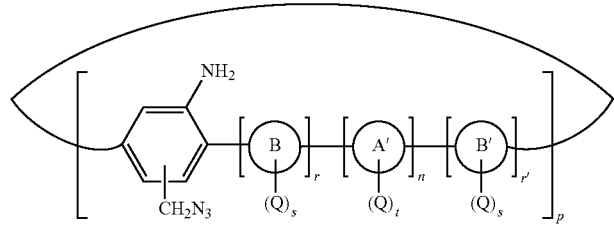
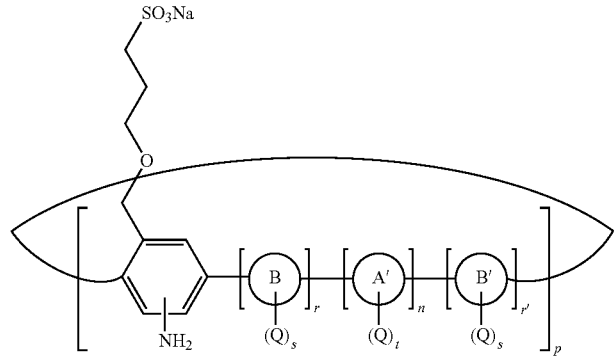

TABLE 5-continued
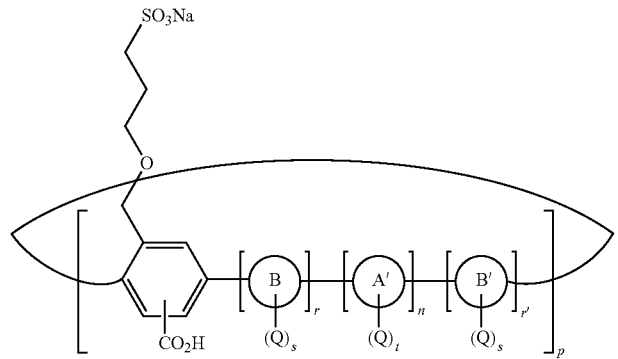
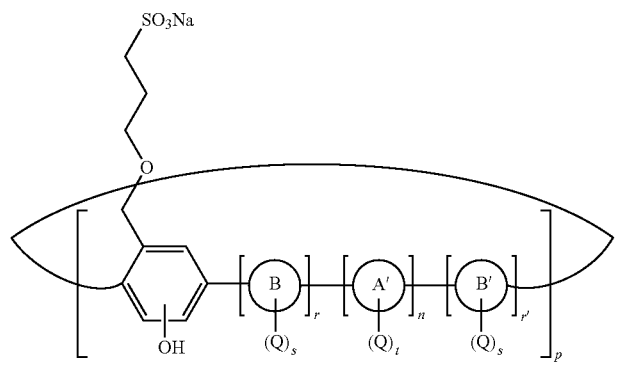
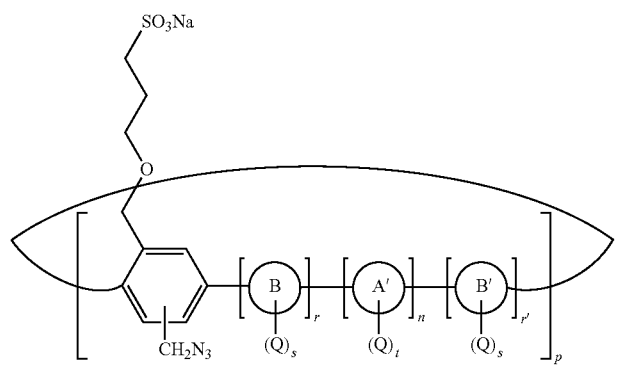
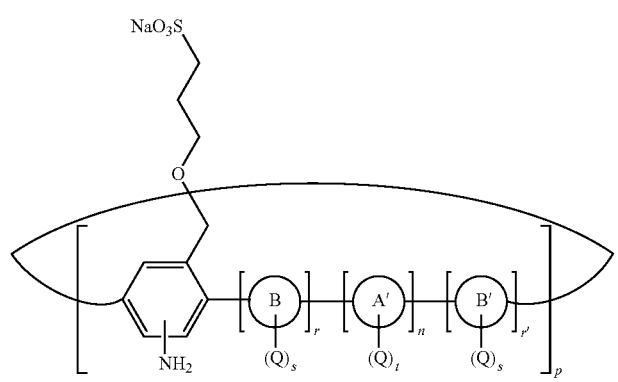

TABLE 5-continued
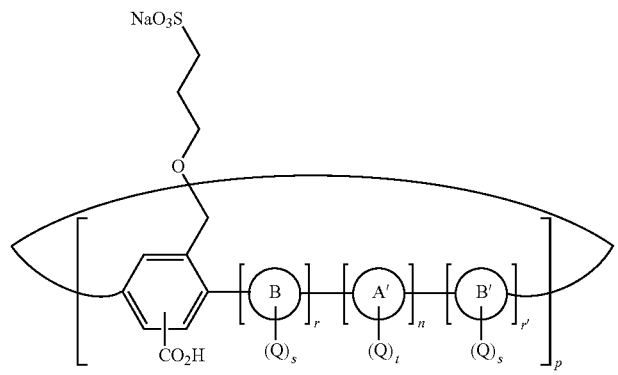
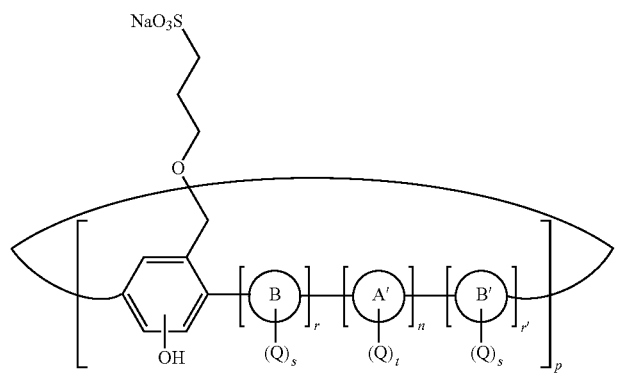
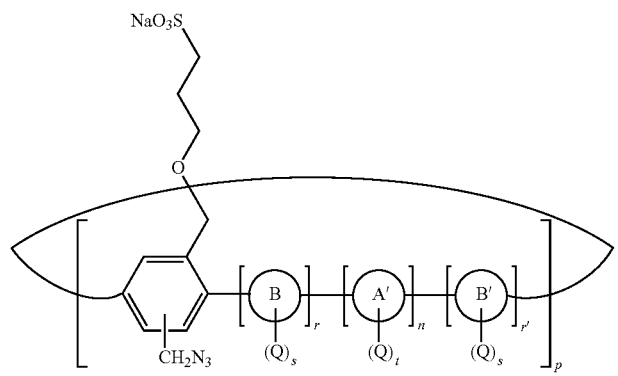
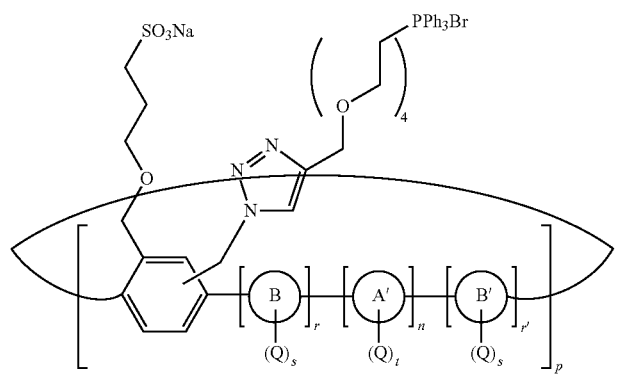

TABLE 5-continued
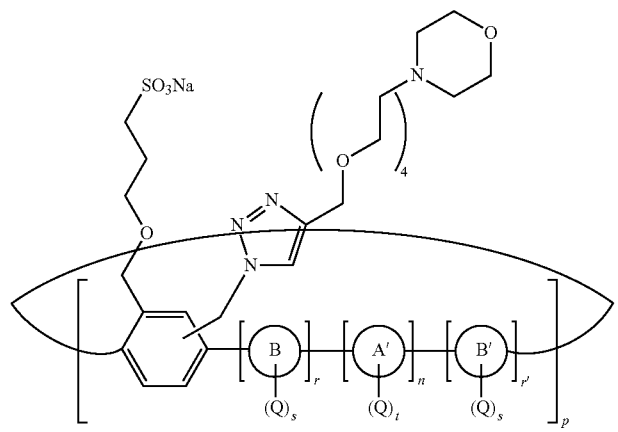
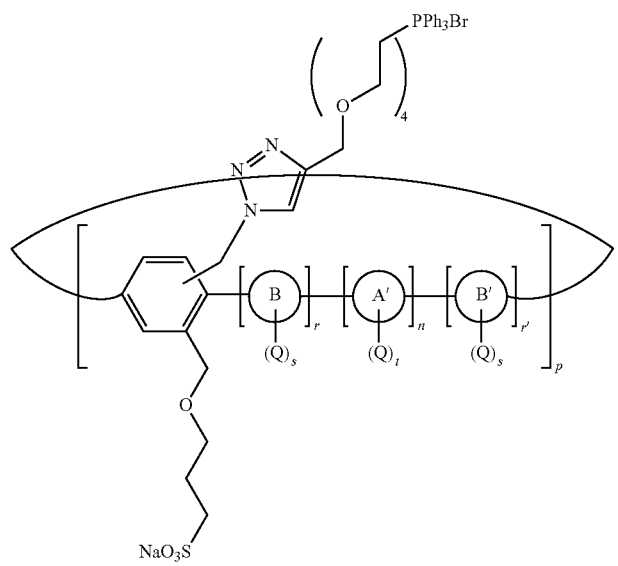
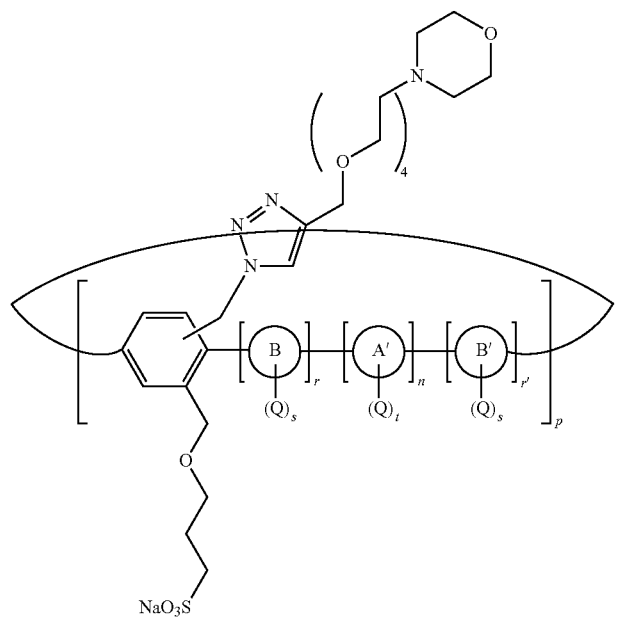

In the formulas illustrated above, the substituents shown on the illustrated phenyl ring can be positioned ortho-substituted to each other, meta-substituted to each other, or para-substituted to each other. Rings B, A', and/or B', if present, can be any of the ring systems disclosed herein. In particular disclosed embodiments, these rings can be five-membered rings, 6-membered rings, 7-membered rings, fused ring systems, and the like. Also, while some substituents are specified as SO$_3$Na, the formulas above (and below) are intended to also cover embodiments wherein other counterions are present in place of Na$^+$ and/or wherein the non-ionized form (SO$_3$H) exists.

Embodiments of representative species of nanohoop compounds are illustrated below in Table 6.

TABLE 6

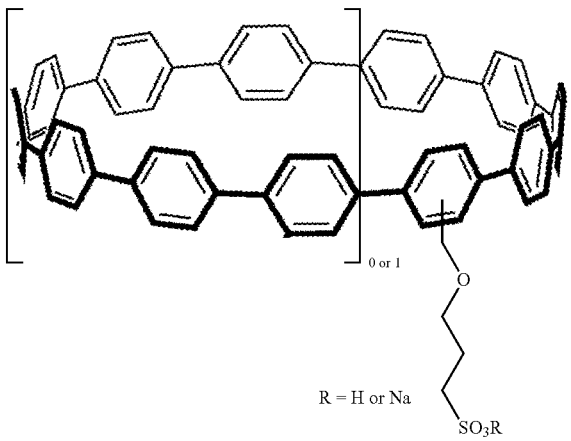

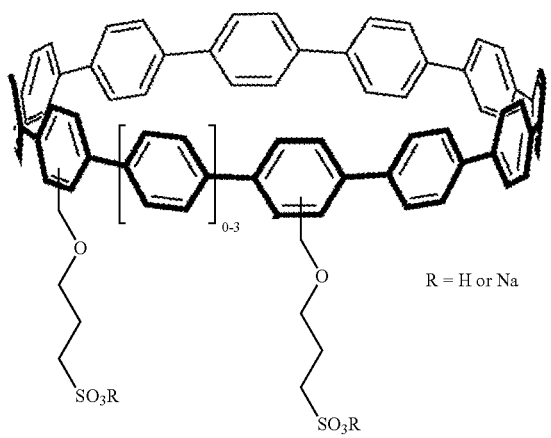

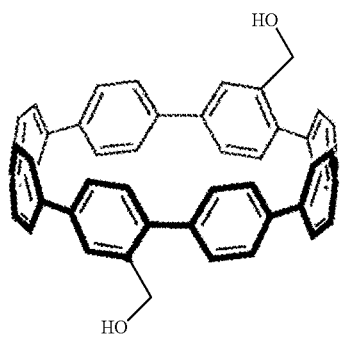

TABLE 6-continued
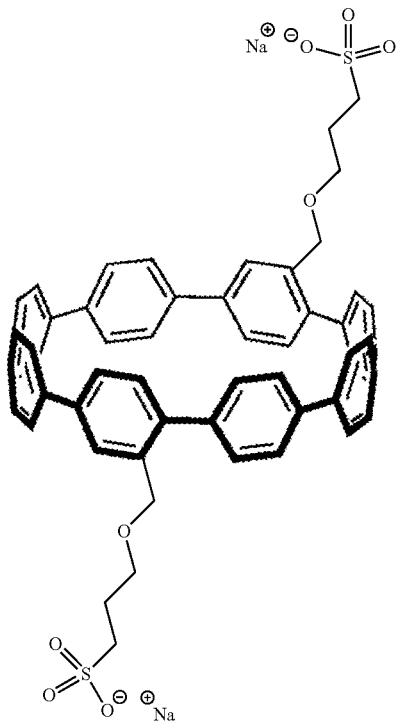
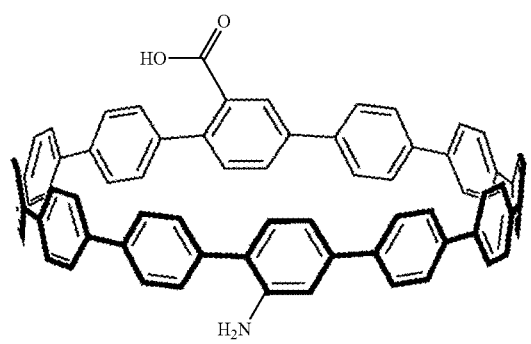
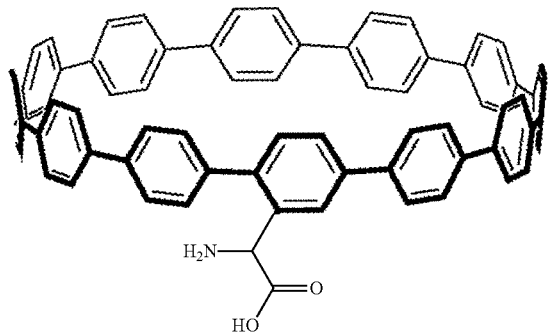

TABLE 6-continued
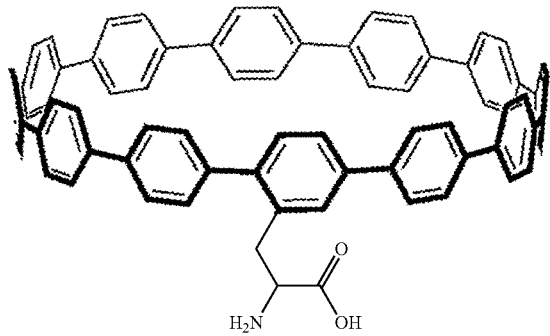
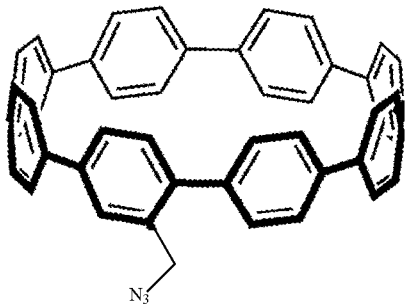
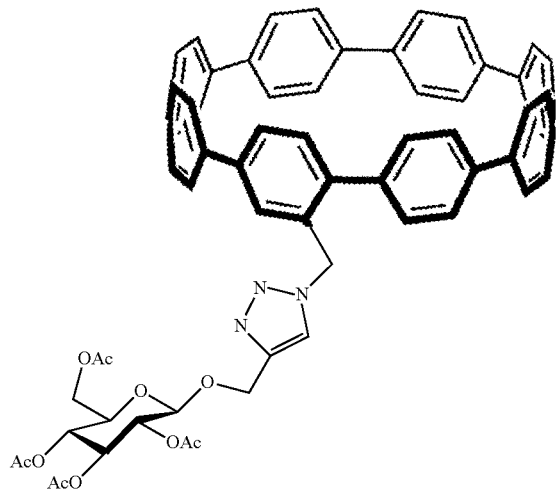
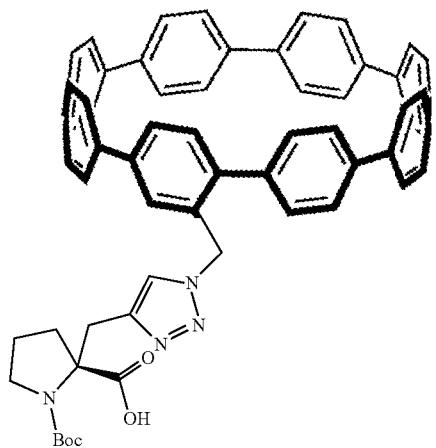 [SMILES: CCn1cc(C[C@@]2(C(=O)O)CCCN2C(=O)OC(C)(C)C)nn1]

TABLE 6-continued
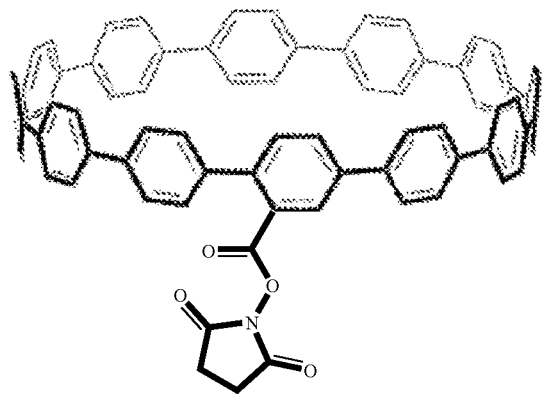
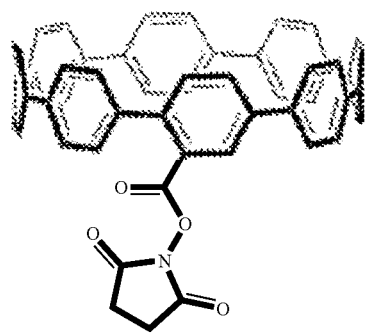
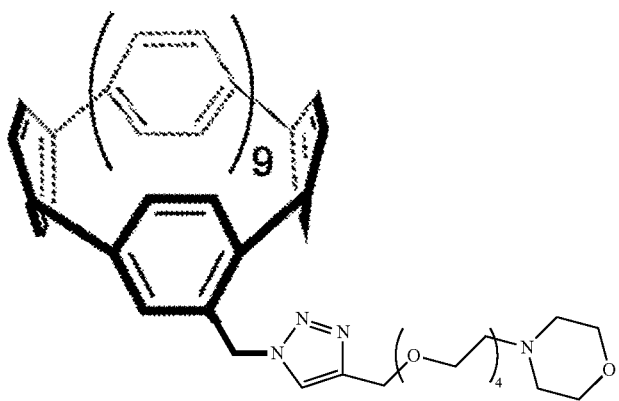
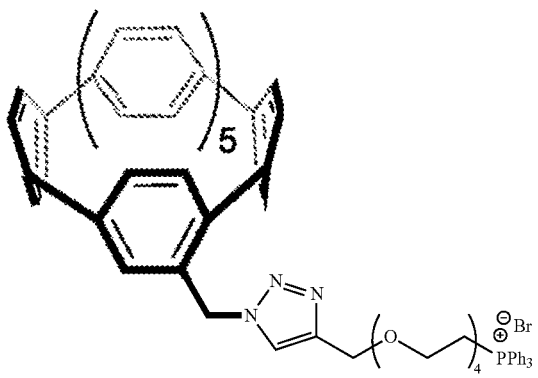

TABLE 6-continued
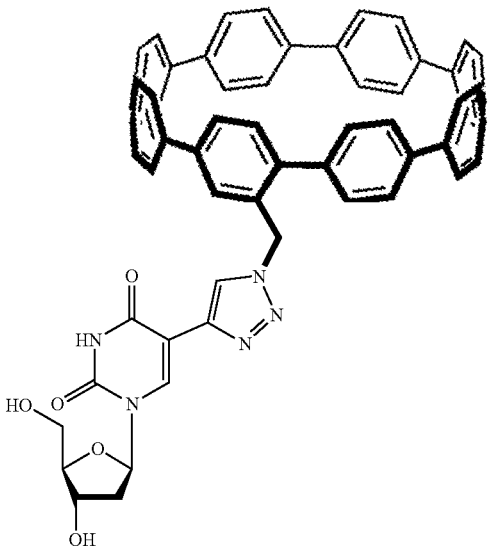
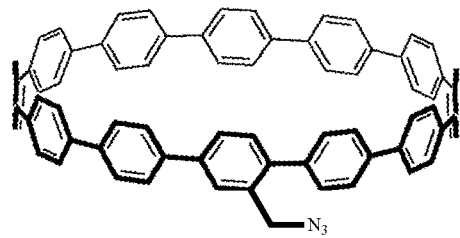
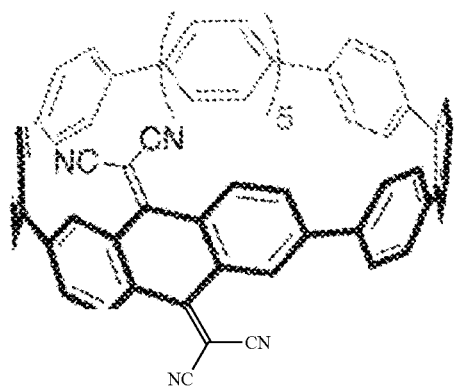
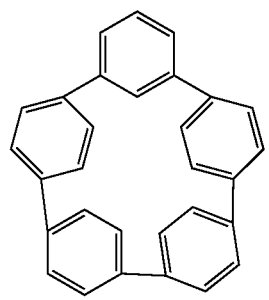 [SMILES: c1cc2cc(c1)-c1ccc(cc1)-c1ccc(cc1)-c1ccc(cc1)-c1ccc-2cc1]

TABLE 6-continued
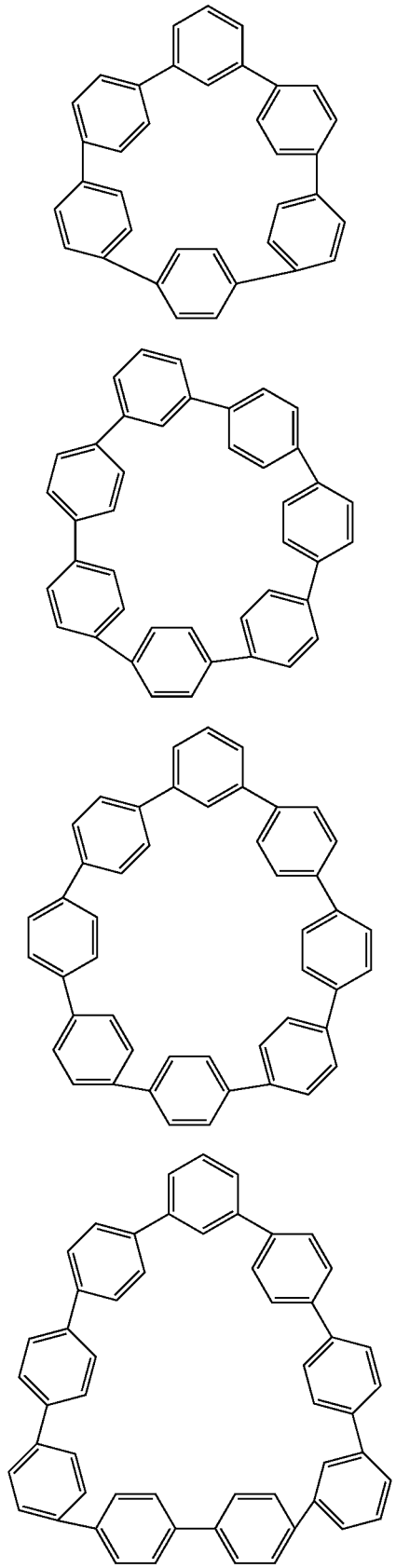

TABLE 6-continued
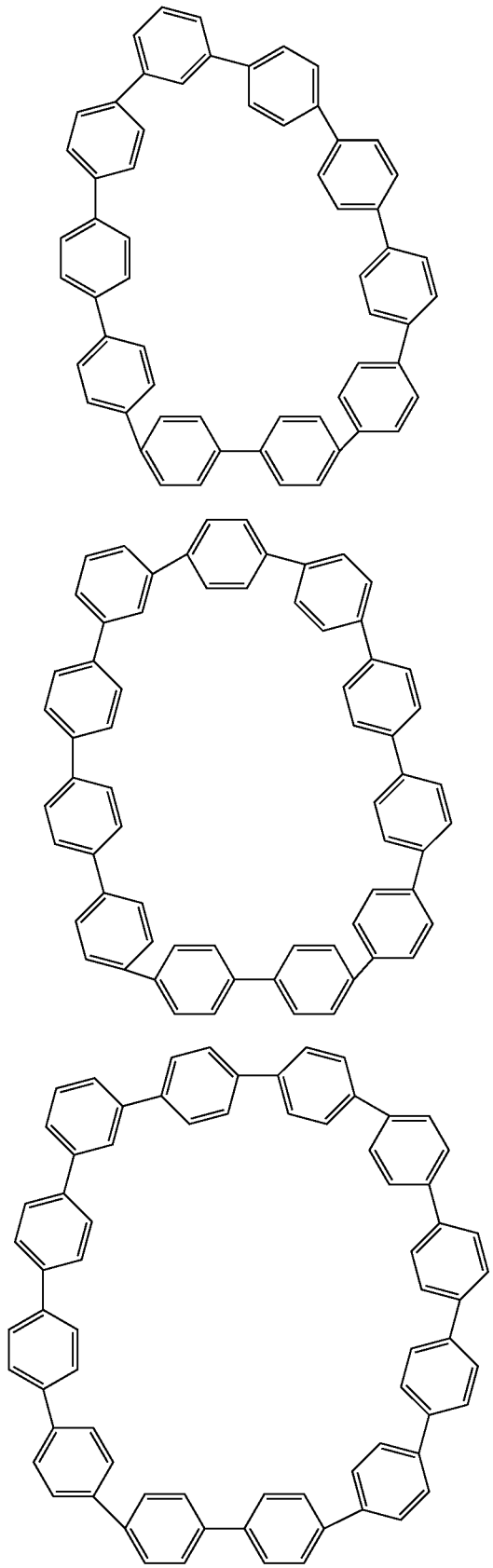

In an independent embodiment, the nanohoop compounds are not, or are other than compounds having the following structures:
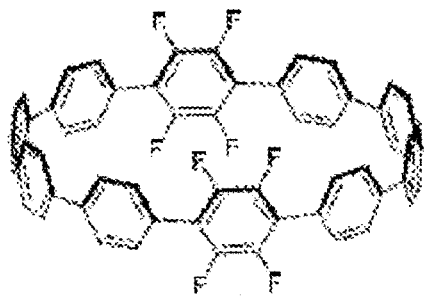
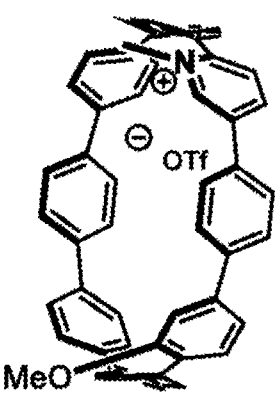
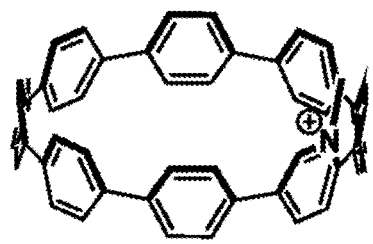
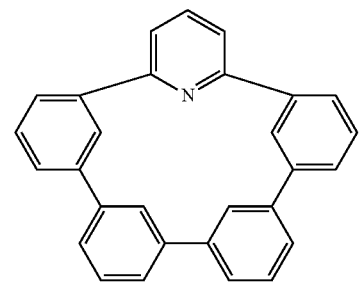
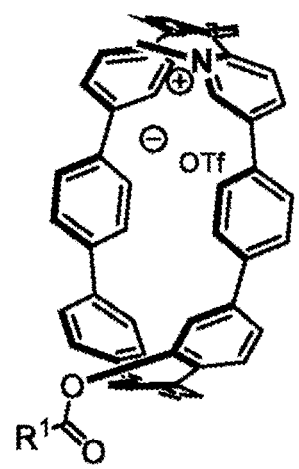
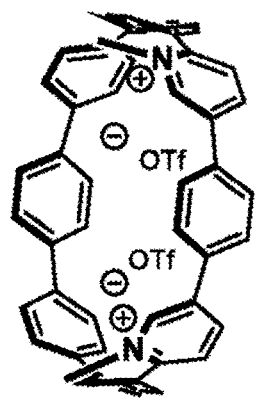
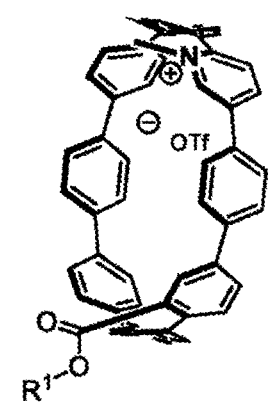

57
-continued
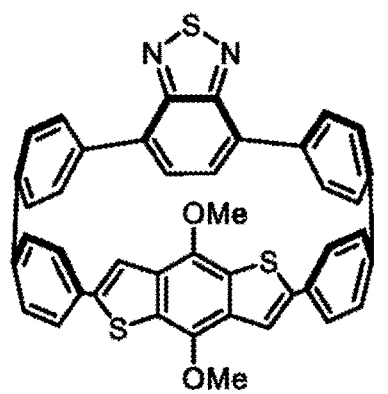
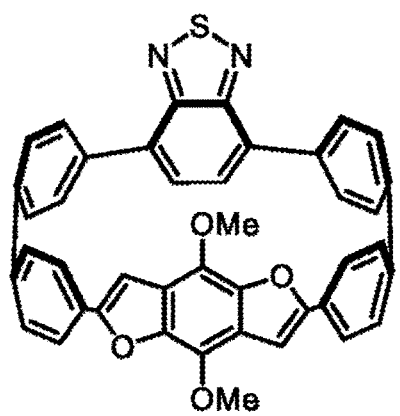
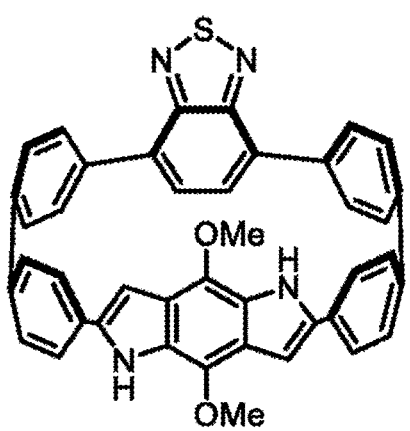
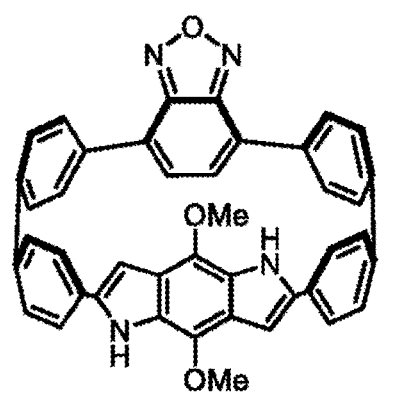
58
-continued
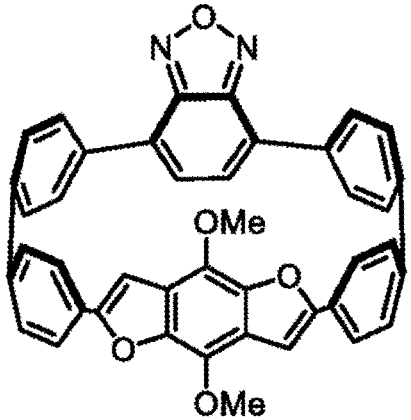
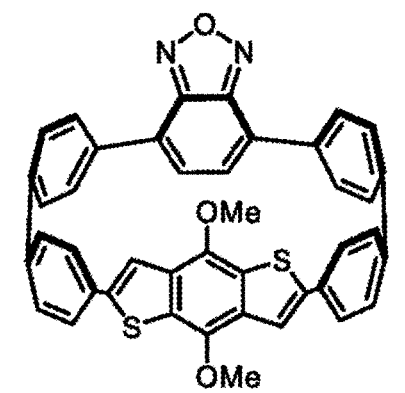
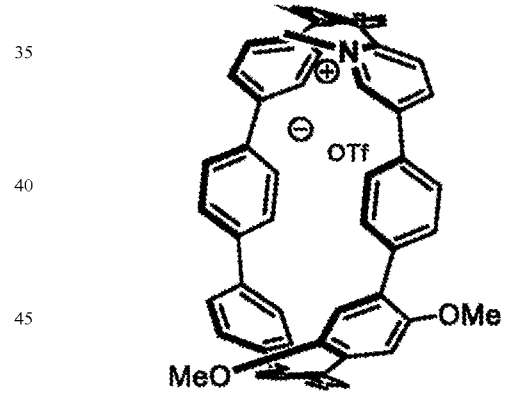
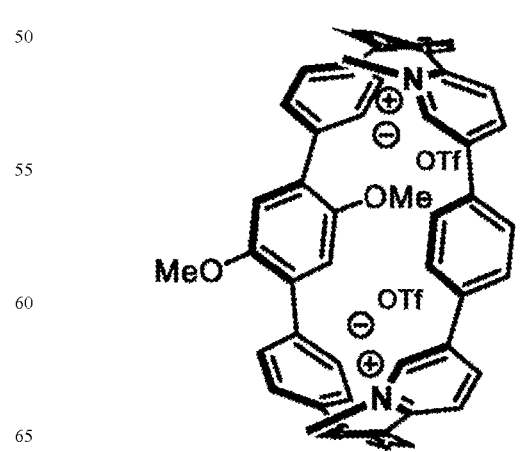

59
-continued
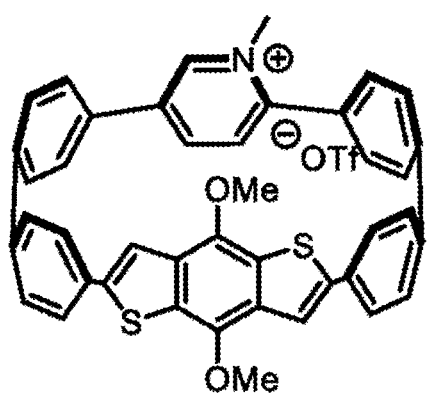
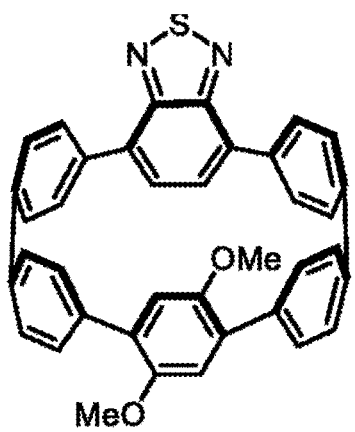
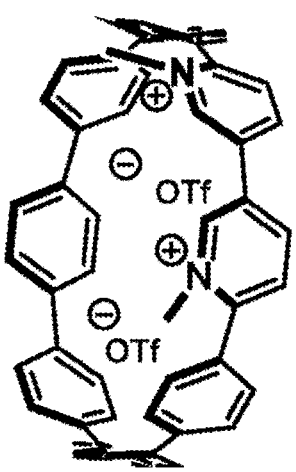
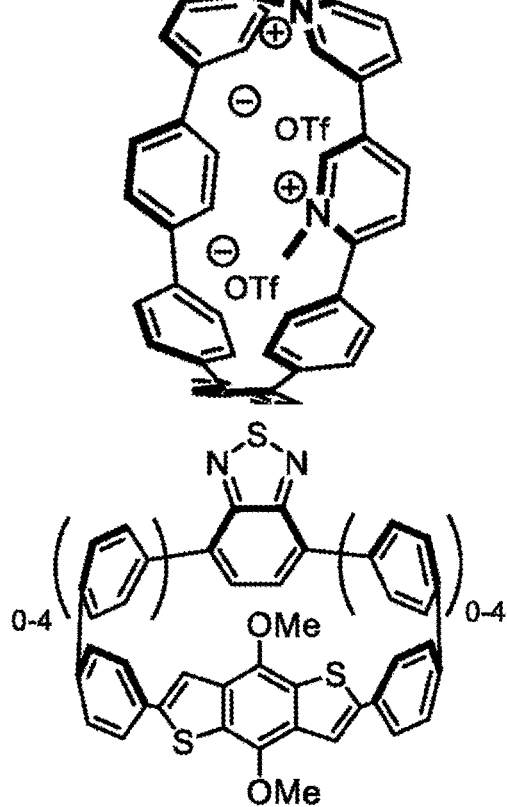
60
-continued
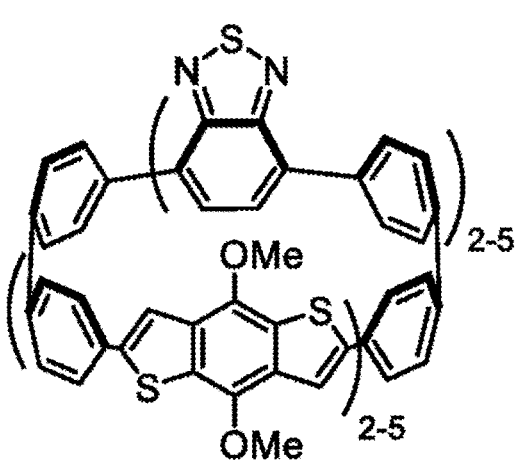
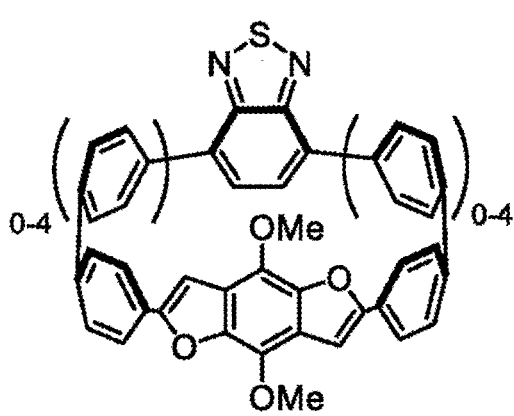
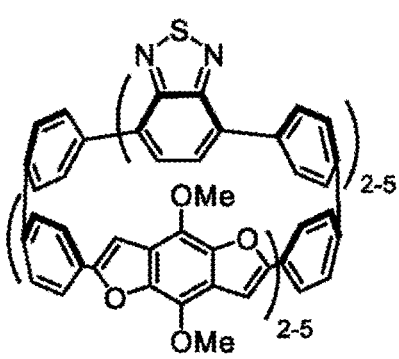

61
-continued
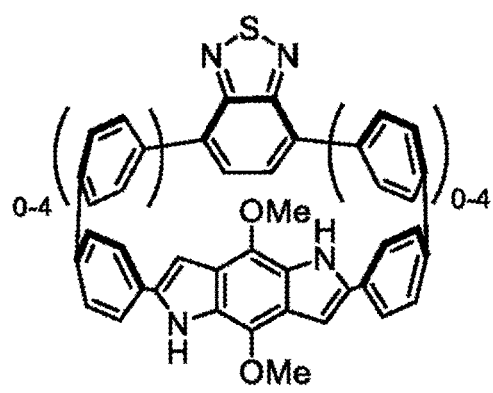
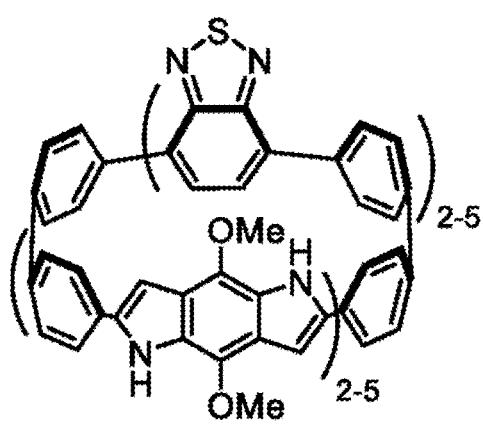
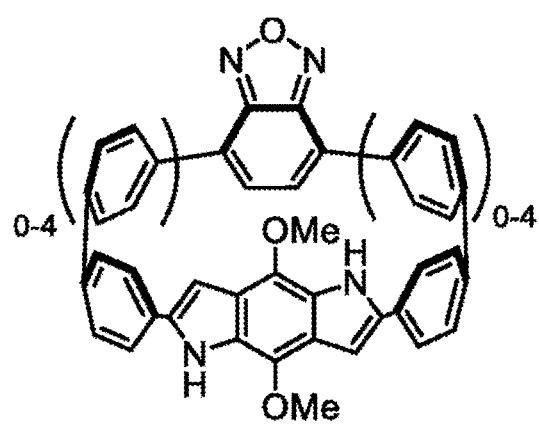
62
-continued
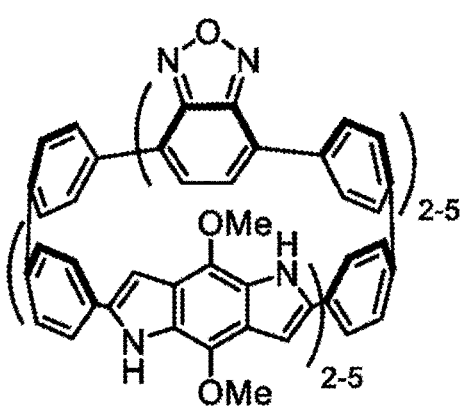
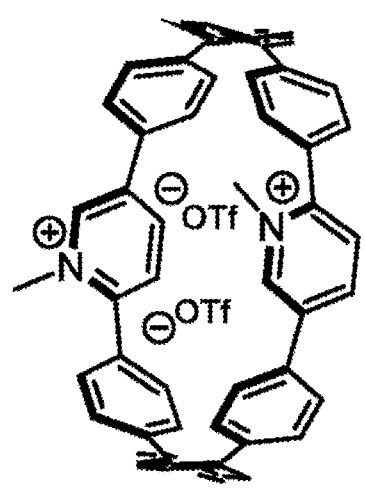
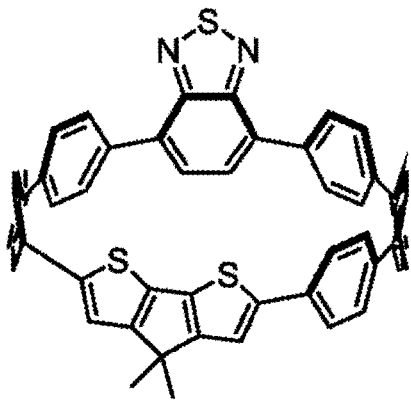

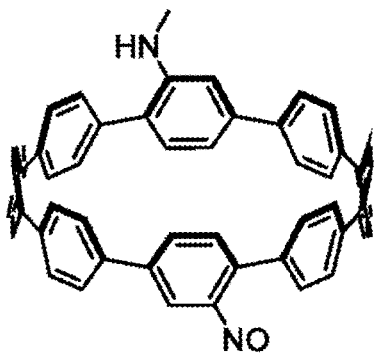

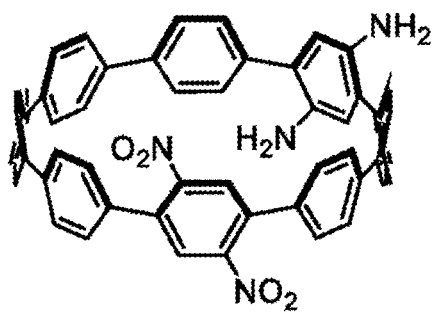

In some embodiments, the disclosed nanohoop compounds provide functionality that allows them to form biological conjugates with one or more biological moieties, but also to one or more additional nanohoop compounds to thereby form a polymeric nanohoop compound. For example, two or more nanohoop monomers can be coupled together to provide polymeric nanohoop compounds comprising a plurality of nanohoop monomers. In some embodiments, two nanohoop compounds independently having structures satisfying Formula I may be coupled to form a dimeric nanohoop compound. As used herein, a nanohoop monomer refers to a compound comprising a single nanohoop. A nanohoop dimer refers to a compound comprising two nanohoops, and a polymeric nanohoop compound comprises at least two nanohoops.

Polymeric nanohoop compounds can be synthesized by covalently coupling the nanohoop monomers together, typically by forming a covalent linkage between one or more rings forming the nanohoop skeleton of each nanohoop monomer directly or through a covalently coupled linker group. In embodiments with a linker, the nanohoop has a structure satisfying formulas described above, wherein R is a linker-Z group and wherein Z is another nanohoop. Covalently coupled linker groups can include, but are not limited to, linker groups discussed above for the linker-Z group of Formula I. In particular disclosed embodiments, the minimal subset of a polymeric nanohoop is a nanohoop dimer, which can comprise a first nanohoop monomer and a second nanohoop monomer. In certain embodiments, a first nanohoop monomer is covalently coupled to a second nanohoop compound via an aliphatic, heteroaliphatic, aryl or heteroaryl linker group. In yet additional embodiments, the first and second nanohoop monomers can be directly coupled together through a bond formed between at least one ring of the first nanohoop monomer and at least one ring of the second nanohoop monomer. Embodiments of polymeric compounds disclosed herein include polymeric nanohoop compounds that comprise a total of 2 to 1000 nanohoop monomers, such as a total of 2 to 750, 2 to 500, 2 to 250, 2 to 100, 2 to 50 and 2 to 20 nanohoop monomers.

Representative nanohoop compounds can have structures satisfying one or more of the formulas illustrated below.

Formula IV

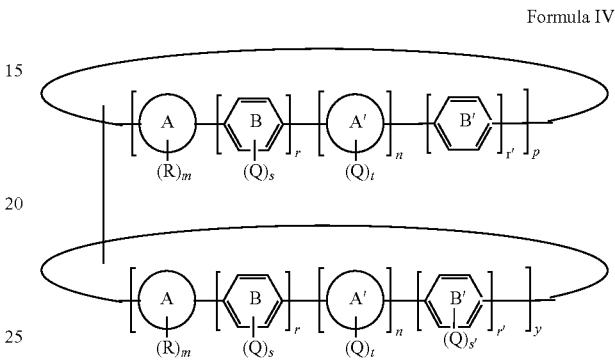

With reference to Formula IV, the illustrated variables are as described above and y is an integer selected from 1 to 25.

In certain embodiments, the first nanohoop monomer is attached to a second nanohoop monomer via the A ring of the first nanohoop. Particular embodiments of a polymeric nanohoop compound comprise a first nanohoop monomer having a structure satisfying Formula I, wherein the first nanohoop monomer is covalently coupled to a second nanohoop monomer having a structure satisfying Formula I through ring A of the first monomer nanohoop and ring A, B, A', or B' of the second nanohoop monomer via an aliphatic, heteroaliphatic, aryl or heteroaryl group, and/or wherein the first nanohoop monomer is covalently coupled to the second nanohoop monomer through ring A', ring B, or ring B' of the first nanohoop monomer and ring A, B, A', or B' of the second nanohoop monomer via an aliphatic, heteroaliphatic, aryl or heteroaryl group. The polymeric nanohoop compounds disclosed herein all have substituents and structures as defined by, and consistent with, the nanohoop compounds of Formula I.

Either, or multiple of, the nanohoop monomers that are linked together to form a polymeric nanohoop compound may be a nanohoop conjugate, such as coupled to a peptide, an oligonucleotide, a nucleoside, a drug, a cell, an antibody, an amino acid, a lipid, a carbohydrate, a liposome, a cyclodextrin, or a porphyrin. Similarly, either or multiple of the nanohoop monomers that are linked together to form a polymeric nanohoop compound may comprise a polymeric nanohoop compound. In some embodiments, the polymeric nanohoop comprises one or more additional nanohoop monomers are covalently coupled to the first and/or second nanohoop monomers.

Particular embodiments of polymeric nanohoop compounds that specify the attachment in more detail are shown in Formulas IVA-IVG below. For example, the polymeric nanohoop compound may have a structure satisfying any one or more of the following formulas illustrated in Table 7.

TABLE 7
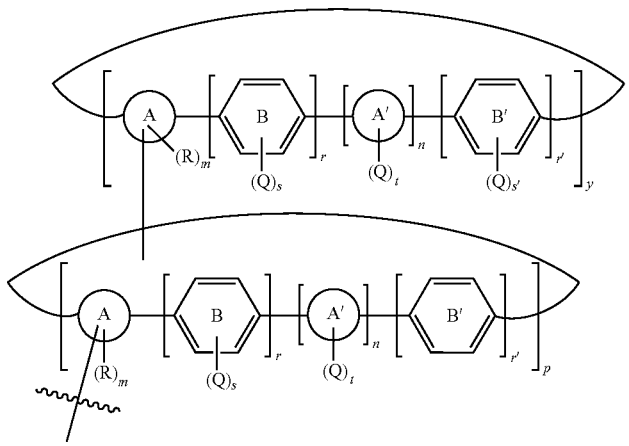
Formula IVA
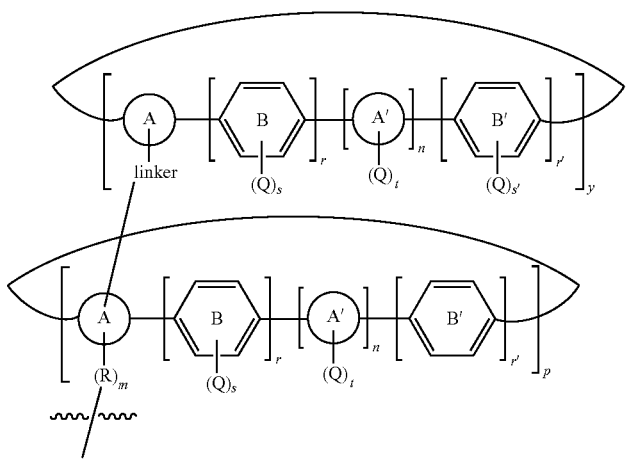
Formula IVB
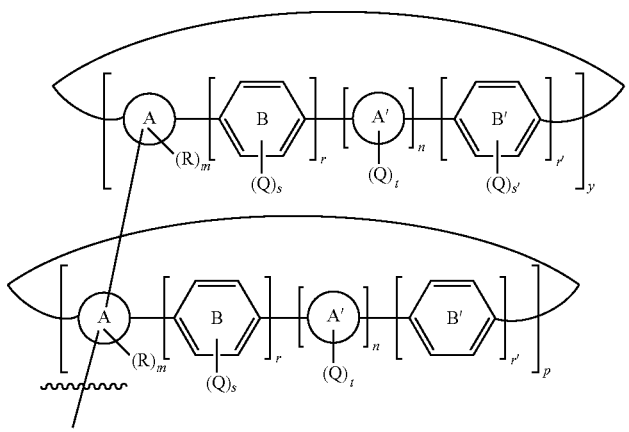
Formula IVC

TABLE 7-continued

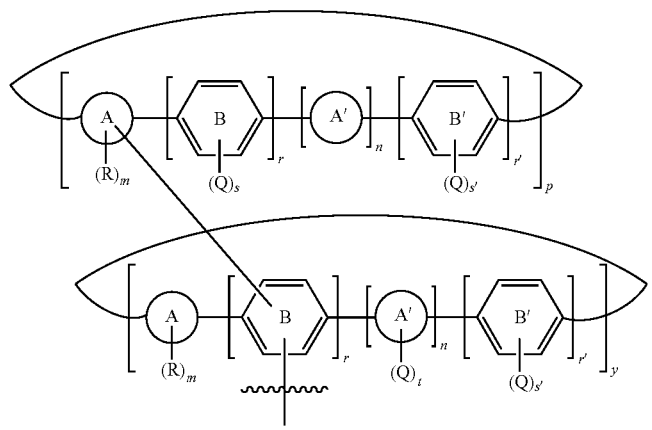

Formula IVD

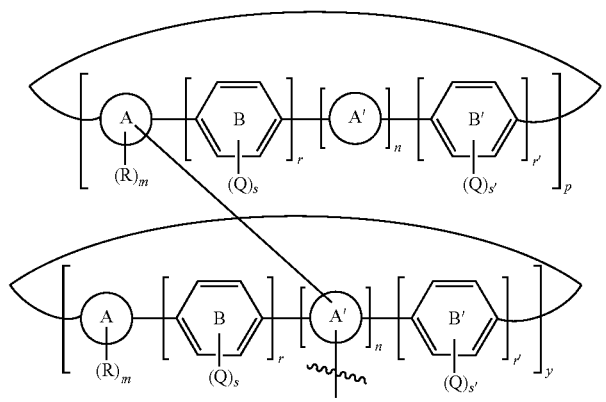

Formula IVE

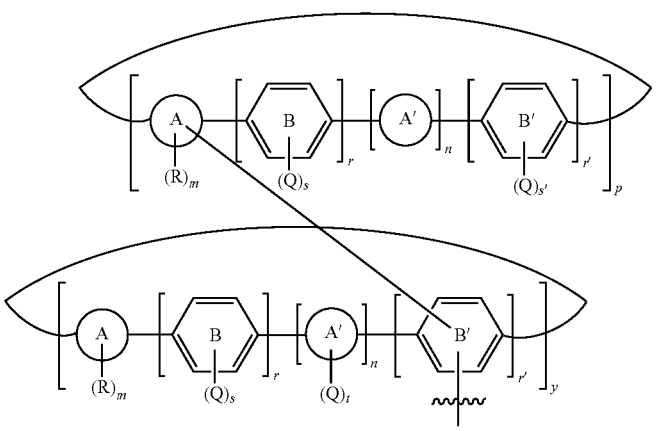

Formula IVF

With reference to the above formulas, each of rings A, B, A', and B'; R; Q; each of n, r and r'; m; w; and p can be as recited herein. In some embodiments, y is an integer selected from 1 to 5, such as 1, 2, 3, 4, or 5.

Also disclosed are species of polymeric nanohoop compounds (e.g., dimer nanohoop compounds) having a structure that satisfies Formula VIA, below, wherein the first nanohoop monomer is covalently coupled to the second nanohoop monomer via a linker group "G," which comprises an aliphatic or aryl group. In some embodiments, the first and/or second nanohoop monomer can be modified to comprise one or more additional nanohoop monomers coupled directly to or indirectly (through a covalently coupled linker group) to the first and/or second nanohoop compound.

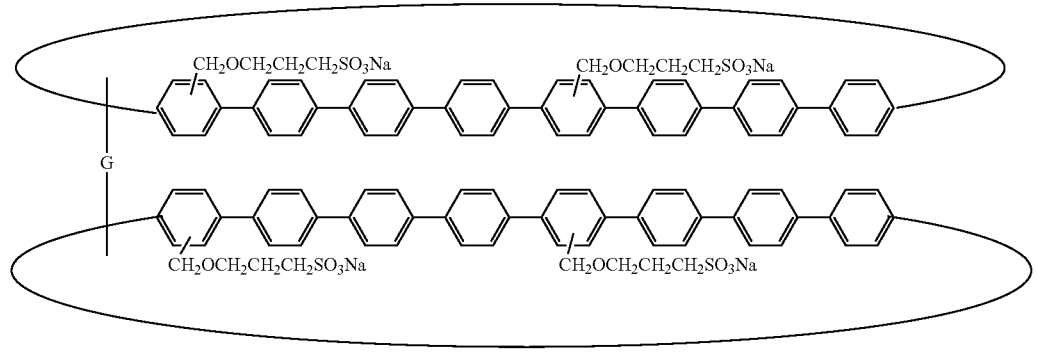
Formula VIA
Particular embodiments of polymeric nanohoop compounds of Formula VIA are shown in Formulas VIIA-VIIP below. In certain embodiments, the polymeric nanohoop compounds disclosed herein has a structure satisfying any one or more of the formulas illustrated below in Table 8.
TABLE 8
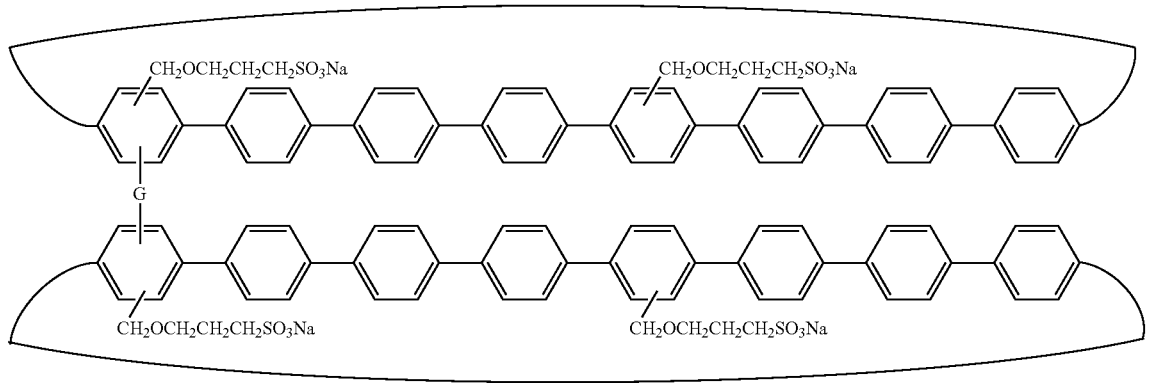
Formula VIIA
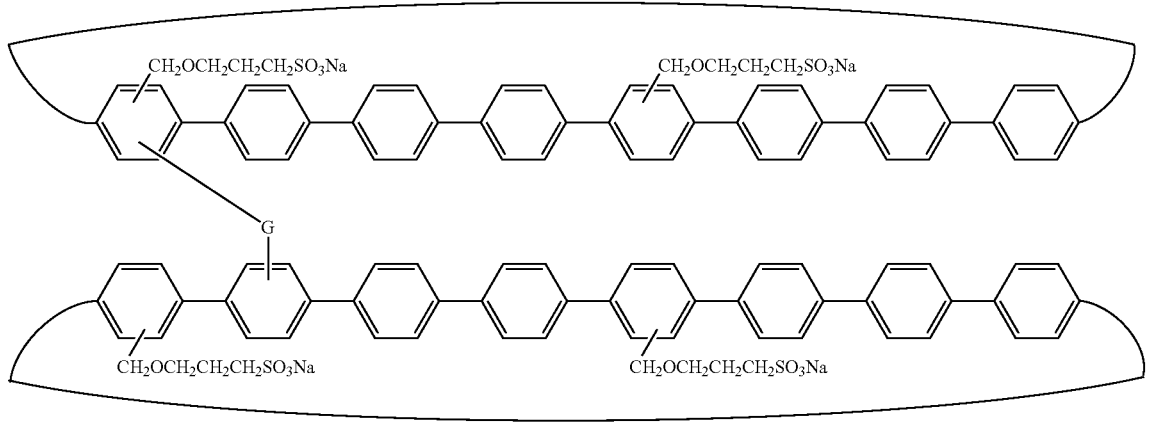
Formula VIIB TABLE 8-continued
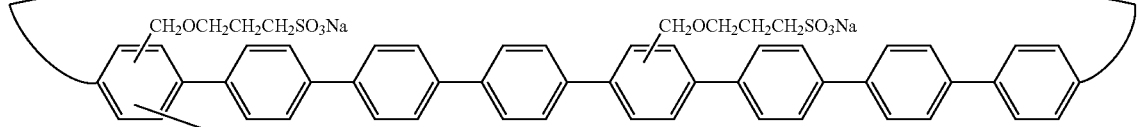
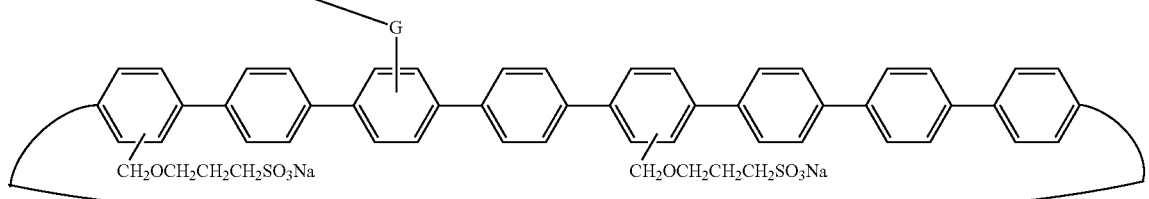
Formula VIIC
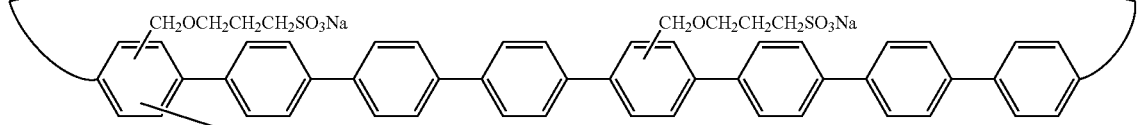
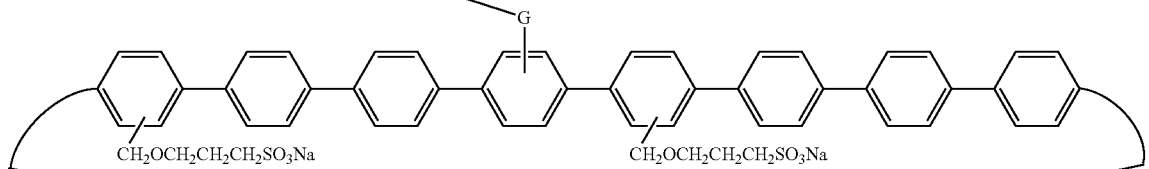
Formula VIID
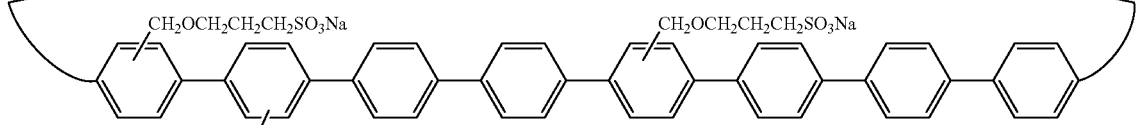
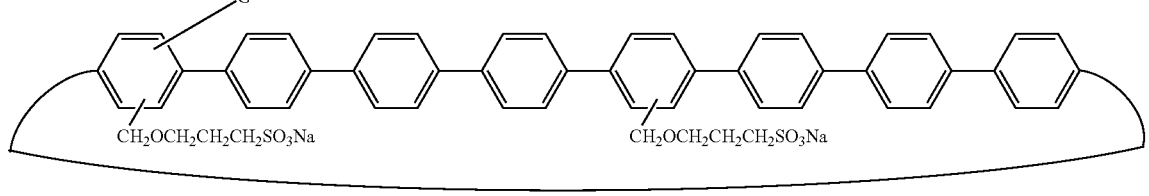
Formula VIIIE TABLE 8-continued
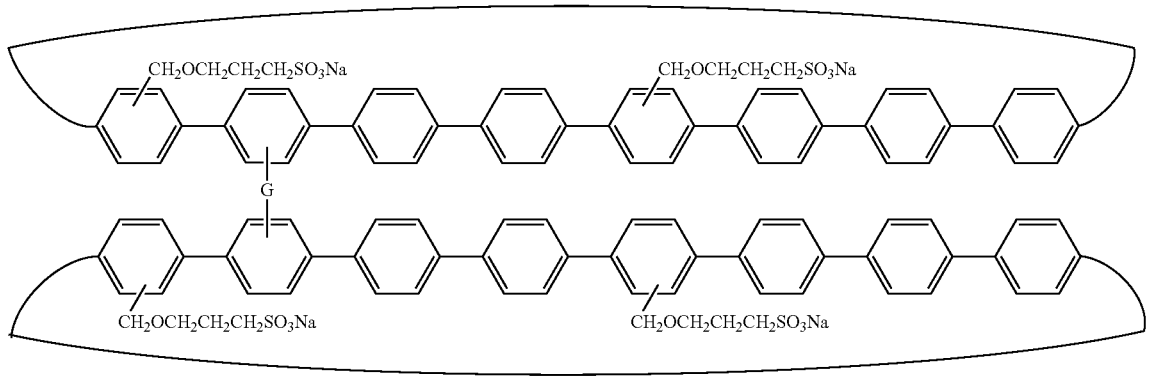
Formula VIIF
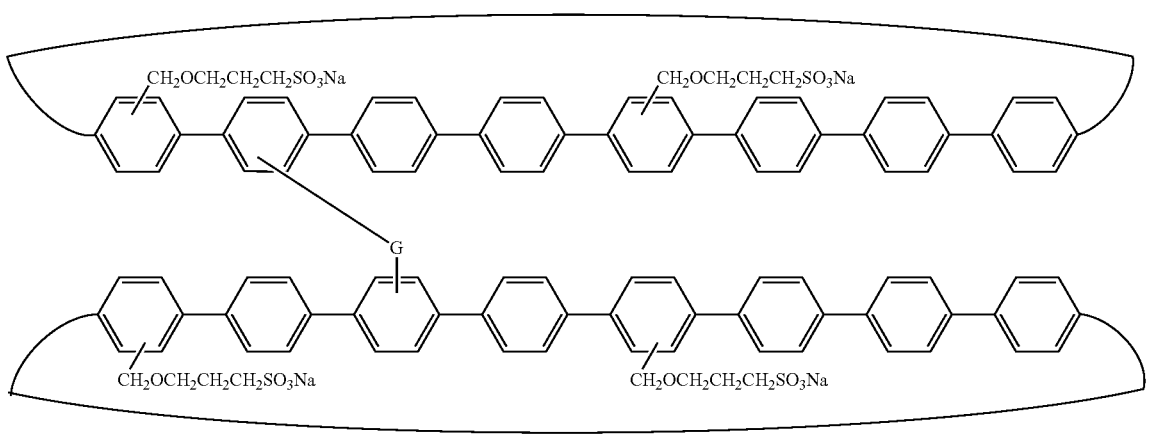
Formula VIIG
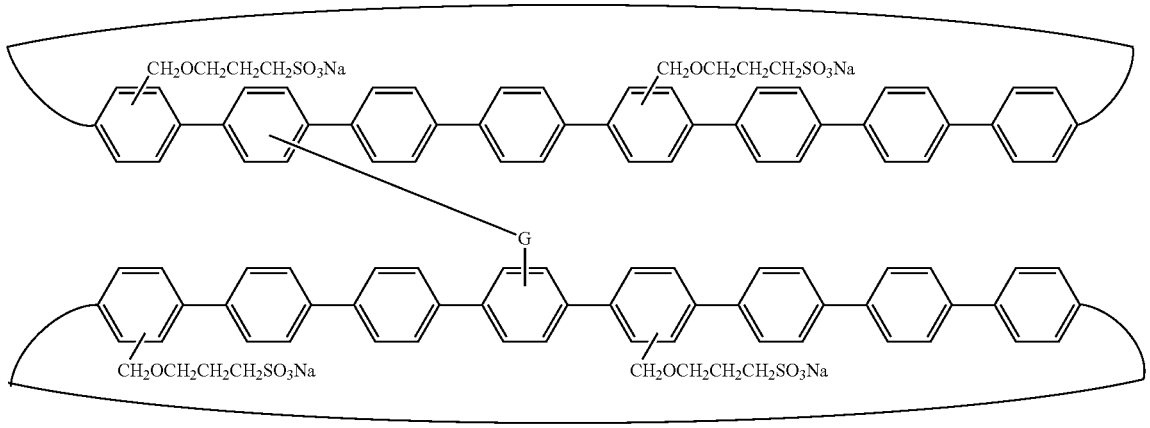
Formula VIIH TABLE 8-continued
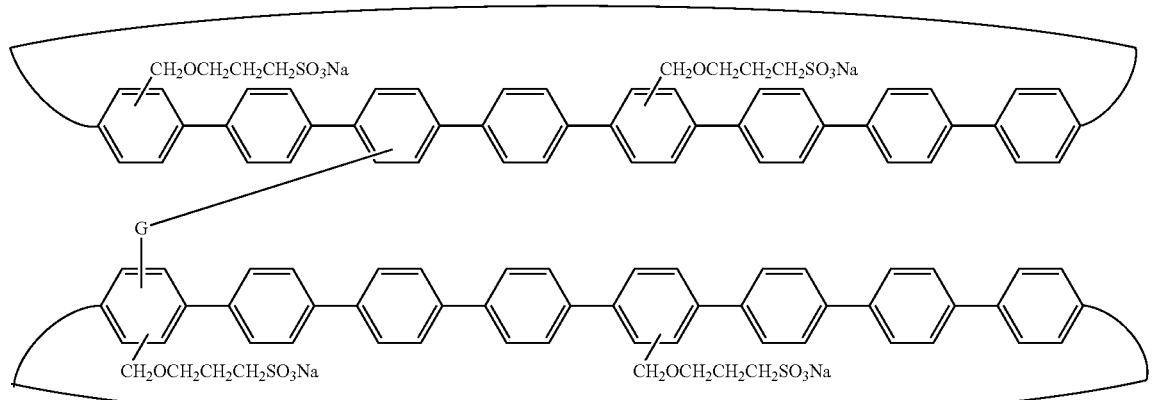
Formula VIII
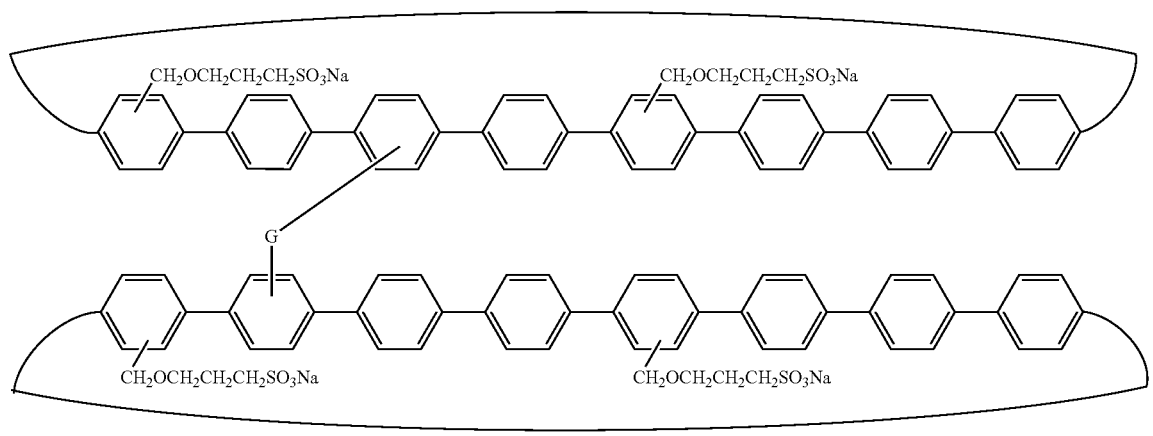
Formula VIIJ
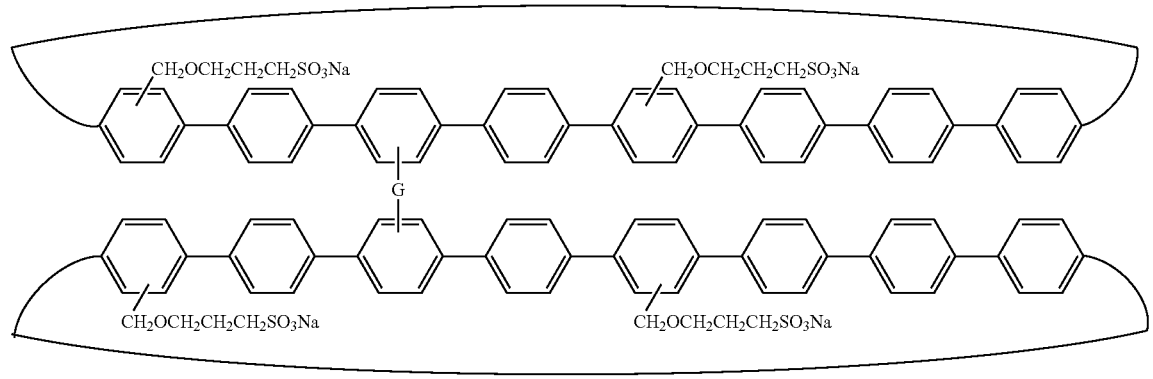
Formula VIIK TABLE 8-continued
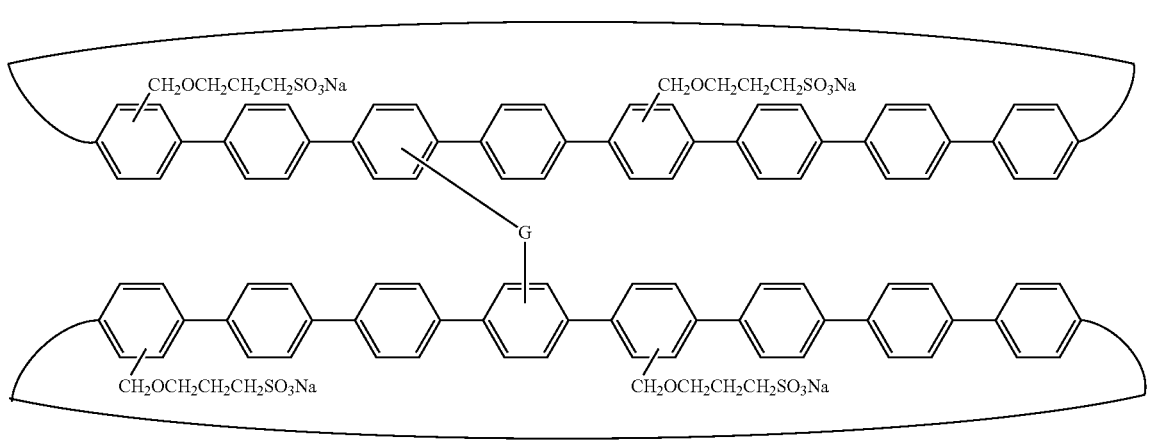
Formula VIIL
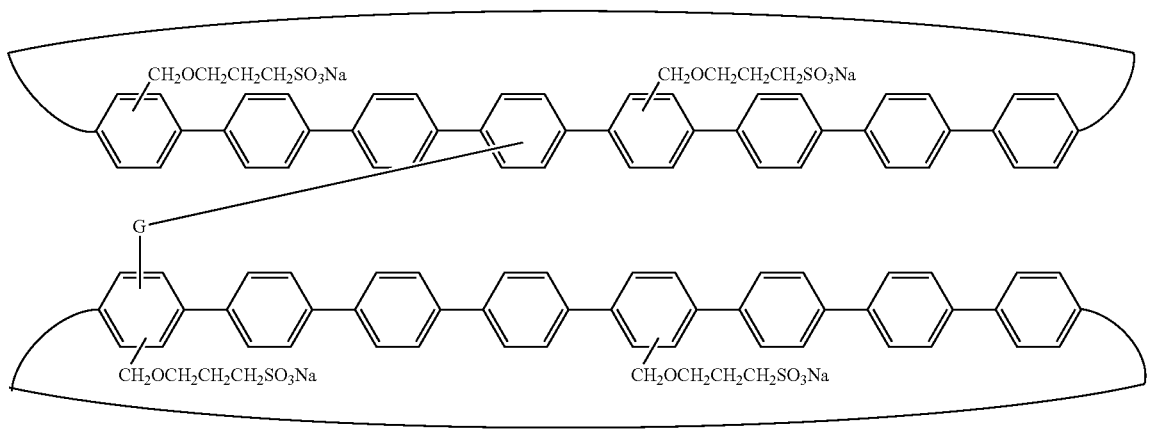
Formula VIIM
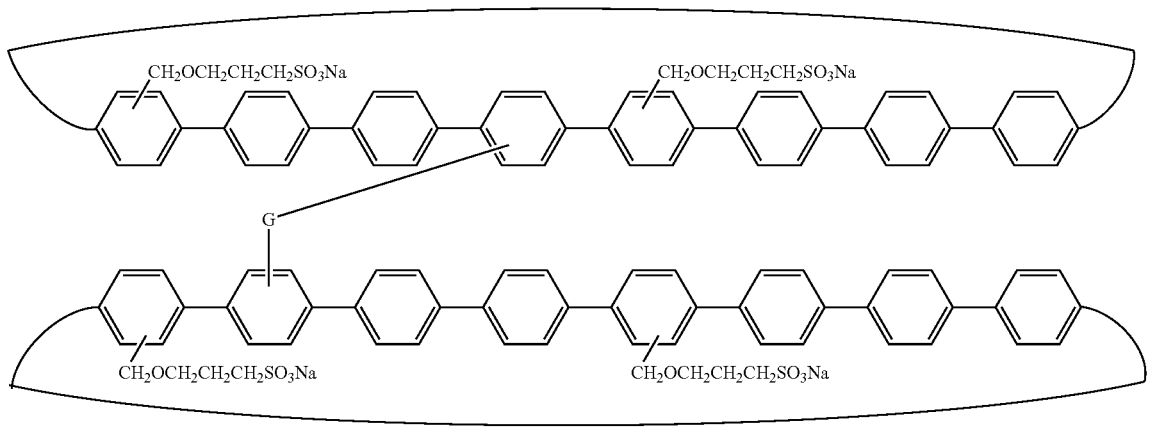
Formula VIIN TABLE 8-continued
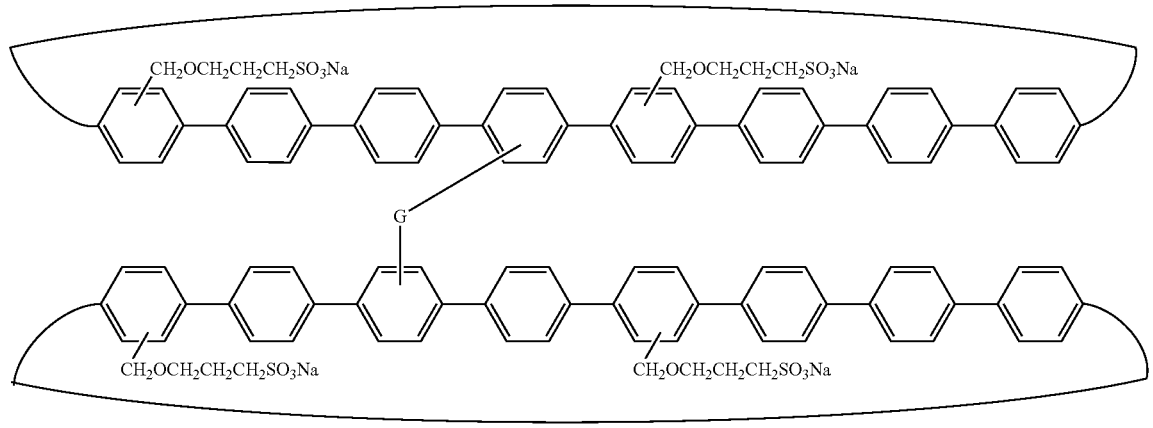
Formula VIIO
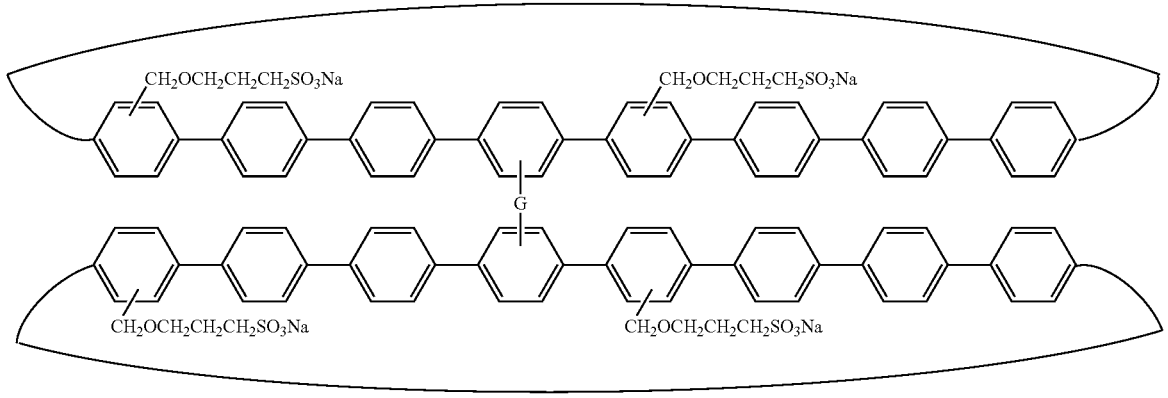
Formula VIIP
In specific embodiments of the compounds of Formulas VIIA-VIIP, G is a bond or phenyl. G, however, can be selected from other linker groups described herein.
In an independent embodiment, the polymeric nanohoop compound is not or is other than the following:
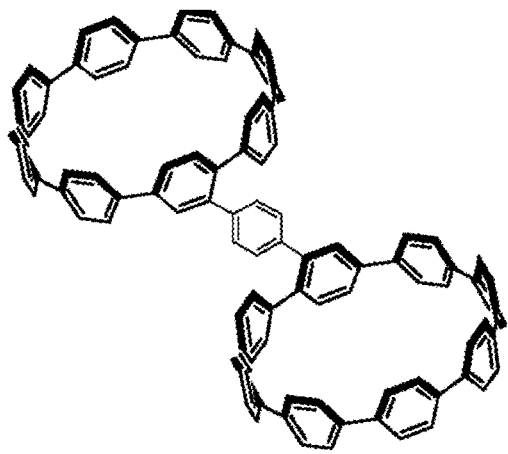
-continued
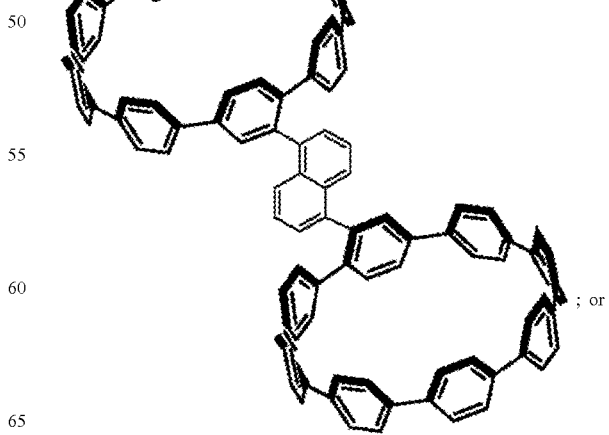
; or -continued

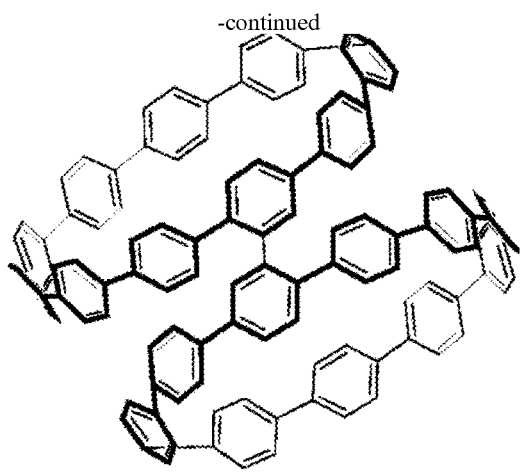

In some embodiments, the nanohoop compounds disclosed herein (and thus conjugates comprising such compounds), including embodiments of the polymeric nanohoop compounds, can exhibit fluorescence. Thus, the nanohoop compounds, conjugates, and polymers described herein may be useful for biological applications as a fluorescent tag, label or probe. In some embodiments, the nanohoop compounds can be conjugated to a biological moiety (e.g., a peptide, a nucleotide, a nucleoside, a drug, a cell, an antibody, an amino acid, a lipid, a carbohydrate, a liposome, a cyclodextrin, a porphyrin, or the like) to thereby facilitate visualizing the presence or absence of the biological moiety in a sample. In some embodiments, nanohoop compound embodiments comprising a ring that is coupled to other rings of the nanohoop via bonds that are meta-substituted relative to one another exhibit bright fluorescence even when lower numbers of rings (e.g., 8 or fewer rings, such as 5 to 7 rings, or 5 to 6 rings) are included in the nanohoop skeleton. In some embodiments, the nanohoop compounds, conjugates, and polymers absorb light of a wavelength between 100 nm and 700 nm. In certain embodiments, the nanohoop compounds, conjugates, and polymers emit light of wavelength between 300 nm and 800 nm. In further embodiments, the nanohoop compounds, conjugates, and polymers absorb light of a wavelength between 100 nm and 700 nm, and emits light of wavelength between 300 nm and 800 nm.

In certain embodiments, the nanohoop compounds, conjugates, and polymers fluoresce with a molar extinction coefficient of between 10,000 and 5,000,000 $M^{-1}$ $cm^{-1}$. In additional embodiments, the nanohoop compounds, conjugates, and polymers fluoresce with a quantum yield of between 0.001 and 0.9 in DBPS, such as 0.01 to 0.77. In some embodiments, the nanohoop compounds, conjugates, and polymers fluoresce with a molar extinction coefficient of between 10,000 and 5,000,000 $M^{-1}$ $cm^{-1}$ and with a quantum yield of between 0.001 and 0.9 in DBPS.

Unexpectedly, in the polymeric nanohoop compounds described herein, the fluorescence of the first nanohoop monomer does not quench the fluorescence of the second nanohoop monomer. This discovery was in contrast to conventional thinking, which postulated that fluorescent compounds having two or more fluorophores, would quench each other and result in the compound having little or no fluorescence.

In some embodiments, the nanohoop compounds, conjugates, and polymers disclosed herein are soluble in water. For example, the disclosed nanohoop compound/conjugate may be soluble in water at a concentration of at least 1 micromolar, at least 5 micromolar, at least 10 micromolar, between 1 micromolar and 1 molar, between 2 and 200 micromolar, or between 5 and 50 micromolar. In certain embodiments, the disclosed nanohoop compound/conjugate has a solubility of 10 micromolar in 0.05% DMSO in water. In view of the ability to render the nanohoop compounds, conjugates, and polymers water-soluble, the nanohoop compound, conjugate, and polymer embodiments described herein can be used for live cell imaging studies and aqueous assay and/or sensor applications.

IV. Methods of Using Nanohoop Compounds and Conjugates

Disclosed herein are embodiments of using the nanohoop compounds, conjugates, and polymers described herein. In particular disclosed embodiments, the nanohoop compounds, conjugates, and polymers disclosed herein exhibit properties superior to conventional dyes that lends to their use in myriad biological applications. The disclosed nanohoop compounds, conjugates, and polymers have structures that provide the ability to tune their fluorescence (e.g., increasing or decreasing hoop size and/or increasing or decreasing the number of nanohoops in a polymer) and further that provide binding pockets (e.g., wherein such pockets reversibly bind guest molecules to turn on/off florescence) and other functionality, which is useful in a biological context.

In particular disclosed embodiments, the nanohoop compound embodiments described herein can be conjugated with peptides, oligonucleotides, nucleosides, nucleotides, proteins, aptamers, drugs, cells, antibodies, amino acids, lipids, carbohydrates, liposomes, cyclodextrins, porphyrins, and the like to form conjugate embodiments described herein. Such nanohoop conjugate (and/or polymer) embodiments described herein can be used as organocatalysts, cell-penetrating peptides, drug delivery compounds, assay/affinity reagents, sensor molecules, catalytic aptamers, primers, DNA/RNA sequencing, and the like. Exemplary methods of using the disclosed nanohoop compounds, conjugates, and polymers are described below.

In some embodiments, the nanohoop compounds disclosed herein can be conjugated with a plurality of amino acids to provide nanohoop-oligopeptide conjugates that comprise a hydrophobic binding pocket provided by the nanohoop compound of the conjugate. These nanohoop-oligopeptide conjugates exhibit superior reactivity as compared to conventional oligopeptides not having a nanohoop conjugated thereto as the disclosed nanohoop-oligopeptide conjugates not only are chiral, but they also have a hydrophobic pocket that can encompass and help solubilize a catalyst comprising hydrophobic amino acids, or help solubilize the catalytic substrate to increase the efficiency of the catalysis. In certain embodiments, the nanohoop compounds disclosed herein can be conjugated with amino acids to provide oligopeptides that comprise a hydrophilic binding pocket.

In particular disclosed embodiments, the nanohoop-oligopeptide conjugates can be used to catalyze carbon-carbon bond forming reactions, such as aldol reactions, Michael reactions, hydrocyanation of aldehydes, and other such reactions often used in organic synthesis. In additional embodiments, the nanohoop-oligopeptide conjugates can catalyze asymmetric organic reactions, such as asymmetric acylations, asymmetric phosphorylations, enantioselective oxidations, enantioselective reductions, enantioselective protonation, and the like. In yet additional embodiments, the nanohoop-oligopeptide conjugates can catalyze hydrolytic reactions. In the catalytic methods described above, the nanohoop-oligopeptide conjugates can be combined with a suitable starting material for the desired transformation (e.g., for an aldol reaction, the starting material would be an aldehyde or the corresponding carbon-containing compound reacted with the aldehyde) and can be provided in amounts ranging from 0.1 mol % to 5 mol %, such as 0.1 mol % to 2.5 mol %, or 0.2 mol % to 2 mol %, or 0.5 mol % to 1 mol %, or 0.5 mol % to 0.75 mol %. Such reactions can be conducted at ambient temperatures (e.g., 23° C. to 26° C., such as 23.5° C. to 25.5° C.), or at temperatures above or below ambient temperatures.

Figure 5:
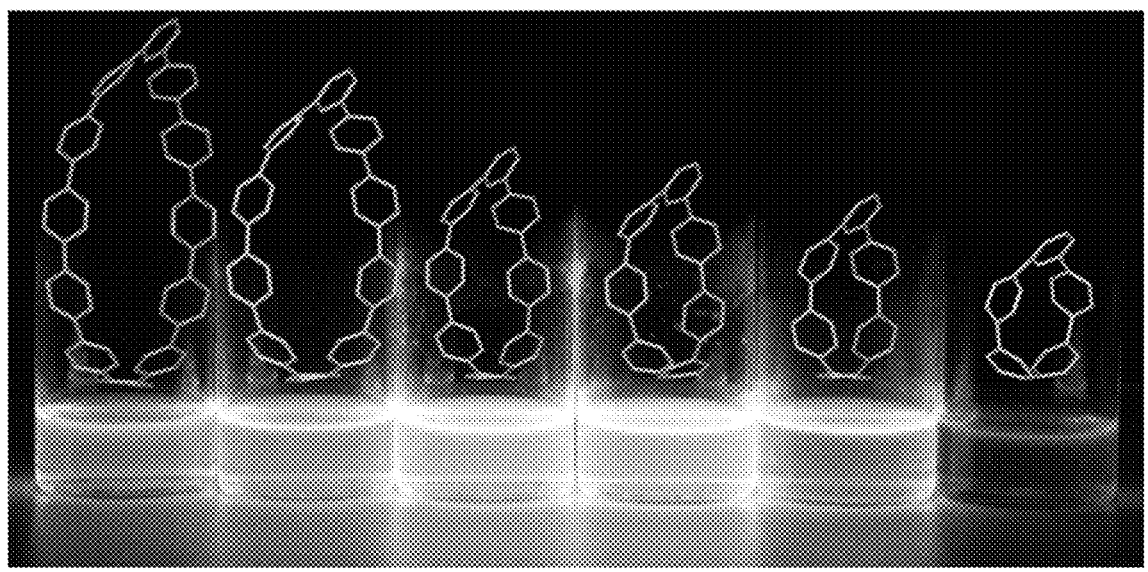
FIG. 5 is a photographic image of solutions of different sized nanohoop compound embodiments comprising meta-substitution showing how fluorescence can be tuned by controlling the size of the nanohoop compound.
Figure 6:
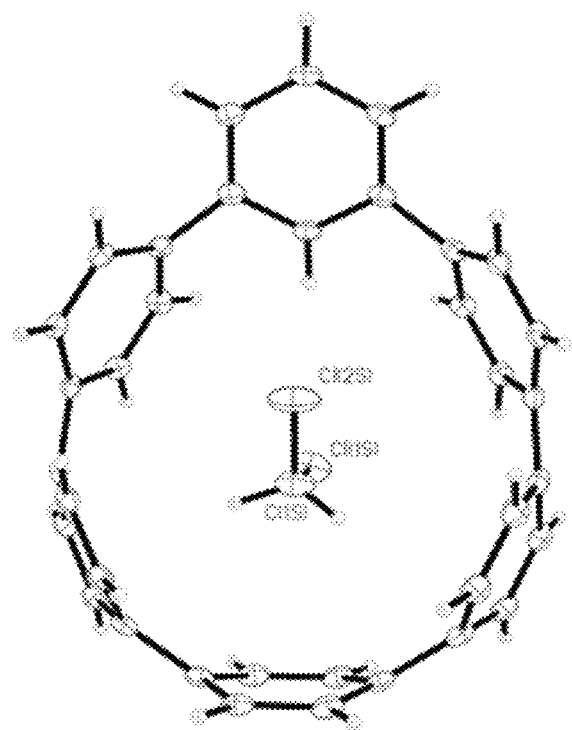
FIG. 6 is an ORTEP representation of an exemplary nanohoop compound ([6]mCPP) comprising a ring that is attached to other rings of the nanohoop compound via bonds that are meta-substituted relative to each other.

In some embodiments, the nanohoop compounds described herein can be conjugated to peptides to form a new class of cell-penetrating peptides (also referred to herein as "CP peptides"). While these types of nanohoop conjugates are referred to herein as nanohoop-based cell-penetrating peptides (or "nanohoop-based CP peptides") they also are able to penetrate other biological structures, such as tissues, mitochondria, and the like. For example, embodiments of the disclosed nanohoop compounds can facilitate the transfer of CP-peptides into cells, or improve the efficiency of cell penetration. In particular disclosed embodiments, the nanohoop compounds can be coupled to short peptides comprising 40 or fewer amino acids. The peptides can be naturally occurring peptides (e.g., truncated versions of full length proteins, such as penetratin, the HIV-1 TAT protein, MAP, transportan/TP10, VP22, MPG, or the like) or synthetic peptides (e.g., peptides made from synthetic sequences and/or peptides having one or more non-naturally occurring amino acids). In some embodiments, the peptide(s) to which the nanohoop compound(s) is coupled comprises only positively charged amino acids. In yet other embodiments, the peptide can be an amphipathic peptide that comprises a hydrophobic domain conjugated to a nuclear localization sequence. In yet additional embodiments, the peptide can be a hydrophobic peptide, a prenylated peptide, or other suitable peptide. The nanohoop-based CP peptides can be used as drug delivery systems and/or as fluorescent label delivery systems. In some embodiments, nanohoop-based CP peptides can be used to deliver drugs or active biomolecules into a cell and at the same time serve as a fluorescent label that can be imaged in the cell due to the ability of the nanohoop portion of the conjugate to naturally fluoresce. As established in Darzi and Jasti, Chem. Soc. Rev., 2015, 44, 6401-6410, non-substituted compounds comprising a different number of phenyl rings connected in a ring exhibited changes in fluorescence. For example, the fluorescence of unsubstituted nanohoop compounds containing 5, 6, 7, 8, 9, 10, 11 and 12 phenyl rings increased as the number of rings increased, and the emission wavelength generally shifted to longer wavelengths (or "redshifted") with increasing ring size; however, at lower rings sizes (e.g., 6 or fewer rings), fluorescence was substantially non-existent. In contrast, novel nanohoop compound embodiments disclosed herein having at least one ring that is coupled to other rings of the nanohoop via bonds that are meta-substituted relative to one another fluoresce with only 5 or 6 (or more) rings in the nanohoop skeleton. This fluorescence of these 5-membered and 6-membered nanohoop rings comprising meta-substitution within the nanohoop is superior to that of similar-sized rings having all para-substituted nanohoop rings within the nanohoop skeleton. FIG. 5 is a photograph showing that these smaller-sized nanohoops comprising meta-substitution exhibit bright fluorescence. Also, FIG. 6 shows the absorption and emission spectra of exemplary nanohoop compound embodiments comprising meta-substitution (referred to as [n]mCPP, wherein n is the number of rings in the nanohoop. Nanohoop compound embodiments disclosed herein also exhibit the ability to tune fluorescence by modifying the number of rings in the nanohoop skeleton and even by modifying the types of rings in the nanohoops skeleton, such as by adding fused ring systems comprising mixtures of phenyl and non-phenyl rings (e.g., 2,2'-(anthracene-9,10-diylidene)dimalononitrile).

In some embodiments, the nanohoop-based CP peptides can be used solely to deliver one or more drug molecules into a cell or solely to serve as a fluorescent label within the cell. The disclosed nanohoop-based CP peptides thus can be used in cancer treatment (e.g., by delivering cytotoxic drugs), muscular dystrophy treatment (e.g., by coupling the nanohoop-based CP peptide to a phosphorodiamidate morpholino oligomer), stroke treatments (e.g., by coupling the nanohoop-based CP peptide to a peptide inhibitor), antiprion treatment (e.g., by coupling the nanohoop compound to a peptide derived from human prion protein), and antiviral treatments (e.g., by coupling the nanohoop-based CP peptide to a phosphorodiamidate morpholino oligomer).

In yet additional embodiments, the nanohoop compounds disclosed herein can be conjugated to one or more drug molecules. Such nanohoop-drug conjugates can be used as biological drug delivery systems. In some embodiments, the nanohoop-drug conjugates can be formed by covalently coupling the nanohoop compound to the drug compound. In yet additional embodiments, the nanohoop-drug conjugates can be formed by non-covalently coupling the drug to the nanohoop compound, such as by housing the drug within the core defined by the nanohoop compound through hydrophobic or electrostatic interactions between the drug and the nanohoop compound. In particular disclosed embodiments, the nanohoop-drug conjugates are able to deliver drug molecules to regions of the body not normally accessed by other drug delivery systems, such as through cell membranes. In particular disclosed embodiments, the nanohoop-drug conjugates not only are able to deliver the drug to a particular region of the body, but it also can simultaneously provide a detectable signal wherein the delivery of the drug can be confirmed by a suitable detection technique. For example, the nanohoop-drug conjugates themselves may not exhibit a fluorescent signal, but such a signal may be produced once the drug is cleaved or otherwise removed from the conjugate. Alternatively, the nanohoop-drug conjugates themselves may exhibit a fluorescence and such a signal may be quenched once the drug is cleaved or otherwise removed from the conjugate. Exemplary drugs that can be delivered using the nanohoop-drug conjugates are discussed above.

In some embodiments, the disclosed nanohoop compounds can be added to an aptamer, such as an oligonucleotide aptamer or a peptide aptamer. In yet additional embodiments, the disclosed nanohoop compounds can be used to form antibody-like affinity reagents for aptamers.

In some further embodiments, the disclosed nanohoop compounds can be added to a cell, such as a diseased cell. The cell may be associated with a nanohoop compound by covalent or non-covalent interactions. The nanohoop compound may, for example, comprise an antibody or peptide that is electrostatically or covalently bound to a cell. Alternatively, the nanohoop compound can be covalently bound to a component in the cell membrane, such as a lipid, or it may be associated with the cell via hydrophobic or electrostatic interactions after being taken up by the cell, In some embodiments, the disclosed nanohoop compounds can be used in enzyme assays. For example, the disclosed nanohoop compounds can be conjugated with a biological moiety to form a conjugate for use in an enzyme assay, such as enzymatic oxidation and/or reduction reactions. In an exemplary embodiment, the nanohoop compound can be coupled to an oligopeptide or an antibody that can further comprise a quenching moiety that quenches fluorescence of the nanohoop compound. Upon exposure of the nanohoop-oligopeptide conjugate (or nanohoop-antibody conjugate) to an enzyme that cleaves the oligopeptide (or the antibody), the nanohoop will provide a detectable fluorescent signal. In an exemplary embodiment, the nanohoop compounds/conjugates described herein can be used in an AIDs protease enzymatic assay.

In some additional embodiments, the nanohoop compounds/conjugates described herein can be used in oligonucleotide hybridization assays (e.g., a gene chip assay), polymerase chain reaction methods (wherein the nanohoop compounds/conjugates can be used as primers), RNAi gene silencing methods, methods associated with clustered regularly interspaced short palindromic repeats (known in the art as "CRISPR" and/or CRISPR-associated gene technologies), and DNA sequencing methods using one or more nanohoop-nucleoside conjugates.

V. Methods of Making Nanohoop Compounds and Conjugates

Methods of making nanohoop compounds are disclosed herein. In some embodiments, the method of making the disclosed nanohoop compounds utilizes precursor compounds as building blocks that can be added in a modular (e.g., ring by ring) or cross coupling (e.g., by cross coupling two components with each component comprising two or more rings that are bound together) fashion to provide nanohoop compounds with varying numbers of rings within the nanohoop skeleton. While representative method embodiments are illustrated below, the method of making the nanohoop compound can be modified using techniques in the art with the benefit of the present disclosure. For example, the method can be modified by using precursors that, when formed into a final nanohoop skeleton, provide a skeleton wherein the rings of the skeleton are linked by para connections, meta connections, ortho connections, or any combination thereof. In some embodiments, any of the precursors used to make the nanohoop compounds can comprise one or more functional groups as described above.

In additional embodiments, any different combination of ring structures can be used. For example, the nanohoop skeleton can comprise a mixture of phenyl rings; fused ring systems wherein all rings are aromatic or a mixture of aromatic and non-aromatic rings; pyridinyl rings, and the like.

As illustrated in Scheme 1 below, two cross-coupling partners 104 and 106 (or 104 and 108) can be used as intermediates to form a nanohoop compound 110. In some embodiments, a halogen-metal-based coupling reacting whereby the precursor compound 100 is exposed to a base (e.g., a lithium-containing base) and a coupling partner 102. After protecting the product from this reaction, intermediate 104 is obtained. Intermediate 104 can also serve as a starting material to produce intermediate 106 by forming a boronate ester from the intermediate. As illustrated by Scheme 1, additional A, B, A', or B' rings (or any combinations thereof) optionally can be added to intermediate 106 using suitable cross-coupling conditions, which are readily recognizable to those of ordinary skill in the art with the benefit of the present disclosure, to form compound 108. The two intermediates 104 and 108 (or intermediate 104 and 106) can then be cross-coupled using suitable cross-coupling conditions, such as transition metal-mediated cross-couplings (e.g., Suzuki-Miyaura cross-coupling conditions). Alternatively, intermediates 104 and/or 108 can be cross-coupled with additional A, B, A', or B' rings (or any combinations thereof) and then an intermolecular cyclization can be used to join the last added ring (or combination of rings) with the remaining terminal ring of intermediate 104 or 108. After a deprotection step, the nanohoop compound 110 is obtained. With reference to Scheme 1, "PG" is a protecting group, which can be selected by those of ordinary skill in the art with the benefit of this disclosure; X is a halogen atom; the other recited variables can be as described above; and each illustrated circle represents a ring, which can be selected from any ring described above for rings A, B, B', and A'. In particular disclosed embodiments, R can be linker Z or Z wherein Z is a functional group that facilitates binding a biological moiety to the nanohoop or wherein Z is a biological moiety. In particular disclosed embodiments, each Q independently can be linker Z or Z wherein Z is a biological moiety, a chemical moiety, or a quenching group.

Scheme 1

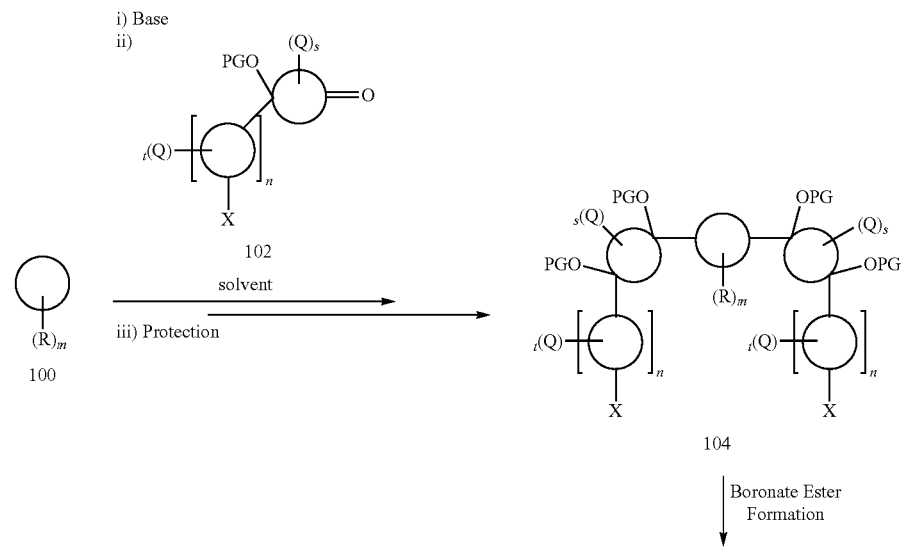

-continued
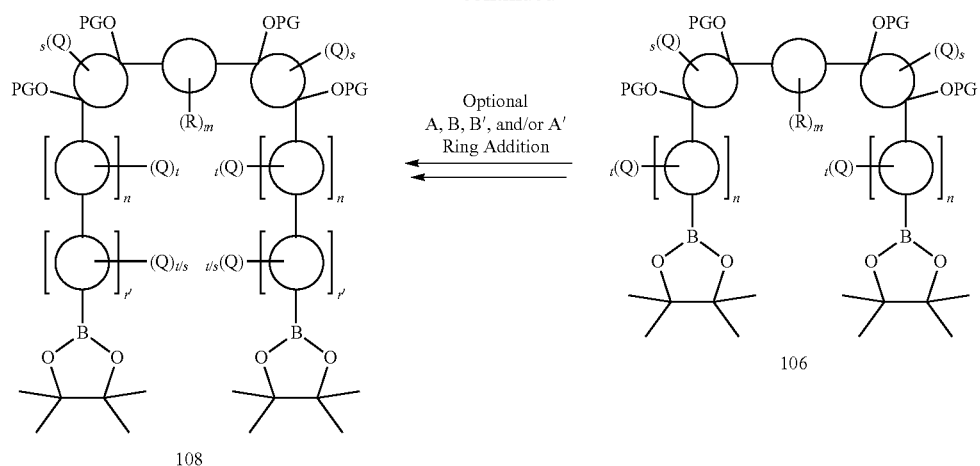
Another representative method embodiment is illustrated below in Scheme 2.
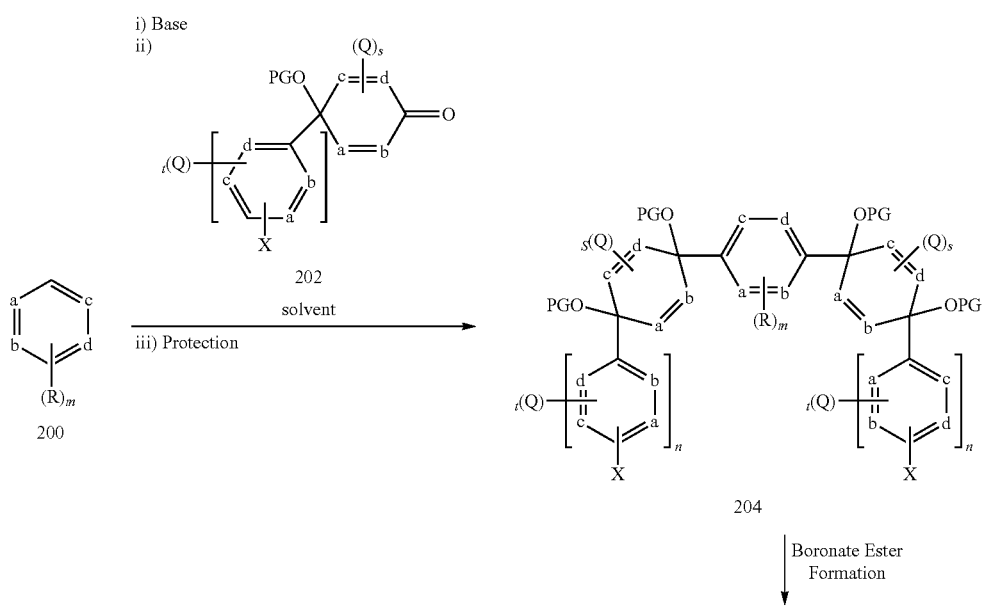

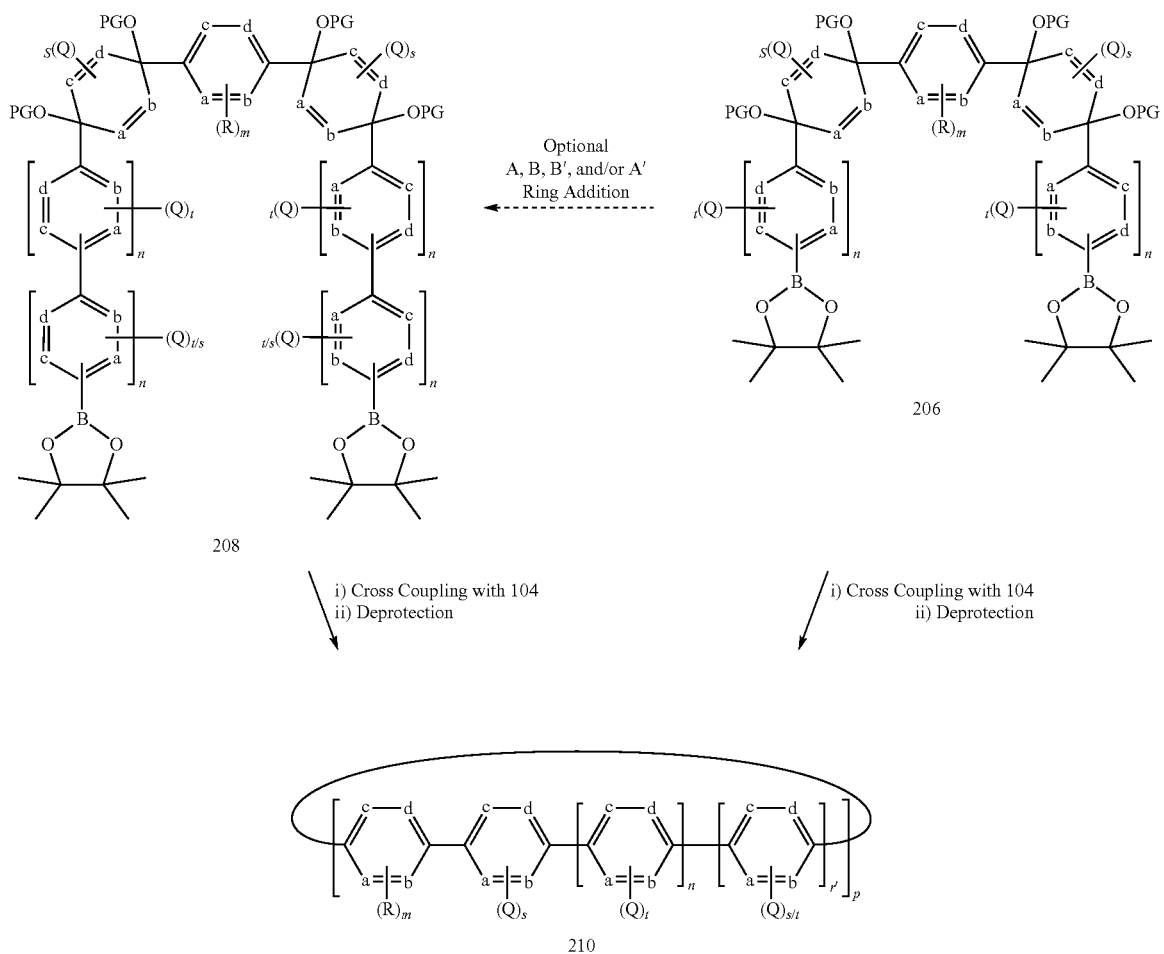

Nanohoop compound embodiments comprising meta-substitution can be made using a method as described below in Schemes 3A and 3B. With reference to Scheme 3, a relatively unstrained macrocycle is synthesized and then the cyclohexadienes are unmasked to reveal phenylenes via reductive aromatization, which imparts the strain of the meta-substituted nanohoops. Without being limited to a single theory of operation, it currently is believed that this strain may facilitate the ability of these compounds to fluoresce. In particular embodiments, a larger masked oligophenylene is prepared via selective additions and cross couplings shown in Scheme 3A. Macrocycles leading to [n]mCPPs (n representing the number of phenylenes) are prepared via Suzuki cross coupling of a meta functionalized benzene with the larger masked oligophenylene (Scheme 3A). Deprotection of the triethylsilyl groups and reductive aromatization unmasks the phenylenes to yield the [n]mCPP. This method can be used to make [n]mCPP embodiments wherein n=6-8, 10, 12. A method for making a [5]mCPP compound embodiment is illustrated in Scheme 3B. A person of ordinary skill in the art will recognize how to make [n]mCPP compound embodiments with other values for [n] with the benefit of the present disclosure.

Scheme 3A

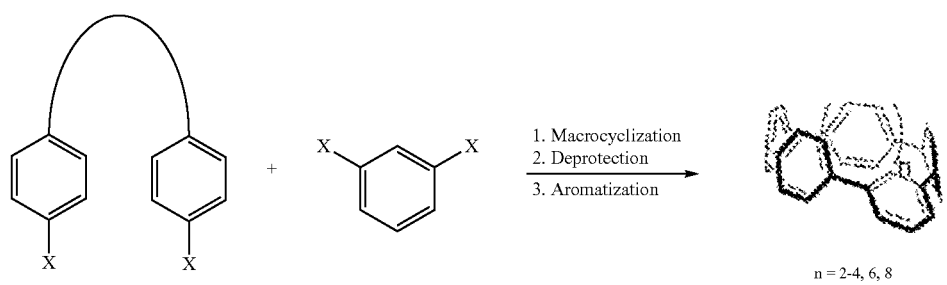

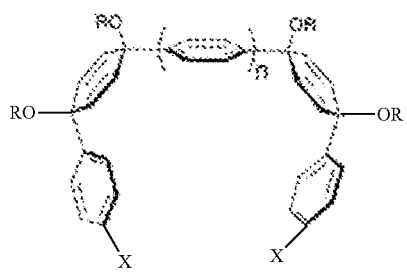

n = 1, 2
R = SiEt$_3$
X = Bpin, Cl

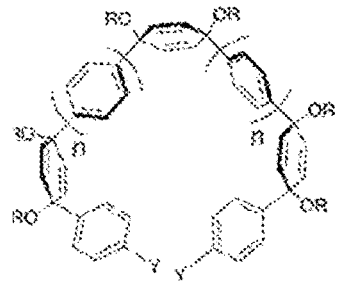

n = 1, 2, 3
R = SiEt$_3$, Me
Y = Br, Cl

Scheme 3B

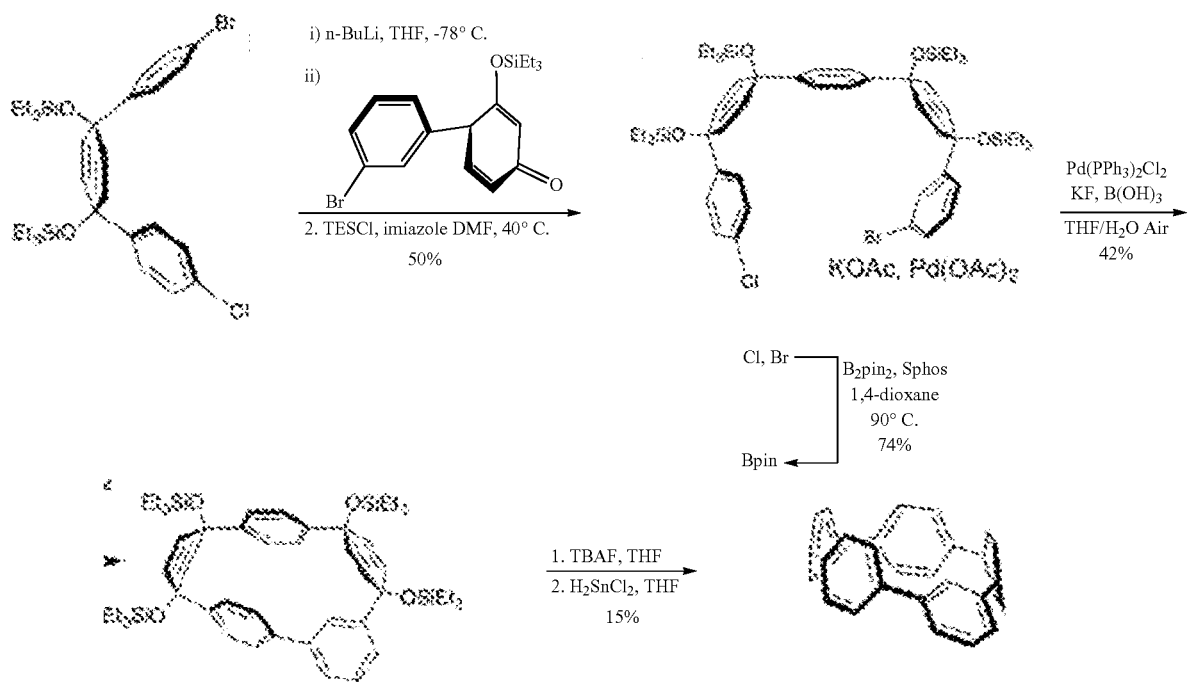

Representative methods of making the nanohoop compounds disclosed herein are provided in the Examples section below. These methods can be modified as needed to arrive at the different compounds disclosed herein by modifying starting materials and/or reagents as would be recognized by a person of ordinary skill in the art with the benefit of the present disclosure.

Also disclosed herein are embodiments of a method for making nanohoop conjugates described herein. In particular disclosed embodiments, the nanohoop conjugates are made by coupling a nanohoop compound described herein with one or more biological moieties. For example, embodiments of the nanohoop compounds having structures satisfying Formula I, wherein Z (either directly coupled to the nanohoop compound or coupled via a linker group, such as in a "linker-Z" moiety) is a functional group that facilitates coupling of the nanohoop compound to one or more of a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin, can be coupled to a biological moiety such that the Z functional group is modified or replaced during formation of a chemical bond with the biological moiety. Solely by way of example, the nanohoop compound can have a structure wherein Z is an amine group (or is a carboxylic acid group) that can be coupled to a carboxylic acid group of a biological moiety (or an amine group of a biological moiety if the Z group is a carboxylic acid) using suitable amide-bond forming reagents, such as a coupling reagent and a base. Exemplary coupling reagents include, but are not limited to, 2-(7-aza-1H-benzotriazol-1-yl)-N,N,N',N'-tetramethylaminium hexafluorophosphate, 2-(1H-benzotriazol-1-yl)-N,N, N',N'-hexafluorophosphate, 2-(6-chloro-1H-benzotriazol-1-yl)-N,N,N',N'-tetramethylaminium hexafluorophosphate, 1-hydroxybenzotriazole, dicyclohexylcarbodiimide, diisopropylcarbodiimide, N-(3-dimethylaminopropyl)-N'-ethylcarbodiimide-HCl, benzotriazol-1-yloxy-tris(dimethylamino)-phosphonium hexafluorophosphate, benzotriazol-1-yloxy-tripyrrolidino-phosphonium hexafluorophosphate, bromo-tripyrrolidino-phosphonium hexafluorophosphate, and the like, or a combination thereof. Bases can be selected from, but are not limited to, di-isopropylethyl amine, isopropyl amine, or other amine-based bases.

As an additional example, the nanohoop compound can have a structure wherein Z is a thiol group (—SH) that can be coupled to another sulfur-containing group of a biological moiety, such as a cysteine, or a pyridyldithiol-containing reagent, forming a disulfide bond. Alternatively, biological moieties having a maleimide group can react with thiols under nearly neutral conditions to form an irreducable thioether bond. Biological moieties having a haloacetyl group, such as a bromoacetyl group, can also react with a thiol, to form a thioether bond. As a further example, the nanohoop compound can have a structure wherein Z is a carbonyl group (—CHO) that can be coupled to a hydrazide group on a biological moiety, to form a hydrazine, or by an alkoxyamine group on a biological moiety, to form an oxime. In yet other embodiments, the Z group of the nanohoop can be a leaving group that becomes displaced by addition of a nucleophilic biological moiety. In additional embodiments, the Z group of the nanohoop can be a leaving group that becomes displaced or modified by a photoreactive group, such as an aryl azide, that forms a nitrene intermediate, which can react with alkenes, amines and nucleophiles in a biological moiety to form a nanohoop conjugate.

In some embodiments, nanohoop compounds described herein can be coupled to a nucleoside triphosphate compound to provide an oliogonucleotide synthesis precursor. Such precursors can be used in standard oligonucleotide synthesizers to provide nanohoop-containing DNA and/or RNA. In additional embodiments, the nanohoop compounds described herein can be coupled to an amino acid and the resulting conjugate can be used in a peptide synthesizer to provide a nanohoop-containing oligopeptide or a nanohoop-containing protein.

VI. Examples

Example 1

Figure 2:
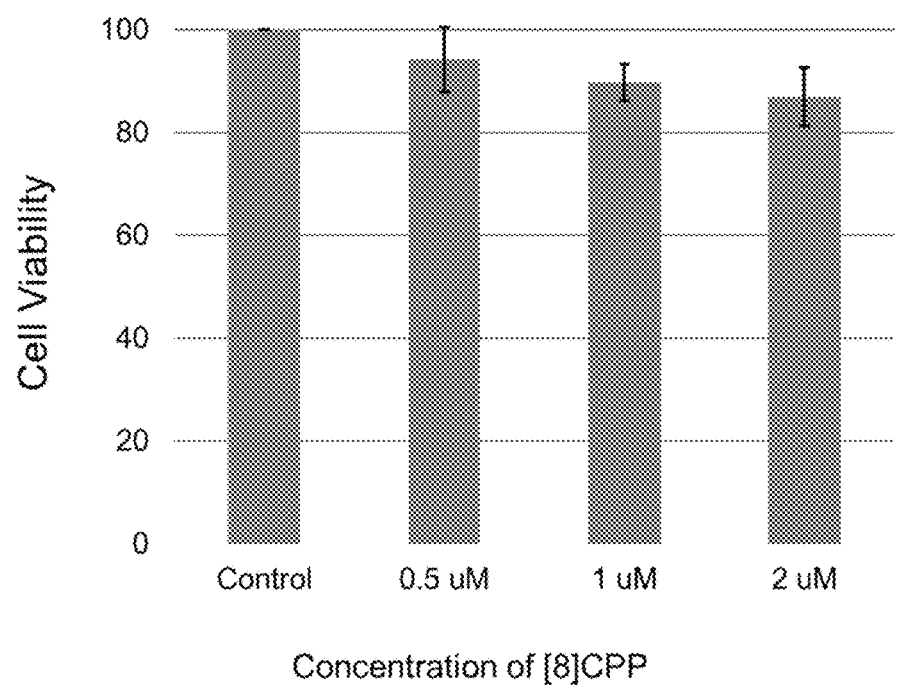
FIG. 2 is graph showing the viability of HeLa cells in the presence of varying concentrations of a nanohoop compound.

HeLa cells were treated with varying concentrations of [8]CPP and [12]CPP in the presence of 5 wt percent Pluronic F108 in DMEM, and their viability was measured using a colorimetric CCK-8 assay (purchased from Dojindo and performed following the assay instructions). Briefly, the cells were treated with the nanohoop compound and the tetrazolium salt WST-8 at each concentration for 2 hours at 37 degrees Celsius, and the optical density of the cells was subsequently measured at 450 nm. The viability of cells treated with the [12]CPP and [8]CPP compounds is illustrated in FIGS. 1 and 2, respectively. The graph in FIG. 1 shows the viability for [12]CPP at concentrations of 0.25 uM, 0.5 uM and 1 uM, and the graph in FIG. 2 shows the viability for [8]CPP at concentrations of 0.5 uM, 1 uM and 2 uM. These results indicate that the nanohoop compounds are not toxic as the nanohoop compounds did not reduce cell viability by more than about 80% in concentrations as high as 1 uM (FIG. 1) or 2 uM (FIG. 2).

Example 2

Compound 1 (shown below) was prepared as described in Example 9:

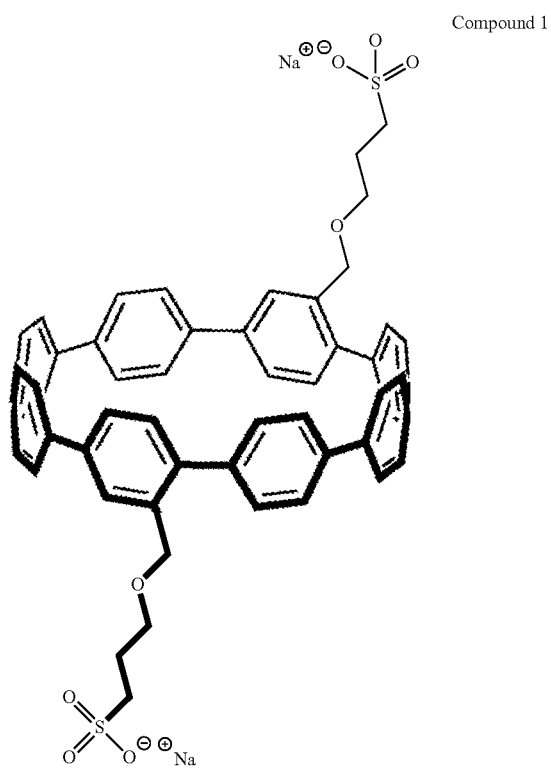

Compound 1

The fluorescence of Compound 1 was evaluated using UV-Vis and fluorescence spectrometry. The quantum yield (QY) was calculated using the protocol described by Horiba Scientific (see also Sisto, et al. J. Am. Chem. Soc. 2011, vol. 133, p. 15800). Briefly, anthracene and 9,10-diphenyl anthracene were used as standards, and the intergrated fluorescence intensity of these samples and Compound 1, after excitation at 340 nm with 1 nm entrance and exit slit widths, was calculated at five concentrations with absorbance intensities less than 0.1 au. All absorbance intensities were measured at 340 nm. The anthracene standard solutions were prepared in ethanol, 9,10-diphenyl anthracene solutions were prepared in cyclohexane, and Compound 1 solutions were prepared in 0.05% DMSO in deionized water. The molar absorptivity was calculated using the absorbance intensity of Compound 1 at 330 nm at a concentration range of 0.5-10 nM in a solution of 0.05% DMSO or less in deionized water. Compound 1 was found to have a quantum yield of 0.13 and a molar absorptivity coefficient (s) of $9.4 \times 10^4$ $M^{-1}$ $cm^{-1}$.

Example 3

Figure 3:
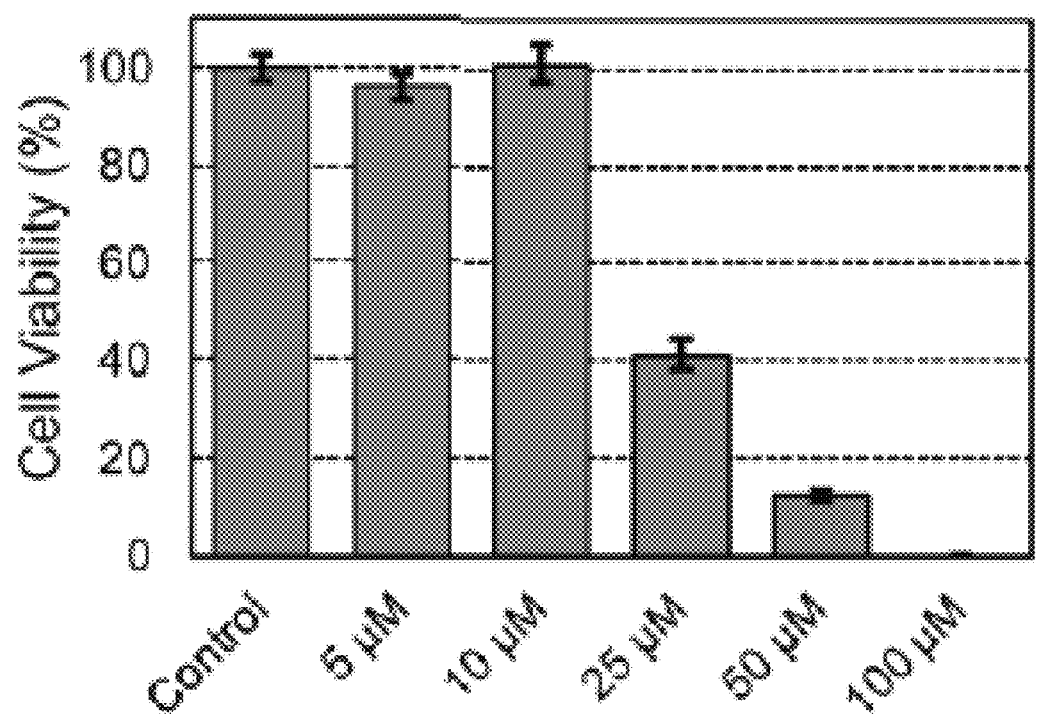
FIG. 3 is graph showing the viability of HeLa cells in the presence of varying concentrations of a representative nanohoop compound comprising a solubilizing group.

In this example, HeLa cells were treated with the disulfonated[8]CPP nanohoop Compound 1 at concentrations of 5 uM, 10 uM, 25 uM, 50 uM and 100 uM and their viability was measured using a standard colorimetric CCK-8 assay, as described above for Example 1. The percentage of living cells remaining after exposure to various concentrations of Compound 1 is illustrated in the graph shown in FIG. 3. As shown in FIG. 3, Compound 1 is not toxic at concentrations less than about 10 uM when incubated with HeLa cells in a solution of 0.05% DMSO in DMEM.

Example 4

Figure 4:
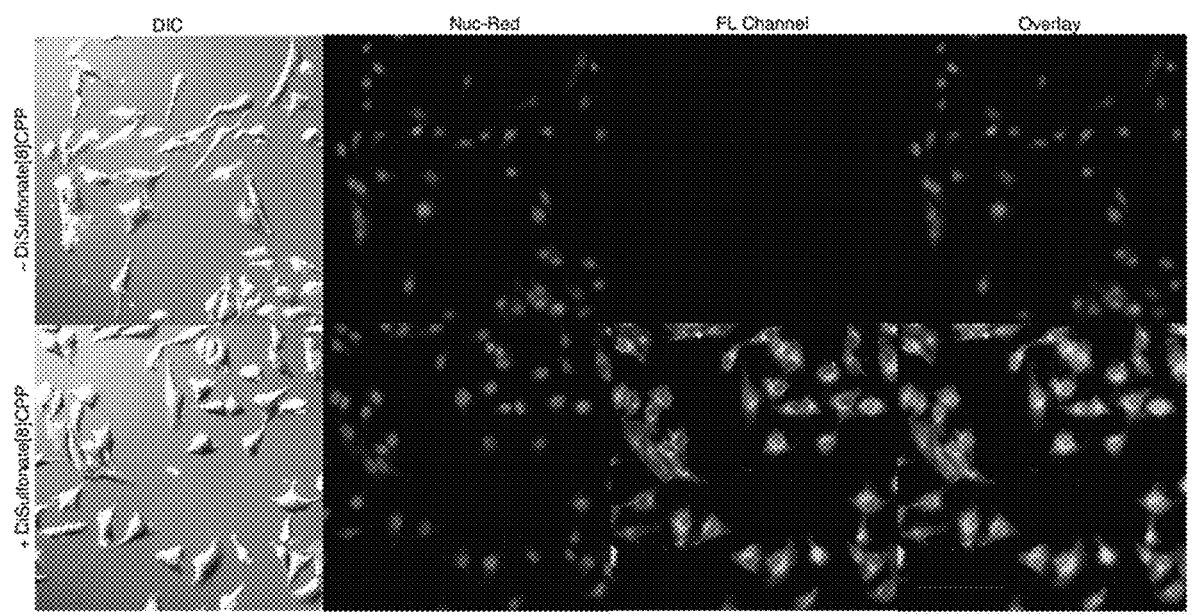
FIG. 4 is a series of micrographs of cells in the presence (lower images) and absence (upper images) of a representative nanohoop compound; the scale bar shown in the lower right corner of FIG. 4 corresponds to 100 micrometers.

HeLa cells were treated with Compound 1 at a concentration of 10 uM for 1 hour at 37 degrees Celsius. A portion of the treated cells were labeled with a nuclear stain (Molecular Probes' NucRed stain), and subsequently imaged. After incubation with Compound 1 and the NucRed stain, cells were rinsed four times with Dulbecco's Phosphate Buffered Saline (Corning cellgro) and treated with this buffer solution during imaging. Images of these cells were compared to non-treated cells. Results are illustrated in FIG. 4. The scale bar shown in the lower right corner of FIG. 4 corresponds to 100 micrometers.

The images in FIG. 4 show that the cellular morphology is unchanged in the presence of the nanohoop compounds, as there is little difference seen when comparing the differential interference contrast (DIC) images of the treated (FIG. 4, left bottom image) and untreated (FIG. 4, left top image) cells. The cell nuclei were unchanged in treated and untreated cells (FIG. 4, center left column of images), indicating that the treated cells were not damaged during treatment. The treated cells are visible in the DAPI-longpass FL channel at 330 nm wavelength (FIG. 4, center right column of images), and can be differentiated from the untreated cells when comparing the overlay images (FIG. 4, right column of images). As seen in FIG. 4, the bright green fluorescence from Compound 1 in the cytosol of the treated cells overlay with the stained nuclei.

Example 5

A particular method of making a nanohoop compound embodiment is illustrated below in Scheme 4.

Scheme 4

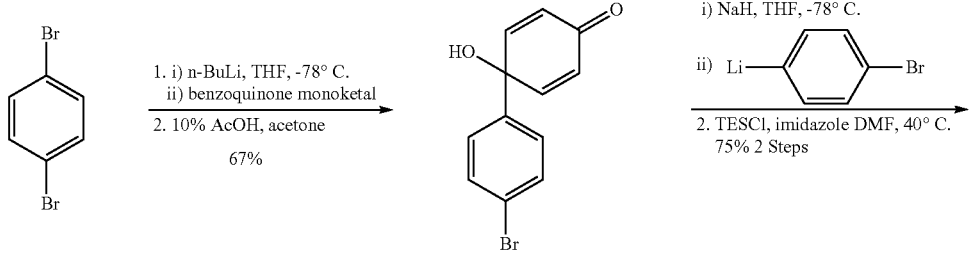

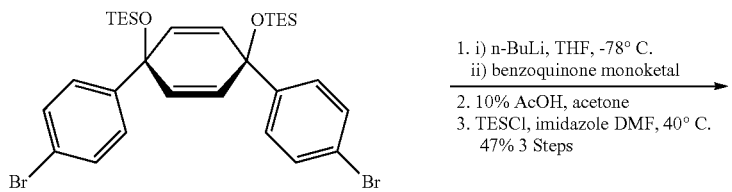

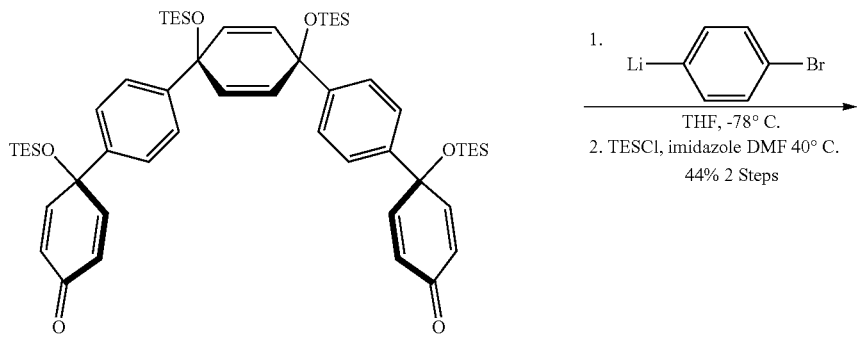

-continued
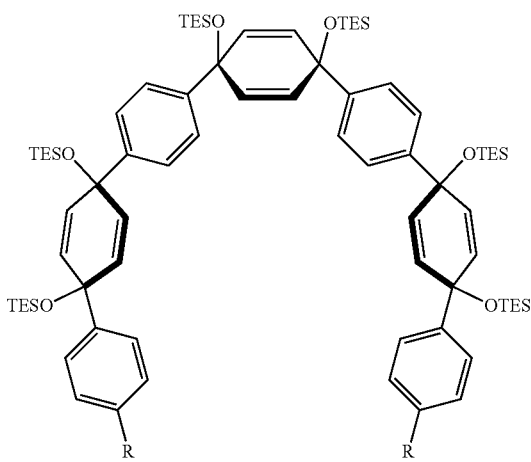
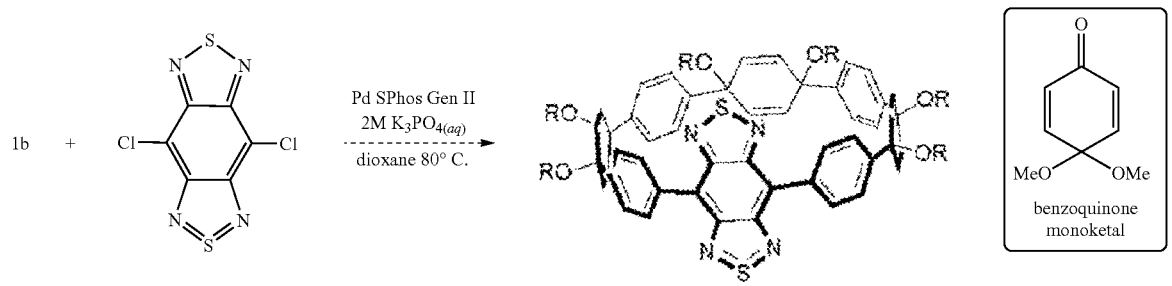 [SMILES: Clc1c2c(c(Cl)c3nsnc13)N=S=N2 ; COC1(OC)C=CC(=O)C=C1]
Example 6
Another representative method for making a nanohoop compound embodiment is illustrated below in Scheme 5.
Scheme 5
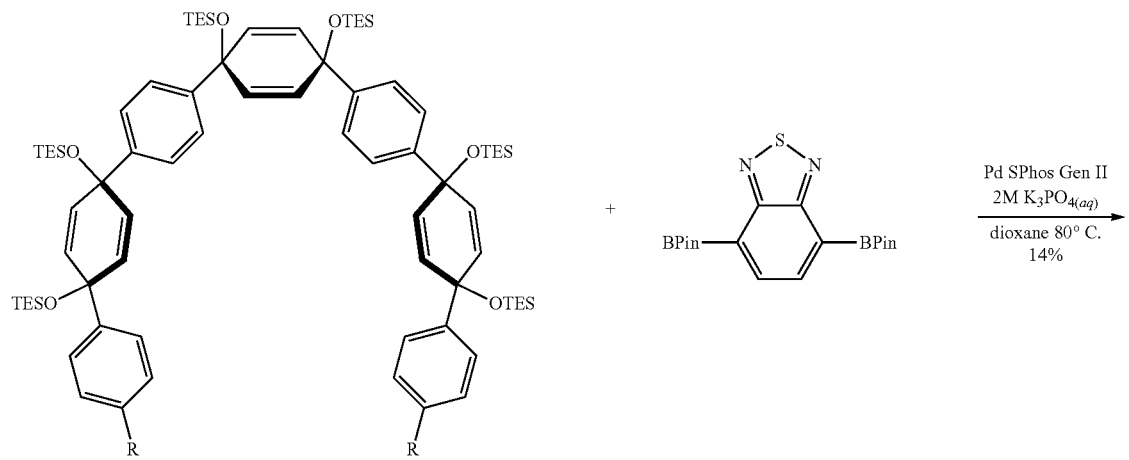

-continued
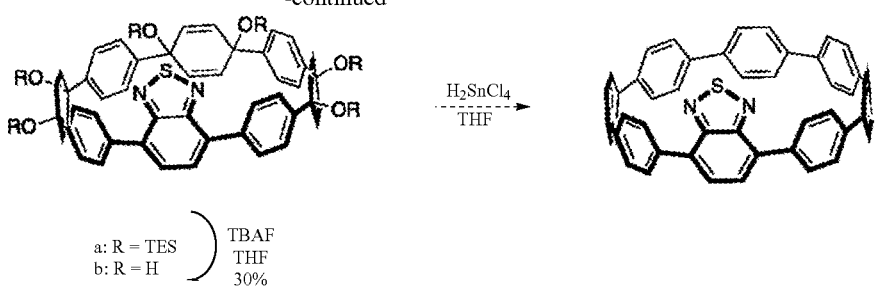
a: R = TES  
b: R = H  
} TBAF THF 30%
Example 7
A representative method of making a nanohoop compound embodiment comprising an exemplary Z functional group that can be coupled to a biological moiety or a solubilizing group is illustrated below in Scheme 6.
Scheme 6
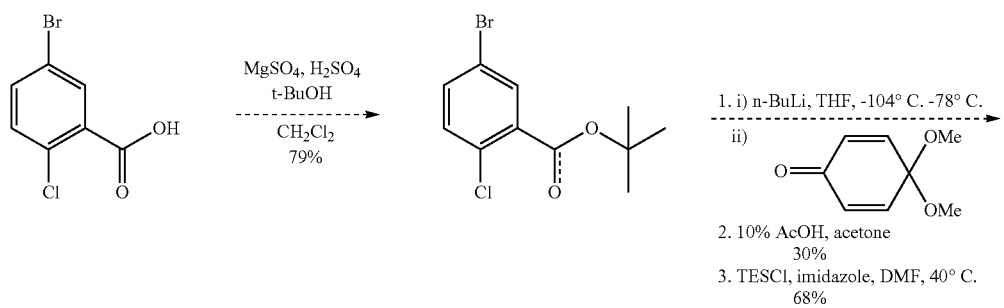
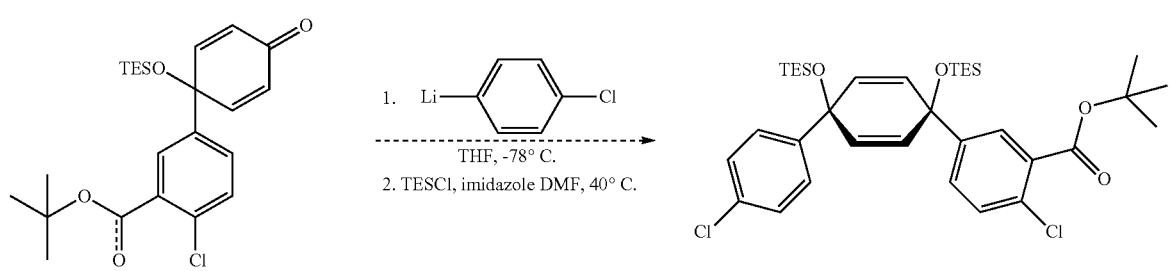
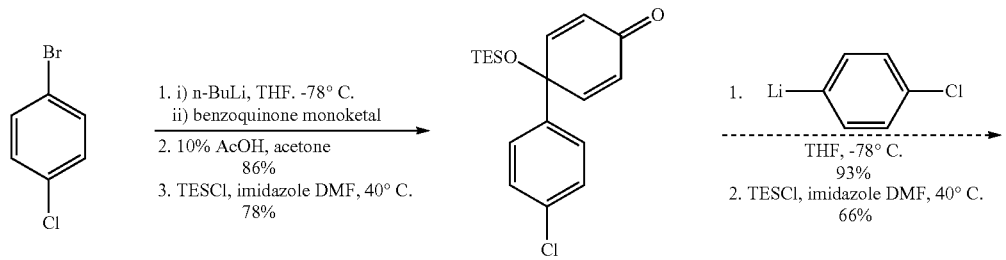
a

101
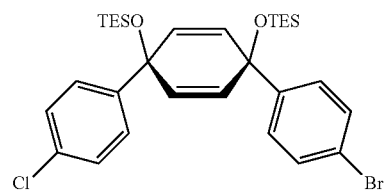
1. i) n-BuLi, THF −78° C.
   ii) a
2. TESCl, imidazole DMF, 40° C.
   37% 2 Steps
102
-continued
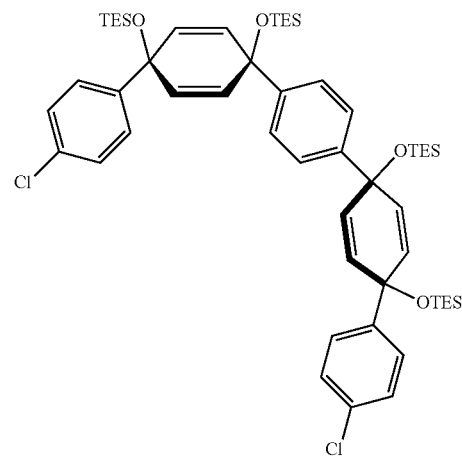
KOAc, Pd(OAc)$_2$
B$_2$Pin$_2$, SPhos dioxane
90° C.
72%
R = Cl
R = BPin
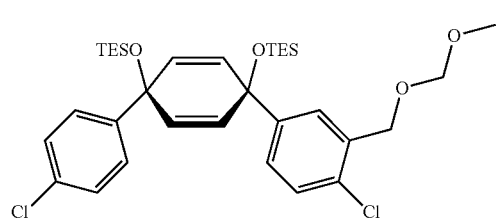
+
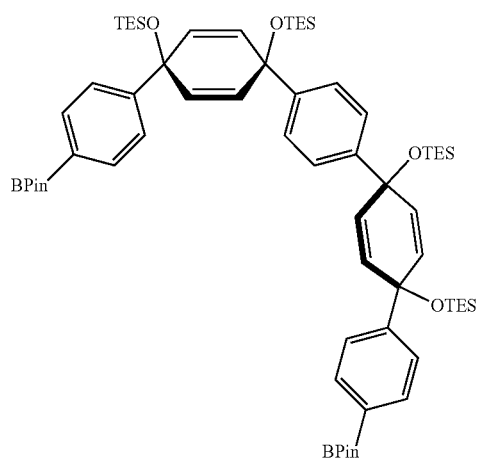
Pd SPhos Gen II
2M K$_3$PO$_{4(aq)}$
dioxane 80° C.
68%
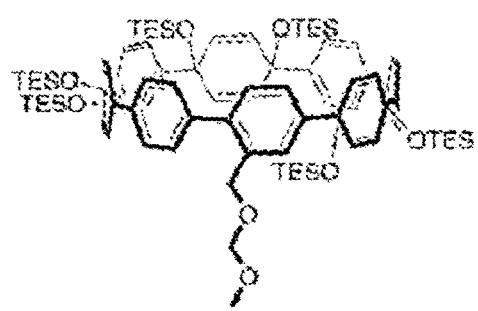
R = TES
R = H
TBAF
THF
43%
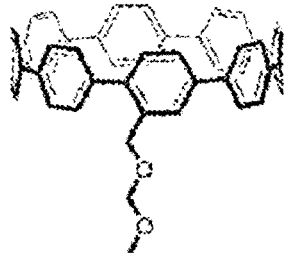
H$_2$SnCl$_4$
THF
26%
TMSBr
DCM
0° C.
4Å sievee
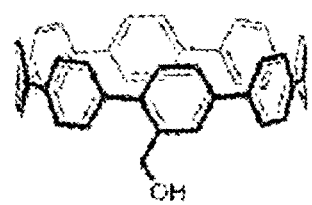

Example 8
A representative method of making a nanohoop compound embodiment comprising two exemplary Z functional groups that can be coupled to one or more biological moieties, one or more solubilizing groups, or both is illustrated below in Scheme 7.
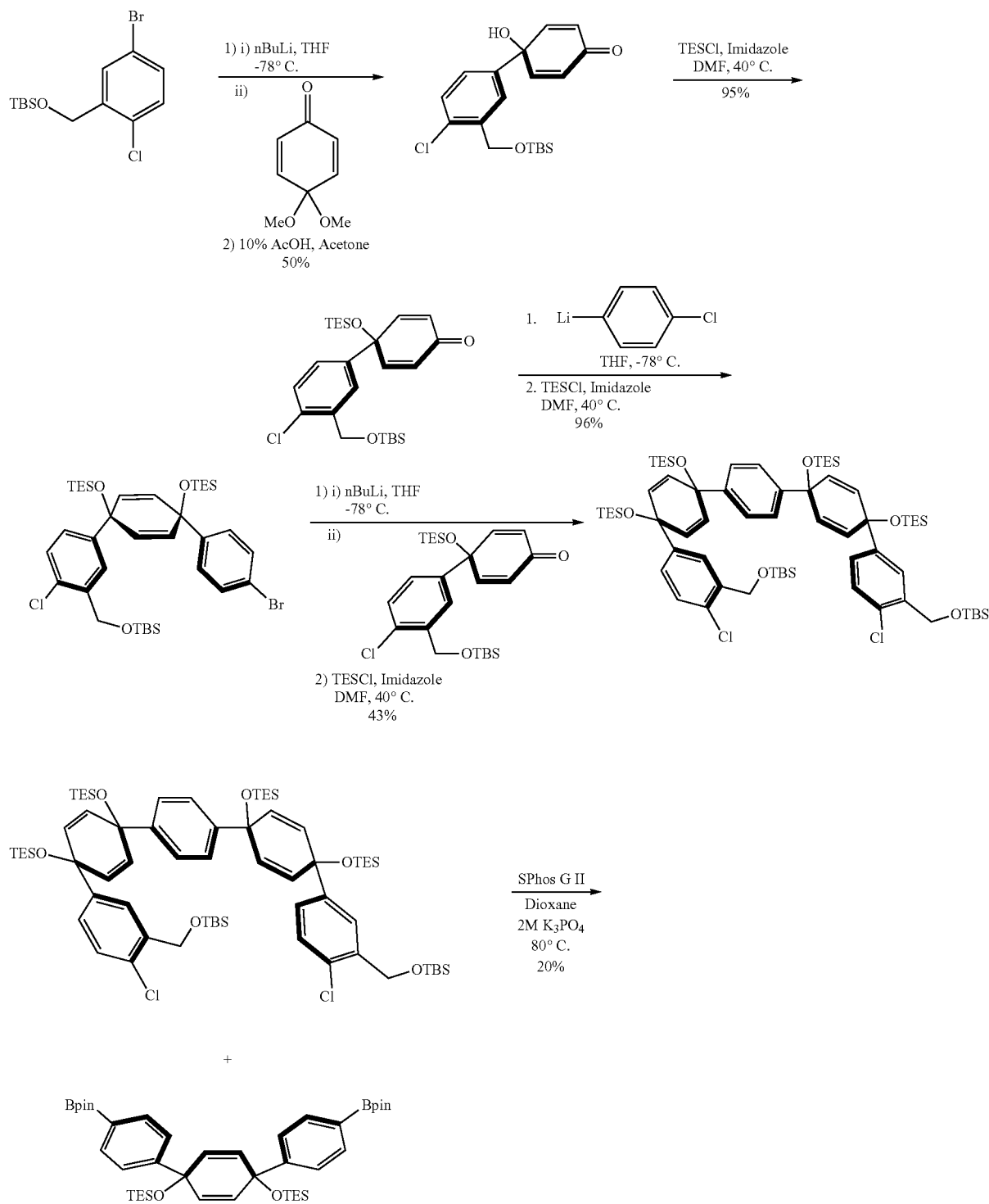

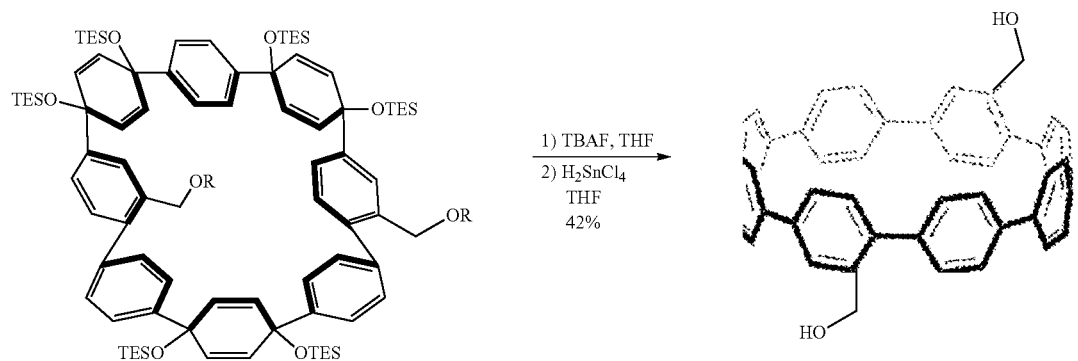
Example 9
This example describes representative methods for making Compound 1, which is an exemplary nanohoop compound comprising a solubilizing group. In this example, the nanohoop compound of Example 8 is coupled with a sulfonate solubilizing group through the hydroxyl group illustrated below, via Scheme 8A, 8B or Scheme 8C.
Scheme 8A
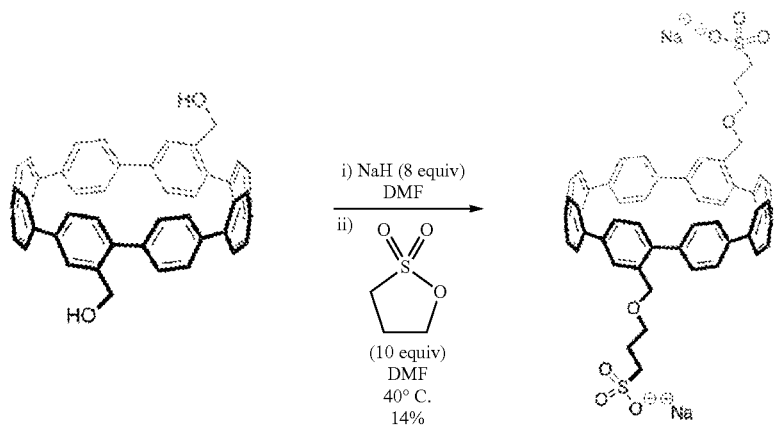
Scheme 8B
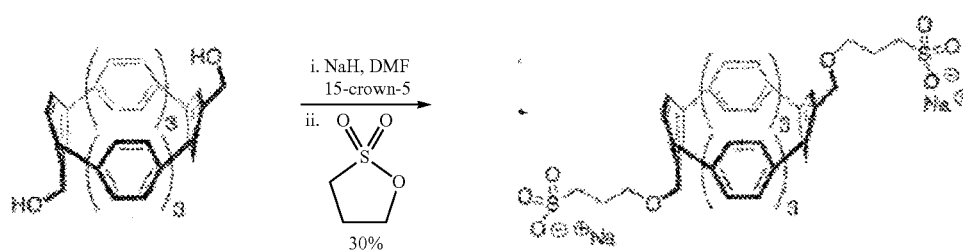

Scheme 8C
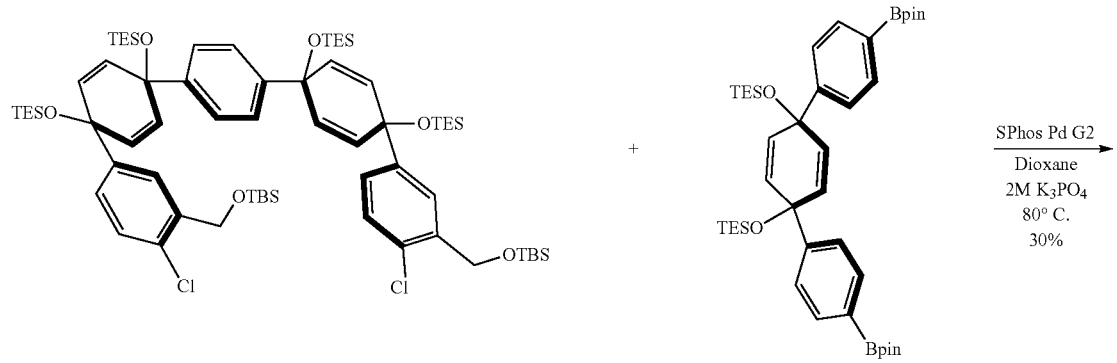
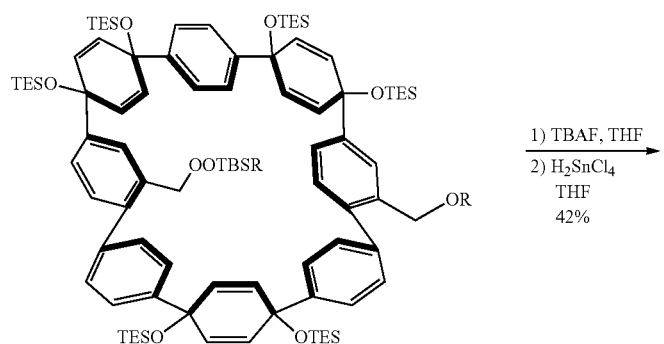
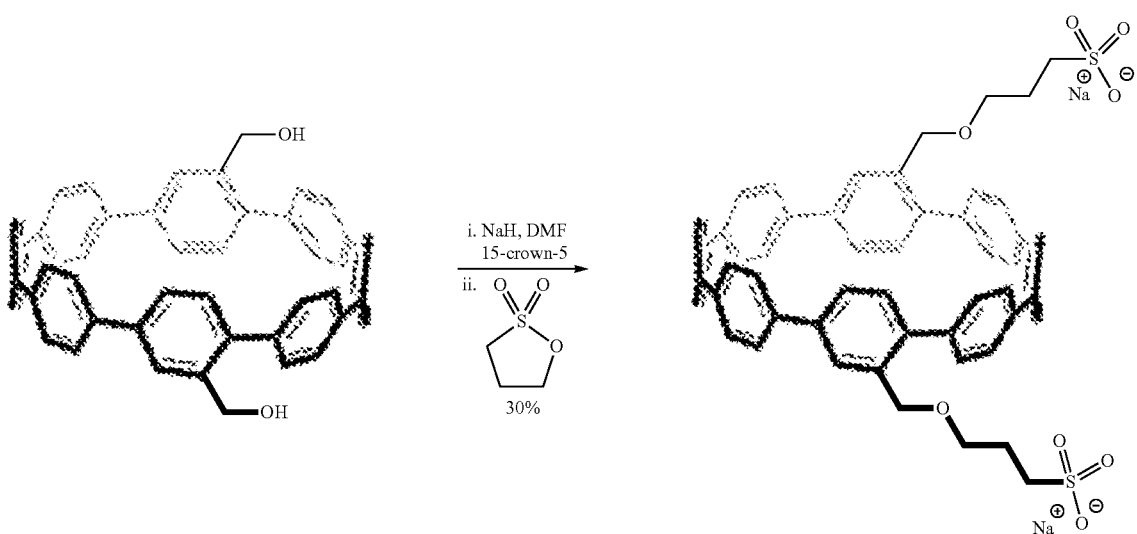
Example 10
This example describes a representative method for making a nanohoop compound comprising a linker-Z moiety wherein the linker is a methylene group and the Z group is an azide group capable of reacting with a functional group of a biological moiety, such as the alkyne-functionalized carbohydrate compound illustrated below in Scheme 9.

Scheme 9
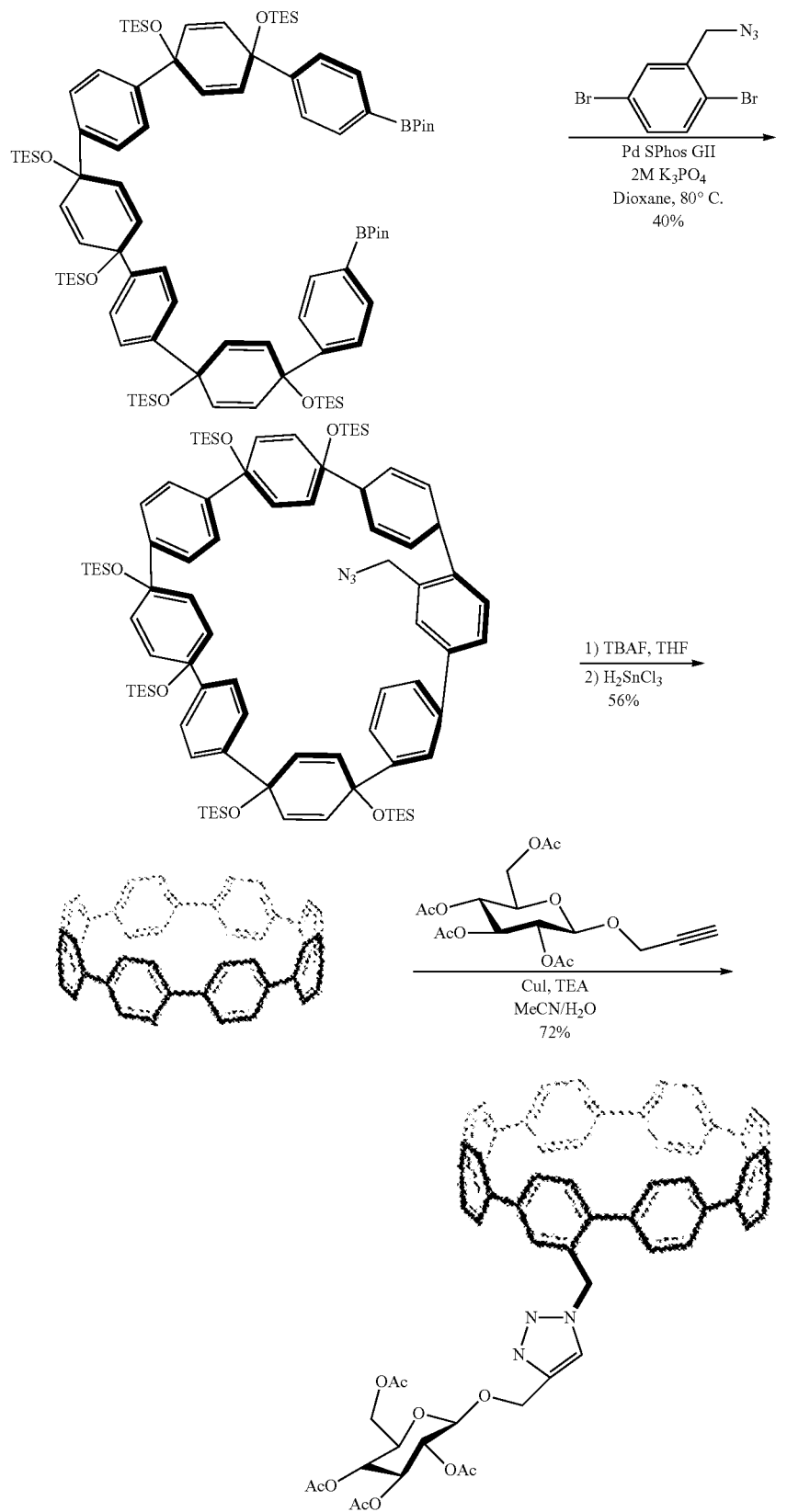

Example 11

This example describes a representative method for making a nanohoop compound comprising a linker-Z moiety wherein the linker is a methylene group and the Z group is an azide group capable of reacting with a functional group of a biological moiety, such as the alkyne-functionalized triphenyl phosphonim compound illustrated below in Scheme 10.

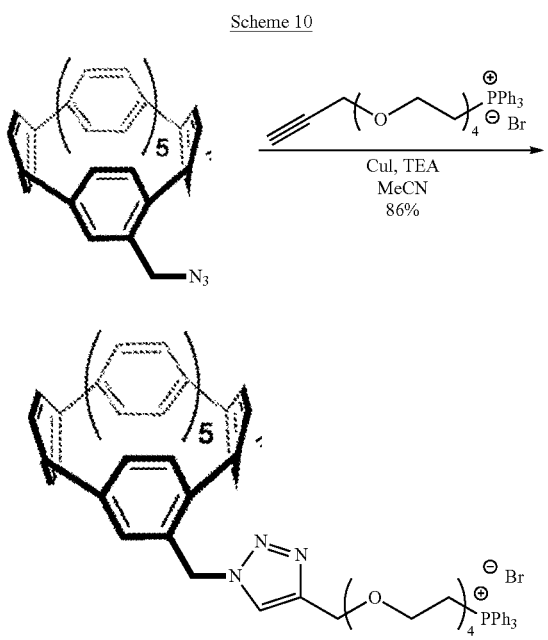

Scheme 10

Example 12

This example describes a representative method for making a nanohoop compound comprising a linker-Z moiety wherein the linker is a methylene group and the Z group is an azide group capable of reacting with a functional group of a biological moiety, such as the alkyne-functionalized morpholino compound illustrated below in Scheme 11.

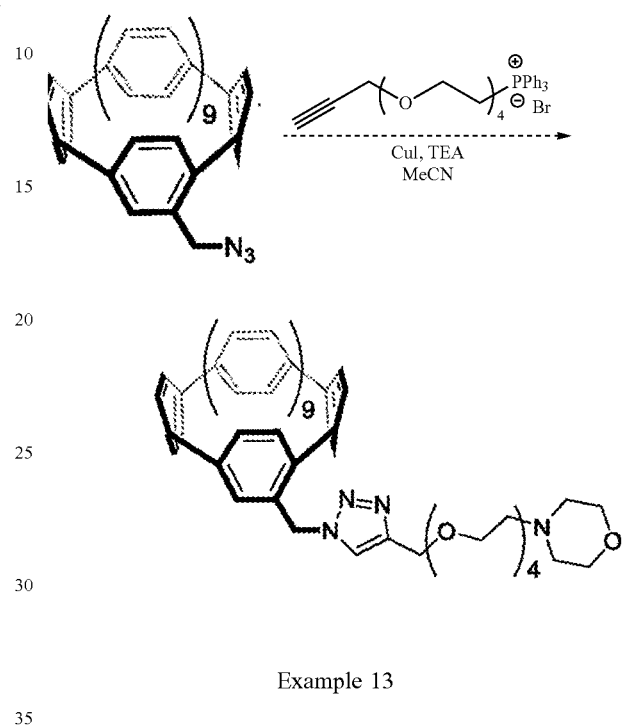

Scheme 11

Example 13

This example describes a representative method for making a nanohoop compound comprising a linker-Z moiety wherein the linker is a carboxyl group and the Z group is an NHS group capable of reacting with a functional group of a biological moiety, such as the antibody conjugated compound illustrated below in Scheme 12.

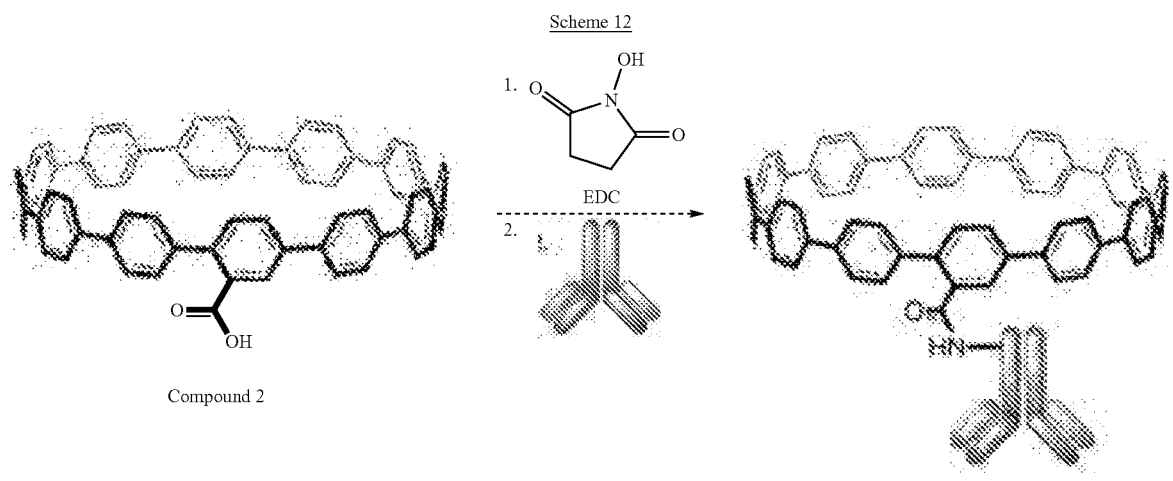

Scheme 12

The incorporation of the N-hydroxysuccinimide (NHS) ester functionality into a nanohoop, conjugation to antibodies and photophysical characterization of the conjugates, and analysis of biomarker detection via flow cytometry, can be performed. N-hydroxy-succinimide (NHS) esters are commonly used for bioconjugation to antibodies. Amine groups of the antibody react with the NHS ester to form a stable amide bond. To prepare an appropriately functionalized CPP, a benzylic alcohol CPP is oxidized with a variety of oxidants in either a one or likely two-step protocol to afford the carboxylic acid [12]CPP shown as Compound 2. The nanohoop compound is be converted to the NHS ester through reaction of the carboxylic acid with NHS in the presence of the coupling agent 1-Ethyl-3-(3-dimethylaminopropyl) carbodiimide (EDC). NHS ester [12]CPP is a bright, reactive probe that is used for conjugation to biological molecules, as shown in Compound 3.

NHS ester [12]CPP is conjugated to an antibody, such as an ca-CD45 antibody. CD45 is a highly abundant glycoprotein antigen that is expressed on all white blood cells and plays an important role in their function. The bioconjugation can take place at pH 8.3 in 0.1 M sodium phosphate buffer to ensure lysine groups of the antibody are in the non-protonated form. A solution of protein is prepared in phosphate buffer and to this is added an aliquot of NHS[12]CPP in DMSO. Conjugates is purified by Bio Rad Bio-Spin® column with Bio-Gel® P-30 resin. The degree of fluorescence labeling is determined by standard procedures using the absorbance of the protein and dye, and is varied by altering the reaction conditions.

Upon staining commercially available peripheral blood mononuclear cells (PBMCs), initial analysis is performed with a Sony SH800 flow cytometer utilizing a 405 nm laser and 450/50 optical filter, or a 355 nm excitation laser. Appropriate controls for the flow cytometry experiment include unconjugated NHS[12]CPP to illustrate specific labeling and an ca-CD45-Alexa Fluor® 350 conjugate to compare brightness. For the lymphocyte cells, the mean fluorescence intensity (MFI) of the CD45 positive population is compared to the MFI of the Alexa Fluor® 350 conjugate. These experiments can help determine that nanohoops is incorporated into standard antibody conjugation protocols, remain strongly fluorescent when conjugated to antibodies, and not disrupt their inherent function.

Proteins not abundantly expressed on cell surfaces are difficult to detect. However, bright fluorophores can observe such low abundant targets. The same conjugation, purification and characterization methods as described above is implemented to conjugate a nanohoop compound to α-CD40. This low abundant target, expressed in several tumor cell lines, is known to play a substantial role in pathogenesis of inflammation and autoimmunity. Upon analysis of the lymphocytes, the MFI of α-CD40-NHS[12]CPP is compared to the α-CD40-Alexa Fluor® 350 MFI.

Example 14

This example describes representative methods for making nanohoop compounds comprising different numbers of rings within the nanohoop skeleton, such as 8, 10, and 12 rings as illustrated in Scheme 13 below.

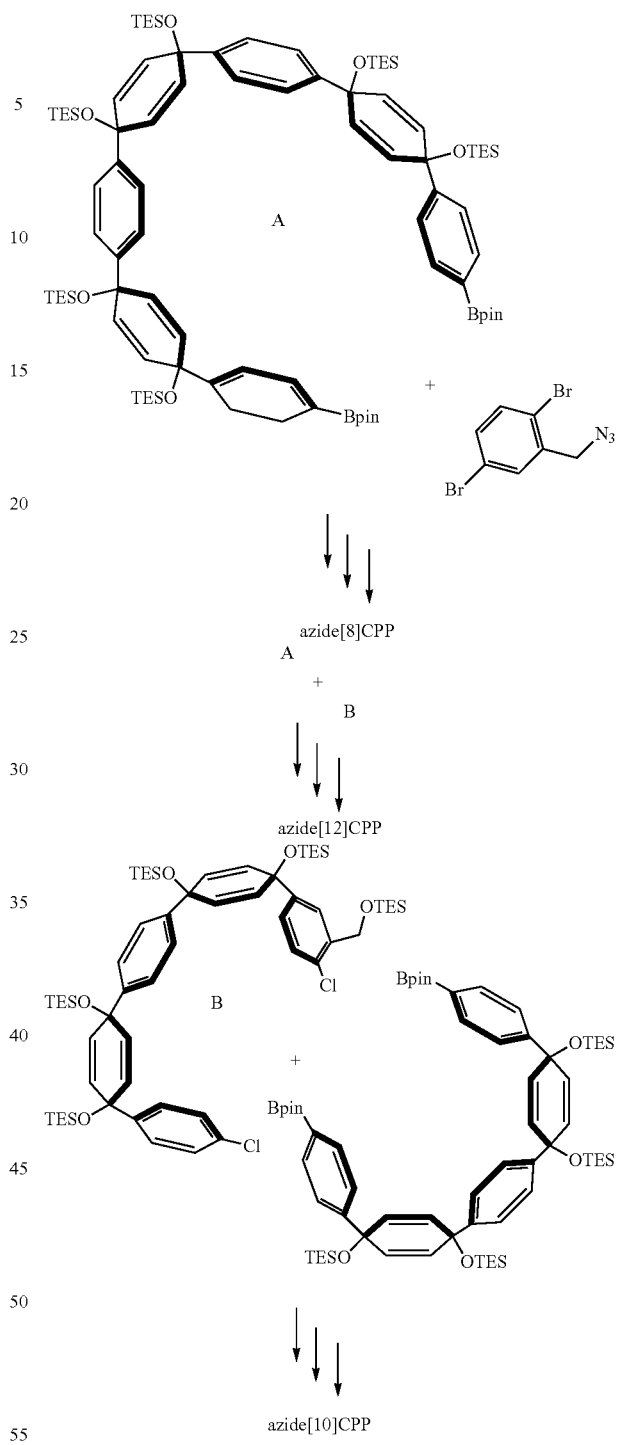

Examples 15-53

In the following examples, all glassware was flame dried and cooled under an inert atmosphere of nitrogen unless otherwise noted. Moisture sensitive reactions were carried out under nitrogen atmosphere using Schlenk and standard syringe/septa techniques. Tetrahydrofuran, dichloromethane, dimethylformamide and 1,4-dioxane were dried by filtration through alumina according to the methods describes by Grubbs. Silica column chromatography was conducted with Zeochem Zeoprep 60 Eco 40-63 μm silica gel. Automated flash chromatography was performed using a Biotage Isolera One. Recycling gel permeation chromatography (GPC) was performed using a Japan Analytical Industry LC-9101 preparative HPLC with JAIGEL-1H/JAI-GEL-2H columns in series using CHCl3. Thin Layer Chromatography (TLC) was performed using Sorbent Technologies Silica Gel XHT TLC plates. Developed plates were visualized using UV light at wavelengths of 254 and 365 nm. $^1$H NMR spectra were recorded at 500 MHz or 600 MHz on a Bruker Advance-II-HD NMR spectrometer. $^{13}$C NMR spectra were recorded 150 MHz on a Bruker Advance-III-HD NMR spectrometer. All $^1$H NMR spectra were taken in CDCl3 (referenced to TMS, δ 0.00 ppm) or DMSO-d6 (referenced to residual DMSO, δ 2.50 ppm). All $^{13}$C NMR spectra were taken in CDCl3 (referenced to chloroform, δ 77.16 ppm) or DMSO-d6 (referenced to DMSO, δ 39.52 ppm). Absorbance and fluorescence spectra were obtained in a 1 cm Quartz cuvette with dichloromethane using an Agilent Cary 100 UV-Vis spectrometer and a Horiba Jobin Yvon Fluoromax-4 Fluorimeter. Fluorescent quantum yield was measured in dichloromethane at room temperature using a Hamamatsu absolute PL quantum yield measurement system. Electrochemical experiments were performed using a Biologic SP-50 potentiostat with a Ag wire reference electrode, Pt wire counter electrode, and glassy carbon working electrode under nitrogen atmosphere in 100 mM solutions of Bu4NPF6 in DCM with ferrocene as a reference. All reagents were obtained commercially unless otherwise noted. Compounds para-benzoquinone mono-methyl ketal, compound A, compound B, PPh$_3$ Pd Gen III, and SPhos Pd Gen 1115 were prepared according to literature procedure.

Example 15

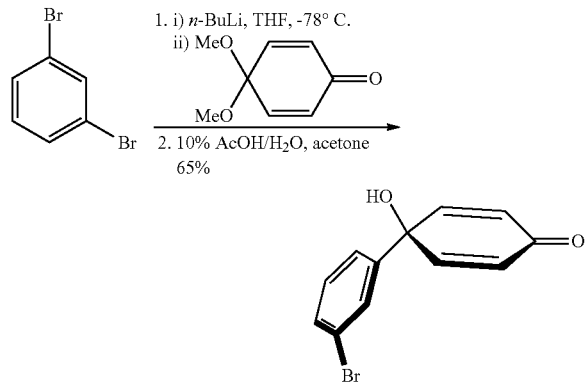

1,3-dibromobenzene (4.3 mL, 35.7 mmol, 1.1 equiv) was added to a 500 mL round bottom flask equipped with a stir bar. The reaction flask was capped with a septa, evacuated and refilled with nitrogen. Tetrahydrofuran (51 mL) was cannulated to the reaction flask, which was cooled to −78° C. over 30 min. n-BuLi (13.6 mL, 34.1 mmol, 1.05 equiv, 2.5 M in hexanes) was added to the reaction mixture dropwise over 10 min. This was followed by the dropwise addition of para-benzoquinone monomethyl ketal (4.6 mL, 32.4 mmol, 1 equiv) and the reaction stirred at −78° C. for 1 h. The reaction was quenched with deionized water (20 mL) at −78° C. and warmed to room temperature. The product was extracted with ethyl acetate (3×20 mL) and washed with brine (30 mL). The organic layers were dried over sodium sulfate, decanted and concentrated to yield the protected product as a slightly yellow solid. The protected product was dissolved in a minimal amount of acetone (20 mL) and a 10% acetic acid solution in water (20 mL) was added. This was stirred at room temperature for 1 h. The reaction was quenched with a saturated solution of sodium bicarbonate (50 mL). The product was extracted with ethyl acetate (3×20 mL), washed with brine (20 mL), dried over sodium sulfate and concentrated to yield the crude product as an orange solid. The product was purified by trituration with hexanes and ethanol to give an off white solid (5.588 g, 65% 2 Steps). $^1$H NMR (600 MHz, Chloroform-d) δ 7.67 (t, J=1.9 Hz, 1H), 7.46 (d, J=7.9 Hz, 1H), 7.37 (d, J=7.9 Hz, 1H), 7.25 (t, J=7.9 Hz, 1H), 6.87 (d, J=10.0 Hz, 2H), 6.23 (d, J=10.0 Hz, 2H), 3.04 (s, 1H). $^{13}$C NMR (151 MHz, Chloroform-d) δ 185.60, 150.34, 140.99, 131.53, 130.45, 128.54, 127.19, 124.04, 123.09, 70.58. HRMS (ESI-TOF) (m/z): [M+H]+ calculated for C$_{12}$H$_{10}$BrO$_2$, 264.9864; found, 264.9871.

Example 16

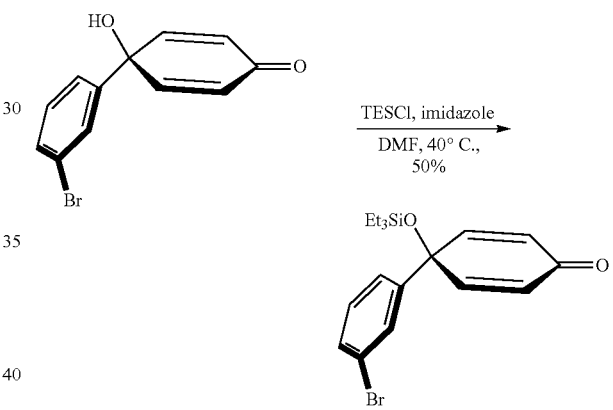

The product from Example 15 (5.588 g, 26.7 mmol, 1 equiv) and imidazole (5.74 g, 84.3 mmol, 4 equiv) were added to a 250 mL round bottom flask equipped with a stir bar and septum. Dimethylformamide (105 mL) was added to the flask followed by triethylsilyl chloride (4.2 mL, 89.8 mmol, 1.2 equiv). The reaction mixture was heated to 40° C. in an oil bath and stirred overnight. The reaction mixture was cooled to room temperature and quenched with a saturated solution of sodium bicarbonate (30 mL). The product was extracted with ethyl acetate (3×100 mL) and washed with 5% lithium chloride solution in water (3×100 mL). The organic layers were dried over sodium sulfate and concentrated to yield the crude product as a yellow oil. The product was purified by automated flash silica gel chromatography (0% to 10% ethyl acetate in hexanes) to give a slightly yellow oil (4.0 g, 50%). $^1$H NMR (600 MHz, Chloroform-d) δ 7.60 (t, J=1.9 Hz, 1H), 7.42 (ddd, J=7.9, 2.0, 1.0 Hz, 1H), 7.34 (ddd, J=7.9, 1.8, 1.1 Hz, 1H), 7.21 (t, J=7.9 Hz, 1H), 6.79 (d, J=10.0 Hz, 2H), 6.24 (d, J=10.0 Hz, 2H), 0.98 (t, J=8.0 Hz, 9H), 0.66 (q, J=7.9 Hz, 6H). $^{13}$C NMR (151 MHz, CDCl3) δ 185.59, 151.35, 142.46, 131.10, 130.25, 128.60, 126.93, 124.08, 122.88, 72.70, 6.90, 6.22. HRMS (ESI-TOF) (m/z): [M+H]+ calculated for C$_{18}$H$_{24}$BrO$_2$Si, 379.0729; found, 379.0732.

Example 17

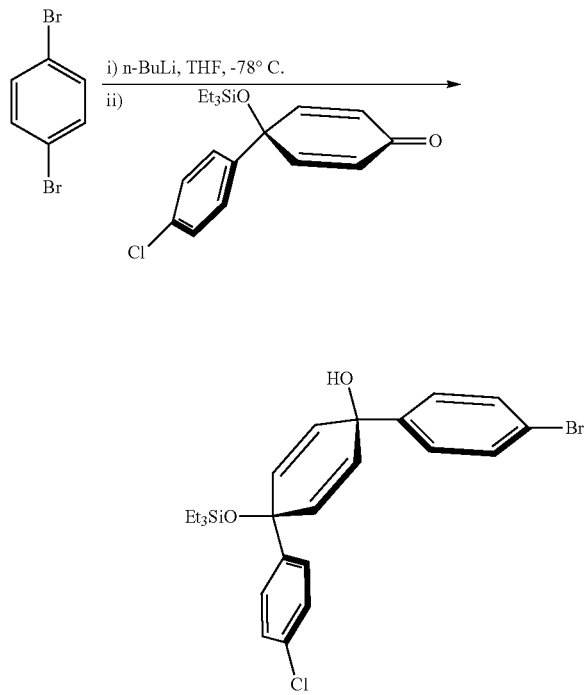

1,4-dibromobenzene (3.9 g, 16 mmol, 1.1 equiv) was added to a 100 mL round bottom flask equipped with a stir bar and septa. The flask was evacuated and filled with nitrogen. Tetrahydrofuran (23 mL) was added to the flask and this was cooled for 30 min at −78° C. n-BuLi (6.5 mL, 16 mmol, 1.05 equiv, 2.4 M in hexanes) was added dropwise over 5 min. The product from Example 16 (4.6 mL, 15 mmol, 1 equiv) was added to the reaction flask dropwise and the reaction was stirred for 1 h at −78° C. The reaction was quenched with deionized water (40 mL) while at −78° C. and warmed to room temperature. The product was extracted with ethyl acetate (3×70 mL) and washed with brine (3×40). The organic layers were dried over sodium sulfate, decanted and concentrated to yield the crude product as a yellow oil. The product was used as is for the next reaction.

Example 18

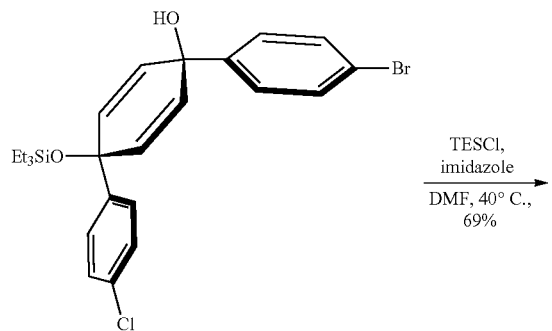

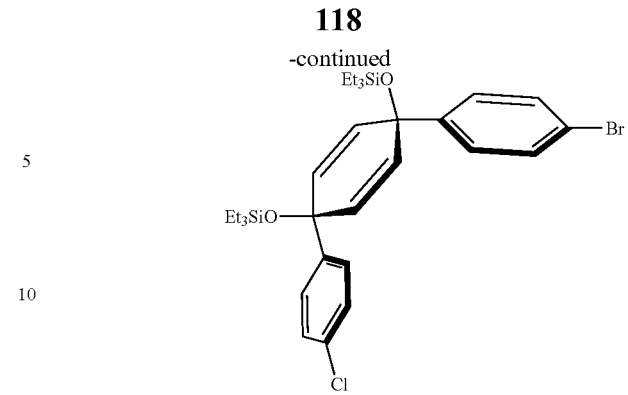

The crude product from Example 17 and imidazole (2.3 g, 25 mmol, 4 equiv) were added to a 250 mL round bottom flask equipped with a stir bar and septum. Dimethylformamide (75 mL) was added to the flask followed by triethylsilyl chloride (3.0 mL, 18 mmol, 1.2 equiv). The reaction mixture was heated to 40° C. in an oil bath and stirred overnight. The reaction mixture was cooled to room temperature and quenched with a saturated solution of sodium bicarbonate (30 mL). The product was extracted with ethyl acetate (3×60 mL) and washed with 5% lithium chloride solution in water (30 mL) and brine (30 mL). The organic layers were dried over sodium sulfate and concentrated to yield the crude product as a yellow oil. The product was purified by automated flash silica gel chromatography (0% to 3% ethyl acetate in hexanes) to give a white solid (6.3 g, 69% 2 steps). $^1$H NMR (600 MHz, Chloroform-d) δ 7.38 (d, J=8.3 Hz, 2H), 7.23 (d, J=0.9 Hz, 4H), 7.17 (d, J=8.3 Hz, 2H), 5.95 (s, 4H), 0.95-0.89 (m, 18H), 0.59 (qd, J=8.0, 2.5 Hz, 12H). $^{13}$C NMR (151 MHz, Chloroform-d) δ 144.97, 144.41, 133.11, 131.46, 131.37, 131.25, 128.31, 127.60, 127.24, 121.29, 71.10, 71.04, 7.02, 6.41. HRMS (EI) (m/z): [M]+ calculated for $C_{30}H_{42}BrClO_2Si_2$, 604.1595; found, 604.1594.

Example 19

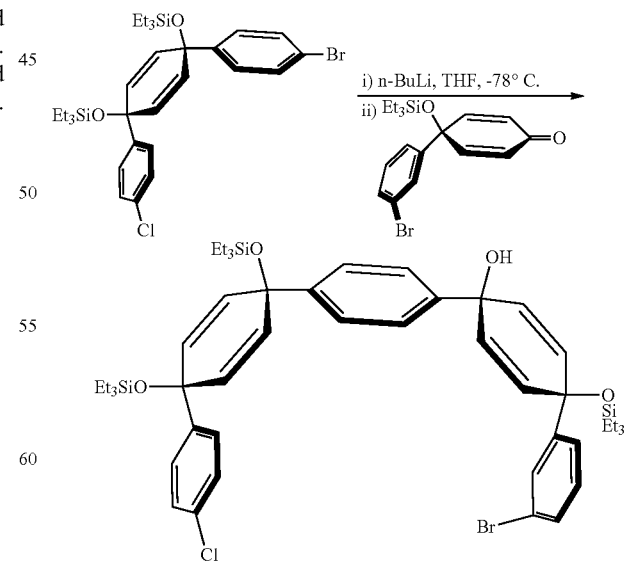

The product of Example 18 (1.5 g, 2.5 mmol, 1.1 equiv) was added to a 25 mL one-neck round bottom flask equipped with a stir bar and septa. The flask was evacuated and filled with nitrogen. Tetrahydrofuran (27 mL) was added to the flask and it was cooled for 30 min at −78° C. n-BuLi (1.0 mL, 2.6 mmol, 1.05 equiv, 2.5 M in hexanes) was added dropwise over 3 min. The product from Example 16 (0.72 mL, 2.5 mmol, 1 equiv) was added to the reaction flask dropwise and the reaction was stirred for 1 h at −78° C. The reaction was quenched with deionized water (10 mL) while at −78° C. and deionized water (5 mL) was added again when the ice bath was removed. The product was extracted with ethyl acetate (3×20 mL) and washed with brine (3×20 mL). The organic layers were dried over sodium sulfate and concentrated to yield the crude product as a colorless oil. The product was not purified.

Example 20

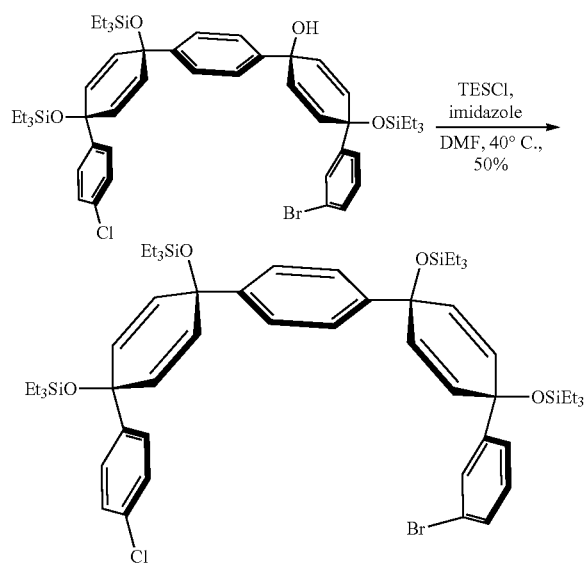

The crude product from Example 19 and imidazole (0.67 g, 9.9 mmol, 4 equiv) were added to a 100 mL round bottom flask equipped with a stir bar and septum. Dimethylformamide (10 mL) was added to the flask followed by triethylsilyl chloride (0.5 mL, 3.0 mmol, 1.2 equiv). The reaction mixture was heated to 40° C. in an oil bath and stirred overnight. The reaction mixture was cooled to room temperature and quenched with a saturated solution of sodium bicarbonate (20 mL). The product was extracted with ethyl acetate (3×100 mL) and washed with 5% lithium chloride solution in water (3×50 mL). The organic layers were dried over sodium sulfate and concentrated to yield the crude product as a yellow oil. The product was purified by automated flash silica gel chromatography (0% to 5% ethyl acetate in hexanes) to give a white solid (1.25 g, 50%, 2 steps). $^1$H NMR (600 MHz, Chloroform-d) δ 7.47 (dd, J=1.5 Hz, 1H), 7.34 (dd, J=7.9, 1.9 Hz, 1H), 7.25-7.22 (m, 6H), 7.21-7.17 (m, 3H), 7.08 (t, J=7.9 Hz, 1H), 6.02 (d, J=10.9 Hz, 2H), 6.00 (d, J=9.9 Hz, 2H), 5.91 (d, J=3.9 Hz, 2H), 5.90 (d, J=3.5 Hz, 2H), 0.97-0.89 (m, 38H), 0.66-0.60 (m, 12H), 0.57 (q, J=7.8 Hz, 13H). $^{13}$C NMR (151 MHz, Chloroform-d) δ 148.41, 144.95, 144.83, 144.70, 131.91, 131.77, 131.06, 130.98, 130.14, 129.60, 129.14, 128.18, 127.28, 125.76, 125.70, 124.29, 122.35, 71.23, 71.15, 7.05, 7.03, 6.46, 6.41. HRMS (ESI-TOF) (m/z): [M+Na]+ calculated for $C_{54}H_{80}BrClNaO_4Si_4$, 1041.3903; found, 1041.3909.

Example 21

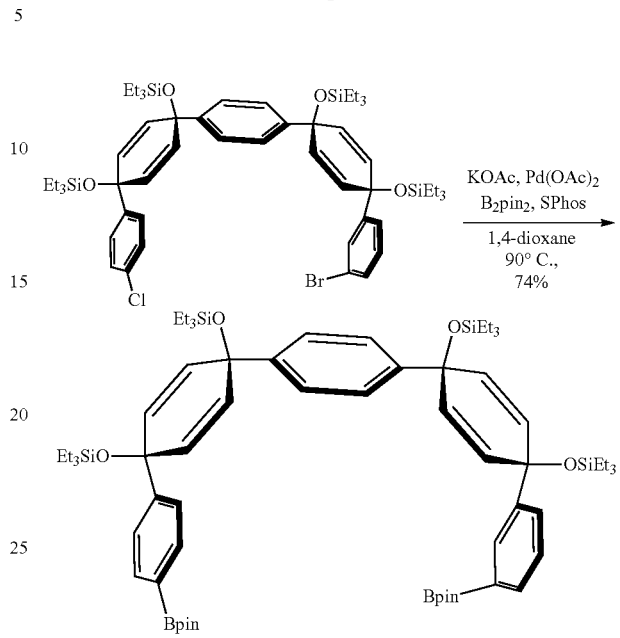

Potassium acetate (KOAc) (634.8 mg, 6.5 mmol, 6.6 equiv) that had been stored in an oven was added to a 25 mL round bottom flask equipped with a stir bar. NOTE: KOAc is extremely hygroscopic and the reaction is water sensitive, therefore it must be dried in an oven and weighed quickly while hot. The KOAc and flask were flame-dried again under vacuum until all apparent moisture was removed. Palladium(II) acetate (1.1 mg, 0.0049 mmol, 0.05 equiv), SPhos (50.3 mg, 0.12 mmol, 0.125 equiv), bis(pinacolato) diboron (994.8 mg, 3.9 mmol, 4 equiv) and the product from Example 20 (1.0 g, 0.98 mmol, 1 equiv) were added to the flask, which was placed under vacuum for 1 h with stirring. The flask was purged with nitrogen and evacuated 3 times. 1,4-dioxane (3.3 mL) was purged with nitrogen for 1 h prior and added to the round bottom flask at room temperature. The round bottom flask was placed in an oil bath while it heated up to 90° C. The reaction mixture changed from yellow to orange to red to a very dark red. The reaction was stirred at 90° C. overnight. Ethyl acetate (EtOAc) was added to the reaction mixture, which was filtered through a fritted suction funnel with 2 cm Celite®. The flask was rinsed several times with EtOAc and sonicated. The filtrate was transferred to a 250 mL flask and concentrated to yield a white waxy solid. This was rinsed with ethanol and suctioned through a Bichner funnel to yield a white solid (843.1 mg, 74%). $^1$H NMR (600 MHz, Chloroform-d) δ 8.01 (s, 1H), 7.70 (d, J=8.0 Hz, 2H), 7.68 (d, J=8.4 Hz, 1H), 7.33 (d, J=7.7 Hz, 2H), 7.29 (d, J=7.9 Hz, 1H), 7.25-7.22 (m, 3H), 7.20 (d, J=8.3 Hz, 2H), 6.02 (d, J=9.8 Hz, 2H), 5.95 (d, J=10.0 Hz, 2H), 5.93 (s, 4H), 1.34 (s, 12H), 1.30 (s, 12H), 0.96-0.88 (m, 36H), 0.65-0.54 (m, 24H). $^{13}$C NMR (151 MHz, CDCl3) δ 149.19, 145.31, 145.06, 144.72, 134.69, 133.60, 132.55, 131.64, 131.58, 131.37, 131.13, 128.62, 127.43, 125.61, 125.54, 125.15, 83.72, 83.61, 71.53, 71.36, 71.29, 71.25, 24.90, 24.88, 7.10, 7.06, 6.47, 6.45, 6.43. HRMS (ESI-TOF) (m/z): [M+Na]+ calculated for $C_{66}H_{104}B_2NaO_8Si_4$, 1181.6892; found, 1181.6926.

Example 22

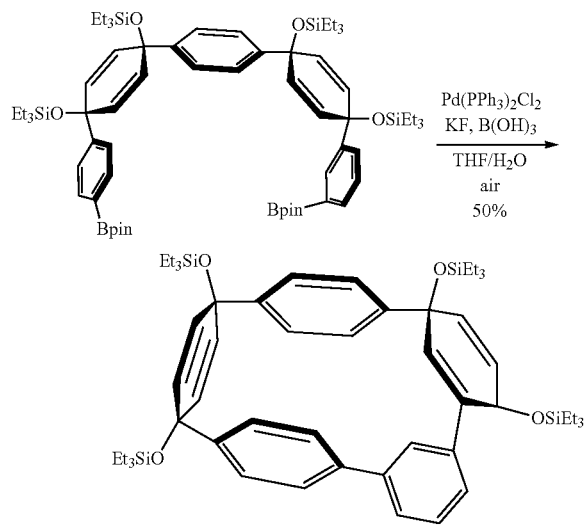

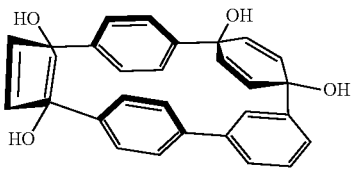

The diboronic ester from Example 21 (400 mg, 0.417 mmol, 1.00 equiv) was added to a round bottom flask followed by bis(triphenylphosphine)palladium(II) dichloride (59 mg, 0.083 mmol, 0.2 equiv) and boric acid (129 mg, 2.09 mmol, 5.00 equiv). The solids were dissolved in tetrahydrofuran (200 mL) and the mixture was stirred vigorously for 10 min. Potassium fluoride (24 mg, 0.417 mmol, 1.00 equiv) dissolved in water (20 mL) was added to the mixture. The reaction was stirred at 40° C. open to the atmosphere overnight. The next day, the mixture was filtered through Celite® washing with EtOAc, dried over sodium sulfate, and concentrated to give the crude product as an orange oil. The product was purified by automated flash silica gel chromatography (0% to 30% dichloromethane in hexanes) to yield a white solid (190 mg, 50%). $^1$H NMR (500 MHz, Chloroform-d) δ 7.65 (d, J=6.6 Hz, 1H), 7.43-7.35 (m, 2H), 7.12 (d, J=6.7 Hz, 2H), 6.92 (d, J=6.7 Hz, 2H), 6.88 (d, J=6.8 Hz, 2H), 6.58 (d, J=6.9 Hz, 2H), 6.47 (s, 1H), 6.40 (d, J=8.3 Hz, 2H), 6.12 (d, J=8.3 Hz, 2H), 5.96 (d, J=8.5 Hz, 2H), 5.86 (d, J=8.5 Hz, 2H), 1.01 (t, J=7.9 Hz, 9H), 0.97 (t, J=7.9 Hz, 9H), 0.87 (t, J=8.0 Hz, 9H), 0.84 (t, J=7.9 Hz, 9H), 0.72 (q, J=7.9 Hz, 6H), 0.64 (q, J=7.9 Hz, 6H), 0.50 (q, J=7.9 Hz, 6H), 0.46 (q, J=7.9 Hz, 6H). $^{13}$C NMR (126 MHz, CDCl3) δ 145.63, 143.99, 143.87, 143.13, 141.22, 141.11, 134.02, 132.79, 132.74, 131.05, 130.66, 128.60, 126.93, 126.75, 125.79, 125.61, 123.22, 122.78, 72.88, 72.53, 72.02, 71.46, 7.12, 7.03, 6.96, 6.95, 6.46, 6.44, 6.41, 6.40.

Example 23

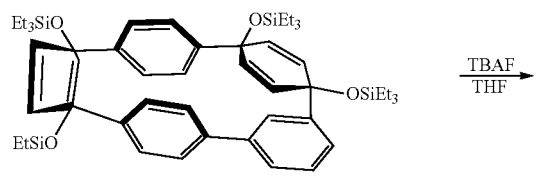

The product from Example 24 (33 mg, 0.036 mmol, 1 equiv) was dissolved in THF (0.9 mL). Tetra-n-butylammonium fluoride (0.22 mL, 0.22 mmol, 6 equiv, 1 M in tetrahydrofuran) was added and the reaction was stirred for 1 h. The reaction was quenched with water (1 mL) and the THF was removed by distillation. The resulting mixture was filtered to afford a white solid that was rinsed with water and dichloromethane. The product was not purified further.

Example 24

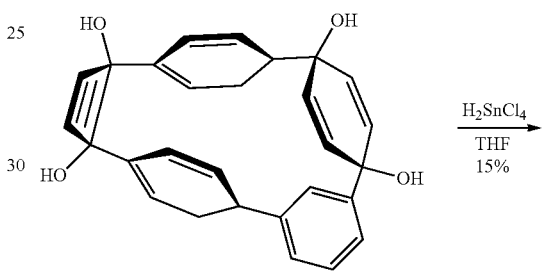

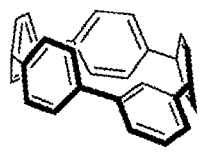

The crude product from Example 23 was dissolved in tetrahydrofuran (0.36 mL). A solution of tin(II) dichloride dihydrate (18 mg, 79 μmol, 2.2 eq) and concentrated hydrochloric acid (12 μL, 150 μmol, 4.2 eq) in THF (710 μL) was added and the reaction was stirred for 1 h at room temperature. A 1 M concentrated solution of NaOH (1 mL) was added and the mixture was extracted with dichloromethane (3×3 mL). The organic layers were concentrated and the product. The product was purified by preparative thin layer chromatography on alumina (50% dichloromethane in hexanes) to yield [5]mCPP as a yellow solid (2.0 mg, 15% 2 steps). $^1$H NMR (500 MHz, Chloroform-d) δ 7.40-7.31 (m, 15H), 7.06 (d, J=8.7 Hz, 4H), 4.80 (s, 1H). $^{13}$C NMR (151 MHz, Chloroform-d) δ 145.23, 142.82, 140.79, 139.05, 136.69, 135.38, 129.88, 128.64, 128.33, 127.54, 126.71, 121.18.

Example 25

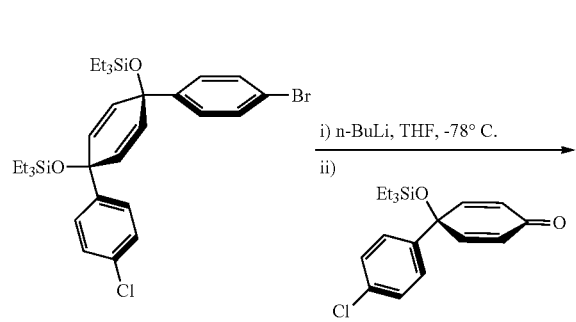

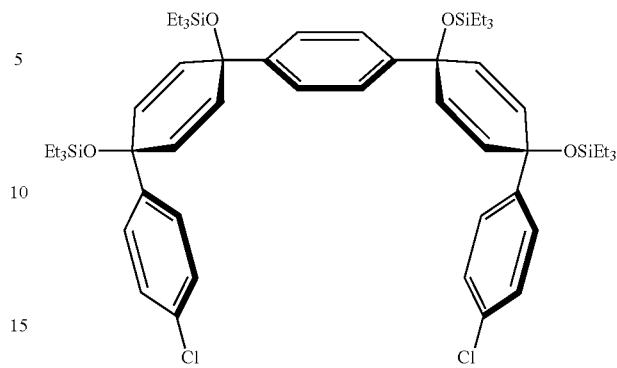

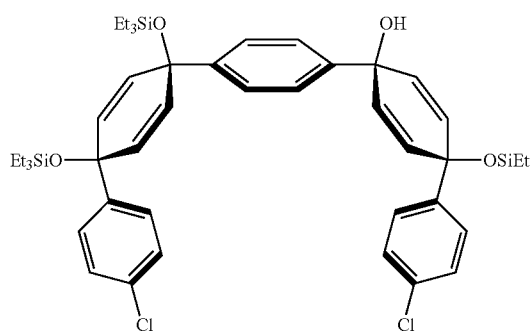

The product from Example 18 (6.0972 g, 10.1 mmol, 1.1 equiv) was added to a 100 mL round bottom flask equipped with a stir bar and septa. The flask was evacuated and filled with nitrogen. Tetrahydrofuran (15 mL) was added to the round bottom flask and was cooled for 30 min at −78° C. n-BuLi (4.2 mL, 10.6 mmol, 1.05 equiv, 2.5 M in hexanes) was added dropwise. Compound A (3.12 mL, 10.1 mmol, 1 equiv) was added to the reaction flask dropwise and the reaction was stirred for 1 h at −78° C. The reaction was quenched with deionized water (15 mL) at −78° C. and warmed to room temperature. The product was extracted with ethyl acetate (3×40 mL) and washed with brine (30 mL). The organic layers were dried over sodium sulfate and concentrated to yield the crude product as a colorless oil. The product was not purified.

Example 26

The crude product from Example 25 (8.67 g, 10.1 mmol, 1 equiv) and imidazole (2.74 g, 40.2 mmol, 4 equiv) were added to a 250 mL round bottom flask and was equipped with a stir bar and septum. Dimethylformamide (50 mL) was added to the flask followed by triethylsilyl chloride (2.0 mL, 12.1 mmol, 1.2 equiv). The reaction mixture was heated to 40° C. in an oil bath and stirred overnight. The reaction mixture was cooled to room temperature and quenched with a saturated solution of sodium bicarbonate (50 mL). The product was extracted with ethyl acetate (3×100 mL) and washed with 5% lithium chloride solution in water (3×100 mL). The organic layers were dried over sodium sulfate and concentrated to yield the crude product as a yellow oil. The product was purified by automated flash silica gel chromatography (0% to 15% ethyl acetate in hexanes) to give a white solid (9.0 g, 92% 2 steps). $^1$H NMR (600 MHz, Chloroform-d) δ 7.24 (s, 4H), 7.22 (d, J=8.4 Hz, 4H), 7.19 (d, J=8.4 Hz, 4H), 6.01 (d, J=10.1 Hz, 4H), 5.91 (d, J=10.1 Hz, 4H), 0.94 (t, J=7.9 Hz, 18H), 0.91 (t, J=7.9 Hz, 18H), 0.62 (q, J=7.9 Hz, 12H), 0.57 (q, J=8.0 Hz, 12H). $^{13}$C NMR (151 MHz, Chloroform-d) δ 144.98, 144.63, 132.91, 131.68, 131.17, 128.15, 127.31, 127.23, 125.73, 71.18, 71.13, 7.05, 7.03, 6.46, 6.40. HRMS (ESI-TOF) (m/z): [M+Na]+ calculated for $C_{54}H_{80}Cl_2NaO_4Si_4$, 997.4409; found, 997.4455.

Example 27

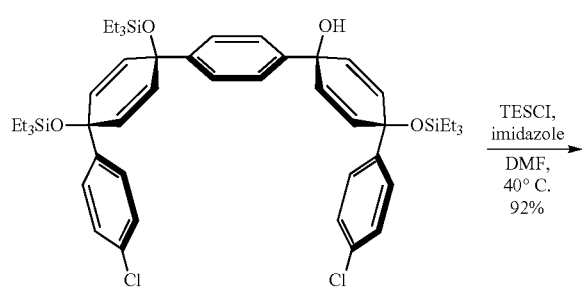

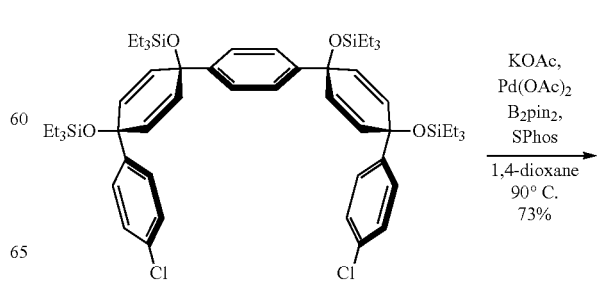

Example 28

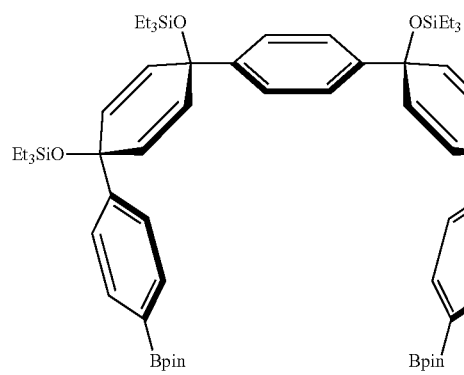

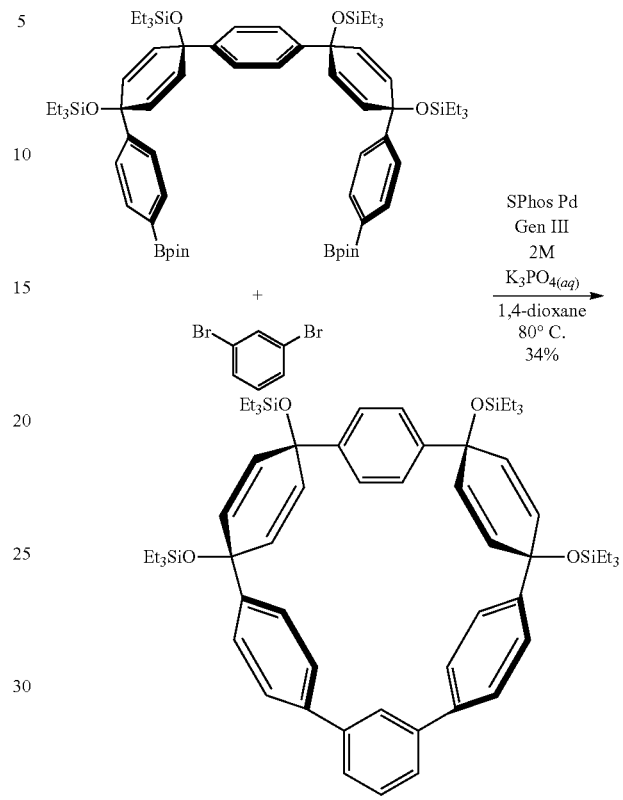

Potassium acetate (KOAc) (1.1 g, 12 mmol, 6.6 equiv) that had been stored in an oven was added to a 25 mL round bottom flask equipped with a stir bar. NOTE: KOAc is extremely hygroscopic and it is important to have none or very little moisture in the reaction, therefore it must be weighed very quickly while it is warm. The KOAc and flask were flame-dried again under vacuum until all apparent moisture was removed. Palladium(II) acetate (20 mg, 0.09 mmol, 0.05 equiv), SPhos (91 mg, 0.2 mmol, 0.13 equiv), bis(pinacolato)diboron (1.8 g, 7 mmol, 4 equiv) and the product from Example 26 (1.7 g, 1.2 mmol, 1 equiv) were added to the flask and was put under vacuum for 1 h with stirring. The flask was purged with nitrogen and evacuated 3 times. 1,4-dioxane (6 mL) was sparged with nitrogen for 1 h, added to the round bottom flask at room temperature and the mixture was stirred for 5 min. The flask was placed in an oil bath and heated to 90° C. The color of the reaction mixture changed from yellow to orange to red to a very dark red. The reaction was stirred at 90° C. over 2 nights. EtOAc was added to the reaction mixture. This was filtered through Celite® in a fritted suction funnel. The reaction flask was rinsed several times with EtOAc with sonication. The filtrate was transferred to a 250 mL round bottom flask and concentrated to yield a white waxy solid. This was rinsed with ethanol and filtered using a Buchner funnel to yield a white solid (1.51 g, 73%). $^1$H NMR (600 MHz, Chloroform-d) δ 7.69 (d, J=8.2 Hz, 4H), 7.32 (d, J=8.2 Hz, 4H), 7.22 (s, 4H), 5.98 (d, J=10.2 Hz, 4H), 5.94 (d, J=10.2 Hz, 4H), 1.33 (s, 24H), 0.95-0.90 (m, 36H), 0.63-0.56 (m, 24H). $^{13}$C NMR (151 MHz, Chloroform-d) δ 149.17, 144.91, 134.65, 131.61, 131.22, 125.68, 125.16, 83.68, 71.60, 71.25, 24.88, 7.07, 6.45. HRMS (ESI-TOF) (m/z): [M+Na]+ calculated for $C_{66}H_{104}B_2NaO_8Si_4$, 1181.6892; found, 1181.6871.

m-dibromobenzene (0.06 mL, 0.08 mmol, 1 equiv), the product from Example 27 (0.5 mg, 0.058 mmol, 1.2 equiv) and SPhos Pd Gen III (38.1 mg, 0.0048 mmol, 0.1 equiv) were added to a 50 mL round bottom flask equipped with a stir bar. The flask was evacuated for 5 min and purged with nitrogen 5 times. 1,4-dioxane and a solution of 2 M $K_3PO_4$ were sparged with nitrogen for over 1 h prior to use. The round bottom flask was equipped with a septa and 1,4-dioxane (160 mL) was added to the round bottom flask and the solution was sparged for 20 min. The round bottom flask was heated to 80° C. for 10 min and $K_3PO_4$ (16 mL, 2 M in deionized water) was added. The reaction was stirred at 80° C. overnight. The reaction mixture was cooled to room temperature. It was filtered through a fritted suction funnel filled with Celite®. The round bottom flask was rinsed with dichloromethane and filtered through the Celite® plug. The filtrate was added to a separatory funnel along with deionized water (10 mL) and the product was extracted (3×30) with dichloromethane. The organic layer was washed with brine (20 mL), dried over sodium sulfate and concentrated to yield an orange oil. The product was purified by automated flash silica gel chromatography (5% to 45% dichloromethane in hexanes) to yield the product as a white solid (193 mg, 34%). $^1$H NMR (600 MHz, Chloroform-d) δ 7.55 (dd, J=7.5, 1.9 Hz, 2H), 7.48-7.44 (m, 5H), 7.30 (d, J=8.3 Hz, 4H), 6.93 (s, 4H), 6.24 (t, J=1.9 Hz, 1H), 6.13 (d, J=10.1 Hz, 4H), 5.72 (d, J=10.1 Hz, 4H), 0.97 (t, J=7.9 Hz, 18H), 0.93 (t, J=7.9 Hz, 18H), 0.69 (q, J=7.9 Hz, 12H), 0.58 (q, J=7.9 Hz, 12H). $^{13}$C NMR (151 MHz, CDCl3) δ 144.92, 144.77, 143.15, 142.47, 141.76, 131.48, 131.43, 128.80, 128.69, 128.06, 125.99, 125.81, 125.73, 125.35, 122.39, 71.19, 70.58, 7.15, 7.04, 6.97, 6.80, 6.61, 6.50, 6.48, 6.42. HRMS (ESI-TOF) (m/z): [M+Na]+ calculated for $C_{60}H_{84}NaO_4Si_4$, 1003.5344; found, 1003.5375.

Example 29

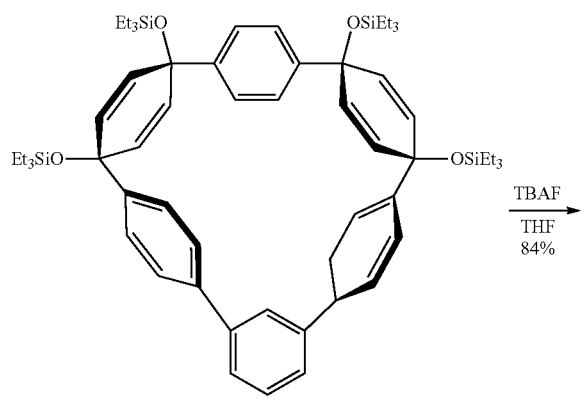

Tetrahydrofuran (1.05 mL) was added to the product from Example 28 (102.9 mg, 0.1 mmol, 1 equiv) and the vial was equipped with a stir bar and septa. Tetra-n-butylammonium fluoride (1.05 mL, 1 mmol, 10 equiv, 1 M in tetrahydrofuran) was added to the reaction flask and this was stirred for 2 h at room temperature. The reaction was quenched with deionized water (5 mL), filtered in a Buchner funnel and washed with deionized water and dichloromethane to yield a white solid (46 mg, 84%). $^1$H NMR (600 MHz, DMSO-d6) δ 7.60 (dd, J=7.6, 1.9 Hz, 2H), 7.51 (t, J=7.6 Hz, 1H), 7.47 (d, J=8.0 Hz, 4H), 7.33 (d, J=7.9 Hz, 4H), 6.88 (s, 4H), 6.17 (t, J=2.0 Hz, 1H), 6.07 (d, J=9.9 Hz, 4H), 5.65 (d, J=9.8 Hz, 4H). $^{13}$C NMR (151 MHz, DMSO) δ 145.94, 144.97, 142.45, 142.38, 131.85, 131.53, 129.54, 128.78, 126.26, 125.54, 122.79, 68.63, 68.09, 23.53, 19.70, 13.98.

Example 30

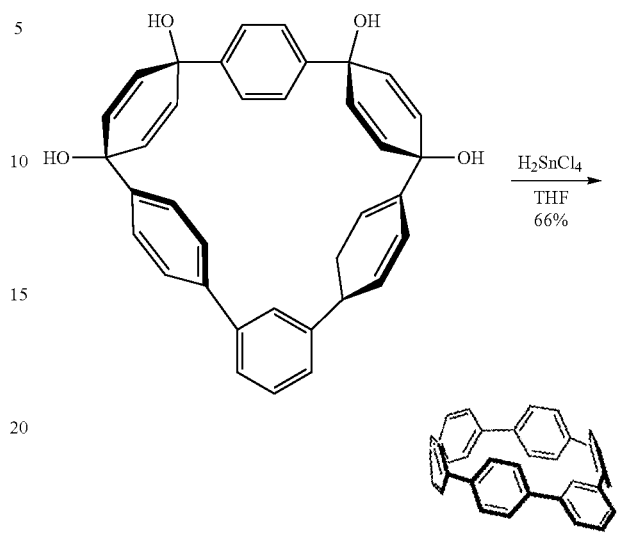

Figure 7:
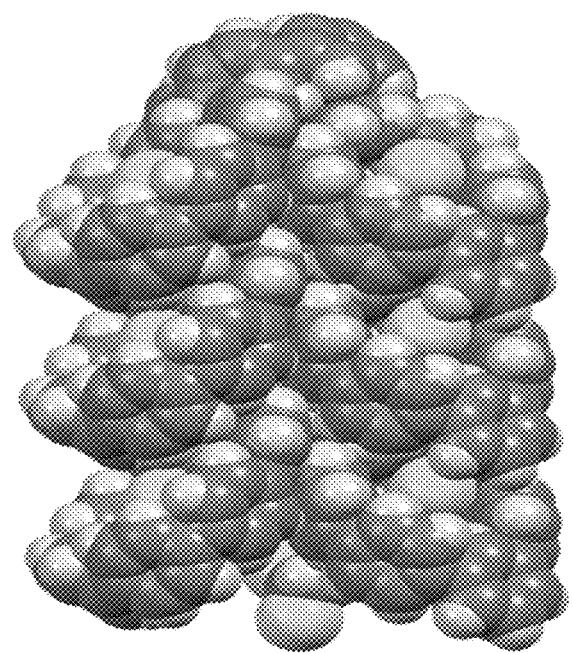
FIG. 7 is a space-filling model of the nanohoop compound illustrated in FIG. 6.
Figure 8:
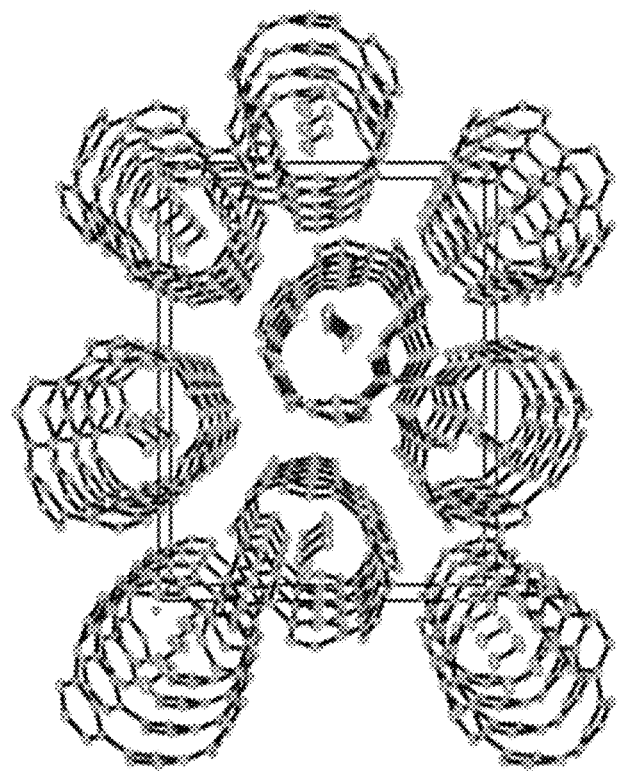
FIG. 8 is an ORTEP representation showing columnar packing of the nanohoop compound of FIG. 6, wherein a single dichloromethane atom is present in the center of each hoop.

SnCl$_2$.H$_2$O (180.6 mg, 0.80 mmol) was added to a 100 mL round bottom flask equipped with a stir bar and septum. Tetrahydrofuran (20 mL) was added to the flask followed by hydrochloric acid (0.13 mL, 1.6 mmol, 12 M). This was stirred at room temperature for 30 min. H$_2$SnCl$_2$ solution (2.1 mL, 0.09 mmol, 2.2 equiv, 0.04 M) was added to the scintillation vial containing the product from Example 29 (20.3 mg, 0.04 mmol, 1 equiv) and was stirred for 1 h at room temperature. The reaction was quenched with saturated sodium bicarbonate (5 mL). The filtrate was transferred to a separatory funnel and the product was extracted with dichloromethane (5×7 mL). The organic layers were washed with brine (10 mL), dried over sodium sulfate and concentrated to give the crude product as a green solid. The product was purified by automated flash alumina column chromatography (10% to 45% dichloromethane in hexanes) to yield [6]mCPP as a green solid (12 mg, 66%). $^1$H NMR (600 MHz, Chloroform-d) δ 7.45-7.38 (m, 19H), 7.15 (d, J=8.6 Hz, 4H), 5.62 (t, J=1.9 Hz, 1H). $^{13}$C NMR (151 MHz, CDCl3) δ 142.79, 139.53, 139.04, 137.43, 136.42, 136.38, 129.45, 128.99, 128.08, 127.85, 127.58, 127.20, 122.20, 77.25, 77.03, 76.82. HRMS (ASAP-TOF) (m/z): [M+H]+ calculated for $C_{36}H_{25}$, 457.1956; found, 457.1956. The ORTEP representation of this compound is provided by FIG. 6. Also, a space-filling model showing herringbone packing is provided by FIG. 7 and the ORTEP representation showing columnar packing of this compound is provided by FIG. 8, wherein a single dichloromethane atom is present in the center of each hoop.

Example 31

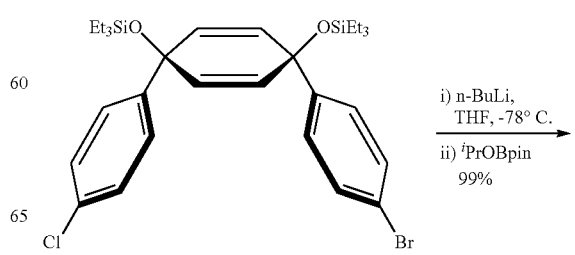

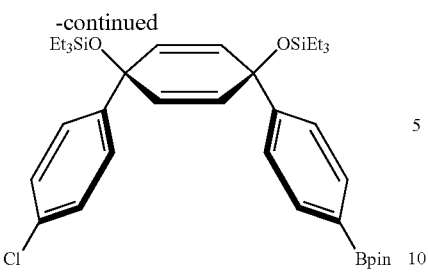

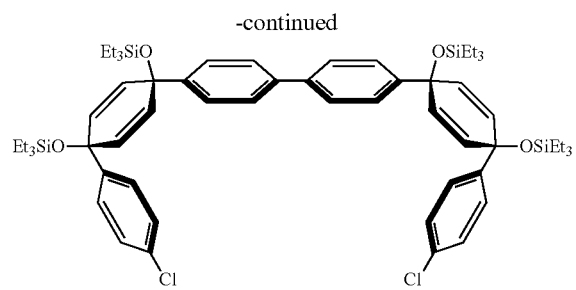

The product of Example 18 (5 g, 8.25 mmol, 1.0 eq) was added to a 100 mL round bottom flask equipped with a stir bar. The reaction flask was capped with a septa and the flask was evacuated and refilled with nitrogen. Tetrahydrofuran (48 mL) was added to the reaction flask and the mixture was cooled for 30 min at −78° C. n-BuLi (3.5 mL, 8.7 mmol, 1.05 eq, 2.5 M in hexanes) was added to the reaction mixture dropwise. This was followed by the dropwise addition of 2-Isopropoxy-4,4,5,5-tetramethyl-1,3,2-dioxaborolane (3.4 mL, 16.5 mmol, 2 eq) and the reaction was stirred at −78° C. for 1 h. The reaction was quenched with deionized water (30 mL) at −78° C. and the reaction mixture was warmed to room temperature. The product was extracted with ethyl acetate (3×50 mL) and washed with brine (3×20 mL). The organic layers were dried over sodium sulfate, decanted into a round bottom flask and concentrated to yield a slightly yellow oil. Ethanol (20 mL) was added to the oil and was sonicated, producing a white precipitate. The product was isolated by suction filtration to yield a white solid (5.3 g, 99%). $^1$H NMR (500 MHz, Chloroform-d) δ 7.72 (d, J=7.8 Hz, 2H), 7.32 (d, J=7.9 Hz, 2H), 7.24 (d, J=8.8 Hz, 2H), 7.22 (d, J=8.7 Hz, 2H), 5.99 (d, J=10.0 Hz, 2H), 5.92 (d, J=10.0 Hz, 2H), 1.34 25 (s, 12H), 0.93 (t, J=8.0 Hz, 9H), 0.91 (t, J=7.9 Hz, 9H), 0.61 (q, J=8.0 Hz, 6H), 0.57 (q, J=7.7 Hz, 6H). $^{13}$C NMR (126 MHz, CDCl3) δ 148.90, 144.59, 134.73, 132.91, 131.60, 131.24, 128.21, 127.27, 125.15, 83.79, 71.45, 71.15, 24.88, 7.03, 6.45, 6.41. HRMS (ESI-TOF) (m/z): [M+Na]+ calculated for $C_{36}H_{54}BClNaO_4Si_2$, 675.324; found, 675.3246.

Example 32

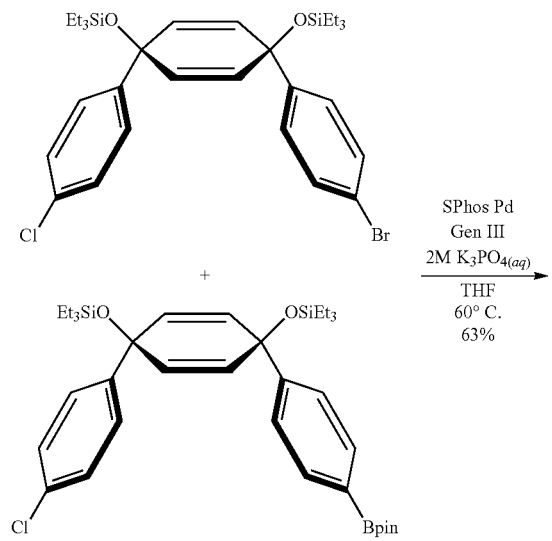

The product from Example 18 (1.00 g, 1.65 mmol, 1 equiv), the product from Example 31 (1.18 g, 1.82 mmol, 1.1 equiv) and PPh$_3$ Pd Gen III (31 mg, 0.050 mmol, 0.03 equiv) dissolved in tetrahydrofuran (16 mL) and warmed to 60° C. K$_3$PO$_4$ (1.6 mL, 2 M in deionized water) was added and the reaction was left overnight. The next day, the reaction was filtered through Celite®, dried over sodium sulfate and the solvent was removed under reduced pressure to yield an oil. The product was purified by automated flash silica column chromatography (0% to 30% dichloromethane in hexanes) to yield a white solid (1.1 g, 63%). $^1$H NMR (500 MHz, Chloroform-d) δ 7.50 (d, J=8.2 Hz, 4H), 7.37 (d, J=8.5 Hz, 4H), 7.28 (d, J=8.3 Hz, 4H), 7.23 (d, J=8.5 Hz, 4H), 6.03 (d, J=10.0 Hz, 4H), 5.96 (d, J=9.8 Hz, 4H), 0.94 (t, J=7.9 Hz, 36H), 0.61 (q, J=8.1 Hz, 24H). $^{13}$C NMR (126 MHz, CDCl3) δ 144.90, 144.66, 139.59, 132.97, 131.78, 131.16, 128.23, 127.33, 126.76, 126.24, 71.27, 71.16, 7.05, 7.04, 6.47, 6.43. HRMS (ESI-TOF) (m/z): [M+Na]+ calculated for $C_{60}H_{84}Cl_2NaO_4Si_4$, 1073.4722; found, 1073.4722.

Example 33

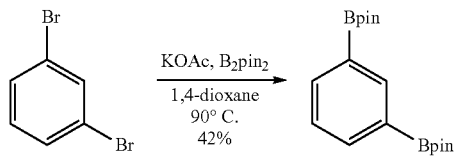

1,3-dibromobenzene (5.0 mL, 9.8 g, 41 mmol, 1 eqiv), Pd(dppf)2Cl2 (169 mg, 0.21 mmol, 0.005 eqiv) and bis (pinacolato)diboron (25 g, 99 mmol, 2.4 equiv) were added to a round bottomed flask. Oven dried hot KOAc (27 g, 270 mmol, 6.6 equiv) was added and the solids were placed under vacuum. The flask was refilled with nitrogen, 1,4-dioxane (40 mL) was added, and the reaction was warmed from room temperature to 90° C. The reaction was stirred at this temperature overnight. The next day, the reaction was filtered through Celite® washing with ethyl acetate (80 mL) and the solvent of the filtrate was removed under reduced pressure until crystallization occurred. The crystals were collected by filtration and washed with cold ethanol to yield a white solid (5.8 g, 42%). $^1$H NMR (500 MHz, Chloroform-d) δ 8.28 (s, 1H), 7.90 (d, J=7.4 Hz, 2H), 7.37 (t, J=7.4 Hz, 1H), 1.34 (s, 24H). $^{13}$C NMR (126 MHz, CDCl3) δ 141.23, 137.62, 127.04, 83.73, 24.88. HRMS (ESI-TOF) (m/z): [M+H]+ calculated for $C_{18}H_{29}B_2O_4$, 331.2252; found, 331.2244.

Example 34

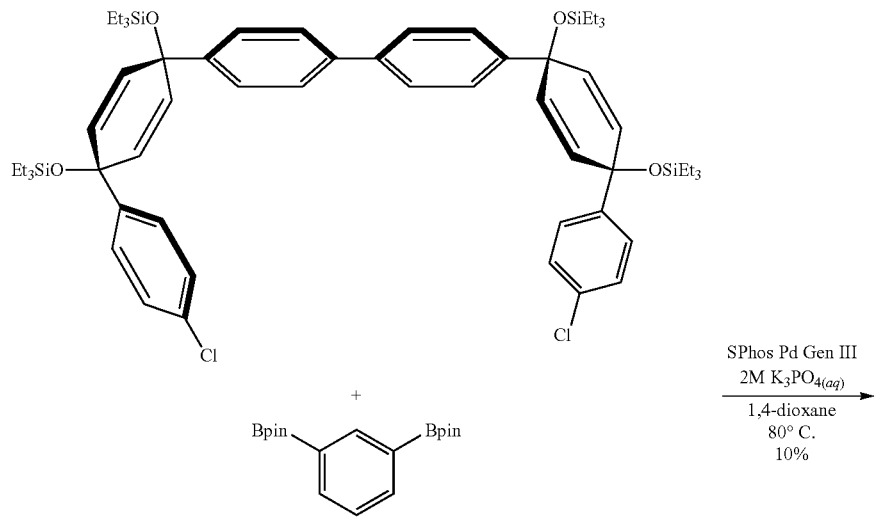

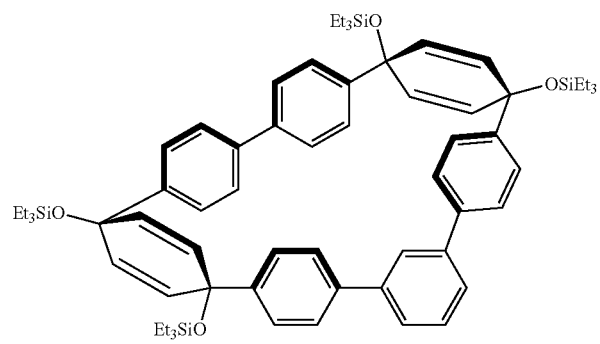

The product from Example 32 (157 mg, 0.475 mmol, 1 equiv), the product from Example 33 (500 mg, 0.475 mmol, 1 equiv), and Sphos Pd Gen III (37 mg, 0.048 mmol, 0.1 equiv) were dissolved in 1,4-dioxane (240 mL) and heated to 80° C. $K_3PO_4$ (24 mL, 2 M in deionized water) was added and the reaction was stirred overnight. The reaction mixture was filtered through Celite® and the solvent was removed under reduced pressure to yield a golden oil. The product was purified by automated flash silica column chromatography (0% to 100% dichloromethane in hexanes) to yield a white solid. The solid was purified by recycling gel permeation chromatography to yield a white solid (50 mg, 10%). $^1$H NMR (600 MHz, Chloroform-d) δ 7.58 (dd, J=7.5, 1.8 Hz, 2H), 7.50 (m, 2H), 7.40 (d, J=8.4 Hz, 4H), 7.26 (d, J=8.4 Hz, 4fH), 7.23 (d, J=8.3 Hz, 4H), 7.04 (d, J=8.3 Hz, 4H), 6.15 (d, J=10.0 Hz, 4H), 6.07 (d, J=10.0 Hz, 4H), 0.99 (t, J=7.9 Hz, 18H), 0.98 (t, J=7.9 Hz, 18H), 0.68 (q, J=7.9 Hz, 12H), 0.66 (q, J=7.9 Hz, 12H). $^{13}$C NMR (151 MHz, CDCl3) δ 143.56, 142.92, 141.63, 140.33, 140.10, 132.46, 131.98, 129.16, 128.78, 127.09, 126.80, 126.68, 126.57, 124.89, 72.54, 72.35, 7.08, 7.06, 6.49. HRMS (ESI-TOF) (m/z): [M+H]+ calculated for $C_{66}H_{89}O_4Si_4$, 1057.5838; found, 1057.5869.

Example 35

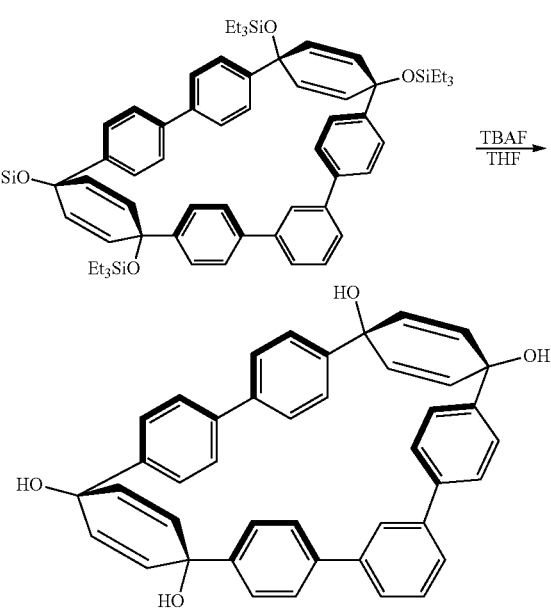

The product from Example 34 (50 mg, 0.047 mmol, 1 equiv) was dissolved in tetrahydrofuran (1.2 mL) and a Tetra-n-butylammonium fluoride (0.21 mL, 0.28 mmol, 6 equiv, 1 M in tetrahydrofuran) was added. The reaction was stirred for 1 h at room temperature and quenched with water. Solvent was removed from this mixture under reduced pressure. Filtration afforded a white solid, which was washed with dichloromethane.

Example 36

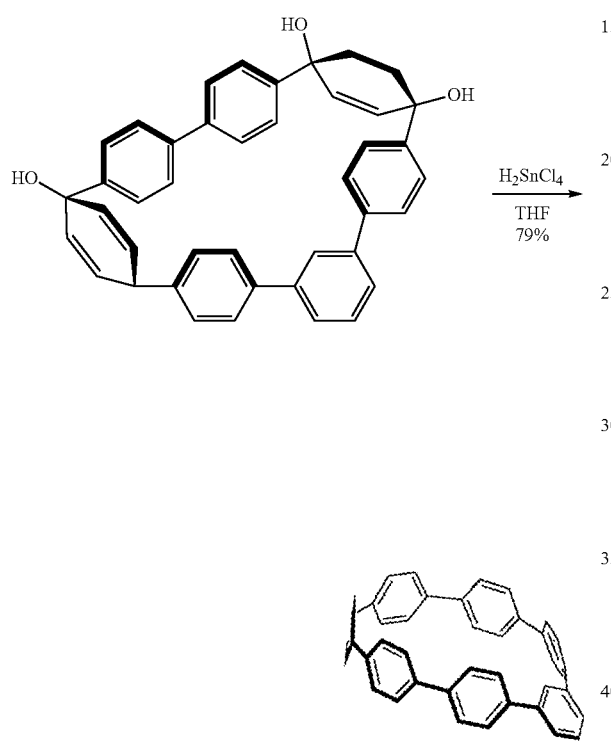

The crude product from Example 35 was dissolved in minimal tetrahydrofuran and to it was added a solution of tin(II) dichloride monohydrate (23 mg, 100 μmol, 2.1 eq) and concentrated aqueous hydrochloric acid (17 μL, 200 μmol, 4.2 eq) in THF (1 mL). The reaction was stirred at room temperature for 1 h and quenched with a 1 M aqueous solution of NaOH. This mixture was extracted with DCM and the combined extracts were dried over anhydrous sodium sulfate. The solvent was removed under reduced pressure and the material was purified by preparative thin layer chromatography on alumina (25% dichloromethane in hexanes) to yield [7]mCPP as a yellow fluorescent solid. (20 mg, 79%) $^1$H NMR (600 MHz, Chloroform-d) δ 7.51-7.43 (m, 19H), 7.42 (d, J=8.5 Hz, 4H), 7.21 (d, J=8.4 Hz, 4H), 6.08 (t, J=1.9 Hz, 1H). $^{13}$C NMR (151 MHz, CDCl3) δ 142.54, 141.91, 138.78, 137.57, 137.37, 137.30, 137.24, 136.58, 129.08, 128.90, 127.69, 127.51, 127.48, 127.43, 127.02, 123.02. HRMS (ASAP-TOF) (m/z): [M+H]+ calculated for $C_{42}H_{29}$, 533.2269; found, 533.2278.

Example 37

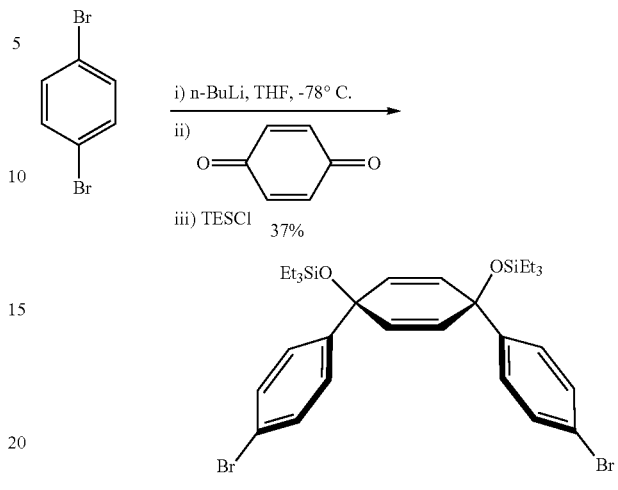

1,4-dibromobenzene (5.00 g, 21.2 mmol, 2.8 equiv) was dissolved in tetrahydrofuran (125 mL) and cooled to −78° C. n-BuLi (8.2 mL, 20.4 mmol, 2.7 equiv, 2.5 M in hexanes) was added followed by 1,4-benzoquinone (818 mg, 7.57 mmol, 1 equiv), which was added in fifths. After each fifth, the reaction turned blue and the next fifth was not added until the reaction became yellow. When the last fifth was added, the reaction was stirred for 1 h, triethylsilyl chloride (4.4 mL, 4.0 g, 26 mmol, 3.5 equiv) was added and the reaction was warmed to room temperature overnight. The next day, the reaction was quenched with water (60 mL) and extracted with ethyl acetate (3×60 mL). The combined extracts were washed with brine (60 mL), dried over anhydrous sodium sulfate and solvent was removed to yield an oil. The product was purified by automated flash silica column chromatography (0% to 20% dichloromethane in hexanes) to yield a clear colorless oil. This was mixed with an equal amount of ethanol and let sit to yield large crystals, which were filtered and washed with ethanol, to yield a white solid (1.80 mg, 37%). $^1$H NMR (500 MHz, Chloroform-d) δ 7.38 (d, J=8.3 Hz, 4H), 7.17 (d, J=8.3 Hz, 4H), 5.95 (s, 4H), 0.92 (t, J=7.9 Hz, 18H), 0.59 (q, J=8.0 Hz, 12H). $^{13}$C NMR (126 MHz, CDCl3) δ 144.94, 131.39, 131.25, 127.60, 121.30, 71.09, 7.01, 6.41. HRMS (EI) (m/z): [M]+ calculated for $C_{30}H_{42}Br_2O_2Si_2$, 648.109; found, 648.1081.

Example 38

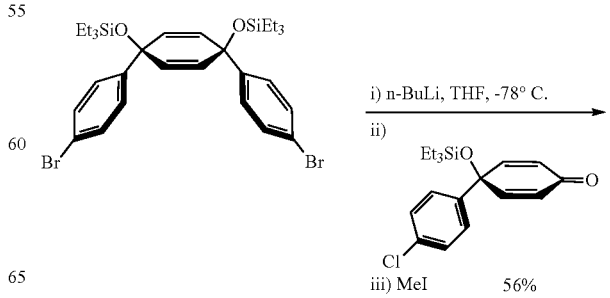

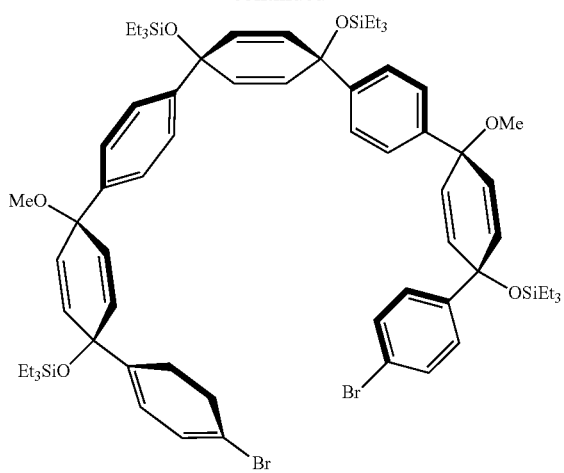

The product from Example 37 (1.63 g, 2.50 mmol, 1 equiv) was dissolved in tetrahydrofuran (50 mL, 100 mM) and cooled to −78° C. n-BuLi (2.0 mL, 5.0 mmol, 2 equiv, 2.5 M in hexanes) was added followed immediately by Compound B (1.5 mL, 1.9 g, 5 mmol, 2 equiv) and the reaction was stirred for 1 h at −78° C. It was quenched with methyl iodide (470 μL, 1.1 g, 7.5 mmol, 3 eq), warmed to room temperature and stirred overnight. The next day, water (20 mL) was added and the product was extracted with ethyl acetate (3×20 mL). The combined extracts were washed with brine (20 mL) and dried over anhydrous sodium sulfate. Solvent was removed under reduced pressure to yield an oil. The product was purified by automated flash silica column chromatography (20% to 80% dichloromethane in hexanes) to yield a white solid (1.8 g, 56%). $^1$H NMR (600 MHz, Chloroform-d) δ 7.34 (d, J=8.6 Hz, 4H), 7.30 (d, J=8.5 Hz, 4H), 7.26 (d, J=8.5 Hz, 4H), 7.16 (d, J=8.6 Hz, 4H), 6.09 (d, J=10.2 Hz, 4H), 5.99 (d, J=10.2 Hz, 4H), 5.96 (s, 4H), 3.33 (s, 6H), 0.96 (t, J=7.9 Hz, 18H), 0.92 (t, J=7.9 Hz, 18H), 0.66 (q, J=7.9 Hz, 12H), 0.60 (q, J=7.9 Hz, 12H). $^{13}$C NMR (151 MHz, CDCl3) δ 145.68, 144.93, 141.99, 135.06, 131.40, 131.11, 129.35, 127.51, 126.02, 125.95, 121.07, 74.30, 71.68, 71.18, 52.06, 7.05, 6.49, 6.44. HRMS (ESI-TOF) (m/z): [M+Na]+ calculated for $C_{68}H_{94}Br_2NaO_6Si_4$, 1299.4392; found, 1299.4379.

Example 39

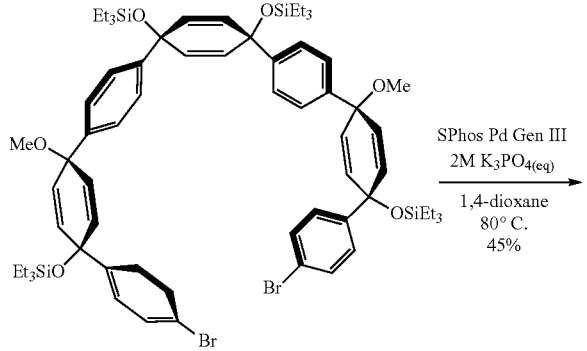

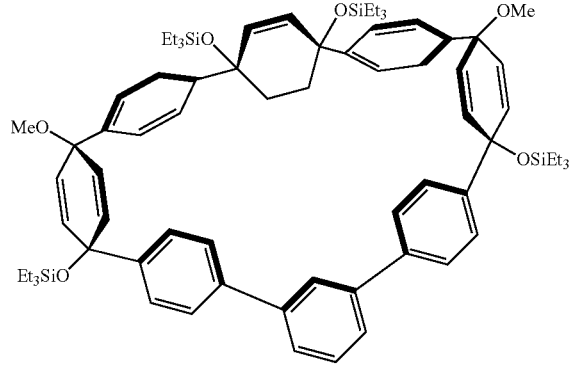

The product from Example 33 (206 mg, 0.63 mmol, 1 equiv), the product from Example 38 (800 mg, 0.63 mmol, 1 equiv), and Sphos Pd Gen III (49 mg, 0.063 mmol, 0.1 equiv) were dissolved in 1,4-dioxane (125 mL) and heated to 80° C. $K_3PO_4$ (12.5 mL, 2 M in deionized water) was added and the reaction was stirred overnight. The reaction mixture was filtered through Celite®, dried over sodium sulfate, and the solvent was removed under reduced pressure to yield a golden oil. The product was purified by automated flash silica column chromatography (20% to 80% dichloromethane in hexanes) to yield a white solid (340 mg, 45%). $^1$H NMR (600 MHz, Chloroform-d) δ 7.65 (s, 1H), 7.58 (dd, J=7.6, 1.8 Hz, 2H), 7.53 (d, J=8.4 Hz, 4H), 7.51 (d, J=8.4 Hz, 4H), 7.48 (d, J=7.5 Hz, 1H), 7.45 (d, J=8.5 Hz, 4H), 7.42 (d, J=8.3 Hz, 4H), 6.15 (s, 4H), 6.12 (d, J=10.1 Hz, 4H), 6.01 (d, J=10.2 Hz, 4H), 3.29 (s, 6H), 1.01 (t, J=7.9 Hz, 18H), 0.89 (t, J=8.0 Hz, 18H), 0.72 (q, J=8.0 Hz, 12H), 0.53 (q, J=8.0 Hz, 12H). $^{13}$C NMR (126 MHz, CDCl3) δ 146.21, 145.04, 142.66, 141.06, 139.60, 135.49, 132.44, 131.12, 128.16, 127.82, 126.87, 126.31, 126.22, 125.87, 124.78, 73.80, 72.04, 69.76, 51.42, 7.12, 6.53.

Example 40

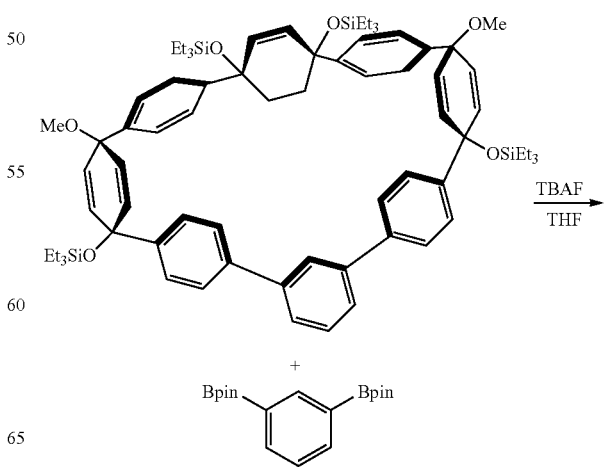

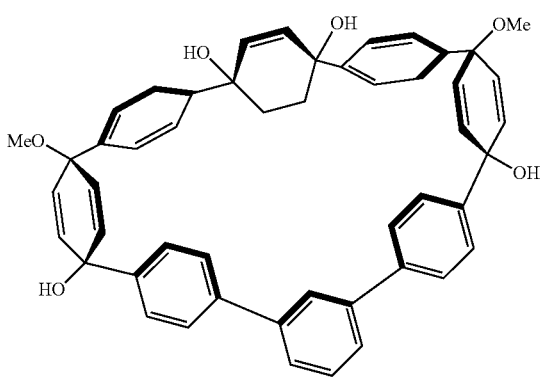

The product from Example 39 (100 mg, 0.084 mmol, 1 equiv) was dissolved in tetrahydrofuran (2.1 mL) and Tetra-n-butylammonium fluoride (0.50 mL, 0.50 mmol, 6 equiv, 1 M in tetrahydrofuran) was added. The reaction was stirred for 1 h at room temperature and was quenched with water. Tetrahydrofuran was removed from this mixture under reduced pressure and filtration afforded a white solid, which was washed with dichloromethane. This crude material was used as is for the next reaction.

Example 41

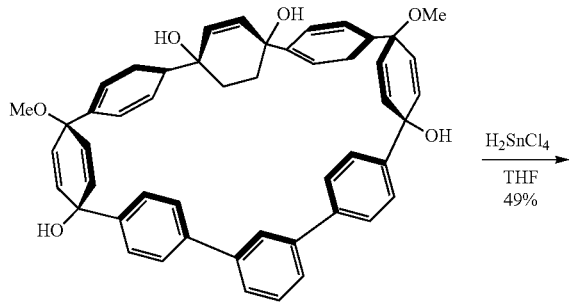

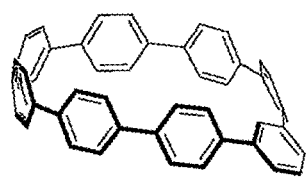

The crude product from Example 40 was dissolved in minimal tetrahydrofuran and to it was added a solution of tin(II) dichloride monohydrate (62 mg, 280 μmol, 3.3 eq) and concentrated aqueous hydrochloric acid (44 μL, 530 μmol, 6.3 eq) in THF (2.1 mL). The reaction was stirred at room temperature for 1 h and quenched with a 1 M aqueous solution of NaOH (1 mL). This mixture was extracted with dichloromethane (3×3 mL) and the combined extracts were dried over anhydrous sodium sulfate. The solvent was removed under reduced pressure and the product was purified by automated flash silica column chromatography (0% to 100% dichloromethane in hexanes) to yield [8]mCPP as a yellow solid (25 mg, 49%). $^{1}$H NMR (600 MHz, Chloroform-d) δ 7.56 (dt, J=7.7, 1.8 Hz, 2H), 7.52-7.44 (m, 17H), 7.40-7.36 (m, 8H), 7.32 (d, J=8.2 Hz, 4H), 6.36 (t, J=1.8 Hz, 1H). $^{13}$C NMR (151 MHz, CDCl3) δ 142.42, 141.12, 139.45, 138.47, 138.00, 137.83, 137.57, 137.23, 135.86, 128.93, 128.51, 127.52, 127.49, 127.27, 127.24, 127.14, 123.24. HRMS (ASAP-TOF) (m/z): [M+H]+ calculated for $C_{48}H_{33}$, 608.2582; found, 609.2585.

Example 42

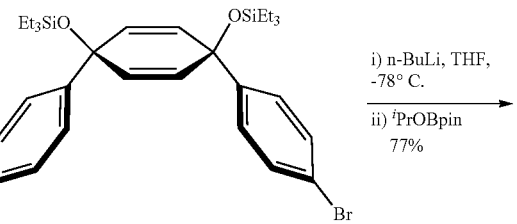

The product from Example 37 (3.00 g, 4.61 mmol, 1 equiv) was dissolved in tetrahydrofuran (50 mL) and cooled to −78° C. n-BuLi (3.9 mL, 9.7 mmol, 2.1 equiv, 2.5 M in hexanes) was added followed immediately by 2-isopropoxy-4,4,5,5-tetramethyl-1,3,2-dioxaborolane (2.1 mL, 1.9 g, 10 mmol, 2.2 equiv). The reaction was stirred for 30 min and warmed to room temperature. The reaction was quenched with water (20 mL) and extracted with ethyl acetate (3×20 mL). The combined extracts were washed with brine (20 mL), dried over anhydrous sodium sulfate, and solvent was removed under reduced pressure to yield an oil. The oil was mixed with an equal amount of ethanol and placed in the freezer until crystals formed, which was filtered to yield a white crystalline powder (2.65 g, 77%). $^1$H NMR (500 MHz, Chloroform-d) δ 7.73 (d, J=7.6 Hz, 4H), 7.37 (d, J=7.7 Hz, 4H), 5.99 (s, 4H), 1.37 (s, 24H), 0.95 (t, J=7.8 Hz, 18H), 0.62 (q, J=7.8 Hz, 12H). $^{13}$C NMR (126 MHz, CDCl3) δ 149.08, 134.69, 131.41, 125.18, 83.72, 71.56, 24.89, 7.04, 6.45. HRMS (ESI-TOF) (m/z): [M+Na]+ calculated for $C_{42}H_{66}B_2NaO_6Si_2$, 767.4482; found, 767.4514.

Example 43

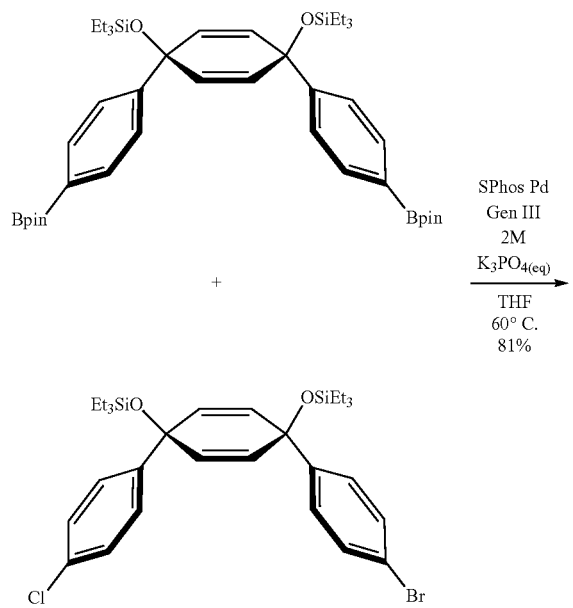

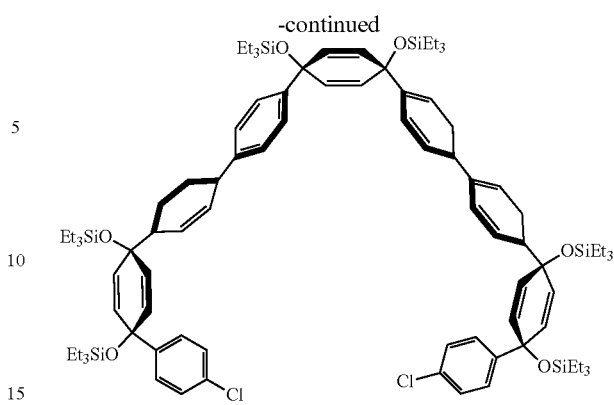

The product from Example 42 (250 mg, 0.34 mmol, 1 equiv), 1 (407 mg, 0.67 mmol, 2 equiv), and PPh$_3$ Pd Gen III (11 mg, 0.017 mmol, 0.05 equiv) were dissolved in tetrahydrofuran (6.7 mL) and heated to 60° C. K$_3$PO$_4$ (0.67 mL, 2 M in deionized water) was added and the reaction was left overnight. The next day, the reaction was cooled to room temperature, filtered through Celite® while rinsing with ethyl acetate (15 mL), and dried over anhydrous sodium sulfate. The solvent was removed under reduced pressure and the product was purified by automated flash silica column chromatography (0% to 50% dichloromethane in hexanes) to yield a white solid (421 mg, 81%). $^1$H NMR (500 MHz, Chloroform-d) δ 7.50 (d, J=8.2 Hz, 8H), 7.42 (d, J=8.0 Hz, 4H), 7.36 (d, J=7.9 Hz, 4H), 7.28 (d, 4H), 7.22 (d, J=7.8 Hz, 4H), 6.04 (s, 4H), 6.03 (d, J=8.8 Hz, 4H), 5.95 (d, J=9.7 Hz, 4H), 0.94 (q, J=8.3 Hz, 54H), 0.67-0.57 (m, 36H). $^{13}$C NMR (126 MHz, CDCl3) 145.18, 144.83, 144.66, 139.70, 139.48, 132.99, 131.80, 131.52, 131.16, 128.23, 127.33, 126.78, 126.74, 126.33, 126.22, 71.38, 71.28, 71.18, 7.09, 7.06, 7.05, 6.51, 6.49, 6.45. HRMS (ESI-TOF) (m/z): [M+Na]+ calculated for $C_{90}H_{126}Cl_2NaO_6Si_6$, 1563.7445; found, 1563.7485.

Example 44

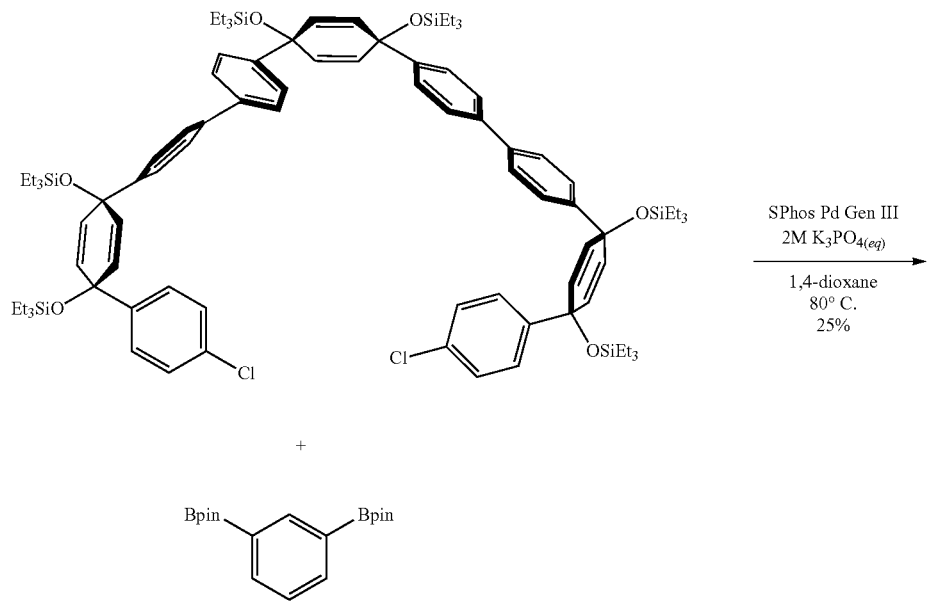

-continued

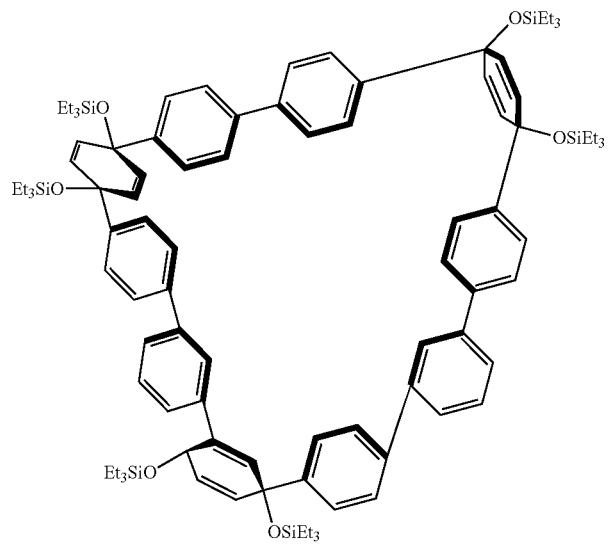

The product from Example 43 (245 mg, 0.16 mmol, 1 equiv), the product from Example 33 (52 mg, 0.16 mmol, 1 equiv), and SPhos Pd Gen III (12 mg, 0.016 mmol, 0.1 equiv) were dissolved in 1,4-dioxane (80 mL) and heated to 80° C. $K_3PO_4$ (8 mL, 2M in deionized water) was added and the reaction was stirred for 3 h. The reaction mixture was filtered through Celite® and dried over anhydrous sodium sulfate. Solvent was removed to yield a brown oil, which was purified by automated flash silica column chromatography (0% to 100% dichloromethane in hexanes) to yield a white solid. The product was purified by recycling gel permeation chromatography (chloroform) to yield a white solid (62 mg, 25%). $^1$H NMR (500 MHz, Chloroform-d) δ 7.74 (s, 1H), 7.58-7.52 (m, 6H), 7.52-7.46 (m, 9H), 7.46-7.39 (m, 8H), 7.35 (d, J=8.3 Hz, 4H), 6.11 (d, J=9.8 Hz, 4H), 6.04-5.97 (m, 7H), 1.03-0.87 (m, 54H), 0.71-0.53 (m, 36H). $^{13}$C NMR (126 MHz, CDCl3) δ 145.29, 145.22, 144.93, 141.64, 140.39, 139.46, 139.42, 131.80, 131.51, 131.36, 131.24, 129.12, 127.25, 126.75, 126.64, 126.51, 126.38, 126.13, 126.10, 71.57, 71.15, 71.11, 7.10, 7.07, 7.05, 6.49, 6.45.

Example 45

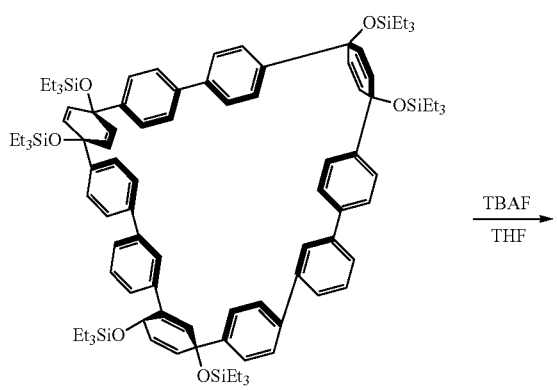

TBAF / THF

-continued

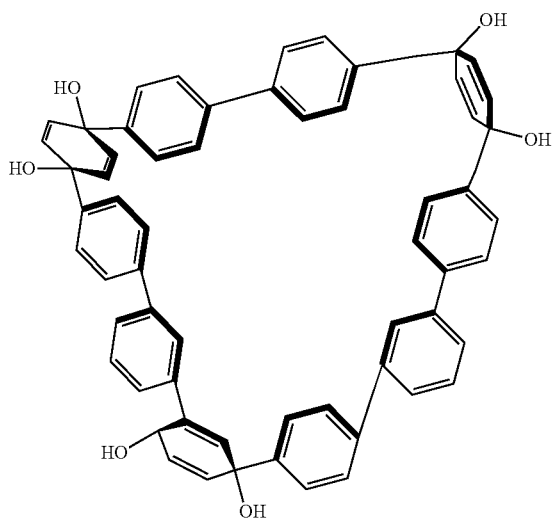

Tetrahydrofuran (1.3 mL) was added to the product from Example 44 (20 mg, 13 µmol, 1 equiv) and the vial was equipped with a stir bar and septa. Tetra-n-butylammonium fluoride (120 µL, 1 mmol, 9 equiv, 1 M in tetrahydrofuran) was added to the reaction flask and stirred for 1 h at room temperature. The reaction was quenched with deionized water (1 mL) and the tetrahydrofuran was removed under reduced pressure. This mixture was filtered through a Buchner funnel, washed with deionized water and dichloromethane yielding a white solid. This solid was used as is for the next reaction.

Example 46

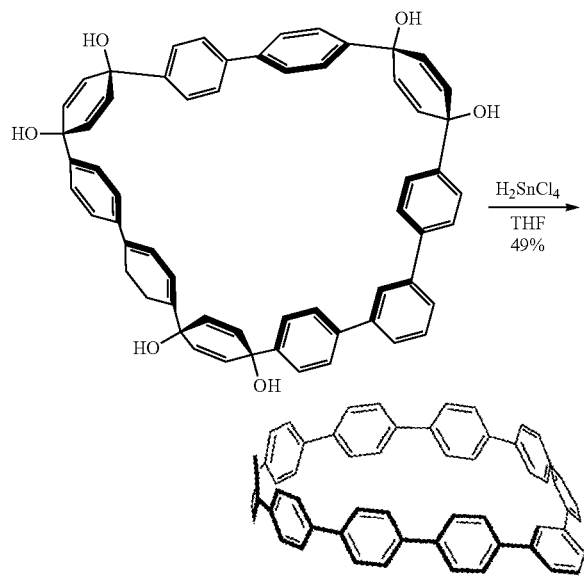

The crude product from Example 45 was dissolved in tetrahydrofuran (300 μL) and to it was added a solution of tin(II) dichloride monohydrate (9.5 mg, 42 μmol, 3.3 eq) and concentrated aqueous hydrochloric acid (6.7 μL, 80 μmol, 6.3 eq) in THF (320 μL). The reaction was stirred at room temperature for 1 h and quenched with a 1 M aqueous solution of NaOH (1 mL). This mixture was extracted with dichloromethane (3×3 mL) and the combined extracts were dried over anhydrous sodium sulfate. The solvent was removed under reduced pressure and the product was purified by preparative thin layer chromatography on alumina (50% dichloromethane in hexanes) to yield [10]mCPP as a white solid (25 mg, 49%). $^1$H NMR (600 MHz, Chloroform-d) δ 7.62 (d, J=8.3 Hz, 8H), 7.60-7.56 (m, 19H), 7.55-7.50 (m, 8H), 7.43 (d, J=7.9 Hz, 4H), 6.86 (s, 1H). $^{13}$C NMR (151 MHz, CDCl3) δ 142.37, 141.12, 139.51, 139.22, 138.49, 138.32, 138.20, 138.13, 138.00, 137.93, 133.39, 129.03, 128.54, 127.65, 127.53, 127.49, 127.45, 127.44, 127.33, 127.24, 127.12, 124.26. LRMS (MALDI) (m/z): [M]+ calculated for $C_{60}H_{40}$, 760.3125; found, 760.244.

Example 47

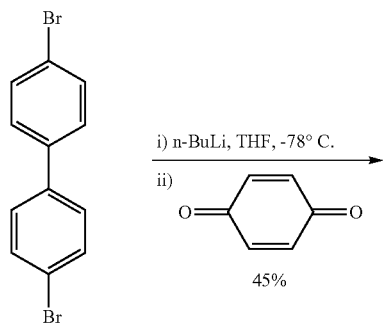

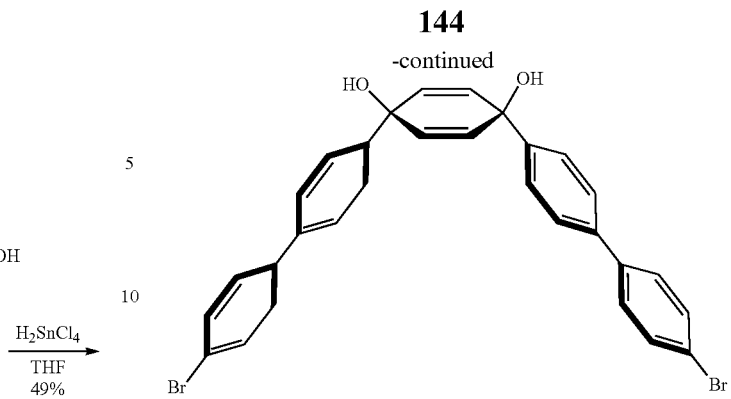

4,4'-Dibromobiphenyl (19 g, 0.061 mol, 3.3 eqiv) was added to a 1000 mL round bottom flask equipped with a stir bar. The reaction flask was capped with a septa and the round bottom flask was evacuated and purged with nitrogen. Tetrahydrofuran (370 mL) was added to the reaction flask and cooled for 30 min at −78° C. n-BuLi (24.1 mL, 0.11 mol, 1.05 equiv, 2.3 M in hexanes) was added to the reaction mixture dropwise over 25 min. The light brown solution was stirred for 15 min producing a white precipitate in a brown solution. p-benzoquinone (14.5 mL, 0.10 mol, 1 equiv) was added to a 9 mL test tube and capped with a septa in order to weigh due to pungent odor. This was added portion-wise by removing the septa from the reaction flask (while a large flow of nitrogen was still flowing into the flask). As the benzoquinone was added, the reaction mixture turns blue momentarily before returning to brown. Benzoquinone was added until the blue color remained (2.3 g total). The reaction was stirred at −78° C. for 3 h. The reaction was quenched with deionized water (160 mL) at −78° C. The reaction mixture was warmed to room temperature. The product was extracted with ethyl acetate (3×200 mL) and washed with brine (3×100 mL). The organic layers were dried over sodium sulfate, decanted and concentrated to yield the crude product as a dark orange solid. This was purified by automated flash silica gel chromatography (10% to 60% ethyl acetate in hexanes). The crude product was used as is for the next reaction.

Example 48

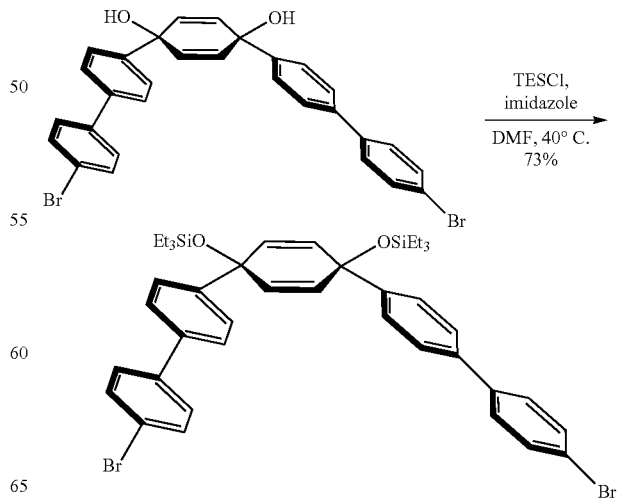

The crude product from Example 47 (4.0 g, 7.0 mmol, 1 equiv) and imidazole (1.9 g, 28 mmol, 4 equiv) were added to a 250 mL round bottom flask equipped with a stir bar and septum. Dimethylformamide (35 mL) was added to the flask followed by triethylsilyl chloride (3.8 mL, 23 mmol, 1.2 equiv). The reaction mixture was heated to 40° C. in an oil bath and stirred overnight. The reaction mixture was cooled to room temperature and quenched with a saturated solution of sodium bicarbonate (30 mL). The product was extracted with ethyl acetate (3×100 mL) and washed with 5% lithium chloride solution in water (5×60 mL). The organic layers were dried over sodium sulfate and concentrated to yield the crude product as a brown solid. The product was purified by automated flash silica gel chromatography (0% to 10% ethyl acetate in hexanes) to give a pale yellow solid (4.10 g, 39% 2 steps). $^1$H NMR (600 MHz, Chloroform-d) δ 7.53 (d, J=8.4 Hz, 4H), 7.47-7.41 (m, 12H), 6.04 (s, 4H), 0.95 (t, J=7.9 Hz, 18H), 0.63 (q, J=7.9 Hz, 12H). $^{13}$C NMR (151 MHz, CDCl3) δ 145.55, 139.66, 138.79, 131.83, 131.51, 128.62, 126.65, 126.45, 121.50, 71.32, 7.07, 6.46. LRMS (MALDI) (m/z): [M]+ calculated for $C_{42}H_{50}Br_2O_2Si_2$, 802.17; found, 802.24.

Example 49

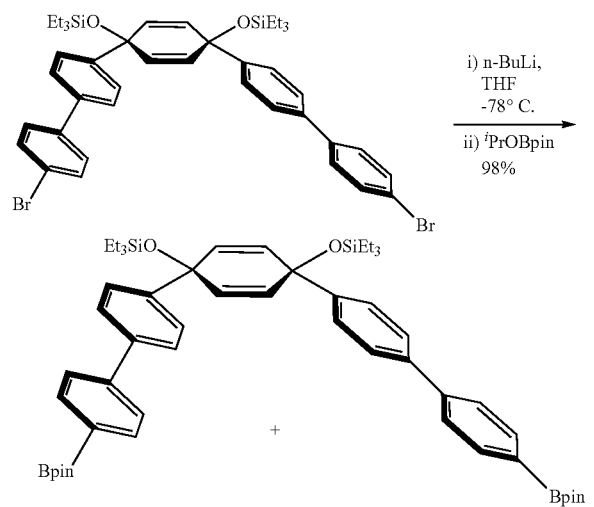

The product from Example 48 (3.0 g, 3.74 mmol, 1.0 eqiv) was added to a 100 mL round bottom flask equipped with a stir bar. The reaction flask was capped with a septa evacuated and refilled with nitrogen. Tetrahydrofuran (19 mL) was added to the reaction flask and the mixture was cooled for 30 min at −78° C. n-BuLi (3.4 mL, 8.2 mmol, 2.2 equiv, 2.4 M in hexanes) was added to the reaction mixture dropwise, followed by the dropwise addition of 2-Iso-propoxy-4,4,5,5-tetramethyl-1,3,2-dioxaborolane (3.0 mL, 14.9 mmol, 4 equiv) and the reaction was stirred at −78° C. for 1 h. The reaction was quenched with deionized water (30 mL) at −78° C. and warmed to room temperature. The product was extracted with ethyl acetate (3×50 mL) and washed with brine (3×20 mL). The organic layers were dried over sodium sulfate and concentrated to yield a yellow solid (3.3 g, 98%). $^1$H NMR (600 MHz, Chloroform-d) δ 7.87 (d, J=7.7 Hz, 4H), 7.63-7.41 (m, 12H), 6.04 (s, 4H), 0.96 (t, J=7.8 Hz, 18H), 0.64 (q, J=8.1 Hz, 12H). $^{13}$C NMR (151 MHz, CDCl3) δ 145.52, 143.50, 139.86, 135.33, 131.59, 127.02, 126.41, 83.84, 71.43, 24.94, 24.88, 7.17, 6.56.

Example 50

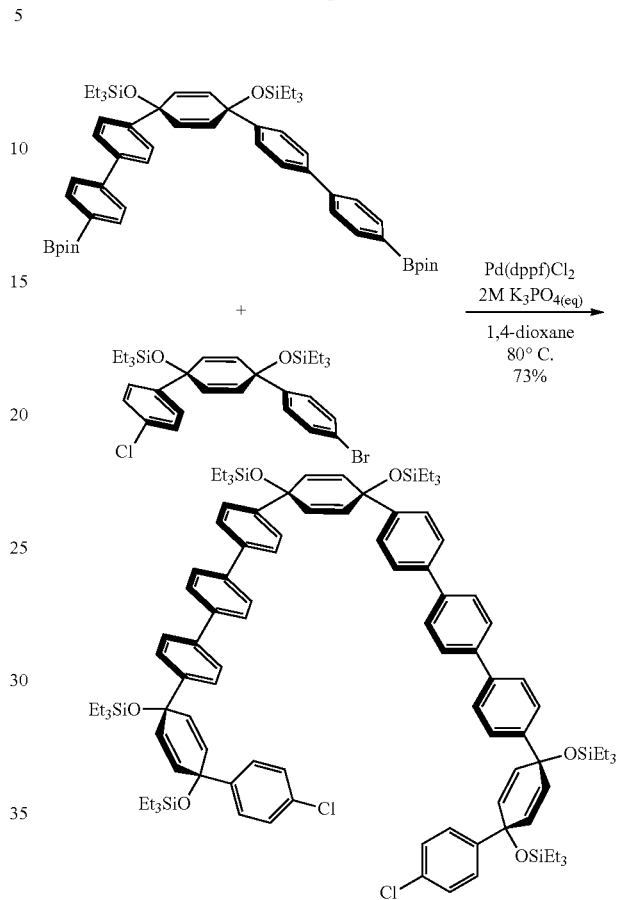

The product from Example 49 (85.8 mg, 0.22 mmol, 1 equiv), the product from Example 18 (270.3 mg, 0.45 mmol, 2 equiv) and Pd(dppf)$_2$Cl$_2$ (25.5 mg, 0.031 mmol, 0.07 equiv) were added to a 10 mL round bottom flask equipped with a stir bar. The flask was evacuated (5 min) and purged with nitrogen 5 times. 1,4-dioxane and 2 M aqueous K$_3$PO$_4$ were sparged with nitrogen for at least 1 h prior to use. The round bottom flask was equipped with a septa and 1,4-dioxane (2.2 mL) was added to the round bottom flask. The round bottom flask was heated to 80° C. over 5 min and K$_3$PO$_4$ (0.22 mL, 2 M in deionized water) was added. The reaction was stirred at 80° C. overnight. The reaction mixture was cooled to room temperature and filtered through a fritted suction funnel filled with Celite®. The round bottom flask was rinsed with dichloromethane, which was filtered through the Celite® plug. The filtrate was added to a separatory funnel along with deionized water (20 mL) and the product was extracted (3×20 mL) with dichloromethane. The organic layer was washed with brine (20 mL), dried over sodium sulfate and concentrated to yield the crude product as a brown solid. The product was purified by automated flash silica gel chromatography (5% to 25% dichloromethane in hexanes to yield a white solid (277 mg, 73%). $^1$H NMR (600 MHz, Chloroform-d) δ 7.65 (s, 8H), 7.55 (t, J=7.7 Hz, 8H), 7.46 (d, J=8.1 Hz, 4H), 7.39 (d, J=8.1 Hz, 4H), 7.30 (s, 4H), 7.23 (d, J=8.4 Hz, 4H), 6.09-6.02 (m, 8H), 5.97 (d, J=9.9 Hz, 4H), 0.99-0.92 (m, 54H), 0.67-0.59

(m, 36H). $^{13}$C NMR (151 MHz, CDCl3) δ 145.26, 144.97, 144.68, 139.72, 139.61, 139.57, 139.48, 133.02, 131.82, 131.58, 131.21, 128.76, 128.28, 127.41, 127.38, 126.78, 126.76, 126.43, 126.32, 71.44, 71.32, 71.19, 18.66, 11.28, 7.14, 7.11, 7.09, 6.53, 6.51, 6.47, 6.34. LRMS (MALDI) (m/z): [M]+ calculated for $C_{102}H_{134}C_{12}O_6Si_6$, 1693.82; found, 1694.838.

Example 51

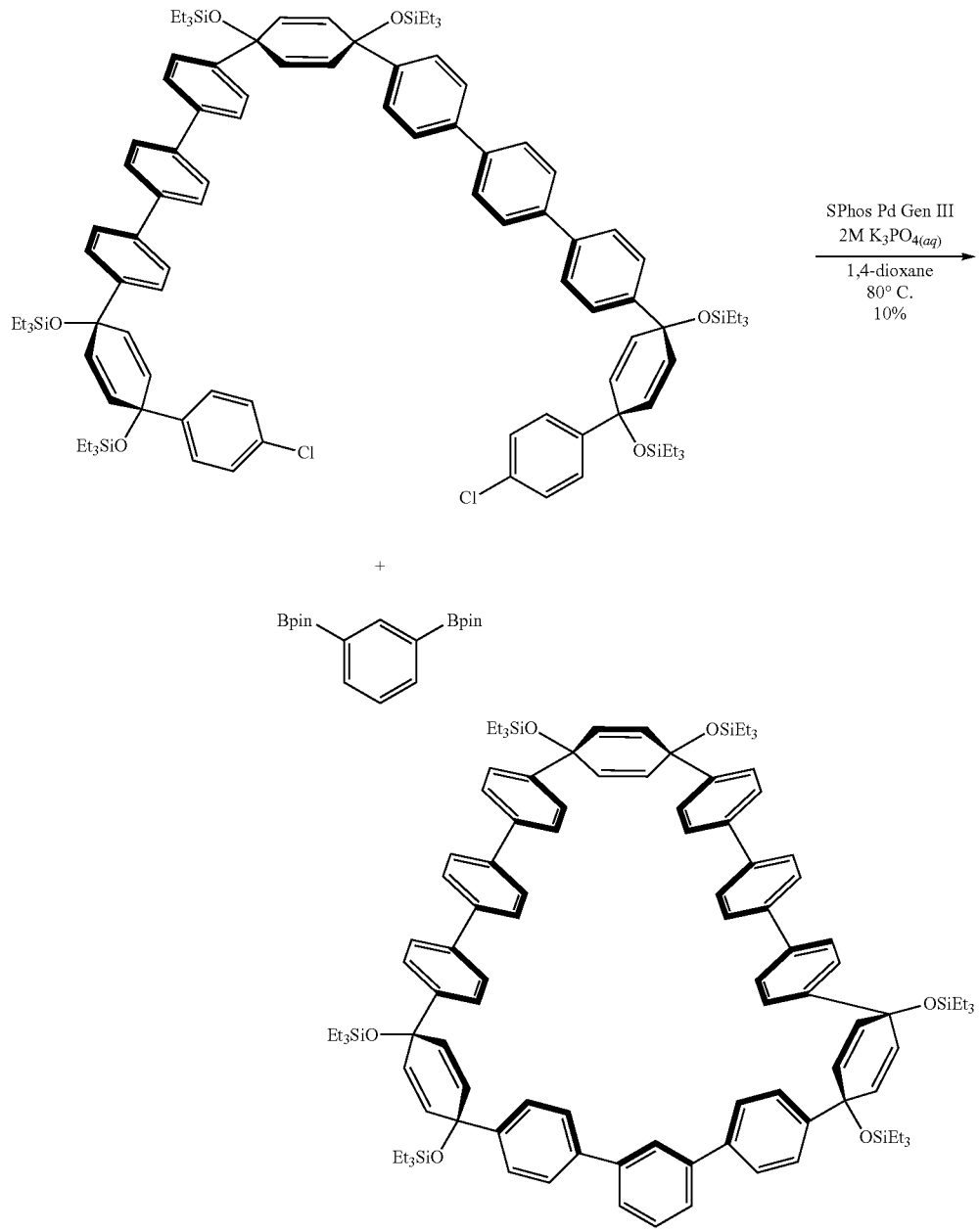

The product from Example 33 (34.7 mg, 0.11 mmol, 1 equiv), the product from Example 50 (101.3 mg, 0.054 mmol, 1.05 equiv) and Pd Sphos Gen III 3.6 mg, 0.0045 mmol, 0.1 equiv) were added to a 100 mL round bottom flask equipped with a stir bar. The flask was evacuated (5 min) and purged with nitrogen 5 times. 1,4-dioxane and aqueous 2 M $K_3PO_4$ were sparged for at least 1 h prior to use. The round bottom flask was equipped with a septum and 1,4-dioxane (33 mL) was added to the round bottom flask and the solution was sparged for 30 min. The round bottom flask was heated to 80° C. over 10 min and $K_3PO_4$ (0.33 mL, 2 M in deionized water) was added. The reaction was stirred at 80° C. overnight. The reaction mixture was cooled to room temperature and filtered through a fritted suction funnel filled with Celite®. The round bottom flask was rinsed with dichloromethane, which was also filtered through the Celite® plug. The filtrate was added to a separatory funnel along with deionized water (30 mL) and the product was extracted (3×30 mL) with dichloromethane. The organic layer was washed with brine (40 mL), dried over sodium sulfate and concentrated to yield a brown oil. The product was purified by flash silica column chromatography (0% to 30% dichloromethane in hexanes) followed by recycling gel permeation chromatography yielding a white solid (18 mg, 10%). ¹H NMR (600 MHz, Chloroform-d) δ 7.77 (t, J=1.7 Hz, 1H), 7.65 (d, J=3.5 Hz, 2H), 7.62-7.45 (m, 25H), 7.36 (d, J=8.1 Hz, 8H), 6.16 (d, J=9.7 Hz, 4H), 6.05 (s, 4H), 6.00 (d, J=9.8 Hz, 4H), 1.00 (t, J=7.9 Hz, 18H), 0.97 (t, J=7.9 Hz, 18H), 0.92 (t, J=7.9 Hz, 18H), 0.71 (q, J=7.9 Hz, 12H), 0.65 (q, J=7.9 Hz, 12H), 0.57 (q, J=7.9 Hz, 12H). ¹³C NMR (151 MHz, CDCl3) δ 145.33, 145.06, 144.75, 141.82, 140.68, 139.63, 139.48, 139.42, 139.27, 132.07, 131.64, 131.10, 127.39, 127.37, 127.30, 127.28, 126.74, 126.61, 126.56, 126.53, 126.18, 71.80, 71.72, 71.01, 7.14, 7.10, 7.05, 6.50, 6.48.

Example 52

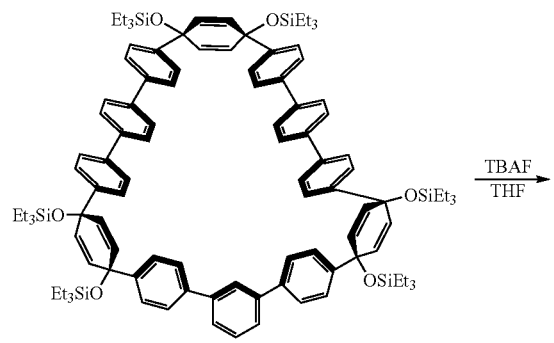

Tetrahydrofuran (0.11 mL) was added to the product from Example 51 (18.2 mg, 0.01 mmol, 1 equiv) and the vial was equipped with a stir bar and septa. Tetra-n-butylammonium fluoride (0.11 mL, 0.1 mmol, 10 equiv, 1 M in tetrahydrofuran) was added to the reaction flask and this was stirred for 2 h at room temperature. The reaction was quenched with deionized water (5 mL) causing the product to precipitate. The resulting solution was filtered in a Buchner funnel, washed with deionized water and dichloromethane yielding a white solid. The crude product was used as is for the following reaction.

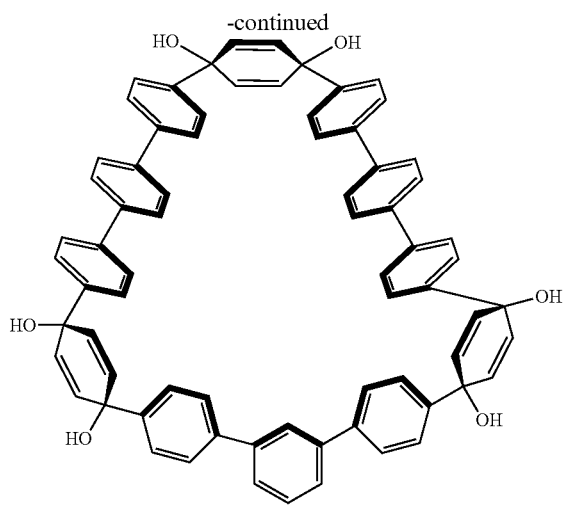

Example 53

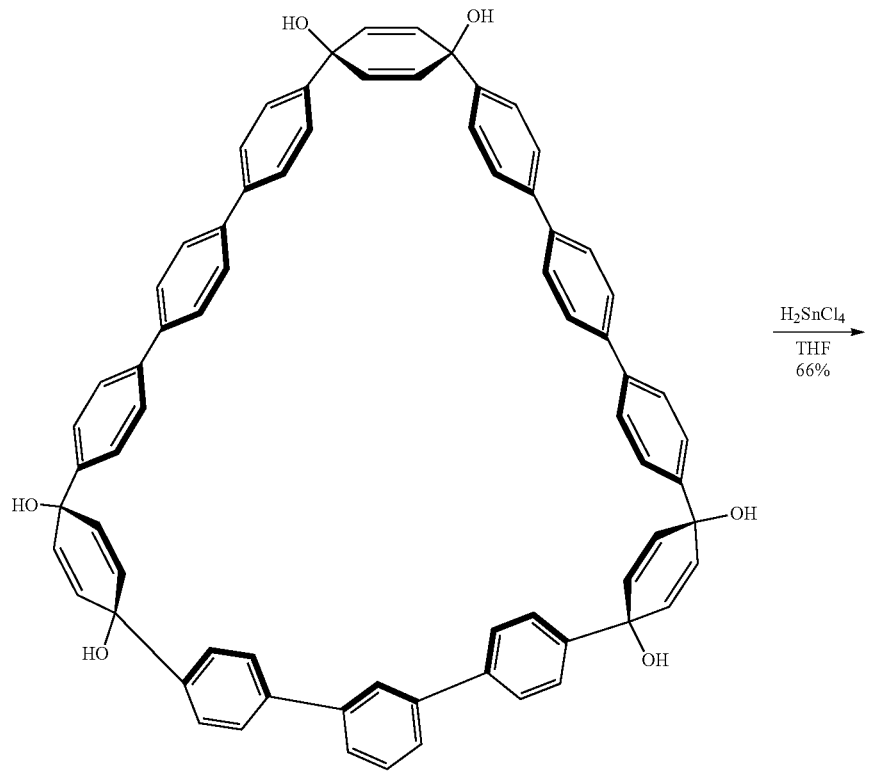

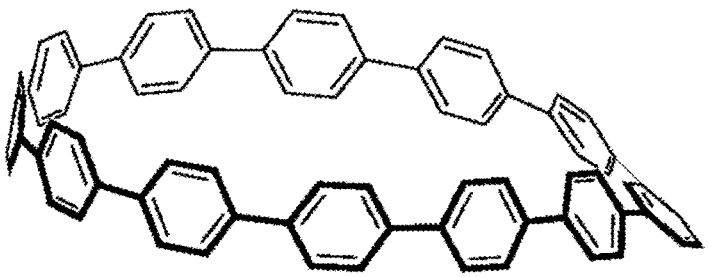

SnCl$_2$*H$_2$O (180.6 mg, 0.80 mmol) was added to a 100 mL round bottom flask equipped with a stir bar and septum. Tetrahydrofuran (20 mL) was added to the flask followed by hydrochloric acid (0.13 mL, 1.6 mmol, 12 M). This was stirred at room temperature for 30 min. H$_2$SnCl$_2$ solution (0.9 mL, 0.04 mmol, 3.3 equiv, 0.04 M) was added to the scintillation vial containing the product from Example 52 (11.1 mg, 0.01 mmol, 1 equiv) and was stirred for 1 h at room temperature. The reaction was quenched with saturated sodium bicarbonate (5 mL). The filtrate was transferred to a separatory funnel and the product was extracted with ethyl acetate (3×7 mL). The organic layers were washed with brine (10 mL), dried over sodium sulfate and concentrated to give the crude product as a yellow solid. The product was purified by preparative thin layer chromatography on alumina (50% dichloromethane in hexanes) and recycling gel permeation chromatography to give [12]mCPP as a pale yellow solid (0.5 mg, 5% 2 steps). $^1$H NMR (600 MHz, Chloroform-d) δ 7.68-7.56 (m, 40H), 7.56-7.53 (m, 3H), 7.51 (d, J=8.4 Hz, 4H), 7.12 (d, J=1.8 Hz, 1H). $^{13}$C NMR (151 MHz, CDCl3) δ 138.55, 128.40, 127.64, 127.45, 127.39, 127.37, 127.31, 127.22, 127.14, 124.63. LRMS (MALDI) (m/z): [M]+ calculated for C$_{72}$H$_{48}$, 912.3751; found, 912.329.

Example 54

In this example, the strain of meta-substituted nanohoop compounds (wherein the meta-substitution refers to the fact that one of the rings of the nanohoop skeleton is connected to other rings of the nanohoop skeleton via bonds that are meta-substituted relative to each other) was evaluated. The most strained of the meta-substituted compounds, [5]mCPP, has a 102 kcal/mol of strain resulting in 20 kcal/mol of strain per phenylene. This places it below [5]CPP (119 kcal/mol) and above [6]CPP (96 kcal/mol) in terms of strain (the [5]CPP and [6]CPP referring to nanohoop compounds wherein all rings of the nanohoop skeleton are connected to one another via bonds that are para-substituted relative to one another). The inherent strain for the series ranges from 43-102 kcal/mol, which equates to 4-20 kcal/mol strain per aryl ring (Table 9).

TABLE 9

| [n]mCPP | Strain energy (kcal/mol) | Strain per aryl ring (kcal/mol) | Dihedral angle (°) |
|---|---|---|---|
| 5 | 102 (119) | 20 (24) | 23 |
| 6 | 78 (96) | 13 (16) | 25 |

TABLE 9-continued

| [n]mCPP | Strain energy (kcal/mol) | Strain per aryl ring (kcal/mol) | Dihedral angle (°) |
|---|---|---|---|
| 7 | 66 (84) | 9 (12) | 28 |
| 8 | 57 (72) | 7 (9) | 30 |
| 10 | 51 (58) | 5 (6) | 31 |
| 12 | 43 (48) | 4 (4) | 34 |

Example 55

Figure 9:
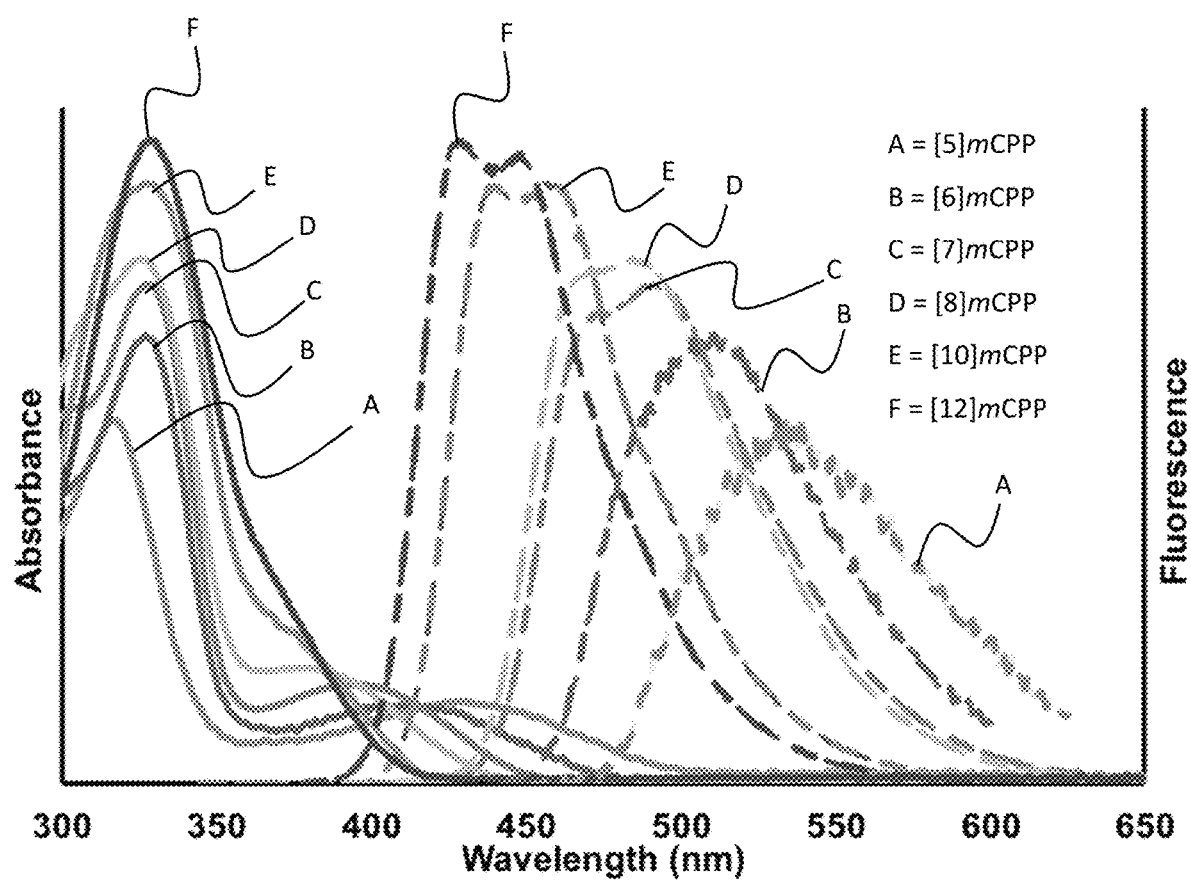
FIG. 9 is a graph of absorbance and fluorescence as a function of wavelength showing absorption spectra (solid lines) and emission spectra (dotted lines) for different sized nanohoop compound embodiments comprising meta-substitution.
Figure 10A:
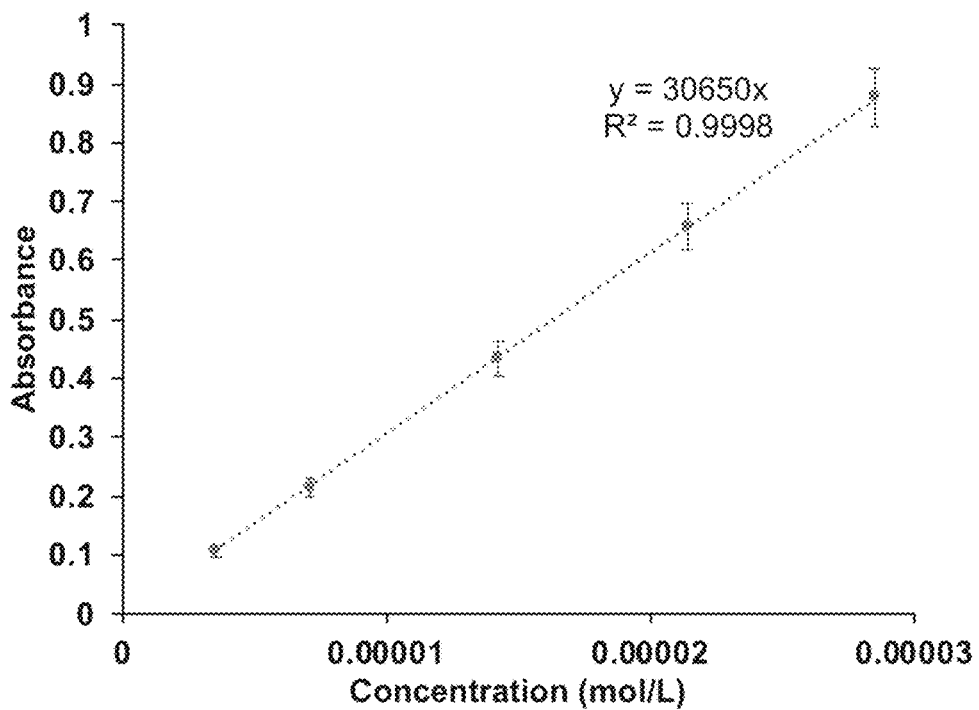
FIGS. 10A and 10B are graphs showing the extinction coefficient determination of a nanohoop compound embodiment ([5]mCPP) comprising a ring that is attached to other rings of the nanohoop compound via bonds that are meta-substituted relative to each other at the absorbance maxima (FIG. 10A) and HOMO→LUMO transition (FIG. 10B).
Figure 10B:
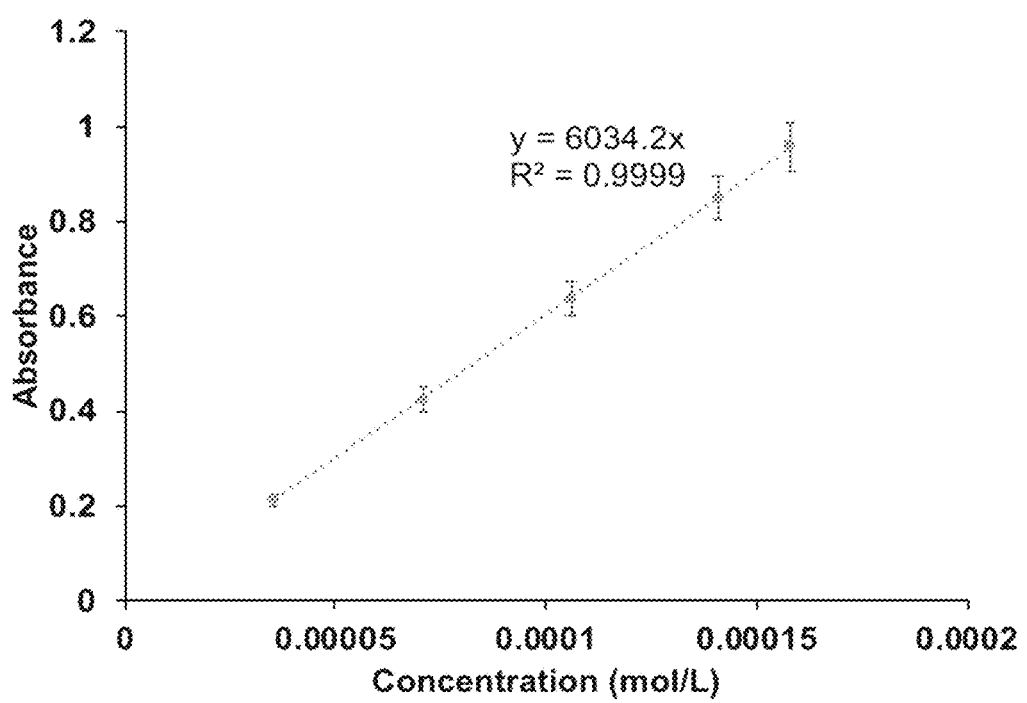
Figure 11A:
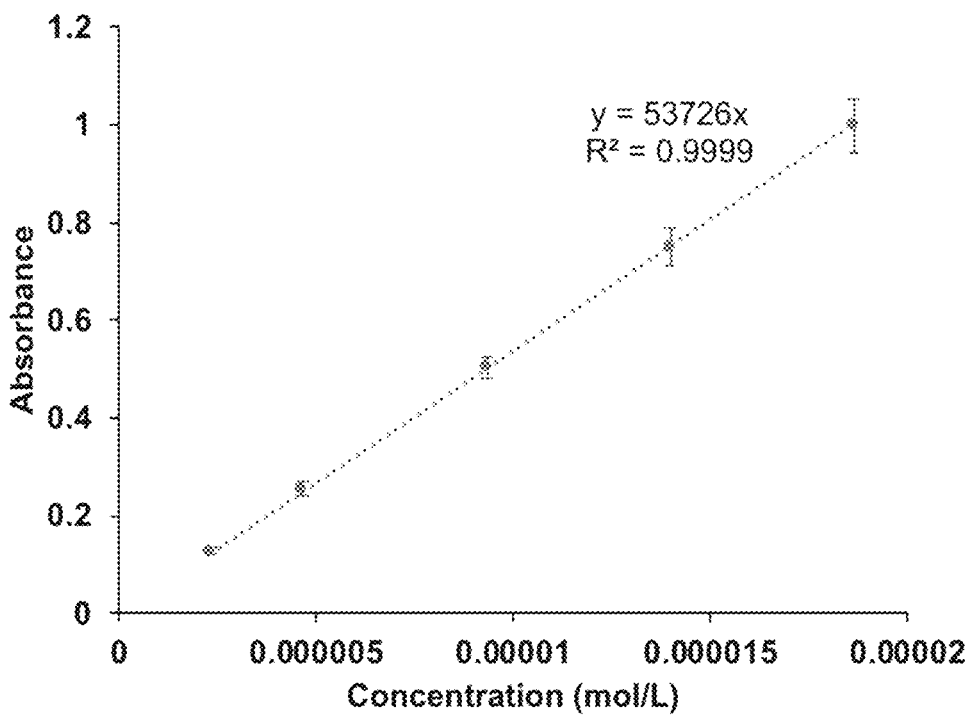
FIGS. 11A and 11B are graphs showing the extinction coefficient determination at the absorbance maxima (FIG. 11A) and HOMO→LUMO transition (FIG. 11B) of a nanohoop compound embodiment ([6]mCPP) comprising a ring that is attached to other rings of the nanohoop compound via bonds that are meta-substituted relative to each other.
Figure 11B:
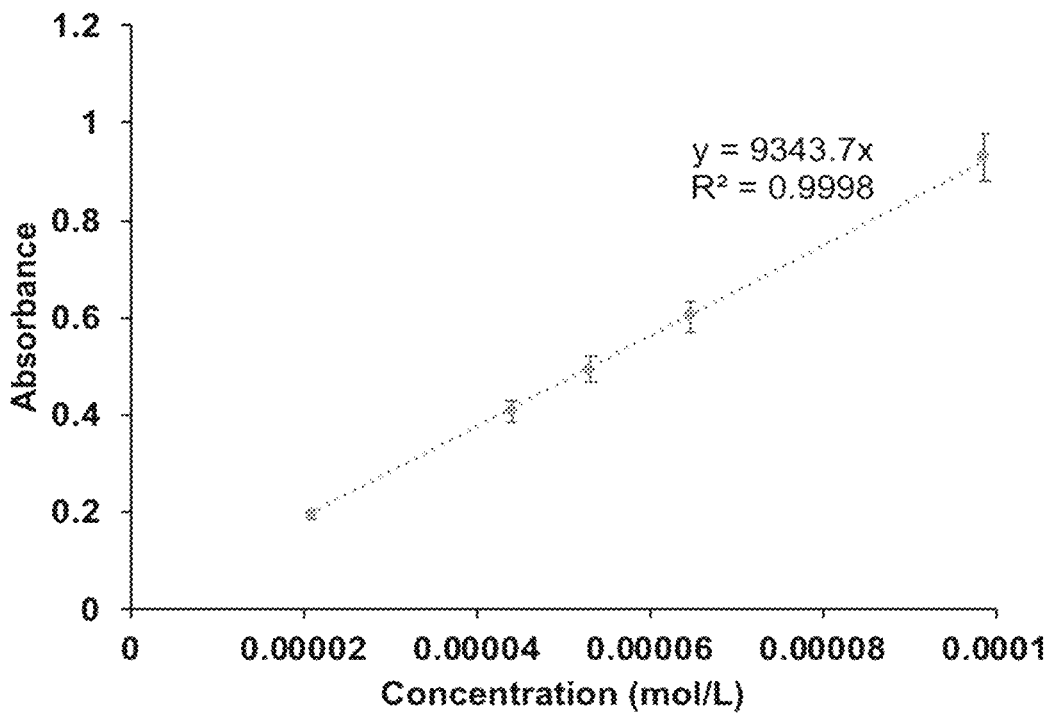
Figure 12A:
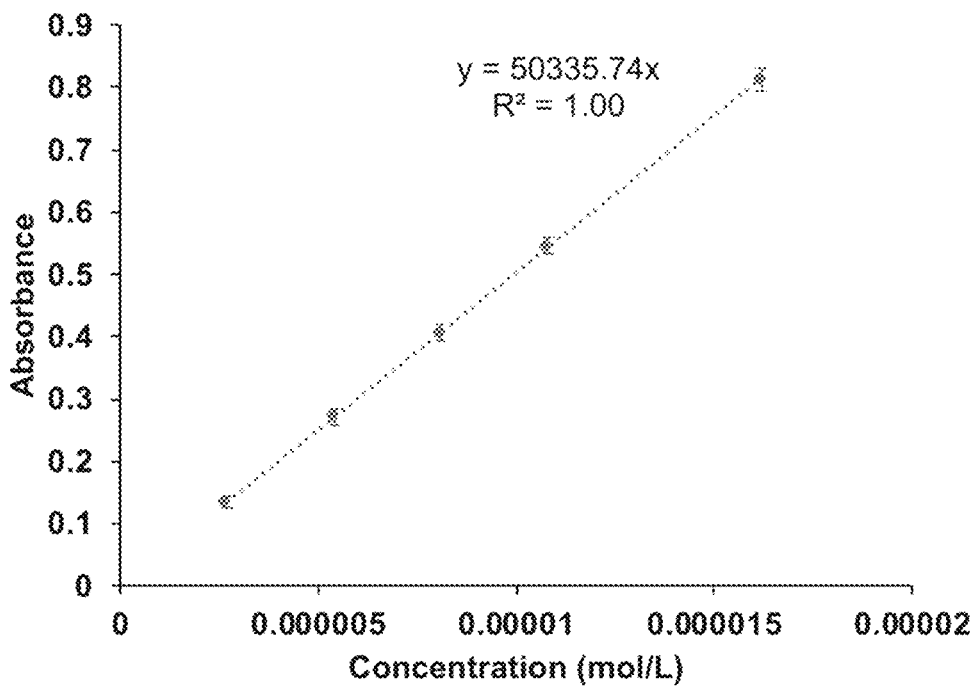
FIGS. 12A and 12B are graphs showing the extinction coefficient determination at the absorbance maxima (FIG. 12A) and HOMO→LUMO transition (FIG. 12B) of a nanohoop compound embodiment ([7]mCPP) comprising a ring that is attached to other rings of the nanohoop compound via bonds that are meta-substituted relative to each other.
Figure 12B:
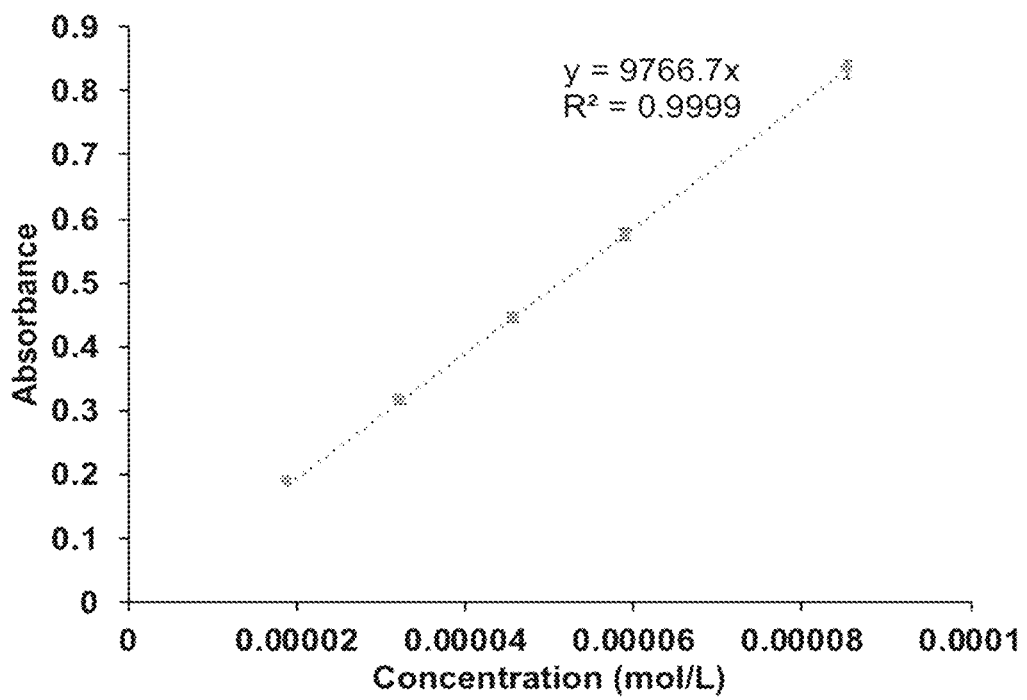
Figure 13A:
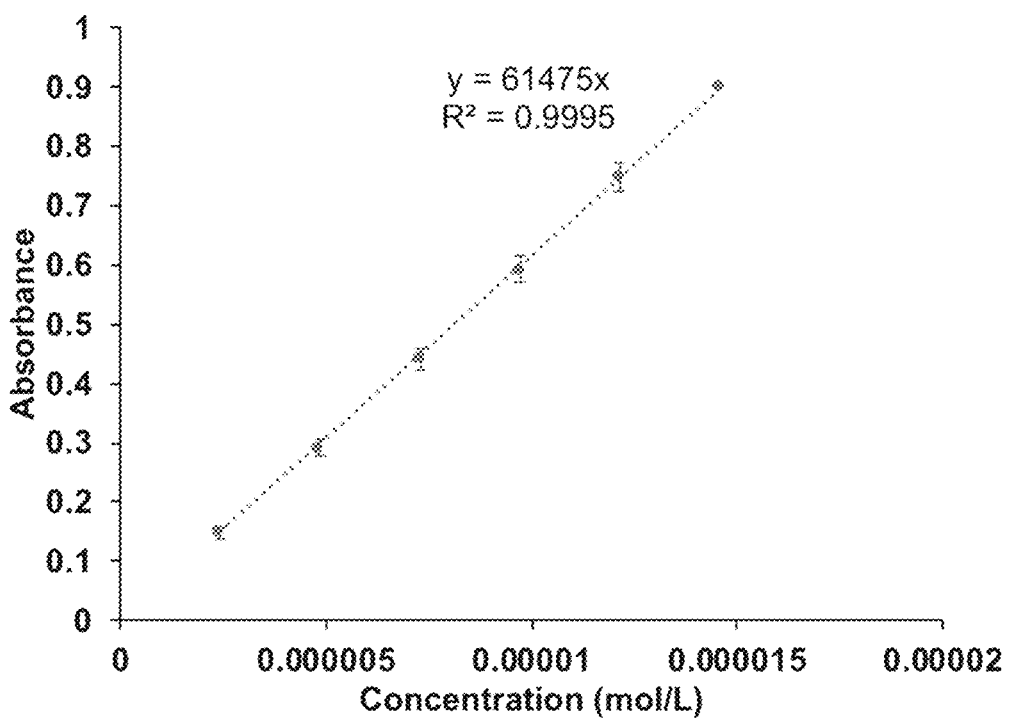
FIGS. 13A and 13B are graphs showing the extinction coefficient determination at the absorbance maxima (FIG. 13A) and HOMO→LUMO transition (FIG. 13B) of a nanohoop compound embodiment ([8]mCPP) comprising a ring that is attached to other rings of the nanohoop compound via bonds that are meta-substituted relative to each other.
Figure 13B:
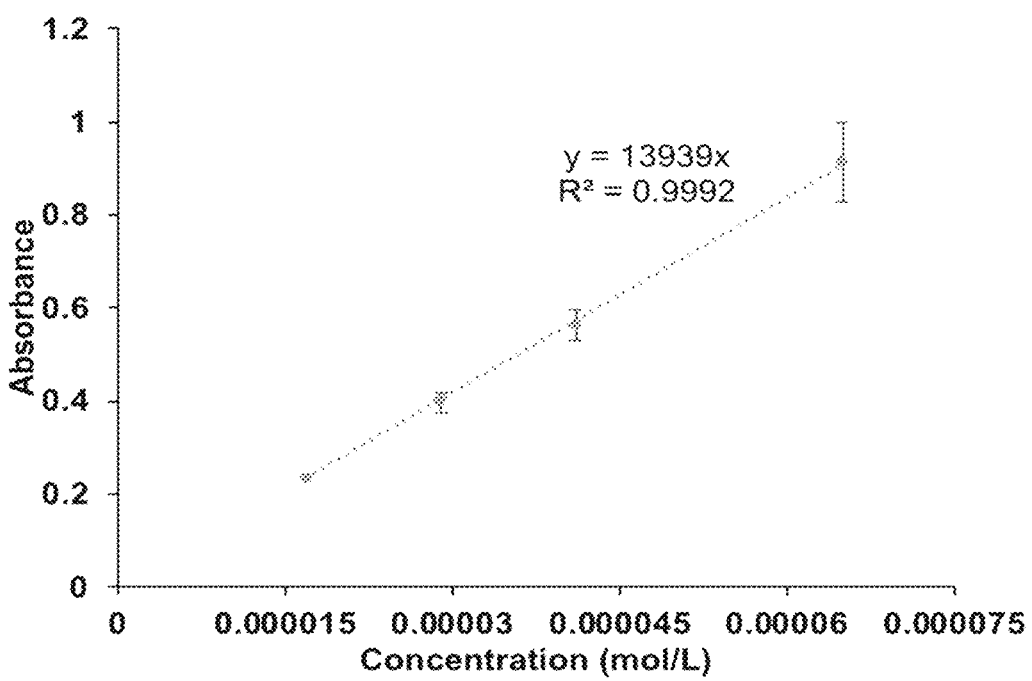
Figure 14:
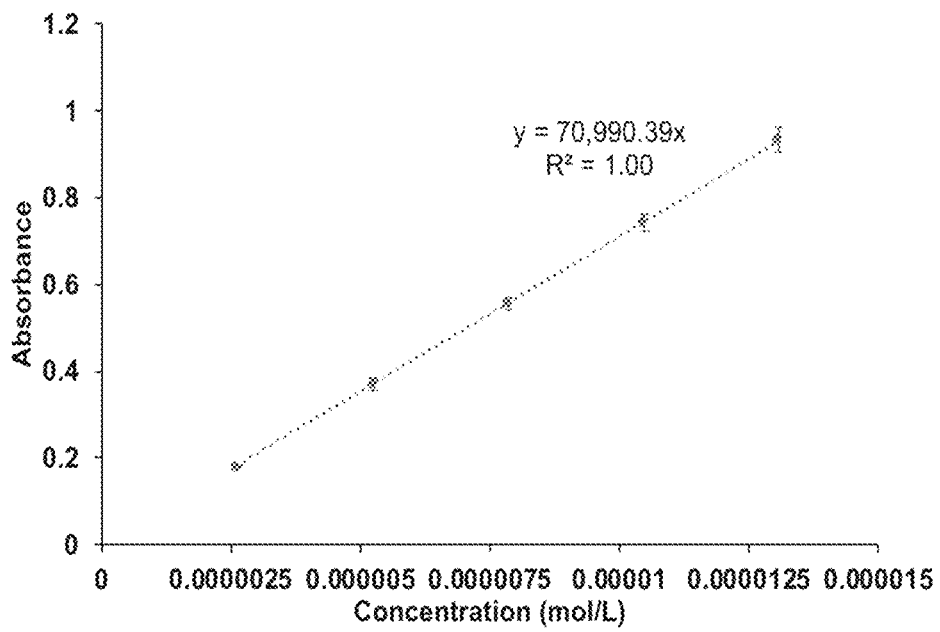
FIG. 14 is a graph showing the extinction coefficient determination at the absorbance maxima of a nanohoop compound embodiment ([10]mCPP) comprising a ring that is attached to other rings of the nanohoop compound via bonds that are meta-substituted relative to each other.
Figure 15:
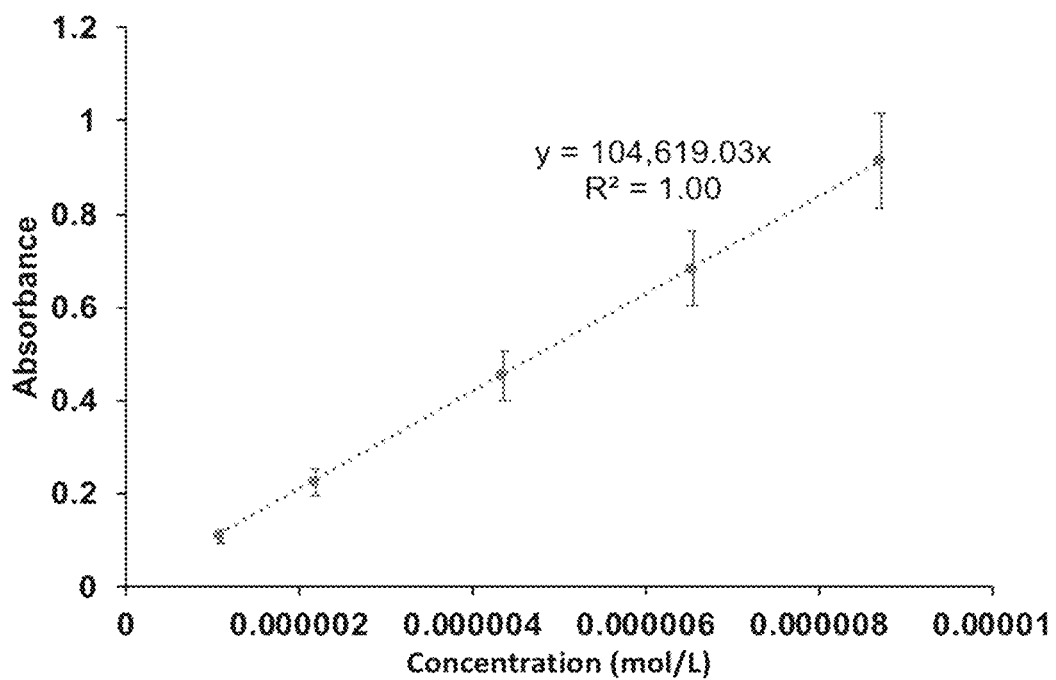
FIG. 15 is a graph showing the extinction coefficient determination at the absorbance maxima of a nanohoop compound embodiment ([12]mCPP) comprising a ring that is attached to other rings of the nanohoop compound via bonds that are meta-substituted relative to each other.

In this example, the photophysical properties of nanohoop compound embodiments comprising meta-substitution (wherein the meta-substitution refers to the fact that one of the rings of the nanohoop skeleton is connected to other rings of the nanohoop skeleton via bonds that are meta-substituted relative to each other) was evaluated. It was determined that disrupting the conjugation of the nanohoop allows the HOMO→LUMO absorption and "turns on" the fluorescence in the smaller sizes (e.g., 6-membered and 5-membered nanohoops). The absorption and emission data as well as extinction coefficients and quantum yields were collected. As seen in FIG. 9, the nanohoops have a common absorption and a red-shifting emission as the size of the hoop decreases. Two absorption transitions can be seen in for the smaller sizes, but the second transition blue-shifts and overlaps with the absorption at 328 nm for [10]- and [12]mCPP. The extinction coefficient of the higher energy transition is larger than that of the lower energy transition in all cases (Table 10). The series shows decreasing, but never vanishing, fluorescence with quantum yields ranging from 0.01 for [5]mCPP to 0.77 for [12]mCPP. Graphs showing the extinction coefficient determination of [5]mCPP at the absorbance maxima and HOMO→LUMO transition are provided in FIGS. 10A and 10B, respectively. Graphs showing the extinction coefficient determination of [6]mCPP at the absorbance maxima and HOMO→LUMO transition are provided in FIGS. 11A and 11B, respectively. Graphs showing the extinction coefficient determination of [7]mCPP at the absorbance maxima and HOMO→LUMO transition are provided in FIGS. 12A and 12B, respectively. Graphs showing the extinction coefficient determination of [8]mCPP at the absorbance maxima and HOMO→LUMO transition are provided in FIGS. 13A and 13B, respectively. Graphs showing the extinction coefficient determination of [10]mCPP and [12]mCPP at the absorbance maxima are provided in FIGS. 14 and 15, respectively.

TABLE 10

| [n]mCPP | Max Abs (nm) | $\varepsilon_{Amax}$ ($M^{-1}cm^{-1}$) | Emission (nm) | $\Phi_{Amax}$ | $\varepsilon_{Amax} \times \Phi_{Amax}$ | CPP $\varepsilon \times \Phi$ |
|---|---|---|---|---|---|---|
| 5 | 316 | $3.1 \times 10^4 \pm 0.2$ | 534 | 0.014 | $4.2 \times 10^2$ | 0 |
| 6 | 328 | $5.4 \times 10^4 \pm 0.3$ | 510 | 0.224 | $1.2 \times 10^4$ | 0 |
| 7 | 328 | $5.1 \times 10^4 \pm 0.09$ | 491 | 0.450 | $2.3 \times 10^4$ | $4.8 \times 10^2$ |
| 8 | 326 | $6.2 \times 10^4 \pm 0.9$ | 484 | 0.595 | $3.7 \times 10^4$ | $1.0 \times 10^4$ |
| 10 | 328 | $7.1 \times 10^4 \pm 0.2$ | 456 | 0.726 | $5.2 \times 10^4$ | $8.5 \times 10^4$ |
| 12 | 328 | $1.0 \times 10^5 \pm 0.1$ | 429 | 0.769 | $7.7 \times 10^4$ | $1.4 \times 10^5$ |

The HOMO→LUMO transition of [n]CPPs (that is, nanohoops that do not comprise at least one ring of the nanohoop skeleton that is connected to other rings of the nanohoop skeleton via bonds that are meta-substituted relative to each other and instead comprise rings that are all para-substituted with respect to one another) is Laporte forbidden due to conservation of orbital symmetry of the ground and excited state. The para-substituted CPPs are therefore excited through HOMO→LUMO+1 and HOMO→LUMO+2 or HOMO-1→LUMO and HOMO-2→LUMO. From these states, internal conversion to a spatially localized $S_1$, state can occur (FIG. 6). Here, the larger para-substituted CPPs (n≥8) exhibit exciton localization over about seven of the phenylenes. When exciton localization occurs, the symmetry is different than the ground state, allowing the $S_{1'}$→HOMO transition. This transition can be responsible for the para-substituted CPP fluorescence. When n≤7 there is complete orbital delocalization over the whole $S_{1'}$ excited state structure; therefore, the ground state symmetry is conserved. In these cases, the $S_{1'}$→HOMO transition is Laporte forbidden, resulting in no fluorescence for [5]CPP and [6]CPP and only weak fluorescence for [7]CPP. In stark contrast, the meta-substituted nanohoop compounds of the present disclosure exhibit strong fluorescence, with a tenfold increase in the absorption when comparing [5]mCPP (6.0× $10^3$ $M^{-1}$ $cm^{-1}$) to [5]CPP (4.5×$10^2$ $M^{-1}$ $cm^{-1}$). The [n]mCPPs retain the common absorption maximum around 328 nm from HOMO-1→LUMO and/or HOMO→LUMO+1 transitions (Table 11).

TABLE 11

| [n]mCPP | H→L Absorbance (nm) | $\varepsilon_{H \to L}$ ($M^{-1}cm^{-1}$) |
|---|---|---|
| 5 | 428 | $6.0 \times 10^3 \pm 0.3$ |
| 6 | 410 | $9.4 \times 10^3 \pm 0.5$ |
| 7 | 394 | $9.9 \times 10^3 \pm 0.08$ |
| 8 | 376 | $1.4 \times 10^4 \pm 0.1$ |

The overall fluorescence of the [n]mCPPs, wherein n is 5 or 6, can be compared to [n]CPPs, wherein n is 5 or 6, by comparing their brightness, which is the product of the extinction coefficient and quantum yield. Additionally, the overall brightness of compounds like [10]- and [12]mCPPs is brighter than many commercial fluorophores like DAPI and Rhodamine 110.

VII. Overview of Several Embodiments

In some embodiments, the nanohoop compounds described herein have structures satisfying Formula I,

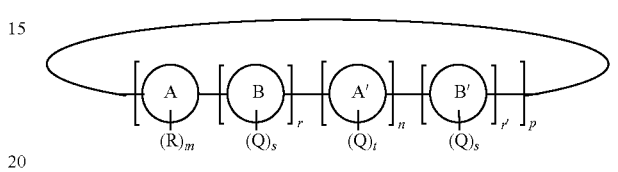

Formula I wherein each of rings A, A', B and B' independently is an aryl ring or a heteroaryl ring;

m is an integer selected from 1 to 10;

each R independently is linker-Z or Z, wherein the linker comprises an aliphatic group, a heteroaliphatic group, or any combination thereof; and Z comprises a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin;

each Q independently is linker-Z or Z;

each of r', r and n independently is an integer selected from 0 to 24;

each of s and t, when present, independently is an integer selected from 0 to 10; and p is an integer selected from 1 to 12, provided that when each of r, r', and n is 0, then p is at least 5, and provided that when p is 1, then at least one of r, r', or n is 4 or r, r', or n independently are integers that when taken together add up to 4.

In such embodiments, the nanohoop compound can have a structure satisfying any one or more of Formulas IIA through IIO as described herein, wherein each of each of a, b, c, and d, independently is selected from C or N; at least one of R or Q independently comprises an anionic group; m is an integer selected from 1 to 4; m' is an integer selected from 0 to 10; each of n, r and r' independently is an integer selected from 0 to 5; each of s and t, when present, independently is an integer selected from 0 to 4; and p is an integer selected from 1 to 5.

In any or all of the above embodiments, the nanohoop compound has a structure satisfying any one or more of Formulas IIA through IIIH, wherein at least one of R or Q independently comprises an anionic group, m is an integer selected from 1 to 4, and each of t, when present, independently is an integer selected from 0 to 4.

In any or all of the above embodiments, the nanohoop compound can comprise a drug selected from aspartame, captopril, enalapril, octreotide, desmopressin, or combinations thereof.

In any or all of the above embodiments, the nanohoop compound can comprise a peptide selected from a cell-penetrating peptide, an oligopeptide, a peptidic drug, an antibody, a protein, or combinations thereof.

In any or all of the above embodiments, the nanohoop compound can comprise a functional group comprising an amine, a carboxylic acid, a hydroxyl, an alkyne, an azide, a thiol, an aldehyde, an aminooxy, a triazole, or combinations thereof.

In any or all of the above embodiments, the nanohoop compound can comprise a nucleotide or nucleoside comprising an aptamer, a Spiegelmer, a somamer, a TNA aptamer, a XNA aptamer, a LNA aptamer, a catalytic aptamer, a phosphorodithioate, an inverted nucleic acid, a 2'-fluoro-, 2'-methoxy- or 2'-amino-modified nucleotide or nucleoside, a nucleotide or nucleotide with a modified base, a primer, an oligonucleoside or oligonucleotide, or combinations thereof.

In any or all of the above embodiments, the nanohoop compound can comprise a solubilizing group comprising an anionic group.

In some embodiments, the anionic group comprises a carboxyl, an organophosphorus group, an organosulfur group, hydroxyl, thiol, or combinations thereof.

In any or all of the above embodiments, the nanohoop compound can comprise an amino acid comprising a proteinogenic amino acid, an unnatural amino acid, a non-proteinogenic amino acid, a homo amino acid, an N-methyl amino acid, an alpha-methyl amino acid, a beta amino acid, a delta amino acid, a gamma amino acid, a D-amino acid, an L-amino acid, a thio amino acid, a seleno amino acid, an amino sulfonic acid, or combinations thereof.

In any or all of the above embodiments, the nanohoop compound comprises a linker that is -($L^a$-X-$L^b$)$_v$- and each of $L^a$ and $L^b$ independently is aliphatic; X is selected from $NR^a$, O and S; $R^a$ is hydrogen or aliphatic; and v is an integer selected from 1 to 50.

In some embodiments, each of $L^a$ and $L^b$ independently is $C_{1-6}$ aliphatic; X is O or S; and v is an integer selected from 1 to 5.

In any or all of the above embodiments, the nanohoop compound comprises a compound wherein each of the rings A, A', B, and B' ring is phenyl; m is 1; R is linker-Z, wherein Z is a solubilizing group and the linker is -($L^a$-X-$L^b$)$_v$-, wherein each of $L^a$ and $L^b$ independently is $C_{1-6}$alkyl; X is O or S; and v is 1; each of n, r, and r' is 1; each of s and t is 0; and p is 2.

In any or all of the above embodiments, the nanohoop compound comprises a solubilizing group comprising an anionic group.

In some embodiments, the anionic group comprises carboxyl, phosphoryl, hydroxyl, thiol, sulfonyl, or combinations thereof.

In any or all of the above embodiments, the nanohoop compound comprises a compound wherein each of the rings A, A', B and B' is phenyl; m, n, and t are each 1; R is Z, wherein Z comprises an amino group; Q comprises a carboxyl group; r and r' are each independently 1, 2, 3, 4, or 5; s is 0; and p is 1, 2 or 3.

In any or all of the above embodiments, the nanohoop compound comprises a compound wherein each of the rings A, A', B, and B' is phenyl; m is 1; each of n, r, and r' independently is 1, 2, 3, or 4; R is Z, wherein Z comprises an amino group and a carboxyl group; each of s and t is 0; and p is 1, 2, or 3.

In any or all of the above embodiments, the nanohoop compound is selected from the compounds having structures satisfying formulas shown in Tables 1-5, 7, or 8, or the compound shown in Table 6.

Also disclosed herein are embodiments of nanohoop compounds or conjugates that fluoresce. Fluorescent molecules can be used as biomarker and/or biological labeling reagents. Embodiments of the nanohoop compounds, and conjugates thereof, that exhibit fluorescence may be useful as a dye, label or probe for biotechnology. Some embodiments of the nanohoop compounds disclosed herein, and conjugates thereof, can be used as a fluorescent dye or fluorescent probe.

In an embodiment, a fluorescent dye or fluorescent probe comprising a nanohoop compound according to any or all of the above embodiments, can absorb light of a wavelength between 100 nm and 700 nm. In certain embodiments, the fluorescent dye or fluorescent probe comprising a nanohoop compound according to any or all of the above embodiments, can emit light of a wavelength between 300 nm and 800 nm. Additional embodiments of a fluorescent dye or fluorescent probe comprising a nanohoop compound according to any or all of the above embodiments, can fluoresce with a molar extinction coefficient of between 10,000 and 5,000,000 $M^{-1}$ $cm^{-1}$, and/or fluoresce with quantum yield of between 0.001 and 0.9 in DBPS.

Embodiments of a particular fluorescent dye or fluorescent probe comprising a nanohoop compound according to any or all of the above embodiments, can absorb light of a wavelength between 100 nm and 700 nm; emit light of a wavelength between 300 nm and 800 nm; fluoresce with a molar extinction coefficient of between 10,000 and 5,000,000 $M^{-1}$ $cm^{-1}$; fluoresce with a quantum yield of between 0.001 and 0.9 in DBPS; or any combination thereof.

Also disclosed herein are embodiments of nanohoop compounds according to any or all of the above embodiments, wherein the compound is soluble in water at a concentration of between 1 micromolar to 1 molar.

Also disclosed herein are embodiments of methods of making a nanohoop conjugate, comprising chemically coupling a biological moiety to a nanohoop compound according to any or all of the above embodiments, through one or more functional groups of any or all of the above embodiments of the nanohoop compound.

In some embodiments, the biological moiety is selected from a peptide, an oligonucleotide, a nucleoside, a drug, a cell, an antibody, an amino acid, a lipid, a carbohydrate, a liposome, a cyclodextrin, and a porphyrin.

In any or all of the above embodiments, the biological moiety can be covalently coupled to the functional group of the nanohoop compound.

In any or all of the above embodiments, the biological moiety can be coupled to the functional group of the nanohoop compound via hydrophobic and/or hydrophilic bonding.

In any or all of the above embodiments, the biological moiety can be coupled to an amine group of the nanohoop compound.

In any or all of the above embodiments, the biological moiety can be coupled to a carboxylic acid group of the nanohoop compound.

Also disclosed herein are embodiments of polymeric nanohoops comprising at least two nanohoop compounds according to any or all of the above embodiments. In some embodiments, the polymeric nanohoop comprises a first nanohoop monomer and a second nanohoop monomer, wherein the first nanohoop monomer is directly and covalently coupled to the second nanohoop monomer or wherein the first nanohoop monomer is indirectly coupled to the second nanohoop monomer through a covalently coupled linker group; wherein the first nanohoop monomer and the second nanohoop monomer independently has a structure satisfying Formula I according to any or all of the above embodiments.

In any or all of the above embodiments, the polymeric nanohoop comprises a compound wherein one or more additional nanohoop monomers are coupled to the first and/or second nanohoop monomers, wherein the one or more additional nanohoop monomers independently has a structure satisfying Formula I according to any or all of the above embodiments.

In any or all of the above embodiments, the polymeric nanohoop comprises a total of 2 to 1000 nanohoop monomers.

In any or all of the above embodiments, the polymeric nanohoop comprises a compound wherein ring A of the first nanohoop monomer is covalently coupled directly or through the covalently coupled linker group to ring A, B, A', or B' of the second nanohoop monomer.

In any or all of the above embodiments, the polymeric nanohoop comprises a compound wherein ring A', ring B, or ring B' of the first nanohoop monomer is covalently coupled directly or through the covalently coupled linker group to ring A, B, A', or B' of the second nanohoop monomer.

In any or all of the above embodiments, the polymeric nanohoop comprises a compound wherein the covalently coupled linker group is selected from an aliphatic, heteroaliphatic, aryl, or heteroaryl group, or combinations thereof.

In any or all of the above embodiments, the polymeric nanohoop comprises a compound satisfying one of more of Formulas IVA-IVF, as described herein, wherein each of a, b, c, and d, independently is selected from C or N; at least one of R or Q independently comprises an anionic group; each of n, r and r' independently is an integer selected from 0 to 4; m is an integer selected from 1 to 4; w is an integer selected from 1 to 5; p is an integer selected from 1 to 5; and y is an integer selected from 1 to 5.

In any or all of the above embodiments, the polymeric nanohoop comprises a compound satisfying Formula VA as described herein, wherein the nanohoop of the first nanohoop monomer is covalently coupled to a second nanohoop monomer through any of rings A, B, A' or B' of the first monomer nanohoop and any of rings A, B, A', or B' of the second nanohoop monomer via an aliphatic, heteroaliphatic, aryl or heteroaryl group; each of n, r and r' independently is an integer selected from 0 to 4; m is an integer selected from 1 to 4; p is an integer selected from 1 to 5; and y is an integer selected from 1 to 5.

In any or all of the above embodiments, the polymeric nanohoop comprises a solubilizing group comprising an anionic group.

In some embodiments, the anionic group comprises carboxyl, an organophosphorus group, an organosulfur group, hydroxyl, thiol, or combinations thereof.

In any or all of the above embodiments, the polymeric nanohoop compound comprises a compound wherein the linker is -(L$^a$-X-L$^b$)$_v$-, and each of L$^a$ and L$^b$ independently is aliphatic; X is selected from NR$^a$, O and S; R$^a$ is hydrogen or aliphatic; and v is an integer selected from 1 to 50.

In some embodiments, the polymeric nanohoop compound comprises a compound wherein L$^a$ and L$^b$ are each independently C$_{1-6}$ aliphatic; X is O or S; and v is selected from 1 to 5.

In any or all of the above embodiments, the polymeric nanohoop compound comprises a compound wherein the fluorescence of the first nanohoop monomer does not quench the fluorescence of the second nanohoop monomer.

In any or all of the above embodiments, the polymeric nanohoop compound comprises a compound wherein the first nanohoop is covalently coupled to the second nanohoop via an aliphatic or aryl group G, and the compound has a structure satisfying Formula VIA as described herein.

In some embodiments, the polymeric nanohoop compound comprises a polymeric nanohoop compound wherein G is a bond or phenyl.

Also disclosed herein are embodiments of kits comprising a nanohoop compound according to any or all of the above embodiments, wherein the kit comprises a container comprising a biological moiety; and a container comprising a nanohoop compound having a structure satisfying Formula I as described herein.

Embodiments of the disclosed nanohoop compounds can further be useful in analytical methods, including for methods of monitoring the presence or absence of a nanohoop compound in an assay or in a subject.

Also disclosed herein are embodiments of methods comprising exposing a sample to a a nanohoop compound according to any or all of the above embodiments, or a composition thereof; and analyzing the sample for the presence or absence of fluorescence after exposing the sample to the compound or composition thereof.

In any or all of the above embodiments, the sample is a biological sample selected from a cell, tissue, or bodily fluid.

In some embodiments, the sample is obtained from a human subject.

In view of the many possible embodiments to which the principles of the present disclosure may be applied, it should be recognized that the illustrated embodiments are only preferred examples and should not be taken as limiting the scope of the present disclosure. Rather, the scope is defined by the following claims. We therefore claim as our invention all that comes within the scope and spirit of these claims.

We claim:

1. A nanohoop compound having a structure satisfying a formula

Formula I

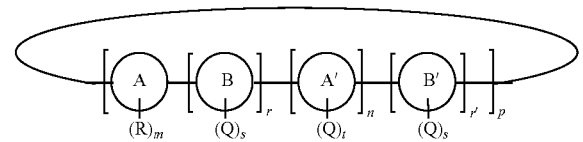

wherein each of rings A, A', B and B' independently is a phenyl ring or a heteroaryl ring selected from pyridinyl, benzo[1,2-b:4,5-b']dithiophenyl, benzo[1,2-b:4,5-b']difuranyl, 4,4-dimethyl-4H-cyclopenta[2,1-b:3,4-b']dithiophene, 1,5-dihydropyrrolo[2,3-f]indolyl, benzo[c][1,2,5]thiadiazolyl, benzo[c][1,2,5]oxadiazolyl, or 2H-benzo[d][1,2,3]triazolyl;

m is an integer selected from 1 to 10;

each R independently is linker-Z or Z, wherein the linker comprises an aliphatic group, a heteroaliphatic group, or any combination thereof; and Z comprises an anionic solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, a quenching moiety, or, (i) a functional group that facilitates coupling of the nanohoop compound with an anionic solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin when R is linker-Z, or (ii) a functional group selected from

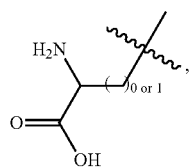

amine, aminooxy, triazole, azide, an NHS ester, or combinations thereof, when R is Z;

each Q independently is linker-Z or Z, wherein
the linker comprises an aliphatic group, a heteroaliphatic group, or any combination thereof; and
Z comprises an anionic solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with an anionic solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin;

each of r', r and n independently is an integer selected from 0 to 24;
each of s and t, when present, independently is an integer selected from 0 to 10; and
p is an integer selected from 1 to 12;
wherein R and Q are the same or different; and
provided that when each of r, r', and n is 0, then p is at least 5; and
provided that when p is 1, then at least one of r, r', or n is 4 or r, r', or n independently are integers that when taken together add up to 4.

2. The nanohoop compound of claim 1, wherein the compound has a structure satisfying any one or more of the following formulas:

Formula IIA

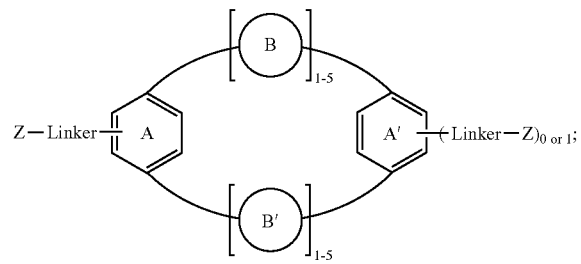

Formula IIB

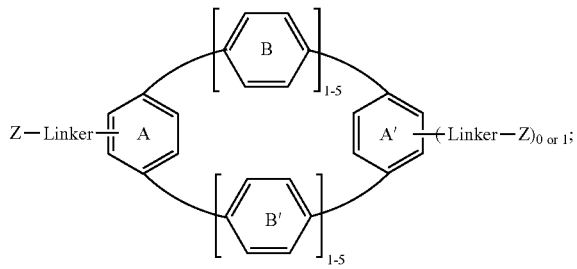

Formula IIC

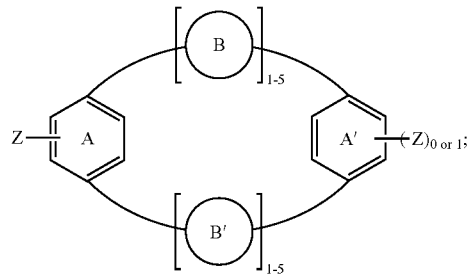

Formula IID

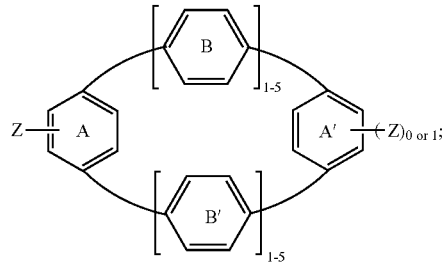

Formula IIE

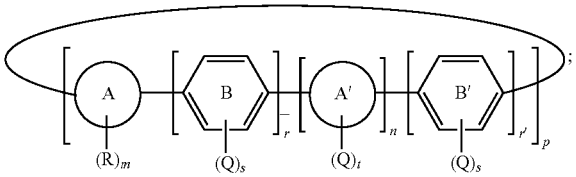

Formula IIF

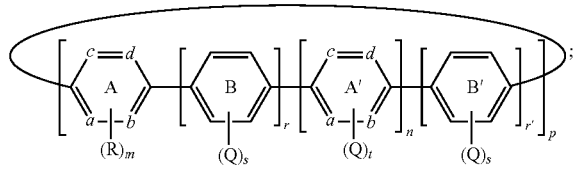

Formula IIG

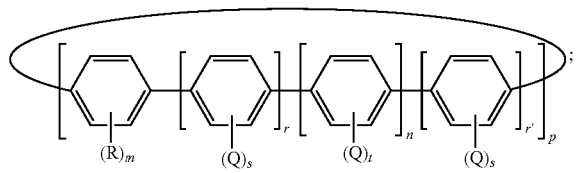

-continued

Formula IIH

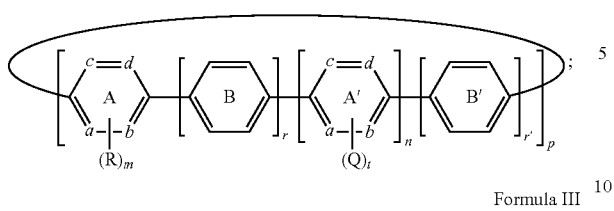

Formula III

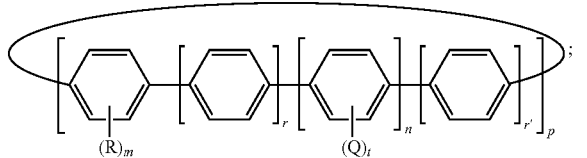

Formula IIJ

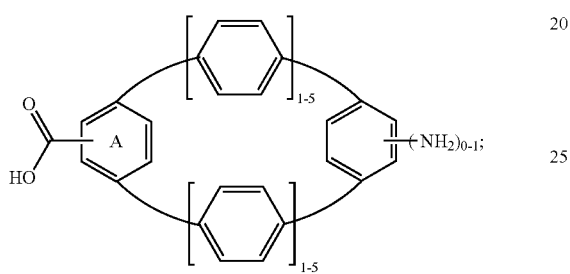

Formula IIK

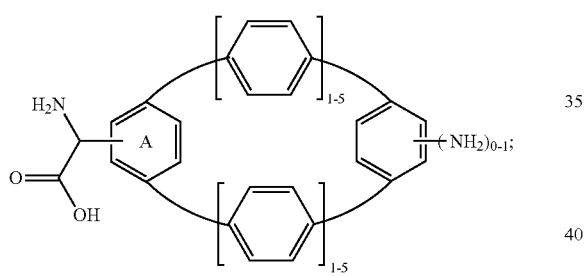

Formula IIL

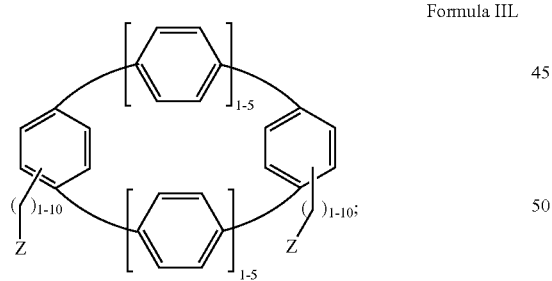

Formula IIN

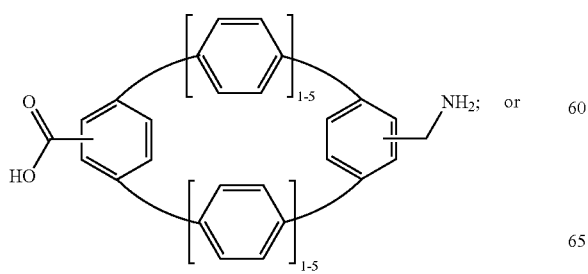
or

-continued

Formula IIO

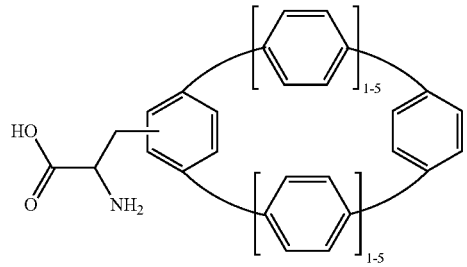

wherein
each of a, b, c, and d, independently is selected from C or N;
at least one of R or Q independently comprises an anionic group;
m is an integer selected from 1 to 4;
m' is an integer selected from 0 to 10;
each of n, r and r' independently is an integer selected from 0 to 5;
each of s and t, when present, independently is an integer selected from 0 to 4; and
p is an integer selected from 1 to 5.

3. The nanohoop compound of claim 1, wherein:
(i) the drug is selected from aspartame, captopril, enalapril, octreotide, desmopressin, or combinations thereof;
(ii) the peptide is a cell-penetrating peptide, an oligopeptide, a peptidic drug, an antibody, a protein, or combinations thereof;
(iii) the functional group that facilitates coupling of the nanohoop compound with the anionic solubilizing group, the peptide, the oligonucleotide, the nucleoside, the nucleotide, the protein, the aptamer, the drug, the quenching moiety, the cell, the antibody, the amino acid, the lipid, the carbohydrate, the liposome, the cyclodextrin, or the porphyrin comprises an amine, a carboxylic acid, a hydroxyl, an alkyne, an azide, a thiol, an aldehyde, an aminooxy, a triazole, or combinations thereof;
(iv) the nucleotide or nucleoside comprises an aptamer; an L-form oligonucleotide; a slow off-rate modified aptamer; a threose nucleic acid (TNA) aptamer; a xeno-nucleic acid (XNA) aptamer; a locked nucleic acid (LNA) aptamer; a catalytic aptamer; a phosphorodithioate; an inverted nucleic acid; a 2'-fluoro-, 2'-methoxy-, or 2'-amino-modified nucleotide or nucleoside; a nucleotide or nucleotide with a modified base; a primer; an oligonucleoside or oligonucleotide; or combinations thereof;
(v) the anionic solubilizing group is selected from a carboxylate, a phosphonate, a sulfonate, or a deprotonated hydroxyl group or thiol group; and/or
(vi) the amino acid comprises a proteinogenic amino acid, an unnatural amino acid, a non-proteinogenic amino acid, a homo amino acid, an N-methyl amino acid, an alpha-methyl amino acid, a beta amino acid, a delta amino acid, a gamma amino acid, a D-amino acid, an L-amino acid, a thio amino acid, a seleno amino acid, an amino sulfonic acid, or combinations thereof.

4. The nanohoop compound of claim 1, wherein

R is linker-Z, wherein the linker is $C_{1-6}$ aliphatic or $-(L^a-X-L^b)_v-$, wherein each of $L^a$ and $L^b$ independently is $C_{1-6}$ aliphatic; X is O or S; and v is an integer selected from 1 to 5; and Z is a functional group that facilitates coupling of the nanohoop and comprises a triazine, —OH, an azide, a carboxyl group, $SO_3H$ or a salt thereof;

each of n, r, and r' is 1;

each of s and t is 0; and p is 2.

5. The nanohoop compound of claim 1, wherein each of the rings A, A', B and B' is phenyl;

m, n, and t are each 1;

R is Z, wherein Z comprises an amino group;

Q comprises a carboxyl group;

r and r' are each independently 1, 2, 3, 4, or 5;

s is 0; and p is 1, 2 or 3.

6. The nanohoop compound of claim 1, wherein each of the rings A, A', B, and B' is phenyl;

m is 1;

each of n, r, and r' independently is 1, 2, 3, or 4;

R is Z, wherein Z is

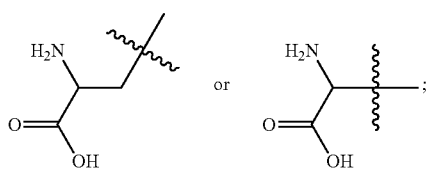

each of s and t is 0; and p is 1, 2, or 3.

7. The nanohoop compound of claim 1, wherein the compound is selected from:

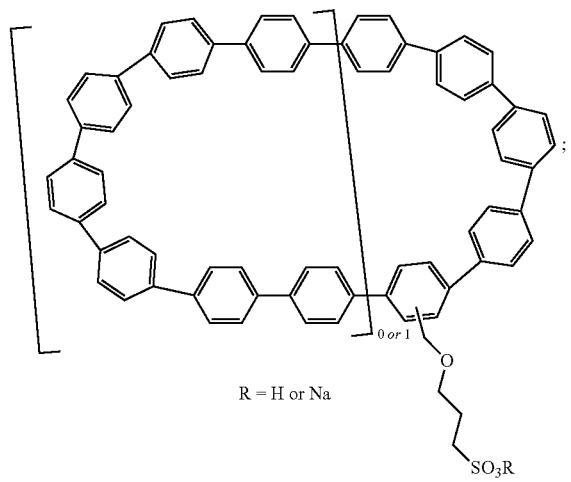

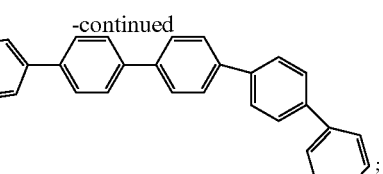

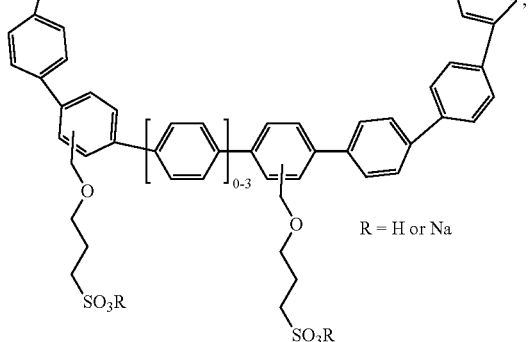

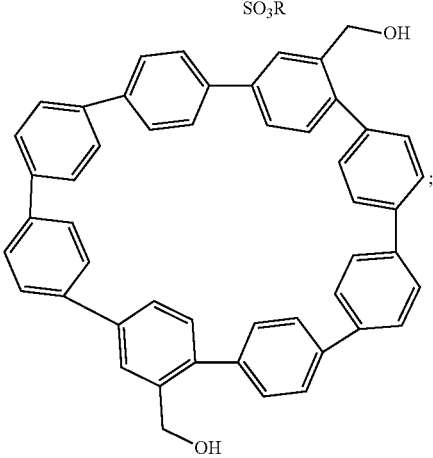

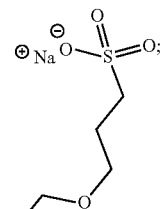

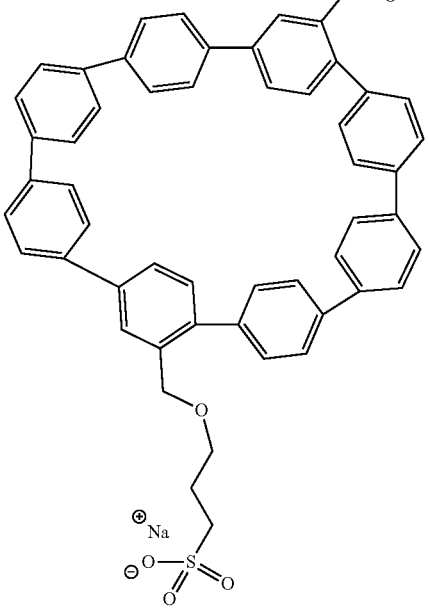

165
-continued
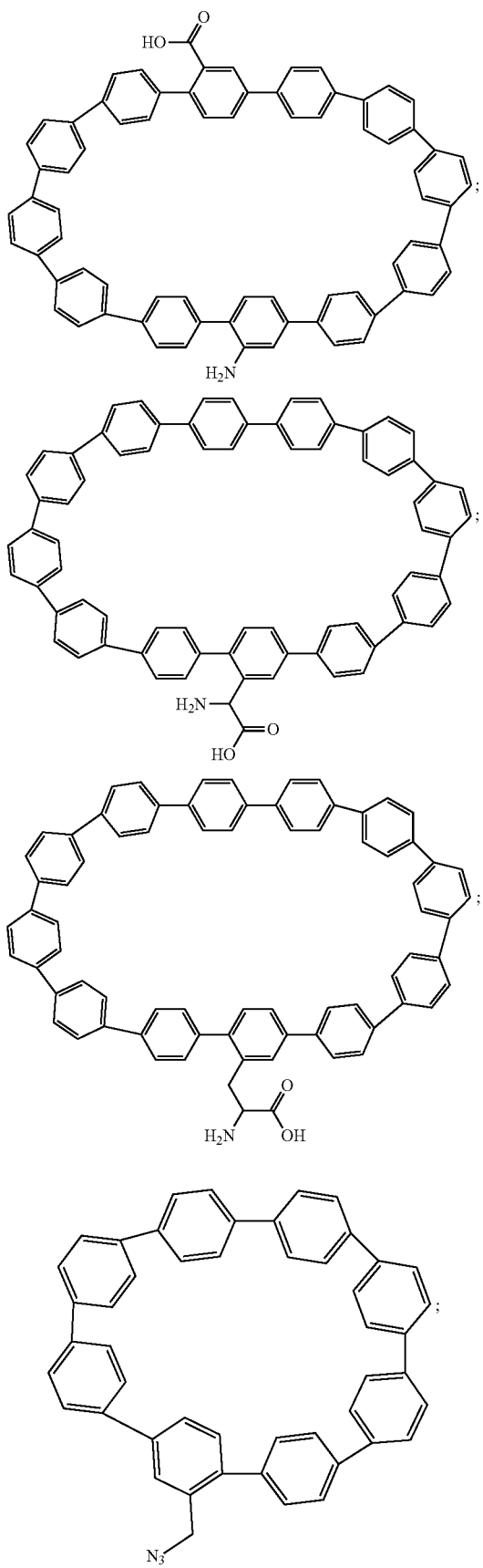
166
-continued
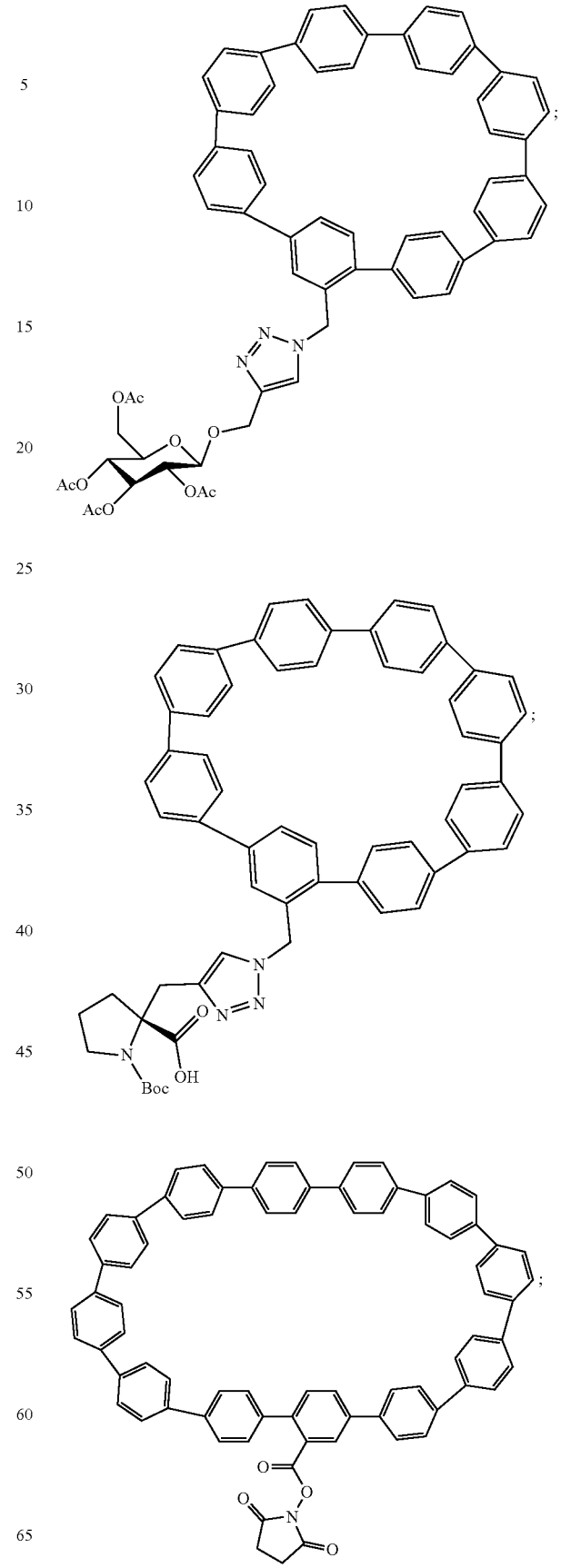

167
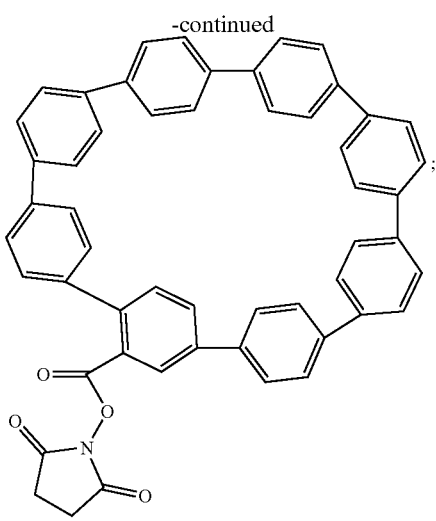
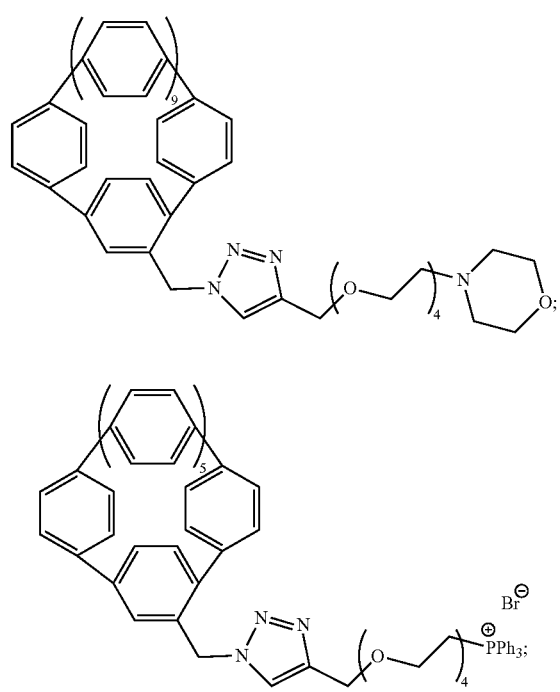
168
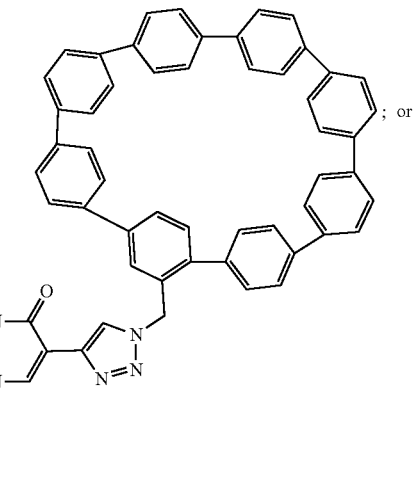
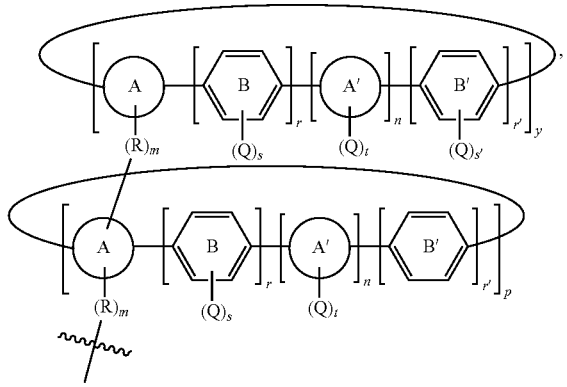
8. A nanohoop compound having a structure satisfying Formula I
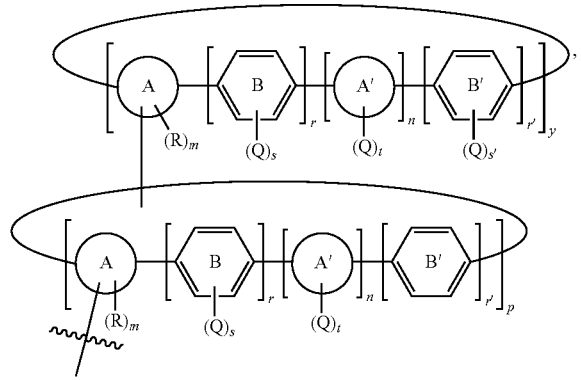

Formula IVC

Formula IVD

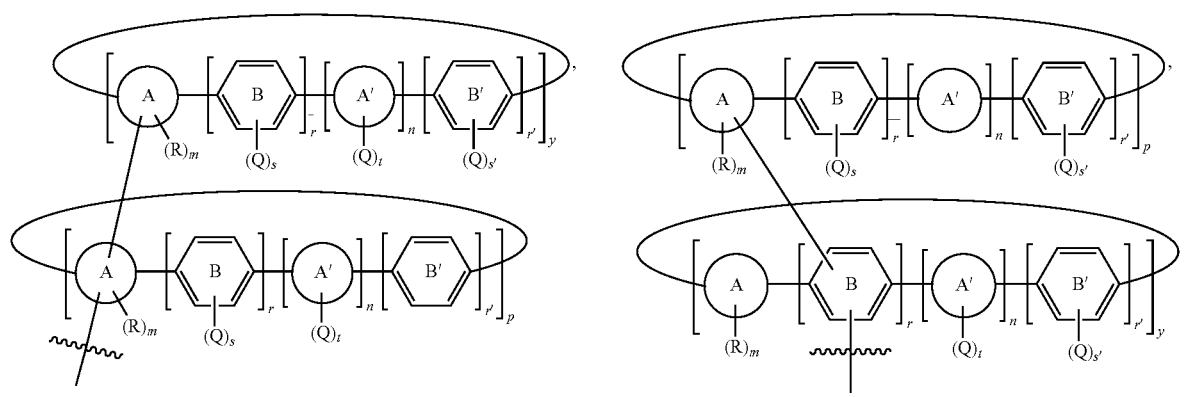

Formula IVE

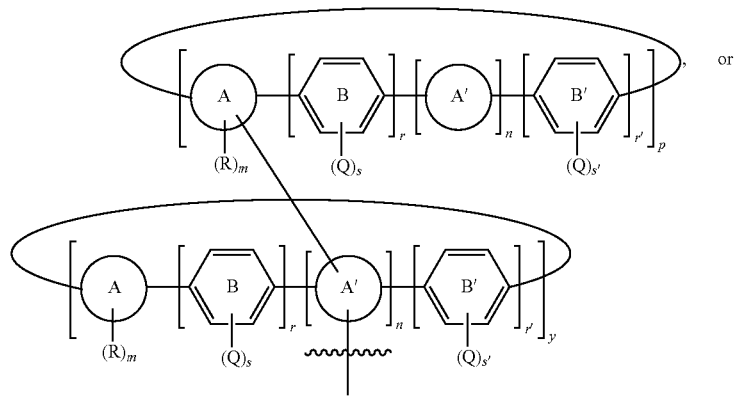

Formula IVF

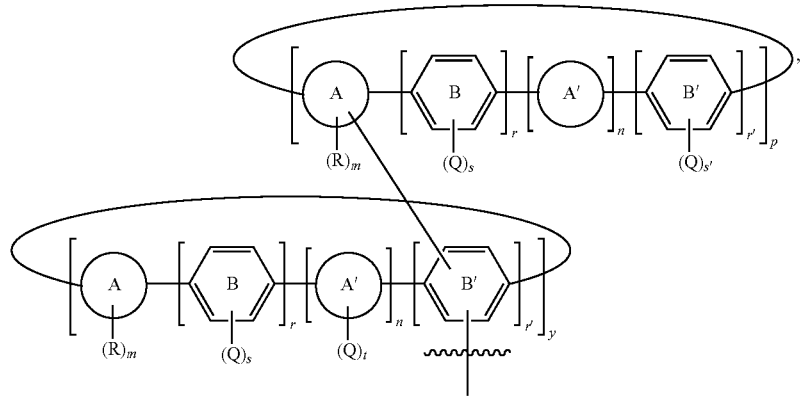

wherein
each of rings A, A', B and B' independently is a phenyl ring or a heteroaryl ring selected from pyridinyl, benzo[1,2-b:4,5-b']dithiophenyl, benzo[1,2-b:4,5-b']difuranyl, 4,4-dimethyl-4H-cyclopenta[2,1-b:3,4-b']dithiophene, 1,5-dihydropyrrolo[2,3-f]indolyl, benzo[c][1,2,5]thiadiazolyl, benzo[c][1,2,5]oxadiazolyl, or 2H-benzo[d][1,2,3]triazolyl;
m is zero and at least one ring A is attached to two other rings of the nanohoop compound by bonds that are meta-substituted relative to one another and wherein the nanohoop compound comprises at least one A, A', B, or B' ring that is attached to two other rings of the nanohoop compound by bonds that are para-substituted relative to one another;
each Q independently is linker-Z or Z, wherein
the linker comprises an aliphatic group, a heteroaliphatic group, or any combination thereof; and
Z comprises a solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, a quenching moiety, or a functional group that facilitates coupling of the nanohoop compound with a solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin;

each of r', r and n independently is an integer selected from 0 to 24;

each of s and t, when present, independently is an integer selected from 0 to 10; and p is an integer selected from 1 to 12;

provided that when each of r, r', and n is 0, then p is at least 5; and provided that when p is 1, then at least one of r, r', or n is 4 or r, r', or n independently are integers that when taken together add up to 4.

9. The nanohoop compound of claim 8 having a structure satisfying Formula IIP

Formula IIP

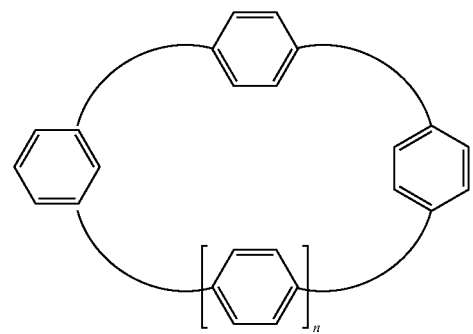

wherein n is an integer ranging from 2 to 9.

10. The nanohoop compound of claim 8, selected from:

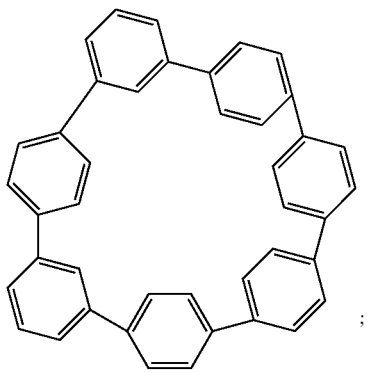

;

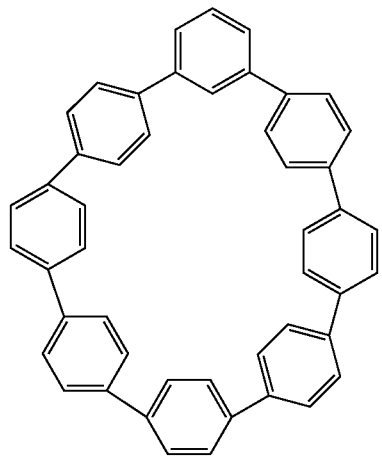

;

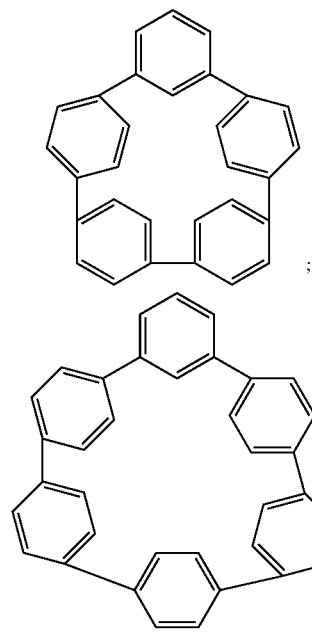

;

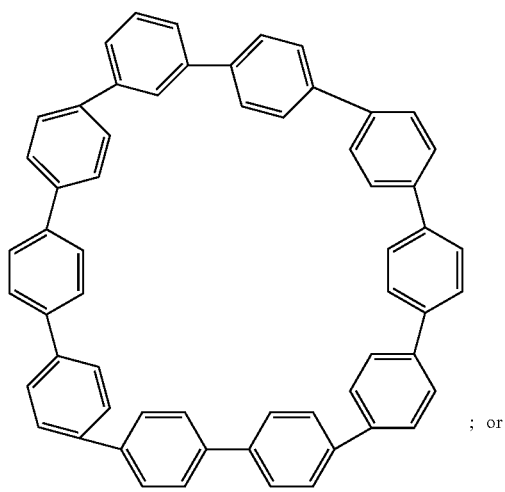

; or

-continued

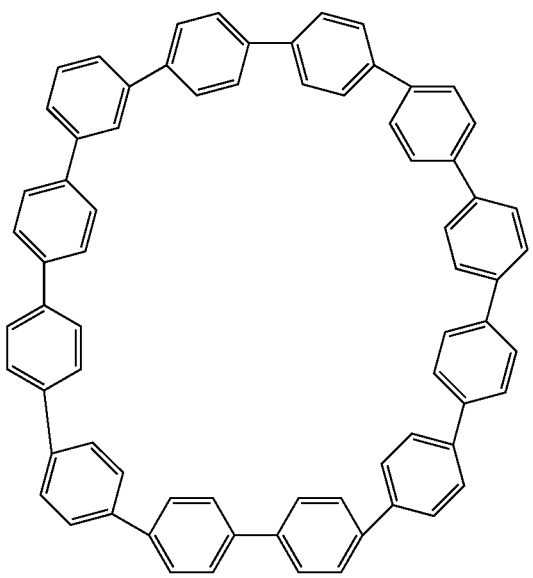

11. A method of making a nanohoop conjugate, comprising covalently coupling a biological moiety to a nanohoop compound having structure satisfying Formula I through one or more functional groups of the nanohoop compound Formula I

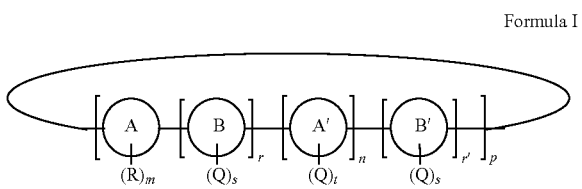

wherein
each of rings A, A', B and B' independently is a phenyl ring or a heteroaryl ring selected from pyridinyl, benzo[1,2-b:4,5-b']dithiophenyl, benzo[1,2-b:4,5-b']difuranyl, 4,4-dimethyl-4H-cyclopenta[2,1-b:3,4-b']dithiophene, 1,5-dihydropyrrolo[2,3-f]indolyl, benzo[c][1,2,5]thiadiazolyl, benzo[c][1,2,5]oxadiazolyl, or 2H-benzo[d][1,2,3]triazolyl;
m is an integer selected from 1 to 10;
each R independently is linker-Z or Z, wherein
  the linker comprises an aliphatic group, a heteroaliphatic group, or any combination thereof; and
  Z comprises aa functional group that facilitates coupling of the nanohoop compound with an anionic solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin when R is linker-Z; or
  (ii) a functional group selected from

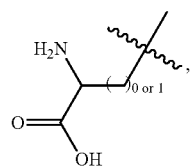

amine, aminooxy, triazole, azide, an NHS ester, or combinations thereof, when R is Z;
each Q independently is linker-Z' or Z', wherein
  the linker comprises an aliphatic group, a heteroaliphatic group, or any combination thereof; and
  Z' is an anionic solubilizing group, a peptide, an oligonucleotide, a nucleoside, a nucleotide, a protein, an aptamer, a drug, a cell, an antibody, an amino acid, a lipid, a carbohydrate, a liposome, a cyclodextrin, a porphyrin, an electron-donating group, an electron withdrawing group, or a quenching moiety;
each of r', r and n independently is an integer selected from 0 to 24;
each of s and t, when present, independently is an integer selected from 0 to 10; and
p is an integer selected from 1 to 12;
provided that when each of r, r', and n is 0, then p is at least 5; and
provided that when p is 1, then at least one of r, r', or n is 4 or r, r', or n independently are integers that when taken together add up to 4.

12. The method of claim 11, wherein the biological moiety is selected from a peptide, an oligonucleotide, a nucleoside, a drug, a cell, an antibody, an amino acid, a lipid, a carbohydrate, a liposome, a cyclodextrin, and a porphyrin and wherein the biological moiety is coupled to an amine group of the nanohoop compound, or to a carboxylic acid group of the nanohoop compound.

13. A polymeric nanohoop compound comprising a first nanohoop monomer and a second nanohoop monomer, wherein the first nanohoop monomer is directly and covalently coupled to the second nanohoop monomer or wherein the first nanohoop monomer is indirectly coupled to the second nanohoop monomer through a covalently coupled linker group; wherein the first nanohoop monomer and the second nanohoop monomer independently have a structure satisfying Formula I of claim 1.

14. The polymeric nanohoop compound of claim 13, wherein the covalently coupled linker group is selected from an aliphatic, heteroaliphatic, aryl, or heteroaryl group, or combinations thereof.

15. The polymeric nanohoop compound of claim 13, wherein the compound has a structure satisfying any one or more of the following formulas Formula IVA

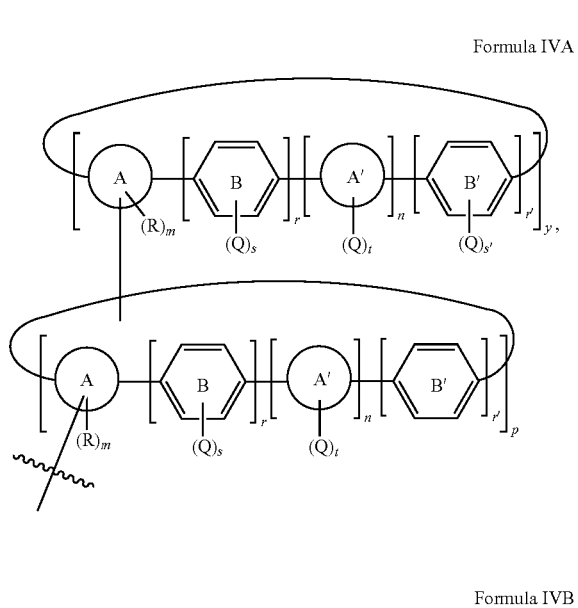

Formula IVB

Formula IVC

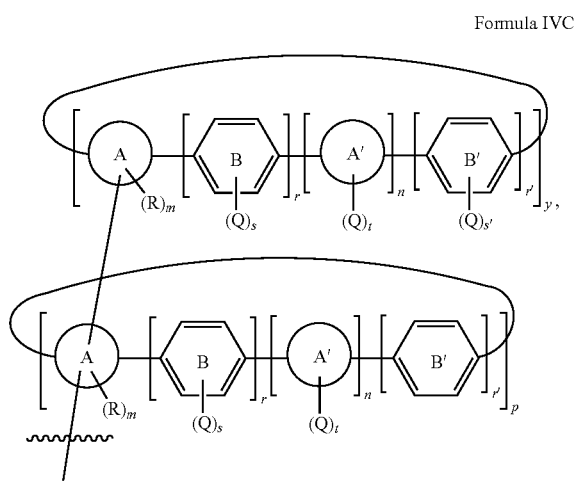

Formula IVD

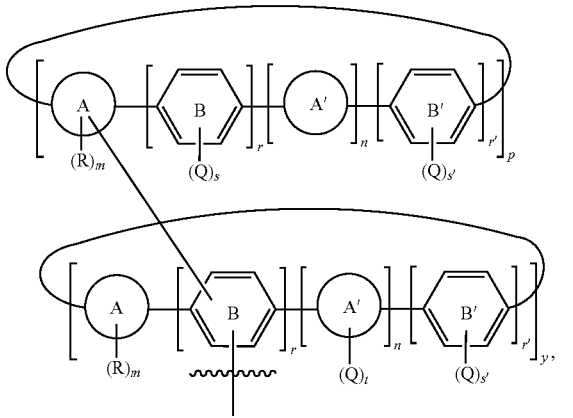

Formula IVE

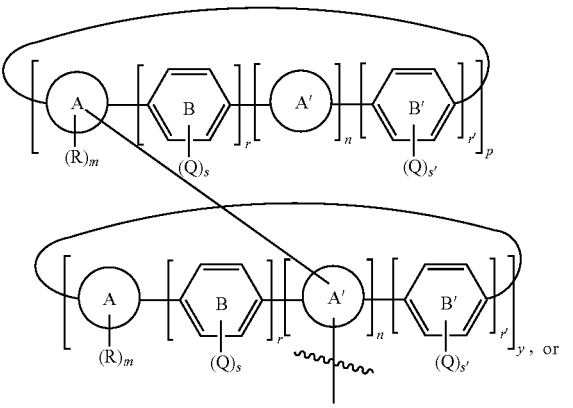

, or

Formula IVF at least one of R or Q independently comprises the anionic solubilizing group;

each of n, r and r' independently is an integer selected from 0 to 4;

m is an integer selected from 1 to 4;

p is an integer selected from 1 to 5; and y is an integer selected from 1 to 5.

16. The polymeric nanohoop compound of claim 13, wherein
the linker of Formula I is -(L$^a$-X-L$^b$)$_v$-, and each of L$^a$ and L$^b$ independently is aliphatic;
X is NR$^a$, O or S;
R$^a$ is hydrogen or aliphatic; and
v is an integer selected from 1 to 50.

17. The polymeric nanohoop compound of claim 16, wherein
L$^a$ and L$^b$ are each independently C$_{1-6}$ aliphatic;
X is O or S; and
v is selected from 1 to 5.

18. The polymeric nanohoop compound of claim 13, wherein the fluorescence of the first nanohoop monomer does not quench the fluorescence of the second nanohoop monomer.

19. The polymeric nanohoop compound of claim 13, having a structure of Formula VIA:

21. A nanohoop compound having a structure satisfying a formula

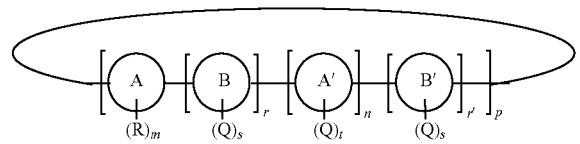

Formula I wherein
each of rings A, A', B and B' independently is a phenyl ring or a heteroaryl ring selected from pyridinyl, benzo[1,2-b:4,5-b']dithiophenyl, benzo[1,2-b:4,5-b']difura-

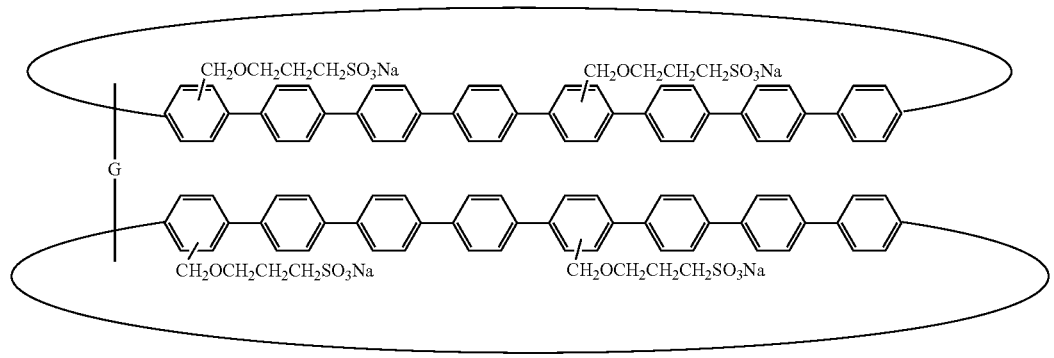

Formula VIA wherein G is a bond or phenyl.

20. A method, comprising:
exposing a biological sample to a nanohoop compound of claim 1 or a composition thereof, wherein R is linker-Z or Z and wherein Z is the anionic solubilizing group, the peptide, the oligonucleotide, the nucleoside, the nucleotide, the protein, the aptamer, the drug, the cell, the antibody, the amino acid, the lipid, the carbohydrate, the liposome, the cyclodextrin, the porphyrin, or the quenching moiety; and
analyzing the biological sample using UV-Vis and/or fluorescence spectrometry to detect
(i) the presence of fluorescence upon delivery of the nanohoop compound to a region of the sample and cleavage of the anionic solubilizing group, the peptide, the oligonucleotide, the nucleoside, the nucleotide, the protein, the aptamer, the drug, the cell, the antibody, the amino acid, the lipid, the carbohydrate, the liposome, the cyclodextrin, the porphyrin, or the quenching moiety from the nanohoop compound, or
(ii) the quenching of fluorescence upon delivery of the nanohoop compound to a region of the sample and cleavage of the anionic solubilizing group, the peptide, the oligonucleotide, the nucleoside, the nucleotide, the protein, the aptamer, the drug, the cell, the antibody, the amino acid, the lipid, the carbohydrate, nyl, 4,4-dimethyl-4H-cyclopenta[2,1-b:3,4-b']dithiophene, 1,5-dihydropyrrolo[2,3-f]indolyl, benzo[c][1,2,5]thiadiazolyl, benzo[c][1,2,5]oxadiazolyl, or 2H-benzo[d][1,2,3]triazolyl;
m is an integer selected from 1 to 10;
each R independently is (i) a triazole moiety, (ii) an aliphatic moiety, (iii) a -(L$^a$-X-L$^b$)$_v$- moiety wherein each of L$^a$ and L$^b$ independently is aliphatic, X is a heteroatom, and v is an integer selected from 1 to 50, or any combination of (i), (ii), and/or (iii); and wherein (i), (ii), (iii), or the combination thereof is bound to Z wherein each Z independently comprises an anionic solubilizing group; a peptide; an oligonucleotide; a nucleoside; a nucleotide; a protein; an aptamer; a drug; a cell; an antibody; an amino acid; a lipid; a carbohydrate; a liposome; a cyclodextrin; a porphyrin; a quenching moiety; or a functional group that facilitates coupling of the nanohoop compound with an anionic solubilizing group, a peptide, an oligonucleotide, a nucleoside, a nucleotide, a protein, an aptamer, a drug, a quenching moiety, a cell, an antibody, an amino acid, a lipid, a carbohydrate, a liposome, a cyclodextrin, or a porphyrin; or each R independently is Z, wherein each Z independently comprises an anionic solubilizing group; a peptide; an oligonucleotide; a nucleoside; a nucleotide; a protein; an aptamer; a drug; a cell; an antibody; an amino acid; a lipid; a carbohydrate; a liposome; a cyclodextrin; a porphyrin; a quenching moiety; or a functional group selected from

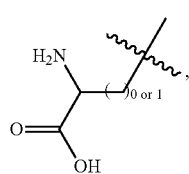

amine, aminooxy, triazole, azide, an NHS ester, or combinations thereof;

each Q independently is linker-Z or Z, wherein the linker comprises an aliphatic group, a heteroaliphatic group, or any combination thereof;

each of r', r and n independently is an integer selected from 0 to 24;

each of s and t, when present, independently is an integer selected from 0 to 10; and p is an integer selected from 1 to 12; and provided that when each of r, r', and n is 0, then p is at least 5; and provided that when p is 1, then at least one of r, r', or n is 4 or r, r', or n independently are integers that when taken together add up to 4.

* * * * *